(12) United States Patent
Verdin et al.

(10) Patent No.: US 8,748,464 B2
(45) Date of Patent: Jun. 10, 2014

(54) USE OF SIRT1 ACTIVATORS OR INHIBITORS TO MODULATE AN IMMUNE RESPONSE

(75) Inventors: Eric M. Verdin, San Francisco, CA (US); Melanie Ott, San Francisco, CA (US); Hye-Sook Kwon, San Mateo, CA (US); Hyungwook Lim, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 519 days.

(21) Appl. No.: 12/838,247

(22) Filed: Jul. 16, 2010

(65) Prior Publication Data
US 2010/0330114 A1 Dec. 30, 2010

Related U.S. Application Data

(63) Continuation-in-part of application No. PCT/US2009/000761, filed on Feb. 5, 2009.

(60) Provisional application No. 61/026,997, filed on Feb. 7, 2008.

(51) Int. Cl.
*A01N 43/78* (2006.01)
*A61K 31/535* (2006.01)

(52) U.S. Cl.
USPC ............ 514/366; 514/229.5; 514/233.2

(58) Field of Classification Search
USPC ........................................... 514/366
See application file for complete search history.

(56) References Cited

U.S. PATENT DOCUMENTS

| | | | |
|---|---|---|---|
| 7,345,178 B2 * | 3/2008 | Nunes et al. ............ | 548/154 |
| 2005/0209300 A1 | 9/2005 | Napper et al. | |
| 2007/0043050 A1 | 2/2007 | Nunes et al. | |
| 2007/0105109 A1 | 5/2007 | Geesaman et al. | |
| 2007/0190073 A1 | 8/2007 | Tuck et al. | |
| 2008/0255382 A1 | 10/2008 | Andrus et al. | |
| 2009/0012080 A1 | 1/2009 | Bemis et al. | |
| 2010/0061984 A1 | 3/2010 | Greene et al. | |

OTHER PUBLICATIONS

Milne et al "Small molecule activators of SIRT1 as therapeutics for the treatment of type 2 diabetes," (2007) Nature 450:712-716.
Ott et al., "Immune hyperactivation of HIV-1-infected T cells mediated by Tat and the CD28 pathway," (1997) Science 275:1481-1485.
Nayagam et al., "SIRT1 modulating compounds from high-throughput screening as anti-inflammatory and insulin-sensitizing agents," (2006) J. Biomol. Screening 11:959-967.
Ott, M. "Role of SIRT1 in T cell Hyperacitivation during HIV infection California HIV/AIDS Research Program," 2008 http://chrp.ucop.edu/funded_research/abstracts/2007_ott.html (2007), para 1-3.
Feige et al., "Specific SIRT1 Activation Mimics Low Energy Levels and Protects against Diet-Induced Metabolic Disorders by Enhancing Fat Oxidation," (2008) Cell Metabolism 8:347-358.
Sakamoto, K. "Silencing Metabolic Disorders by Novel SIRT1 Activators," (2008) Cell Metabolism 7:3-4.
Pacholec et al., "SRT1720, SRT2183, SRT1460, and Resveratrol are not Direct Activators of SIRT1," Published on Jan. 8, 2010 as Manuscript M109.088682 The latest version is at http://www.jbc.org/cgi/doi/10.1074/jbc.M109.088682—25 pages.
Sundrud et al., "Synergistic and combinatorial control of T cell activation and differentiation by transcription factors," ScienceDirect www.sciencedirect.com, Current Opinion in Immunology (2010) 22:1-7.
Tao et al., "Deacetylase inhibition promotes the generation and function of regulatory T cells," (2007) Nat. Med. 13 (11):1299-1307.
Saouaf et al., "Deacetylase inhibition increases regulatory T cell function and decreases incidence and severity of collagen-induced arthritis," (2009) Exp. Mol. Pathol. 87:99-104.
Van Loosdregt et al., "Regulation of Treg functionality by acetylation-mediated Foxp3 protein stabilization" (2010) Blood 115(5):965-974.
Wang et al., "Using histone deacetylase inhibitors to enhance Foxp3+ regulatory T-cell function and induce allograft tolerance," (2009) Immunol. Cell Biol. 87:195-202.
Pagans, et al. "SIRT1 Regulates HIV Transcription via TAT Deacetylation", PLoS Biology, Feb. 2005, vol. 3, Issue 2, pp. 0210-0220.

* cited by examiner

*Primary Examiner* — Sreeni Padmanabhan
*Assistant Examiner* — Timothy E Betton
(74) *Attorney, Agent, or Firm* — Paula A. Borden; Bozicevic, Field & Francis LLP.

(57) ABSTRACT

The present disclosure provides a method of increasing an immune response in an individual, the method involving administering to an individual in need thereof an inhibitor of SIRT1. The present disclosure provides a method of reducing an immune response, e.g., to treat chronic immune hyperactivity, the method generally involving administering to an individual in need thereof an activator of SIRT1. The present disclosure provides a method of modulating activation and differentiation of CD4$^+$ T cells.

7 Claims, 13 Drawing Sheets

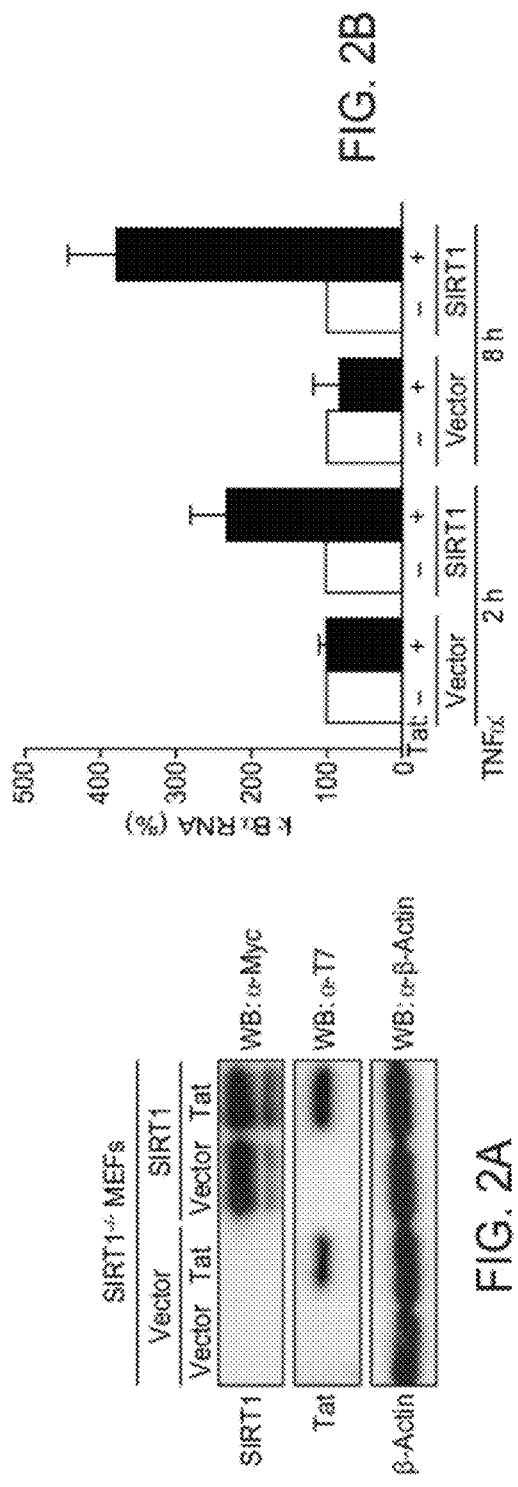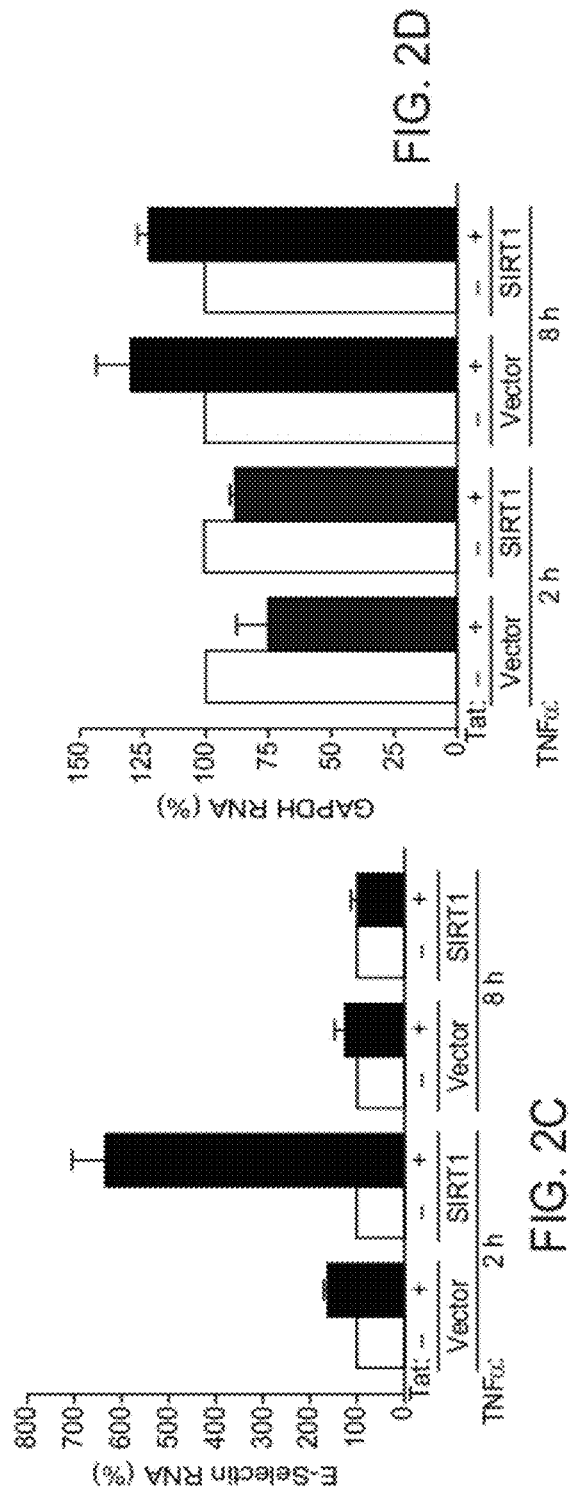
FIG. 2A  FIG. 2B  FIG. 2C  FIG. 2D

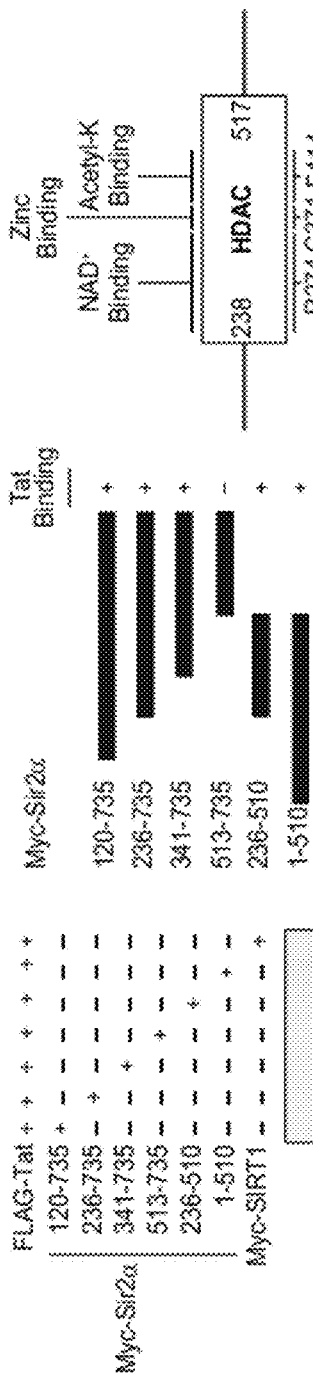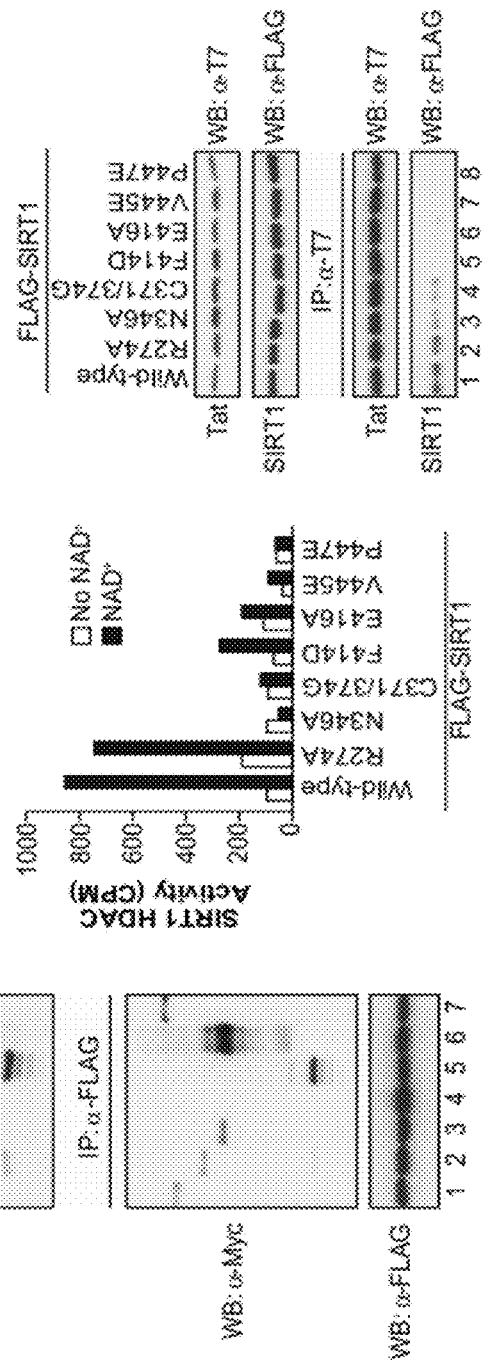

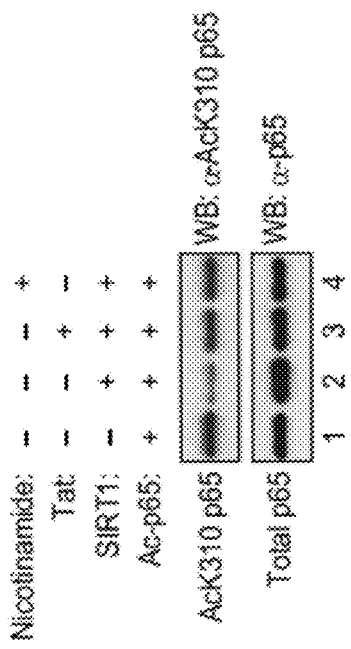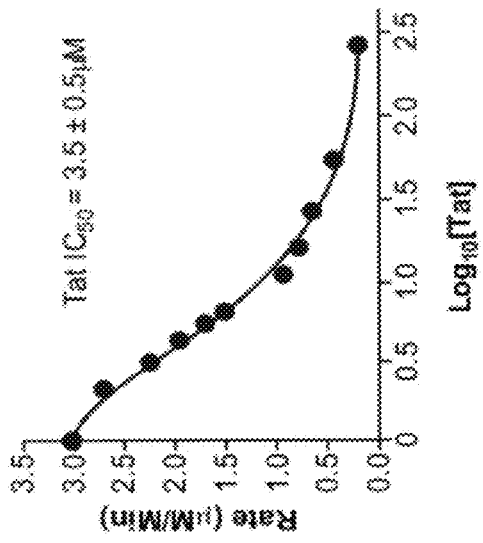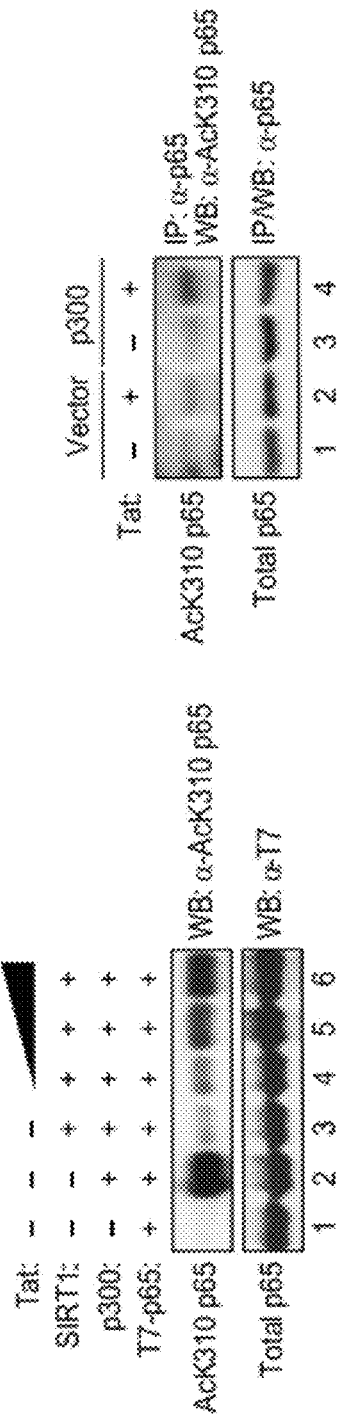
FIG. 5A
FIG. 5B
FIG. 5C
FIG. 5D

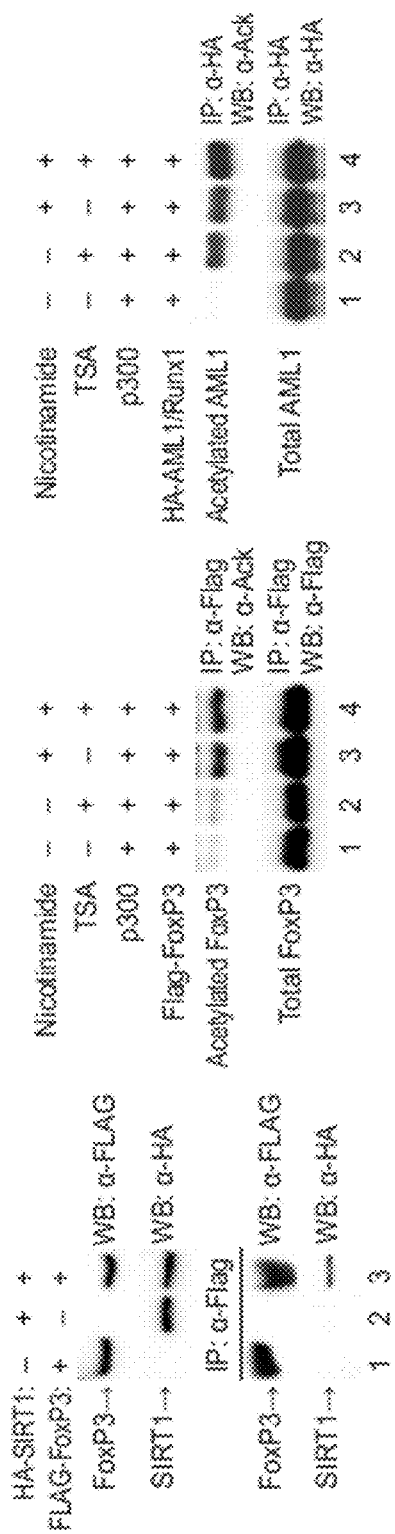
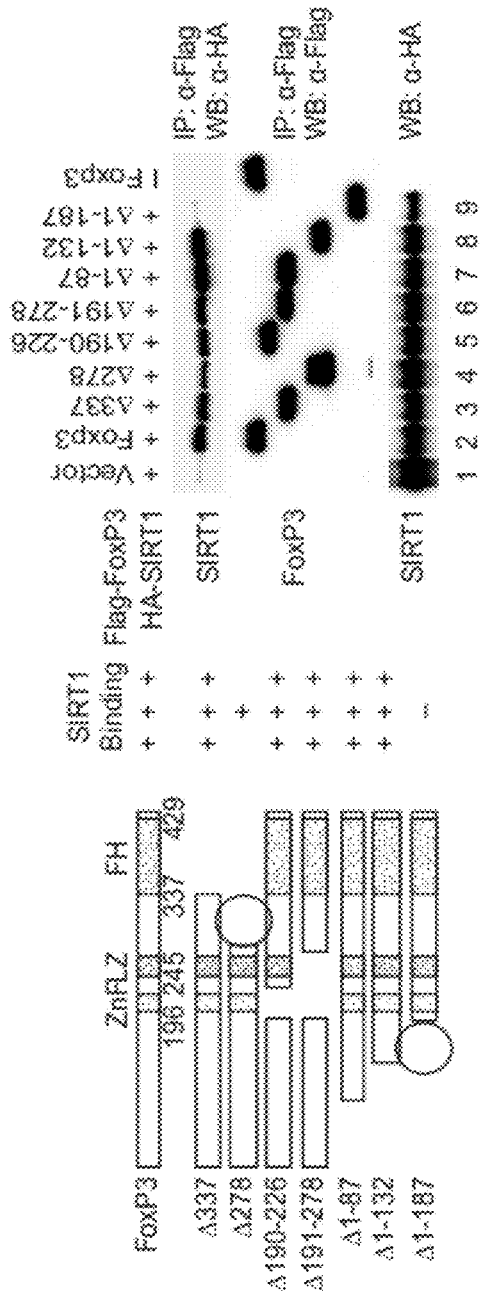

```
Human   MPNPRPGKPS APSLALGPSP GASPSWRAAP KASDLLGARG PGGTFQGRDL RGGAHASSSS   60
Cow     MPNTRPRAKPL APSLVLSPSP GASPSWRAAP KASDQLGTKS PGTTTQGRDL RSGAHTSSSS   60
Mouse   MPNPRPAKPM APSLALGPSP GVLPSWKTAP KGSELLGTRG SGGPFQQRDL RSGAHTSSS-   59

Human   LNPMPPSQLQ LPTLPLVMVA PSSGARLGFLP HLQALLQDRP HFMMQLSTVD AHARTPVLQV   120
Cow     LNDMPPSQLQ MPTYPLVMVA PSGARLGPSP HLQALLQDRP HFYHQLSTVD AHARTPVLQV   120
Mouse   LNPLPPSQLQ LPTVPLVMVA PSSGARLGPSP HLQALLQDRP HFMMQLSTVD AHAQTPVLQV   119

Human   HPLESPAMIS LTPPTTATGV FSLKAPPGLP PGINVASLEW VSREPALLCT FPNPSAPFKD   180
Cow     RPLQSPAMIS LPPPTAATGL FSLKAPPGLP PGINVASLEW VSREPALLCT FPSPGMPPKD   180
Mouse   RPLDNPAMIS LPPPSAATGV FSLKAPPGLP PGINVASLEW VSREPALLCT FPRSGTPPKD   179

Human   STLSAVPQSS YPLLANGVCK WPGCEKVFEE FEDFLKHCQA DHILDEKGRA QCLLQREMVQ   240
Cow     STLSTVPQGS YSLLANGVCK WPGCEKVFKE PEDFLKHCQA DHILDEKGRA QCLLQREVVQ   240
Mouse   SNLLAAPQGS YPLLANGVCK WPGCEKVFEE FEEFLKHCQA DHILDEKGKA QCLLQREVVQ   239

Human   SLEQQLVLEK ERLSAMQAHL AGKMAITKAS SVASSDKGSC CIVAAGSQGP VVPAWSGPRE   300
Cow     SLEQQLVLEK ERLGAMQAHL AGKNAQTKAP SAASSDKGSC CIVATGTPGT TVPAWPGFQE   300
Mouse   SLEQQLELER ERLGAMQAHL AGKRALAKAP SVASMDKSSC CIVATSTQGS VLPAWSAFRE   299

Human   APDS-LFAVR RHLWGSHGNS TFPEFLHNMD YTKFHNMRPP FTYATLIRWA ILEAPEKQRT   359
Cow     APDG-LFAVR RHLWGSHGNS TFPFFNED YTKFHNMRPP FTYATLIRWA ILEAPEKQRT   359
Mouse   APDGGLFAVR RHLWGSHGNS SFPFFHNMD YFKYHNMRPP FTYATLIRWA ILEAPEKQRT   359

Human   LNEIYHWFTR MFAFFRNHPA TWKNAIRHNL SLHKCFVRVE SEKGAVWTVD ELEFRKKRSQ   419
Cow     LNEIYHWFTR MFAFFRNHPA TWKNAIRHNL SLHKCFVRVE SEKGVVWTVD EFEFRKKRSQ   419
Mouse   LNEIYHWFTR MFAYFRNHPA TWKNAIRHNL SLHKCFVRVE SEKGAVWTVD EFEFRKKRSQ   419

Human   RPSRCSNPTPGP 431 (SEQ ID NO:3)
Cow     RPSRCSNPTPGP 431 (SEQ ID NO:4)
Mouse   RPNKCSNPCP-- 429 (SEQ ID NO:5)
```

FIG. 13

USE OF SIRT1 ACTIVATORS OR INHIBITORS TO MODULATE AN IMMUNE RESPONSE

CROSS-REFERENCE

This application is a continuation-in-part of International Patent Application No. PCT/US2009/000761, which claims the benefit of U.S. Provisional Patent Application No. 61/026,997, filed Feb. 7, 2008, which applications are incorporated herein by reference in their entirety.

STATEMENT REGARDING FEDERALLY SPONSORED RESEARCH

This invention was made with government support under grant no. R01 A1067118-01A awarded by the National Institutes of Health. The government has certain rights in the invention.

BACKGROUND

Immune activation is a hallmark of human immunodeficiency virus-1 (HIV-1) infection and a significant factor that promotes continuous viral replication and CD4+ T-cell depletion. In HIV-infected individuals, levels of circulating activation markers correlate with accelerated disease progression and shortened survival. HIV infection is critically dependent on the activated state of CD4+ T cells since the virus cannot replicate efficiently in resting T cells. Quiescent T cells in blood are refractory to infection because of blocks at the level of reverse transcription and proviral integration. In addition, T-cell activation enhances viral transcription through the activation of various transcription factors, notably nuclear factor κB (NF-κB).

SIRT1 is a mammalian homologue of the yeast transcriptional repressor silent information regulator 2 (Sir2), an important factor governing longevity in yeast. Like Sir2, SIRT1 requires nicotinamide adenine dinucleotide (NAD$^+$) as a cofactor, which links its activity to the metabolic state of the cell. In addition to its enzymatic activity on histone substrates in vitro, recent experimental evidence suggests that SIRT1 predominantly targets nonhistone proteins for deacetylation. It has been reported that Tat is a substrate for the deacetylase activity of SIRT1. Acetylation of lysine 50 (K50) in Tat is mediated by the histone acetyltransferase activities of p300 and human GCN5 and generates binding sites for the bromodomains of PCAF and Brg1. SIRT1 binds and deacetylates Tat at K50, a process necessary to recycle nonacetylated Tat protein for binding to TAR RNA and the cellular positive transcription elongation factor b (P-TEFb).
Literature Milne et al., (2007) *Nature* 450:712-716; U.S. Patent Publication No. 2007/0043050; U.S. Pat. No. 7,345,178; Ott et al. (1997) *Science* 275:1481; U.S. Patent Publication No. 2009/0012080; U.S. Patent Publication No. 2008/0255382; Nayagam et al. (2006) *J. Biomol. Screening* 11:959; U.S. Patent Publication No. 2007/0105109; U.S. Patent Publication No. 2007/0190073; U.S. Patent Publication No. 2005/0209300.

SUMMARY OF THE INVENTION

The present disclosure provides a method of increasing an immune response in an individual, the method involving administering to an individual in need thereof an inhibitor of SIRT1. The present disclosure provides a method of reducing an immune response, e.g., to treat chronic immune hyperactivity, the method generally involving administering to an individual in need thereof an activator of SIRT1. The present disclosure provides a method of modulating activation and differentiation of CD4$^+$ T cells.

BRIEF DESCRIPTION OF THE DRAWINGS

FIGS. 2A-D depict the Tat-mediated superinduction of NF-κB-responsive genes.

FIGS. 4A-E depict binding of Tat to the acetyl lysine-binding site in SIRT1.

FIGS. 5A-D depict the effect of Tat on SIRT1 deacetylase activity.

FIGS. 10A-D depict interaction of SIRT1 with FoxP3, and the effect of inhibition of SIRT1 deacetylase activity on acetylation of FoxP3.

FIG. 13 depicts an alignment of amino acid sequences of human FoxP3 (GenBank Accession Nos. NP_054728 and NM_014009), mouse FoxP3 (GenBank Accession Nos. NM_054039 and NP_473380), and cow FoxP3 (GenBank Accession Nos. NM_001045933 and NP_001039398).

DEFINITIONS

Figure 1A:
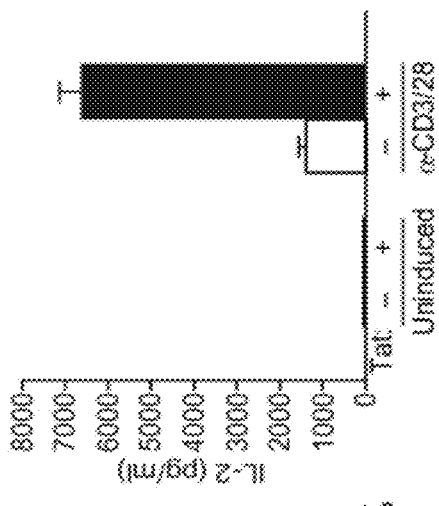
FIGS. 1A-F depict data showing the effect of Tat and nicotinamide on T cell hyperactivation.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The term "effective amount" or "therapeutically effective amount" means a dosage sufficient to provide for treatment for the disease state being treated or to otherwise provide the desired effect (e.g., induction of an effective immune response, reduction of chronic immune hyperactivity, etc.). The precise dosage will vary according to a variety of factors such as subject-dependent variables (e.g., weight, age, etc.), the disease, and the treatment being effected.

The terms "individual," "host," "subject," and "patient," used interchangeably herein, refer to a mammal, including, but not limited to, murines, felines, simians, humans, etc. In some embodiments, an individual is a human. In some embodiments, an individual is a rodent (e.g., a mouse, a rat, etc.) or a lagomorph.

A "pharmaceutically acceptable excipient," "pharmaceutically acceptable diluent," "pharmaceutically acceptable carrier," and "pharmaceutically acceptable adjuvant" means an excipient, diluent, carrier, or adjuvant that is useful in preparing a pharmaceutical composition that is generally safe, non-toxic and neither biologically nor otherwise undesirable, and include an excipient, diluent, carrier, or adjuvant that is acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, a "pharmaceutical composition" is meant to encompass a composition suitable for administration to a subject, such as a mammal, e.g., a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intra-peritoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a SIRT1 modulator" includes a plurality of such modulators and reference to "the SIRT1 inhibitor" includes reference to one or more SIRT1 inhibitors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method of increasing an immune response in an individual, the method involving administering to an individual in need thereof an inhibitor of SIRT1. The present disclosure provides a method of reducing an immune response (e.g., to treat chronic immune hyperactivity, to treat an autoimmune disorder), the method generally involving administering to an individual in need thereof an activator of SIRT1. The present disclosure provides a method of modulating activation and differentiation of CD4$^+$ T cells, the method generally involving contacting the CD4$^+$ T cell with a SIRT1 inhibitor.

As used herein, "SIRT1" refers to a polypeptide exhibiting nicotinamide adenosine dinucleotide (NAD)-dependent deacetylase activity, and having an amino acid sequence that is at least about 70%, at least about 75%, at least about 80%, at least about 85%, at least about 90%, at least about 95%, at least about 98%, at least about 99%, or 100%, identical to the amino acid sequence of a known SIRT1 polypeptide. A SIRT1 protein includes yeast Sir2 (GenBank Accession No. P53685); *C. elegans* Sir-2.1 (GenBank Accession No. NP_501912); human SIRT (see, e.g., GenBank Accession No. NM_012238 or NP_036370 (or AF083106); Frye ((1999) *Biochem. Biophys. Res. Comm.* 260:273); and GenBank Accession Nos. Q96EB6, AAH12499, NP_036370, and AAD40849); mouse SIR1 (see, e.g., GenBank Accession Nos. Q923E4 and NP_062786); and equivalents and fragments thereof. For example, a SIRT1 polypeptide comprises an amino acid sequence having at least about 70%, at least about 75%, at least about 80%, at least about 85%, at least about 90%, at least about 95%, at least about 98%, at least about 99%, or 100%, amino acid sequence identity with a contiguous stretch of from about 500 amino acids (aa) to about 550 aa, from about 550 aa to about 600 aa, from about 600 aa to about 650 aa, from about 650 aa to about 700 aa, or from about 700 aa to about 747 aa, of the amino acid sequence set forth in SEQ ID NO:1.

SIRT1 Modulators

A suitable SIRT1 modulator modulates an enzymatic activity of a SIRT1 polypeptide. For example, a suitable SIRT1 modulator modulates Tat deacetylase activity of SIRT1. SIRT1 Tat deacetylase activity can be determined using known methods. For example, a Tat polypeptide (e.g, a synthetic Tat polypeptide) that is acetylated is used as a substrate. A reaction sample can include an acetylated Tat polypeptide, $NAD^+$, a SIRT1 polypeptide, and a SIRT1 modulator. Acetylated Tat polypeptides include Tat polypeptides having one or more acetylated lysine residues, e.g., acetylated K28, acetylated K41, and acetylated K50. A suitable acetylated Tat polypeptide includes the amino acid sequence Ser-Tyr-Gly-Arg-AcLys-Lys-Lys-Arg-Arg-Gln-Arg (SEQ ID NO:02), where AcLys is acetylated lysine. An acetylated Tat protein can be generated as described in, e.g., Doerr et al. (2002) *EMBO J.* 21:2715-2723; or Peloponese (1999) *J. Biol. Chem.* 274:11473-11478. Suitable acetylated Tat polypeptides are described in, e.g., U.S. Pat. No. 7,485,416 and U.S. Patent Publication No. 2005/0287597.

The effect of the SIRT1 modulator on SIRT1 Tat deacetylase activity can be determined by measuring the amount of deacetylated Tat polypeptide produced by action of the SIRT1 polypeptide in the presence of the SIRT1 modulator, compared to the amount of deacetylated Tat polypeptide produced by action of the SIRT1 polypeptide in a control reaction sample that does not include the SIRT1 modulator. As an alternative to, or in addition to, measuring the amount of deacetylated Tat polypeptide, the amount of remaining acetylated Tat can be measured. Methods of determining the level of acetylated Tat in a sample include immunological assays using antibody that is specific for acetylated form of Tat, and that therefore distinguishes between acetylated Tat and deacetylated Tat. Any of a variety of immunological assays can be used, including, e.g., enzyme linked immunosorbent assay (ELISA), radioimmunoassay (RIA), protein blot ("Western" blot) assays, and the like. In some embodiments, mass spectroscopy is used. SIRT1 activity can also be determined by measuring the level of NAD in the test sample. The action of SIRT1 on acetylated Tat can be coupled to a second enzymatic reaction that reduces NAD to NADH, and measuring fluorescence of NADH at, e.g., 340 nm. See U.S. Pat. No. 7,485,416 and U.S. Patent Publication No. 2005/0287597 for descriptions of methods of determining SIRT1 Tat deacetylase activity.

In some embodiments, a suitable SIRT1 modulator (a SIRT1 activator or a SIRT1 inhibitor) is a selective SIRT1 modulator. For example, in some embodiments, a suitable SIRT1 activator is a selective SIRT1 activator; and in some embodiments, a suitable SIRT inhibitor is a selective SIRT1 inhibitor. For example, in some embodiments, a suitable SIRT1 activator increases the enzymatic activity of a SIRT1 polypeptide, but does not substantially increase the enzymatic activity of any other sirtuin. For example, in some embodiments, a suitable SIRT1 activator increases the enzymatic activity of a SIRT1 polypeptide, but does not substantially increase the enzymatic activity of SIRT2, SIRT4, or SIRT5. In some embodiments, a suitable SIRT1 inhibitor reduces the enzymatic activity of a SIRT1 polypeptide but does not substantially reduce the enzymatic activity of any other sirtuin. For example, in some embodiments, a suitable SIRT1 inhibitor reduces the enzymatic activity of a SIRT1 polypeptide, but does not substantially reduce the enzymatic activity of SIRT2, SIRT4, or SIRT5.

In some embodiments, a suitable SIRT1 modulator modulates the activity of SIRT1, and can also modulate the activity of one or more additional sirtuins. For example, in some embodiments, a suitable SIRT1 activator increases the enzymatic activity of a SIRT1 polypeptide, and can also increase the enzymatic activity of SIRT5. As another example, in some embodiments, a suitable SIRT1 inhibitor reduces the enzymatic activity of a SIRT1 polypeptide, and can also reduce the enzymatic activity of SIRT5.

A suitable SIRT1 activator can increase the enzymatic activity of SIRT1 by at least about 25%, at least about 50%, at least about 75%, at least about 2-fold, at least about 2.5-fold, at least about 5-fold, at least about 10-fold, at least about 20-fold, or more than 20-fold. A suitable SIRT1 activator can increase the enzymatic activity of SIRT1 by from about 25% to about 50%, from about 50% to about 75%, from about 75% to about 2-fold, from about 2-fold to about 5-fold, from about 5-fold to about 10-fold, from about 10-fold to about 20-fold, or more than 20-fold.

A suitable SIRT1 inhibitor can reduce the enzymatic activity of SIRT1 by at least about 5%, at least about 10%, at least about 15%, at least about 20%, at least about 25%, at least about 30%, at least about 35%, at least about 40%, at least about 45%, at least about 50%, at least about 60%, at least about 65%, at least about 70%, at least about 75%, or more than 75%. A suitable SIRT1 inhibitor can reduce the enzymatic activity of SIRT1 by from about 5% to about 10%, from about 10% to about 15%, from about 15% to about 20%, from about 20% to about 25%, from about 25% to about 30%, from about 35% to about 40%, from about 40% to about 50%, from about 50% to about 60%, from about 60% to about 75%, or more than 75%.

A suitable SIRT1 activator can increase SIRT1 enzymatic activity at an $EC_{50}$ (half maximal effective concentration) of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

A suitable SIRT1 activator can increase SIRT1 enzymatic activity at an $EC_{1.5}$ (concentration of compound required to increase enzyme activity by 50%) of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM. For example, a suitable SIRT1 activator can have an $EC_{1.5}$ of from about 0.01 µM to about 100 µM, e.g., from about 0.01 µM to about 0.1 µM, from about 0.1 µM to about 0.5 µM, from about 0.5 µM to about 1.0 µM, from about 1.0 µM to about 10 µM, from about 10 µM to about 25 µM, from about 25 µM to about 50 µM, or from about 50 µM to about 100 µM.

A suitable SIRT1 inhibitor can have an $IC_{50}$ of less than 50 µM, e.g., a suitable SIRT1 inhibitor can have an $IC_{50}$ of from about 50 µM to about 5 nm, or less than 5 nM. For example, in some embodiments, a suitable SIRT1 inhibitor has an $IC_{50}$ of from about 50 µM to about 25 µM, from about 25 µM to about 10 µM, from about 10 µM to about 5 µM, from about 5 µM to about 1 µM, from about 1 µM to about 500 nM, from about 500 nM to about 400 nM, from about 400 nM to about 300 nM, from about 300 nM to about 250 nM, from about 250 nM to about 200 nM, from about 200 nM to about 150 nM, from about 150 nM to about 100 nM, from about 100 nM to about 50 nM, from about 50 nM to about 30 nM, from about 30 nM to about 25 nM, from about 25 nM to about 20 nM, from about 20 nM to about 15 nM, from about 15 nM to about 10 nM, from about 10 nM to about 5 nM, or less than about 5 nM.

SIRT1 modulators are known in the art, and any modulator of SIRT1 can be used. For example, Ota et al. ((2006) *Oncogene* 25:176) discusses sirtinol; resveratrol is discussed in, e.g., de la Lastra (2005) *Mol. Nutr. Food Res.* 49:405; Napper et al. ((2005) *J. Med. Chem.* 48:8045) discusses indole compounds that are SIRT1 inhibitors; Solomon et al. ((2006) *Mol. Cell. Biol.* 26:28) discusses EX-527, a SIRT1 inhibitor; U.S. Patent Publication Nos. 2007/0043050, 2007/0037865, and 2007/0037809 discuss SIRT1 modulators; and U.S. Patent Publication No. 2008/0021063 discusses SIRT1 modulators.

Whether a given agent (e.g., a SIRT1 modulator, such as a SIRT1 inhibitor or a SIRT1 activator) is effective in modulating an immune response (e.g., increasing an immune response; e.g., reducing an immune response, such as reducing chronic immune hyperactivity) can be readily determined using well known methods to assess one or more immune response parameters. Immune response parameters include, but are not limited to, CD4 count; serum cytokine levels, e.g., serum levels of IL-2; serum antibody levels; levels of an autoantibody; and the like.

Methods of Reducing an Immune Response

In some embodiments, the present disclosure provides methods of reducing an immune response, the methods generally involving administering to an individual in need thereof an effective amount of a SIRT1 activator.

In some embodiments, an effective amount of a SIRT1 activator is an amount that, when administered to an individual in one or more doses, is effective to reduce the level of a cytokine associated with an immune response. Cytokines associated with an immune response include, e.g., interleukin-2 (IL-2), tumor necrosis factor-alpha (TNF-α), interleukin-4 (IL-4), interferon gamma (IFN-γ), and interleukin-12 (IL-12). In some embodiments, an effective amount of a SIRT1 activator is an amount that, when administered to an individual in one or more doses, is effective to reduce the level in the individual of a cytokine associated with an immune response by at least about 10%, at least about 15%, at least about 20%, at least about 25%, at least about 30%, at least about 35%, at least about 40%, at least about 50%, at least about 60%, at least about 70%, or at least about 80%, compared to the level of the cytokine in the absence of treatment with the SIRT1 activator.

In some embodiments, an effective amount of a SIRT1 activator is an amount that, when administered to an individual in one or more doses, is effective to reduce the level of IL-2 (e.g., circulating IL-2, e.g., a serum level of IL-2) in the individual by at least about 10%, at least about 15%, at least about 20%, at least about 25%, at least about 30%, at least about 35%, at least about 40%, at least about 50%, at least about 60%, at least about 70%, or at least about 80%, compared to the level of IL-2 in the individual in the absence of treatment with the SIRT1 activator.

Methods of reducing an immune response are useful for treating chronic immune hyperactivation. Thus, the instant disclosure provides methods for treating chronic immune hyperactivation, the methods generally involving administering to an individual in need thereof an effective amount of a SIRT1 activator. In some embodiments, the instant disclosure provides a method for treating chronic immune hyperactivation, the method comprising administering to an individual in need thereof an effective amount of a selective SIRT1 activator. In some embodiments, the instant disclosure provides a method for treating chronic immune hyperactivation that results from infection with an immunodeficiency virus, e.g., a human immunodeficiency virus (e.g., HIV-1), the method comprising administering to an individual in need thereof an effective amount of a SIRT1 activator, where in some embodiments, the SIRT1 inhibitor is a selective SIRT1 activator.

SIRT1 Activators

Examples of SIRT1 activators that are suitable for use in a subject method include, but are not limited to, resveratrol ((E)-5-(p-Hydroxystyryfiresorcinol (E)-5-(4-hydroxystyryl) benzene-1,3-diol); or 3,5,4'-trihydroxy-trans-stilbene); butein (3,4,2',4'-tetrahydroxychalcone); piceatannol (3,5,3', 4'-tetrahydroxy-trans-stilbene); isoliquiritigenin (4,2',4'-trihydroxychalcone); fisetin (3,7,3',4'-tetrahydroxyflavone); quercetin (3,5,7,3',4'-pentahydroxyflavone); a SIRT1 activator as described in U.S. Pat. No. 7,345,178; a SIRT1 activator as described in U.S. Patent Publication No. 2008/02555382; and a SIRT1 activator as described in U.S. Patent Publication No. 2009/0012080. Pharmaceutically acceptable salts of any of the foregoing SIRT1 activators are also suitable for use in a subject method.

For example, a suitable SIRT1 activator is a compound of any one of Formulas I-XXVIII as described in U.S. Pat. No. 7,345,178, where substituents are as described in U.S. Pat. No. 7,345,178, or a pharmaceutically acceptable salt of a compound of any one of Formulas I-XXVIII as described in U.S. Pat. No. 7,345,178, provided that the compound activates SIRT1 activity. For example, a suitable SIRT1 activator includes a compound shown in Table 4 of U.S. Pat. No. 7,345,178.

For example, suitable SIRT1 activators are shown in Table 1, below.

TABLE 1

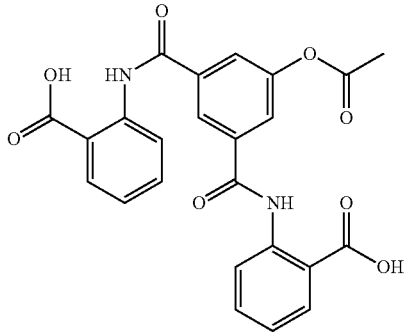 [SMILES: CC(=O)Oc1cc(C(=O)Nc2ccccc2C(=O)O)cc(C(=O)Nc2ccccc2C(=O)O)c1]

Compound 1

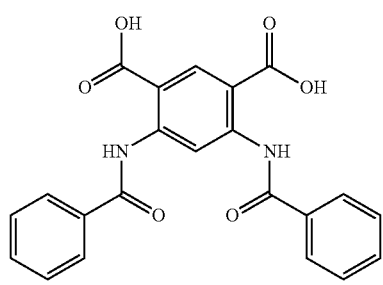 [SMILES: O=C(Nc1cc(NC(=O)c2ccccc2)c(C(=O)O)cc1C(=O)O)c1ccccc1]

Compound 2

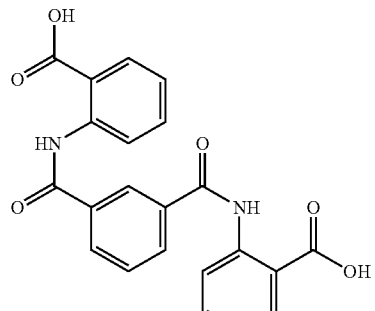

Compound 3

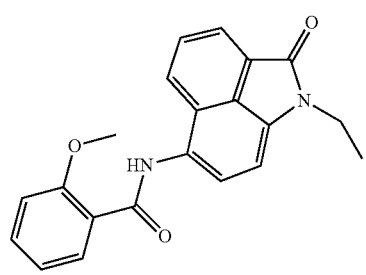 [SMILES: CCN1C(=O)c2cccc3c(NC(=O)c4ccccc4OC)ccc1c23]

Compound 4

TABLE 1-continued

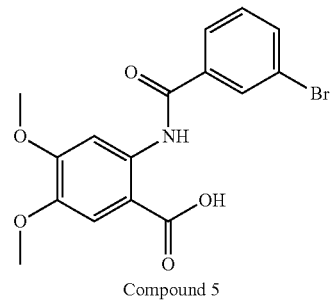

Compound 5

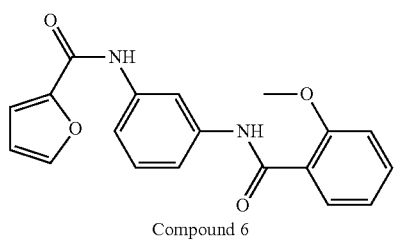

Compound 6

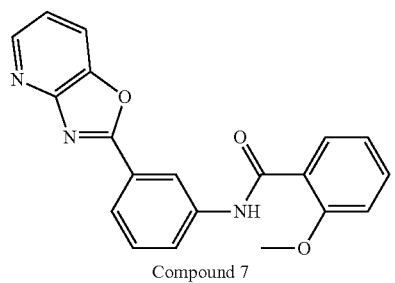

Compound 7

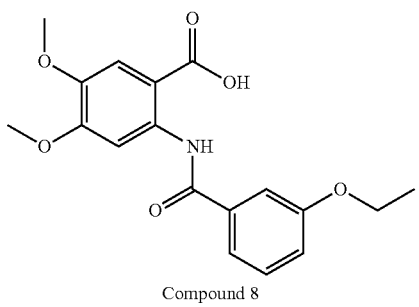

Compound 8

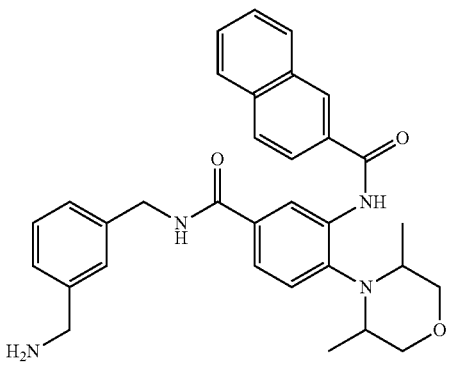 [SMILES: CC1COCC(C)N1c1ccc(C(=O)NCc2cccc(CN)c2)cc1NC(=O)c1ccc2ccccc2c1]

Compound 9

TABLE 1-continued
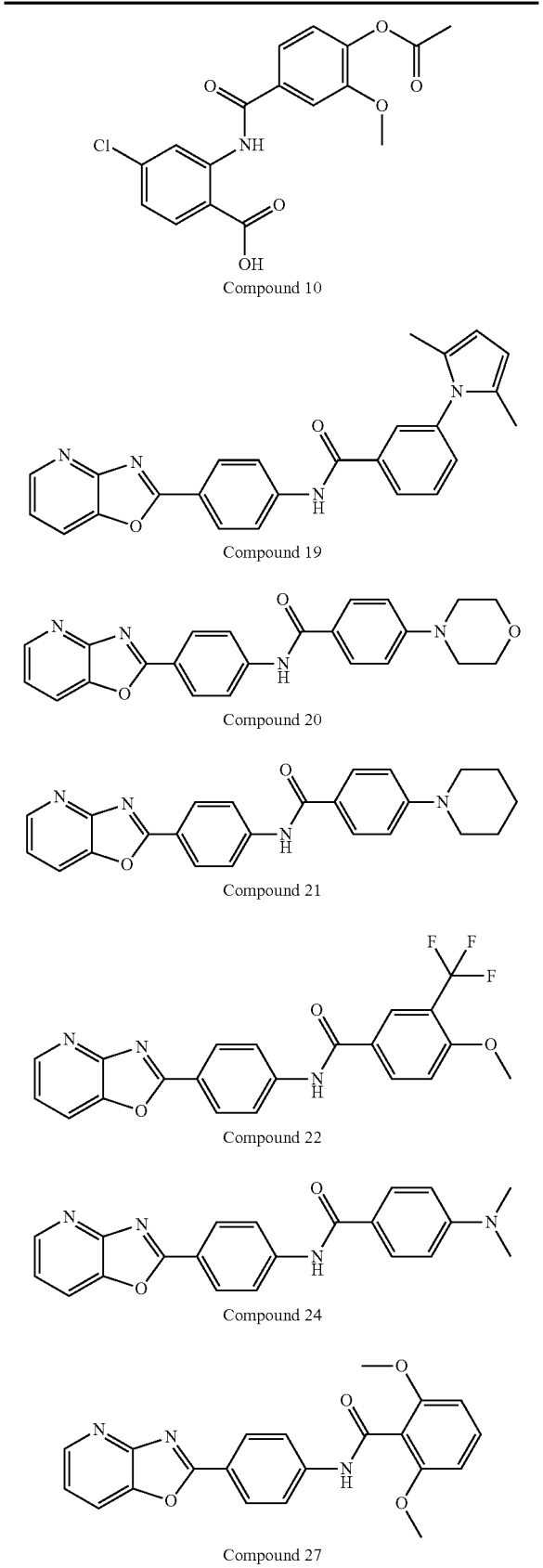
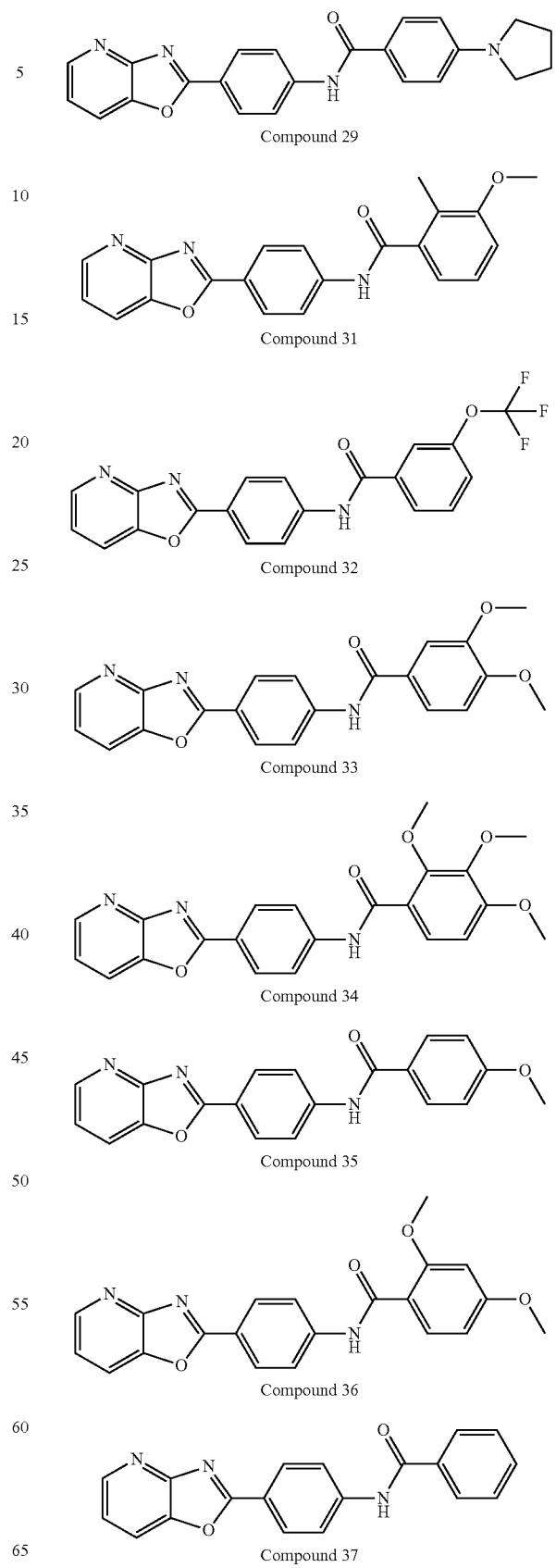

TABLE 1-continued
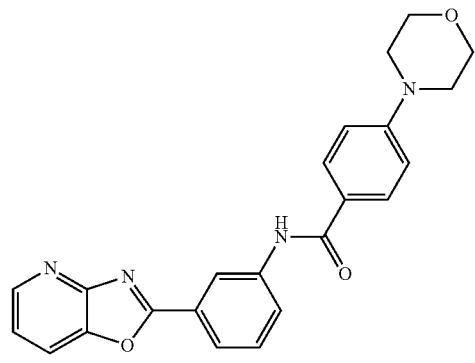 [SMILES: O=C(Nc1cccc(-c2nc3ncccc3o2)c1)c1ccc(N2CCOCC2)cc1]
Compound 38
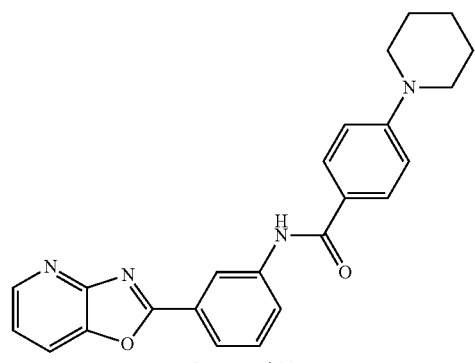
Compound 39
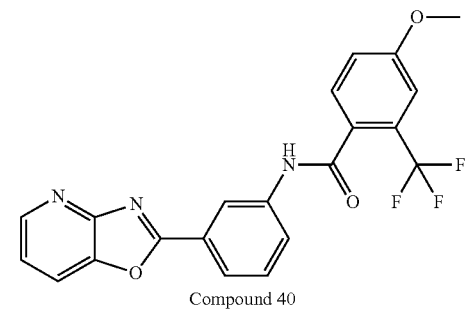
Compound 40
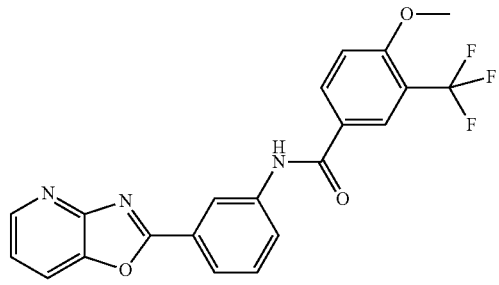 [SMILES: COc1ccc(C(=O)Nc2cccc(-c3nc4ncccc4o3)c2)cc1C(F)(F)F]
Compound 41
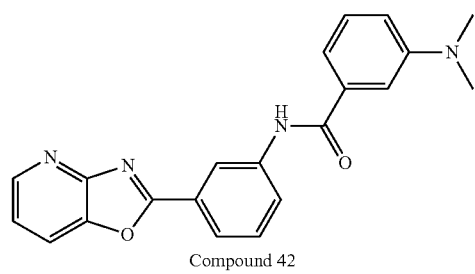
Compound 42
TABLE 1-continued
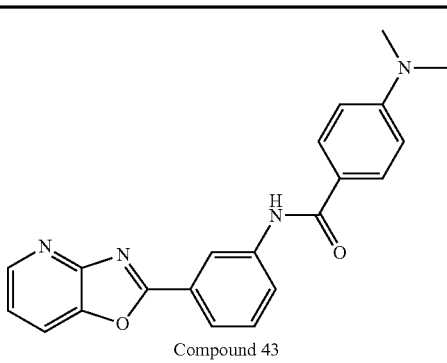
Compound 43
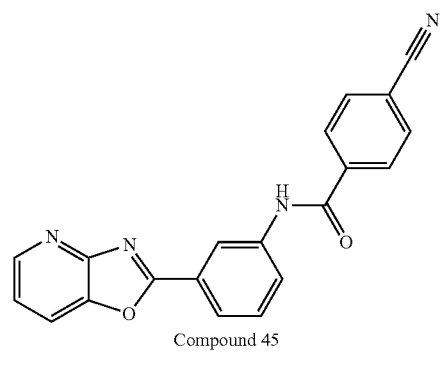
Compound 45
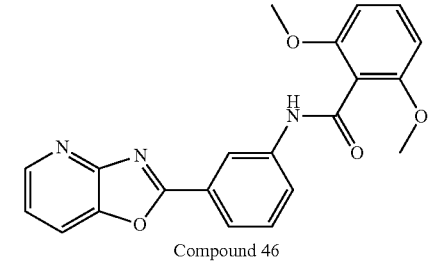
Compound 46
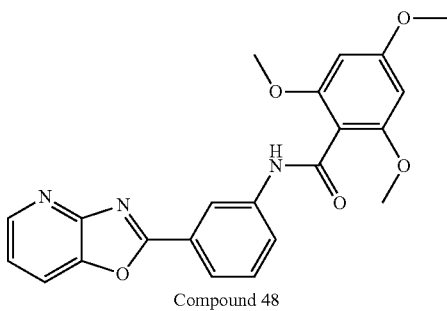
Compound 48
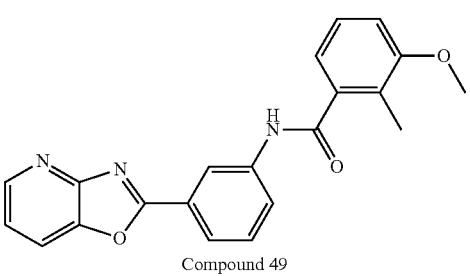
Compound 49

TABLE 1-continued
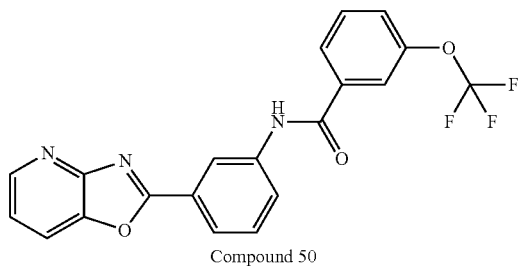
Compound 50
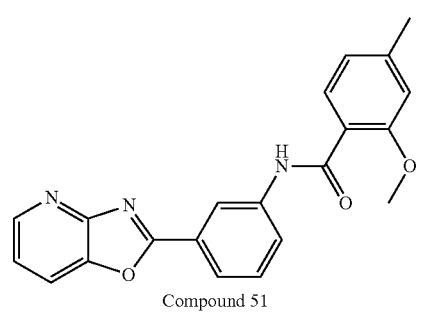
Compound 51
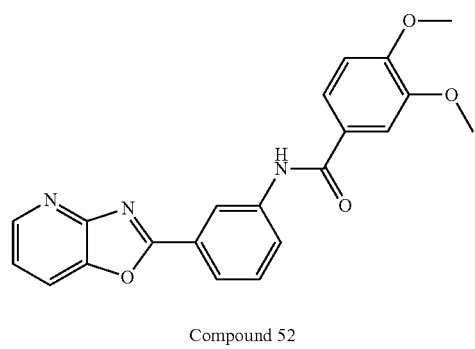
Compound 52
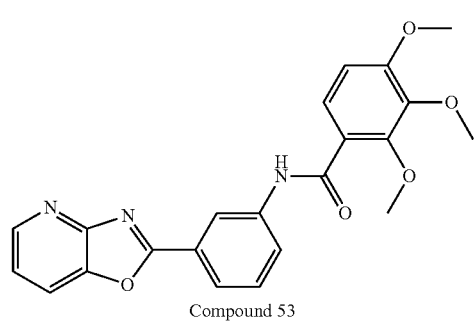
Compound 53
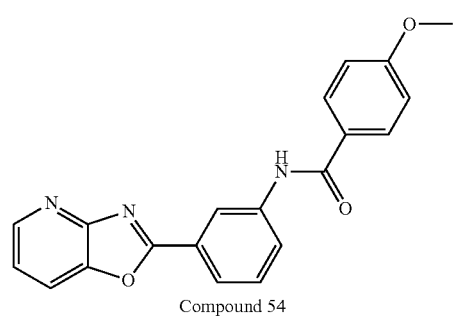
Compound 54
TABLE 1-continued
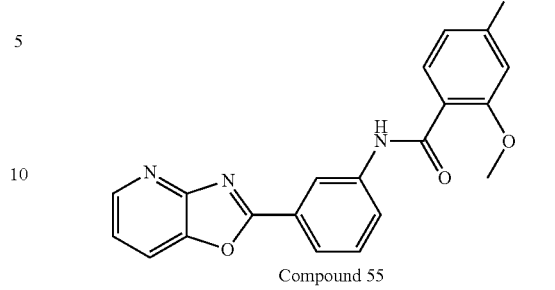
Compound 55
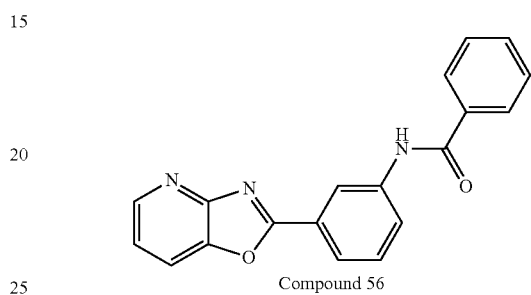
Compound 56
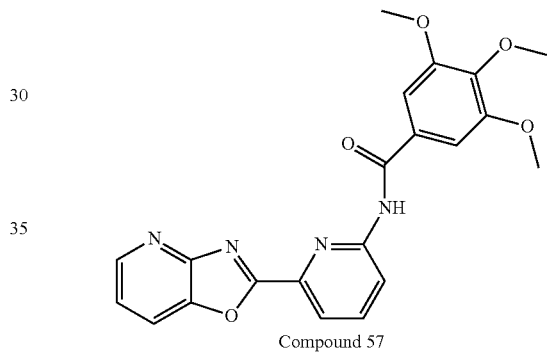
Compound 57
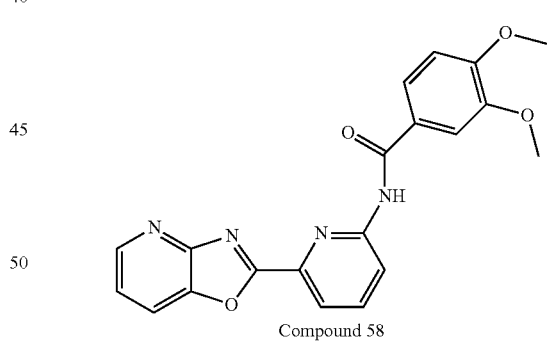
Compound 58
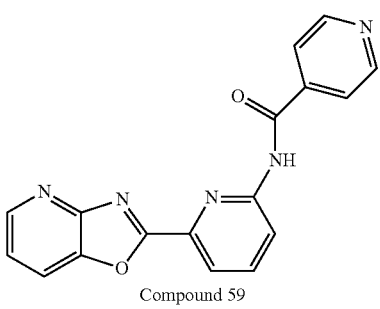
Compound 59

TABLE 1-continued
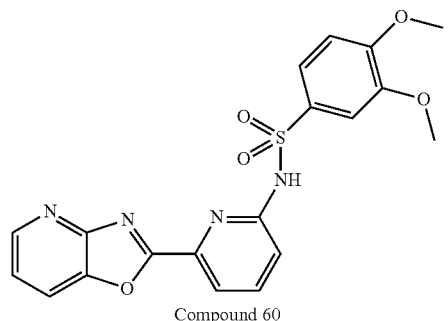
Compound 60
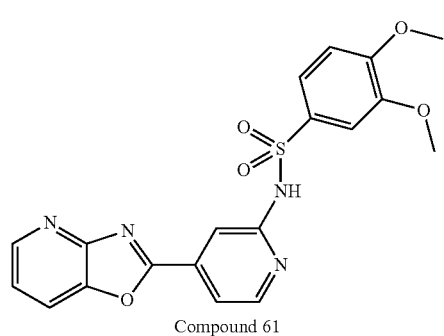
Compound 61
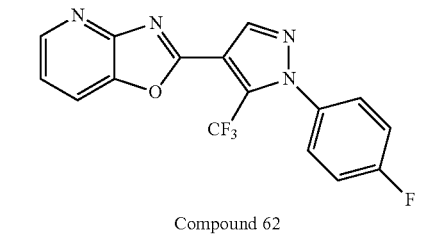
Compound 62
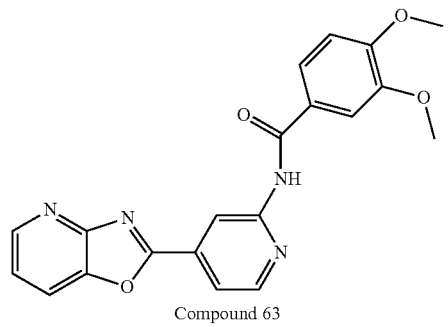
Compound 63
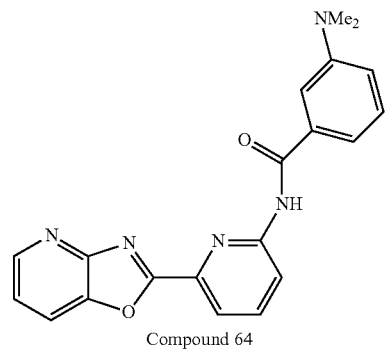
Compound 64
TABLE 1-continued
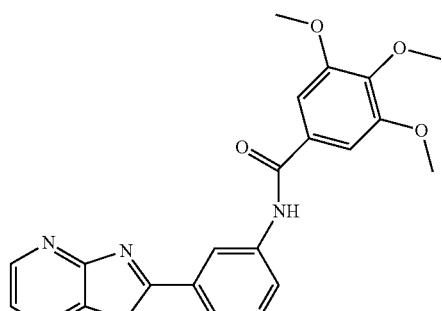
Compound 66
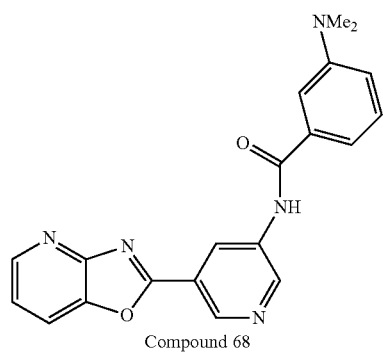
Compound 68
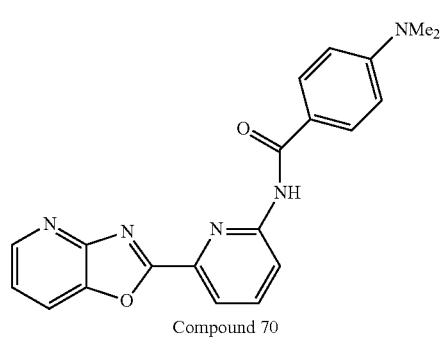
Compound 70
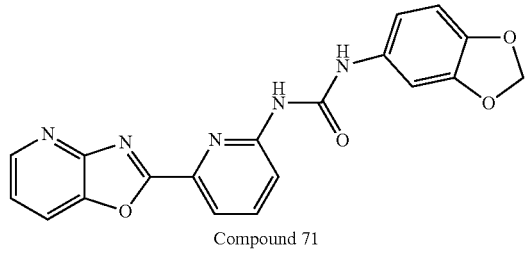
Compound 71
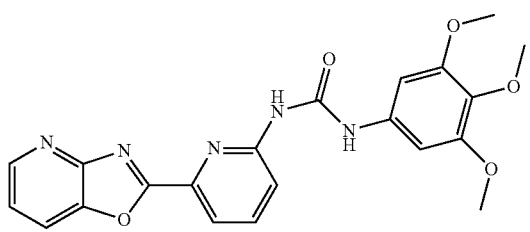 [SMILES: COc1cc(NC(=O)Nc2cccc(-c3nc4ncccc4o3)n2)cc(OC)c1OC]
Compound 72

TABLE 1-continued
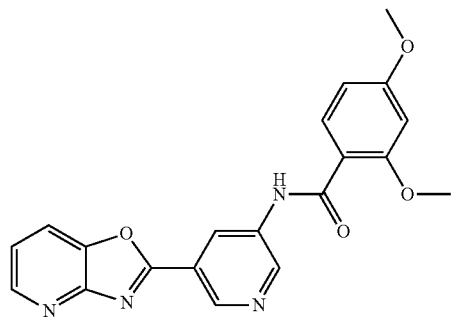 [SMILES: COc1ccc(C(=O)Nc2cncc(-c3nc4ncccc4o3)c2)c(OC)c1]
Compound 73
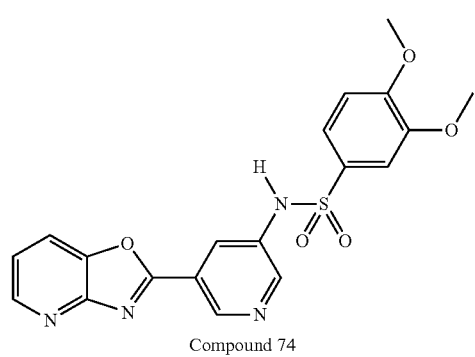
Compound 74
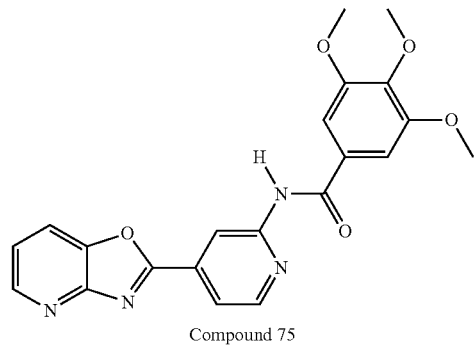
Compound 75
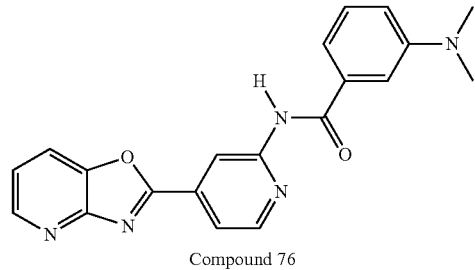
Compound 76
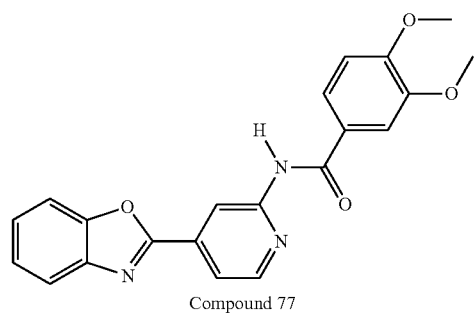
Compound 77
TABLE 1-continued
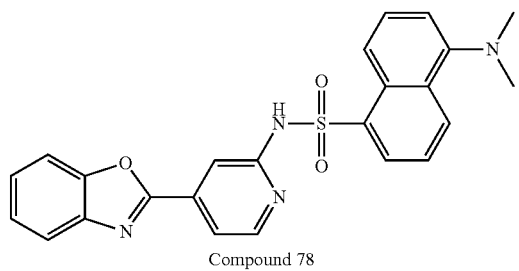
Compound 78
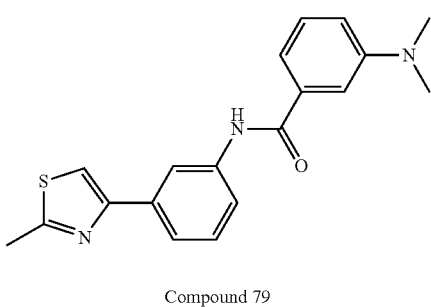
Compound 79
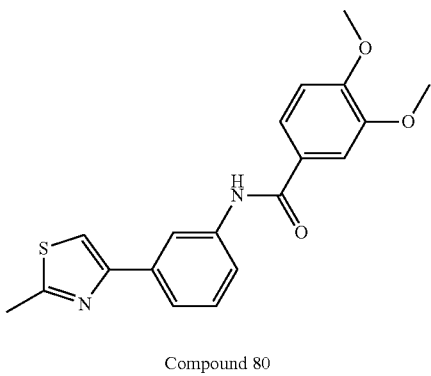
Compound 80
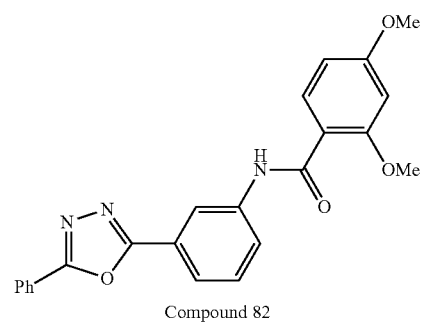
Compound 82
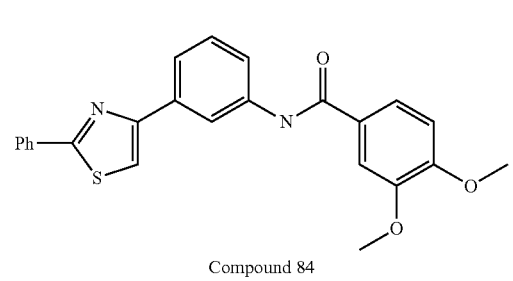
Compound 84

TABLE 1-continued
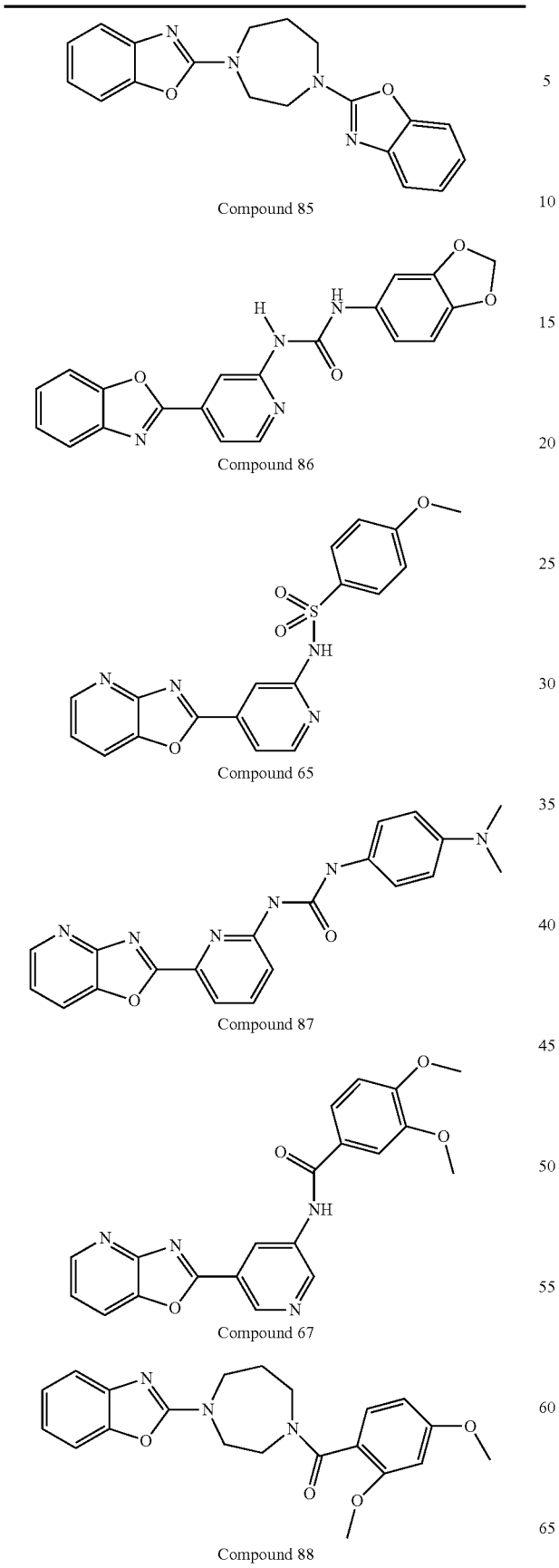
Compound 85
Compound 86
Compound 65
Compound 87
Compound 67
Compound 88
TABLE 1-continued
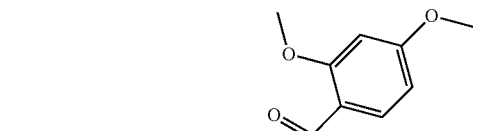
Compound 69
Compound 89
Compound 90
Compound 91
Compound 92
Compound 93

TABLE 1-continued
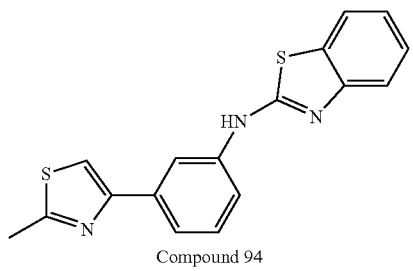
Compound 94
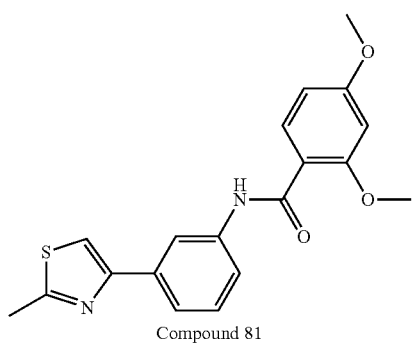
Compound 95
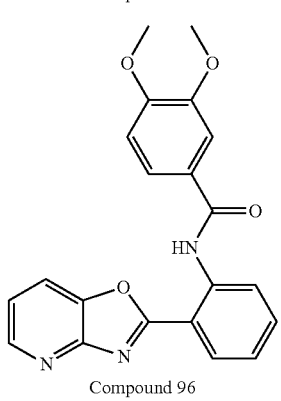
Compound 81
Compound 83
Compound 96
TABLE 1-continued
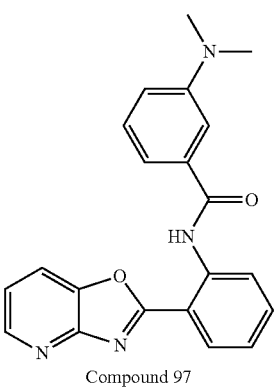
Compound 97
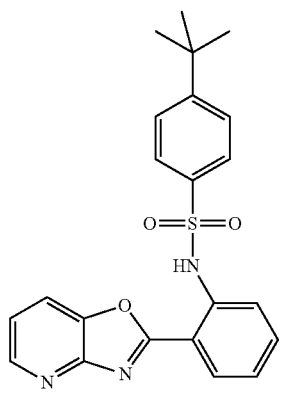 [SMILES: CC(C)(C)c1ccc(S(=O)(=O)Nc2ccccc2-c2nc3ncccc3o2)cc1]
Compound 98
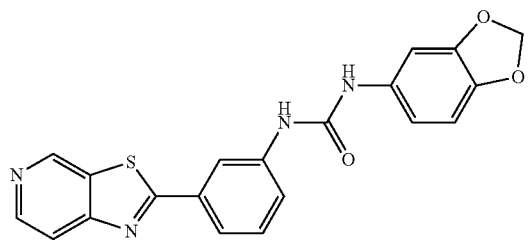 [SMILES: O=C(Nc1cccc(-c2nc3ccncc3s2)c1)Nc1ccc2c(c1)OCO2]
Compound 99
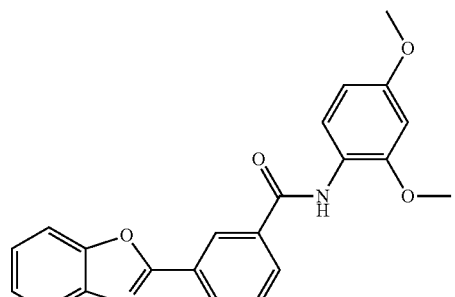
Compound 100

TABLE 1-continued
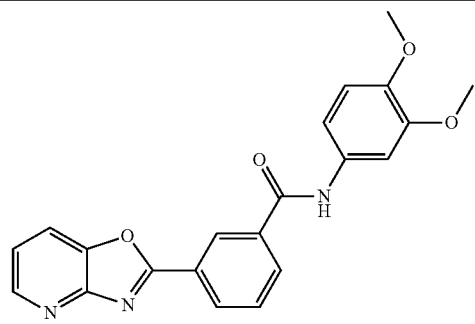
Compound 101
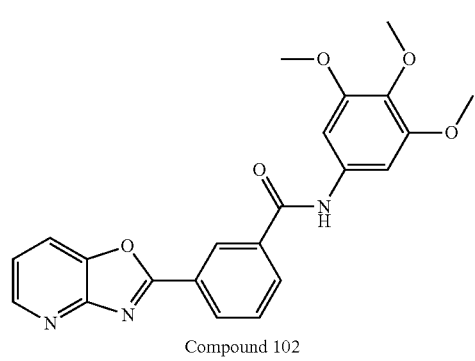
Compound 102
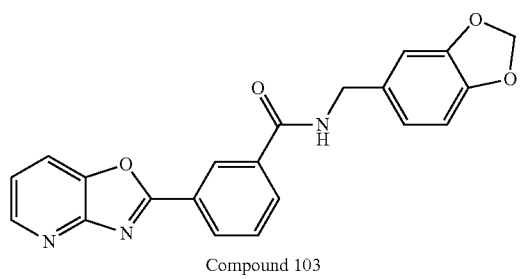
Compound 103
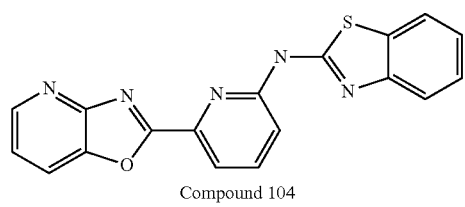
Compound 104
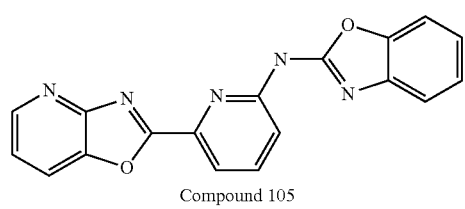
Compound 105
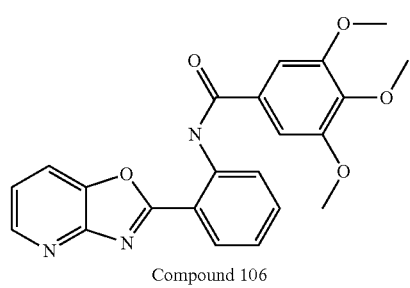
Compound 106
TABLE 1-continued
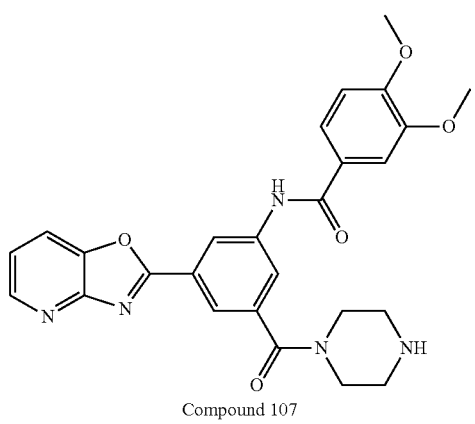
Compound 107
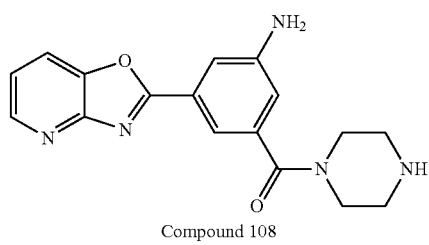
Compound 108
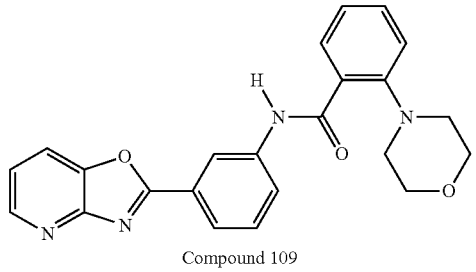
Compound 109
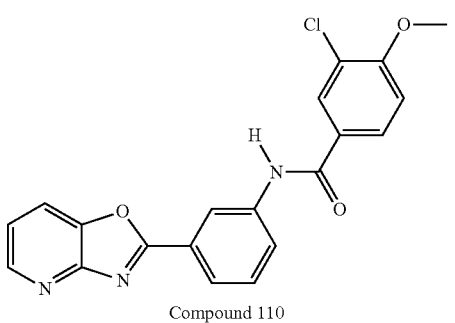
Compound 110
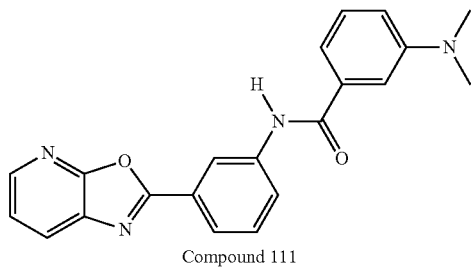
Compound 111

TABLE 1-continued
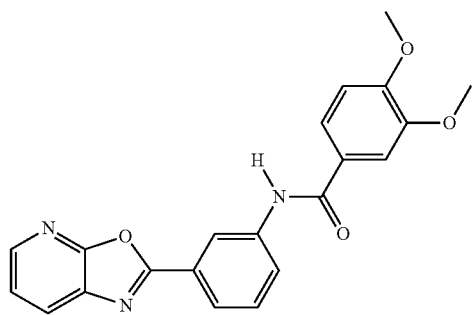 [SMILES: COc1ccc(C(=O)Nc2cccc(-c3nc4cccnc4o3)c2)cc1OC]
Compound 112
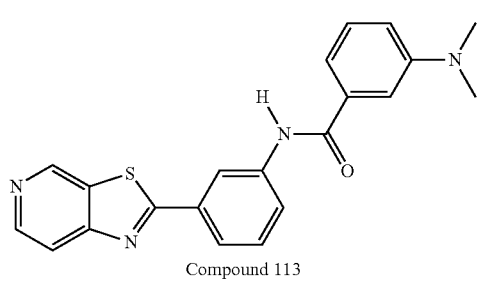
Compound 113
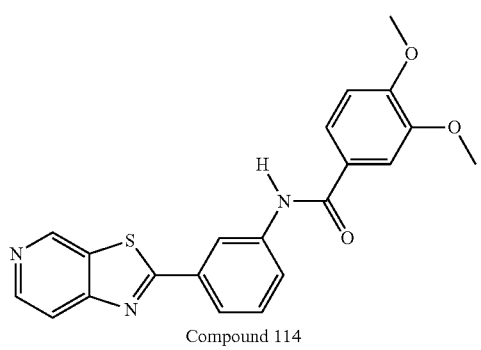
Compound 114
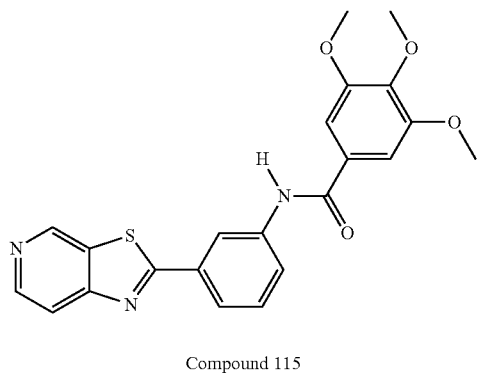
Compound 115
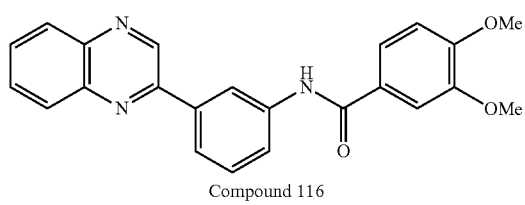
Compound 116
TABLE 1-continued
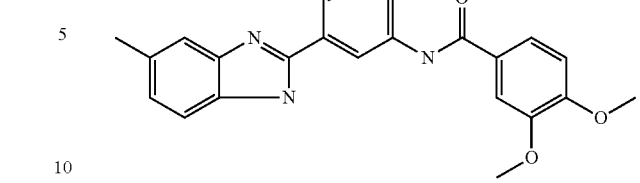
Compound 117
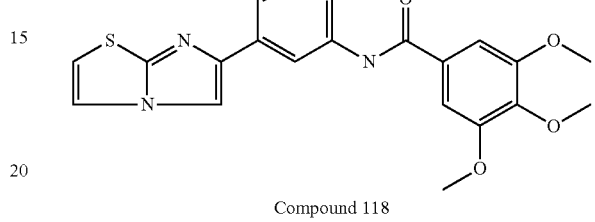
Compound 118
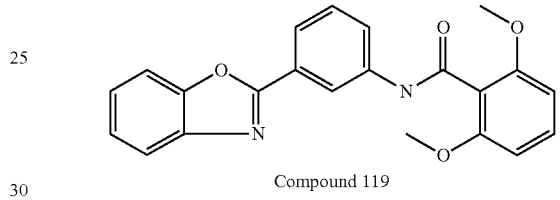
Compound 119
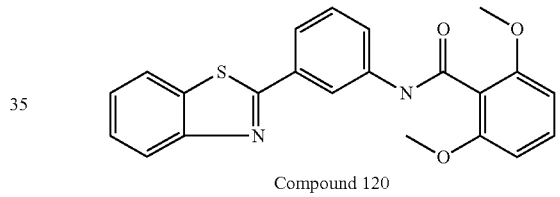
Compound 120
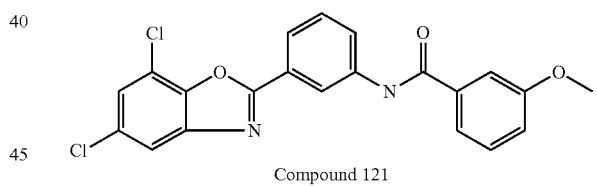
Compound 121
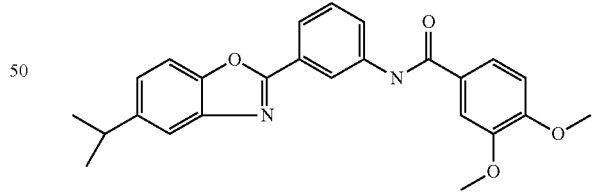
Compound 122
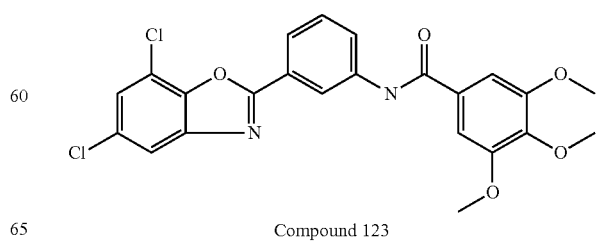
Compound 123

TABLE 1-continued
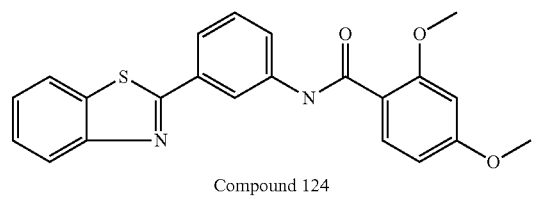
Compound 124
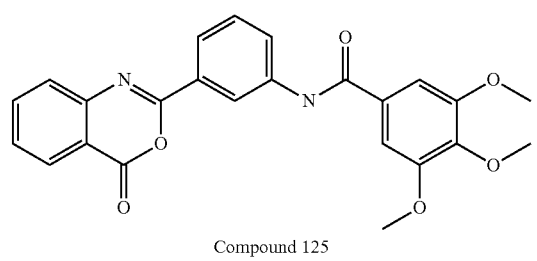
Compound 125
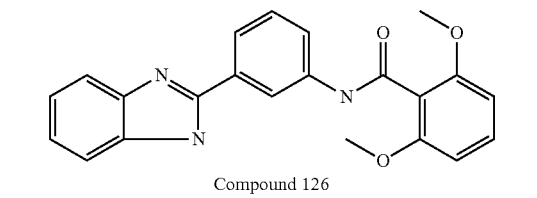
Compound 126
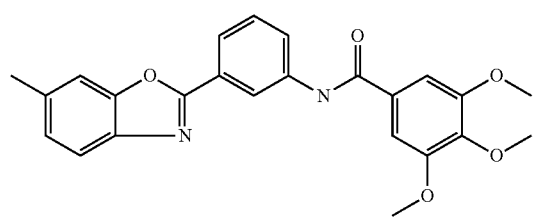
Compound 127
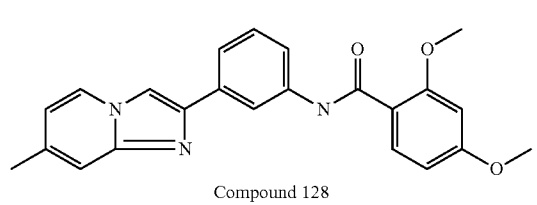
Compound 128
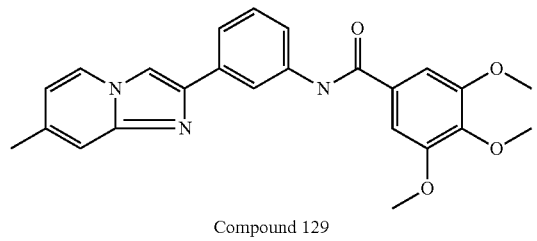
Compound 129
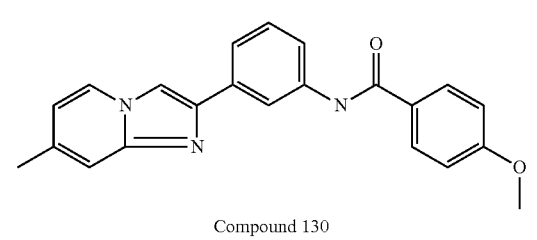
Compound 130
TABLE 1-continued
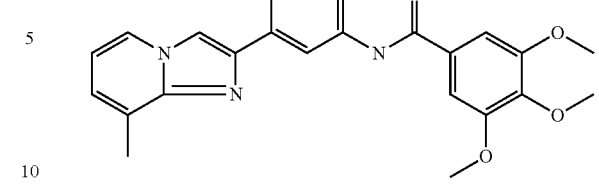
Compound 131
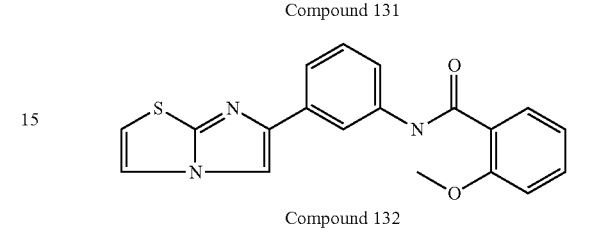
Compound 132
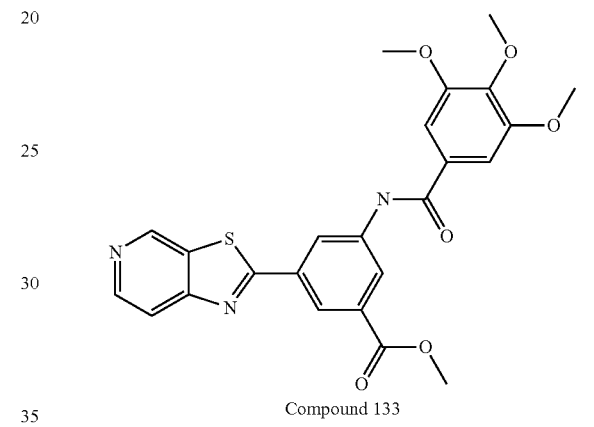
Compound 133
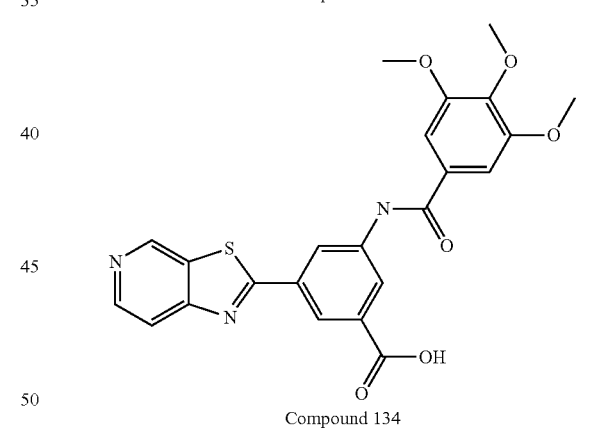
Compound 134
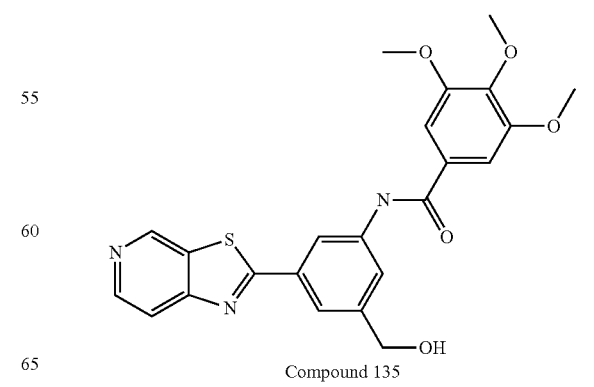
Compound 135

TABLE 1-continued
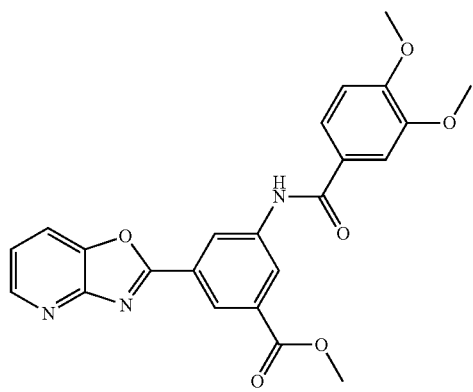 [SMILES: COC(=O)c1cc(NC(=O)c2ccc(OC)c(OC)c2)cc(-c2nc3ncccc3o2)c1]
Compound 136
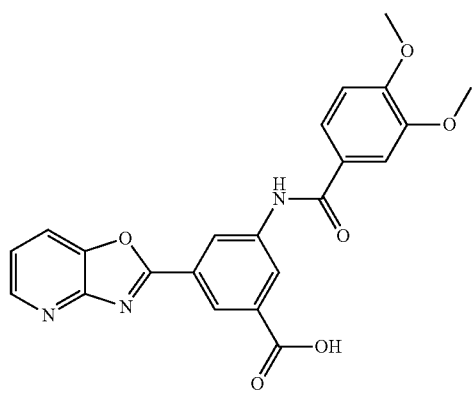 [SMILES: COc1ccc(C(=O)Nc2cc(C(=O)O)cc(-c3nc4ncccc4o3)c2)cc1OC]
Compound 137
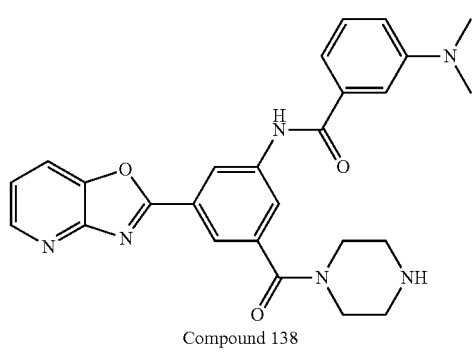
Compound 138
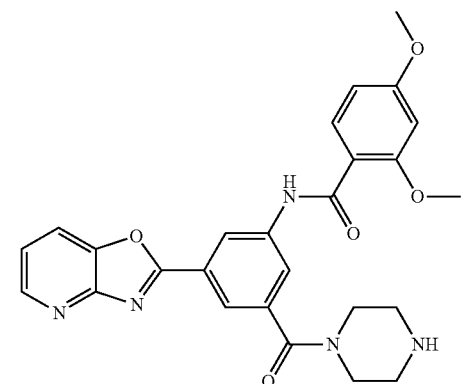 [SMILES: COc1ccc(C(=O)Nc2cc(C(=O)N3CCNCC3)cc(-c3nc4ncccc4o3)c2)c(OC)c1]
Compound 139
TABLE 1-continued
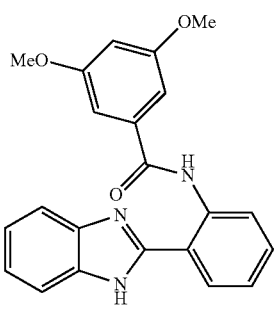 [SMILES: COc1cc(OC)cc(C(=O)Nc2ccccc2-c2nc3ccccc3[nH]2)c1]
Compound 141
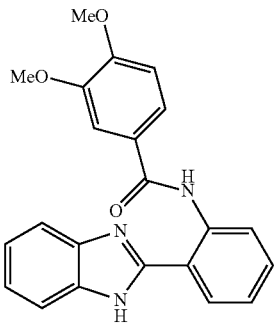 [SMILES: COc1ccc(C(=O)Nc2ccccc2-c2nc3ccccc3[nH]2)cc1OC]
Compound 142
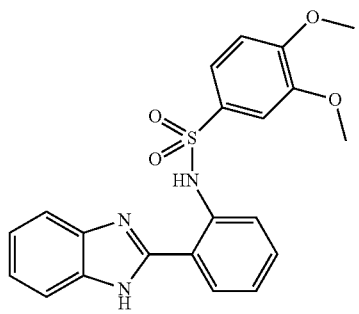 [SMILES: COc1ccc(S(=O)(=O)Nc2ccccc2-c2nc3ccccc3[nH]2)cc1OC]
Compound 143
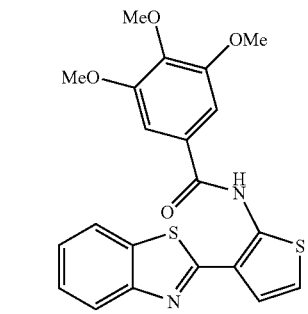 [SMILES: COc1cc(C(=O)Nc2sccc2-c2nc3ccccc3s2)cc(OC)c1OC]
Compound 144

TABLE 1-continued
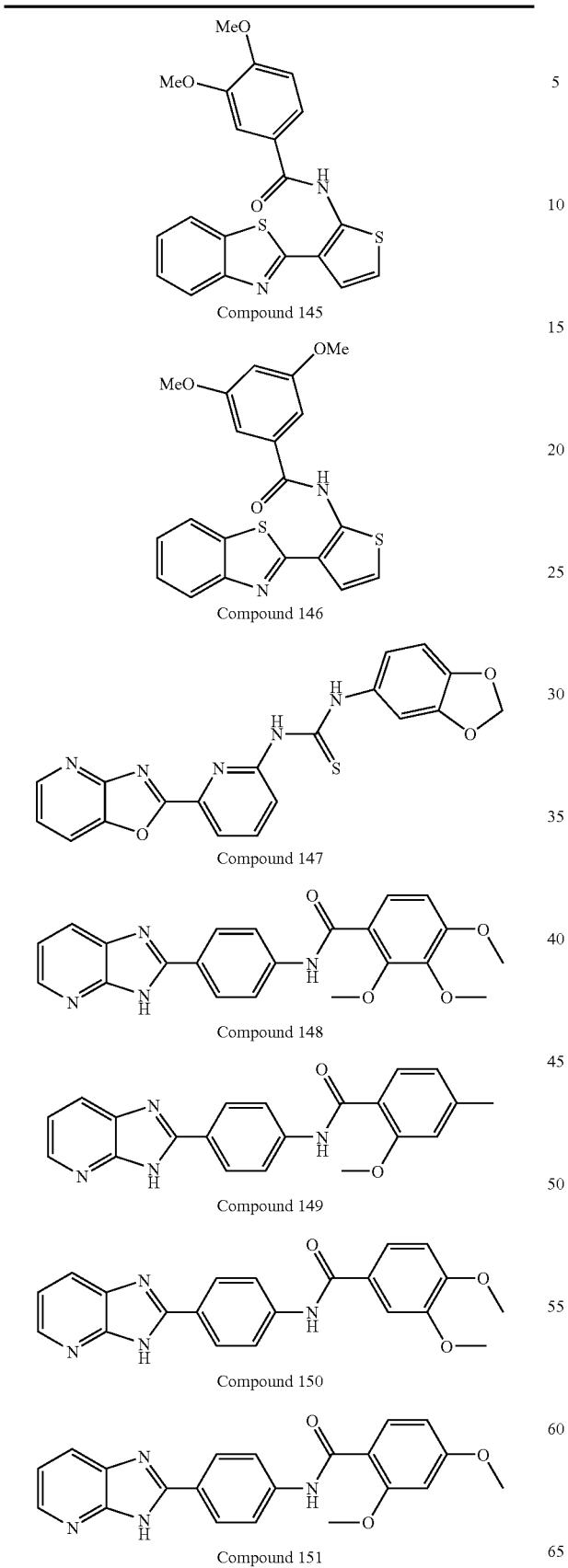
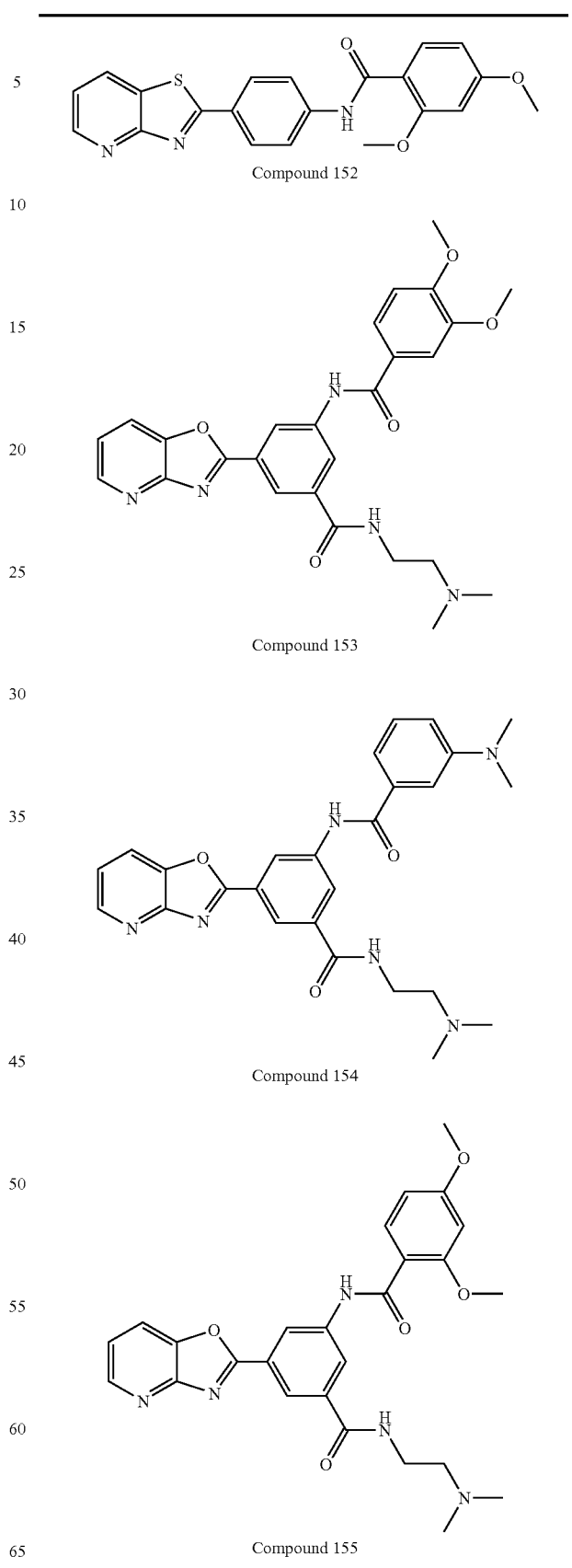

TABLE 1-continued
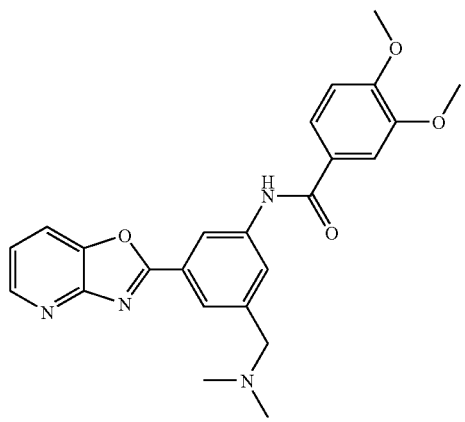 [SMILES: COc1ccc(C(=O)Nc2cc(CN(C)C)cc(-c3nc4ncccc4o3)c2)cc1OC]
Compound 156
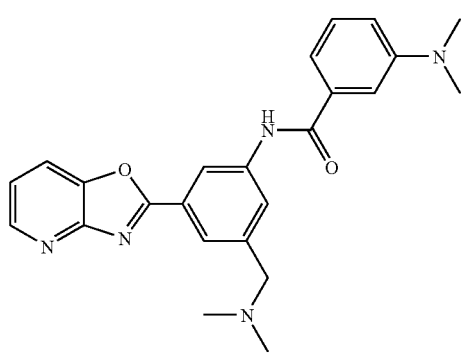 [SMILES: CN(C)Cc1cc(NC(=O)c2cccc(N(C)C)c2)cc(-c2nc3ncccc3o2)c1]
Compound 157
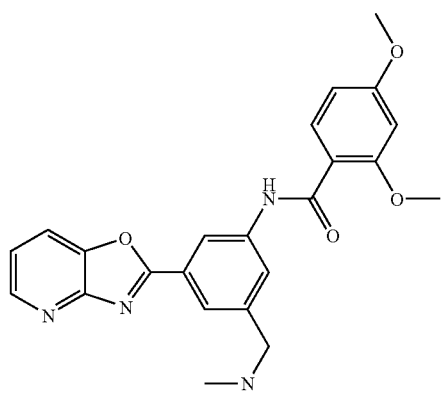
Compound 158
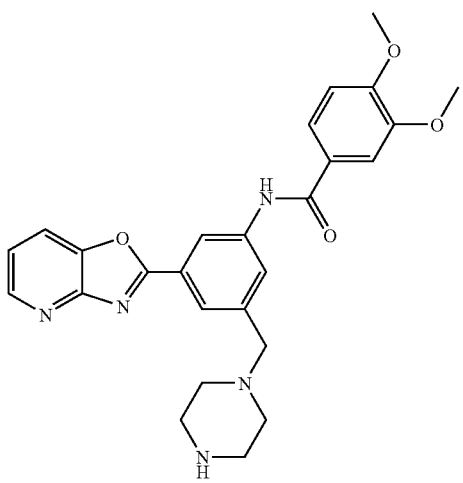 [SMILES: COc1ccc(C(=O)Nc2cc(CN3CCNCC3)cc(-c3nc4ncccc4o3)c2)cc1OC]
Compound 159
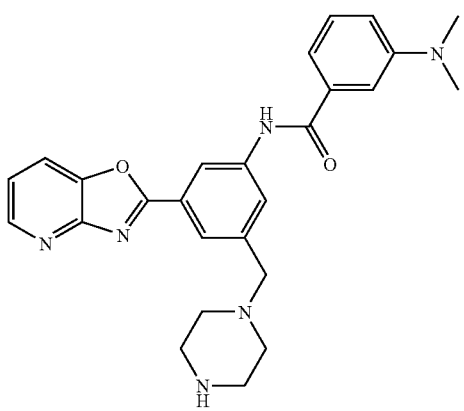 [SMILES: CN(C)c1cccc(C(=O)Nc2cc(CN3CCNCC3)cc(-c3nc4ncccc4o3)c2)c1]
Compound 160
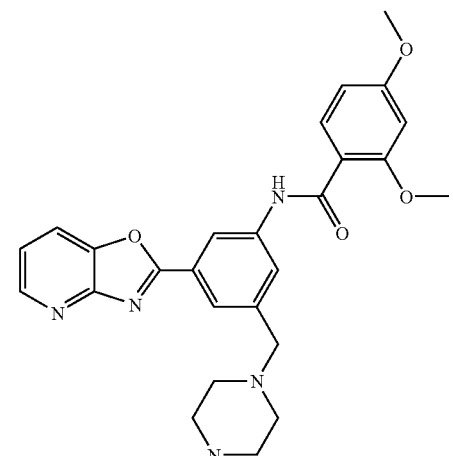
Compound 161

TABLE 1-continued
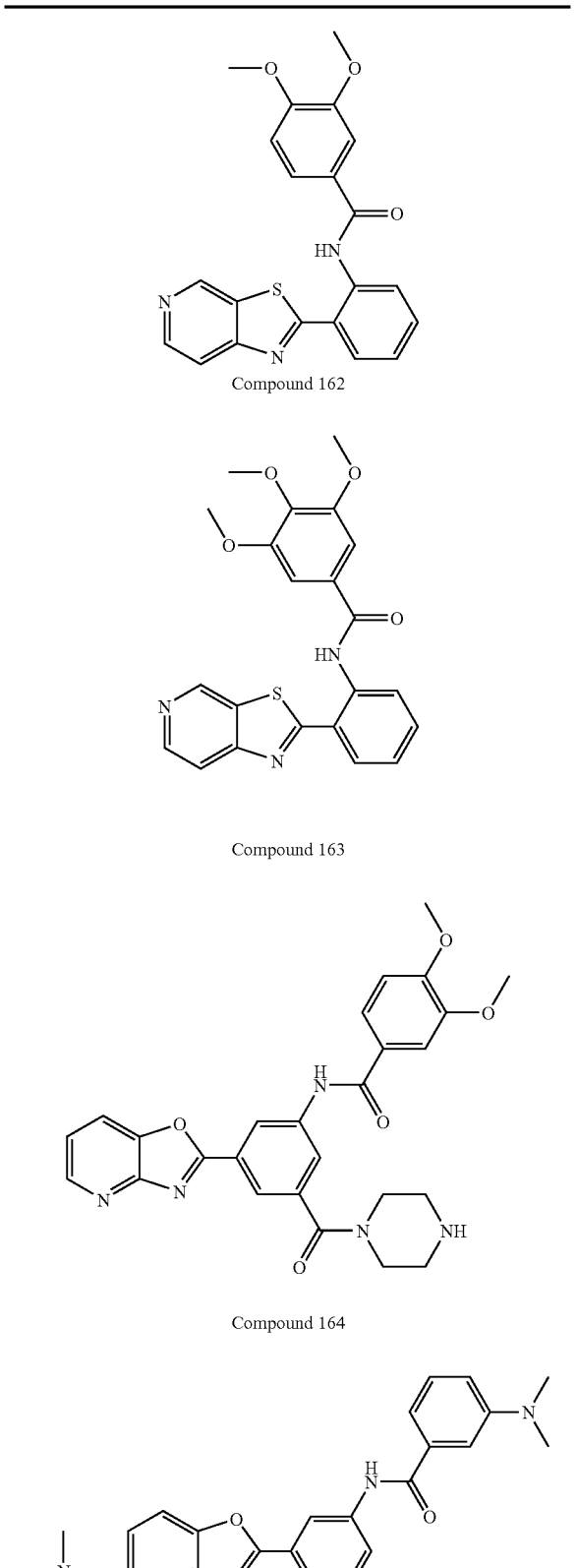
Compound 162
Compound 163
Compound 164
Compound 165
TABLE 1-continued
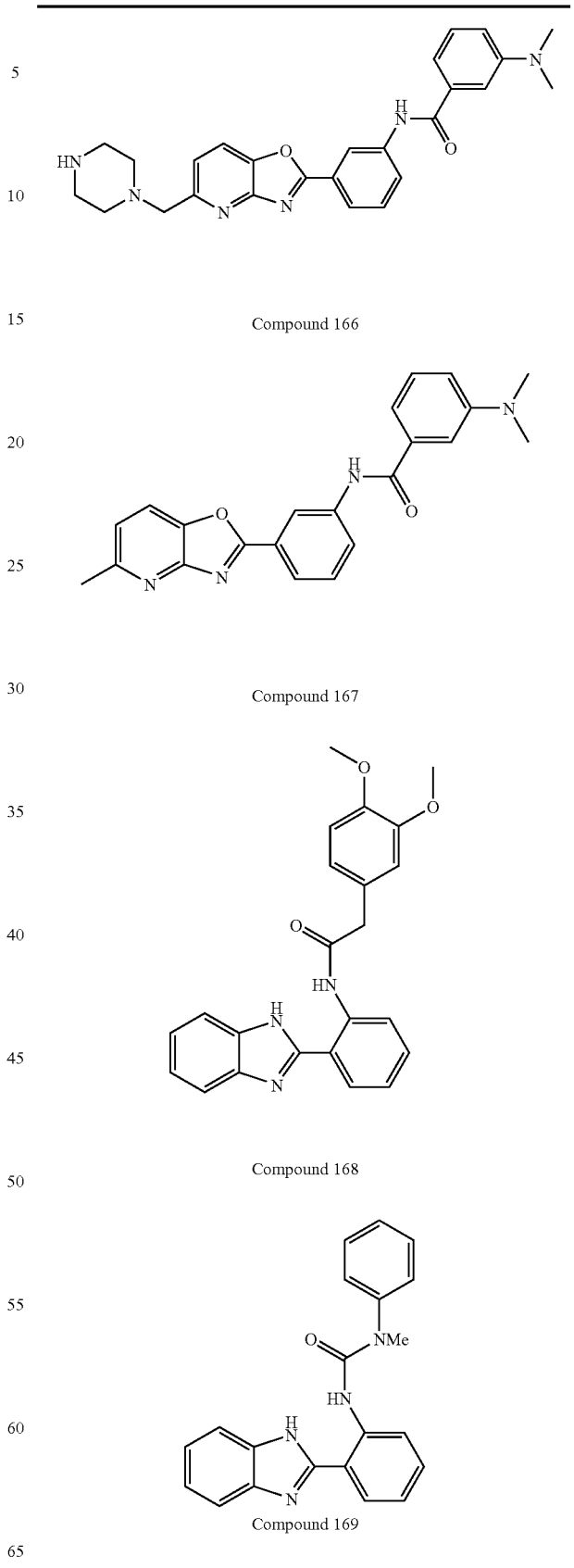
Compound 166
Compound 167
Compound 168
Compound 169

TABLE 1-continued
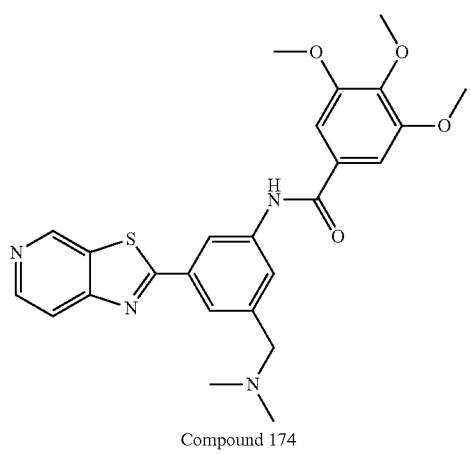
Compound 174
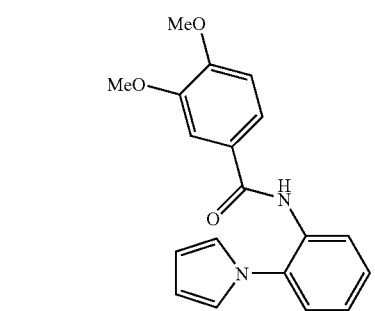
Compound 175
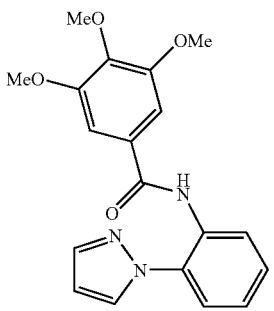 [SMILES: COc1cc(C(=O)Nc2ccccc2-n2cccn2)cc(OC)c1OC]
Compound 176
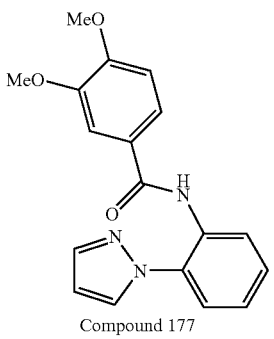
Compound 177
TABLE 1-continued
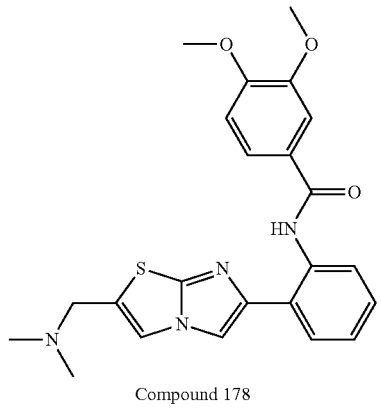
Compound 178
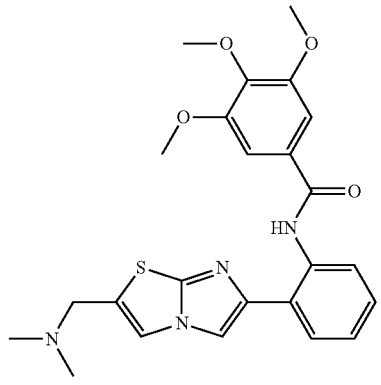 [SMILES: COc1cc(C(=O)Nc2ccccc2-c2cn3cc(CN(C)C)sc3n2)cc(OC)c1OC]
Compound 179
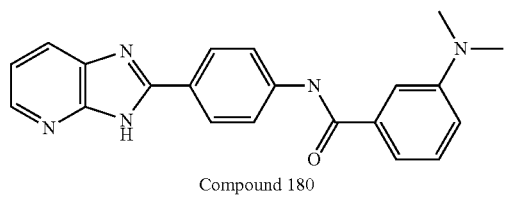
Compound 180
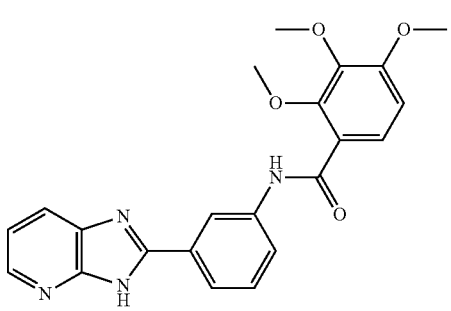 [SMILES: COc1ccc(C(=O)Nc2cccc(-c3nc4cccnc4[nH]3)c2)c(OC)c1OC]
Compound 181
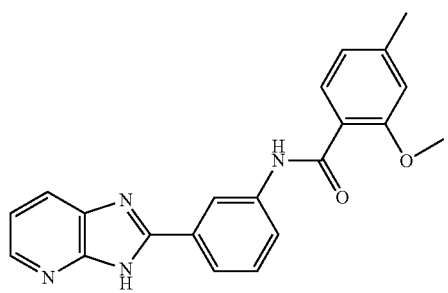 [SMILES: COc1cc(C)ccc1C(=O)Nc1cccc(-c2nc3cccnc3[nH]2)c1]
Compound 182

TABLE 1-continued
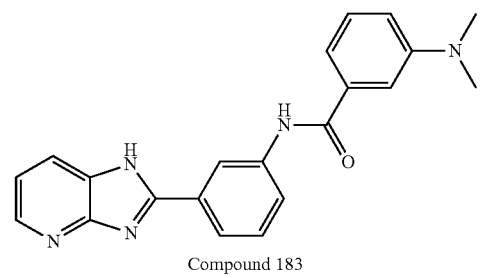
Compound 183
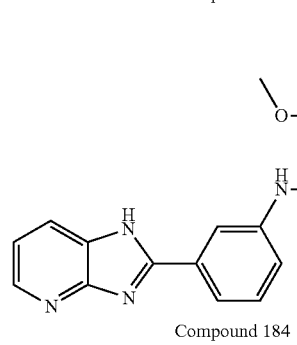
Compound 184
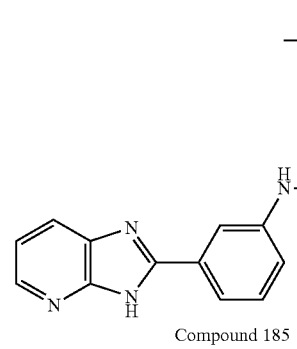
Compound 185
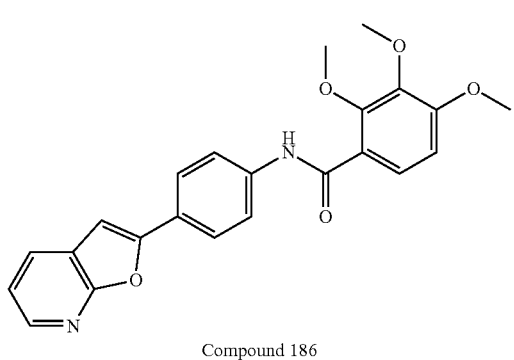
Compound 186
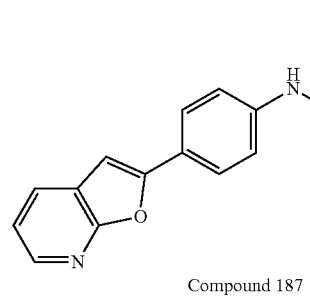
Compound 187
TABLE 1-continued
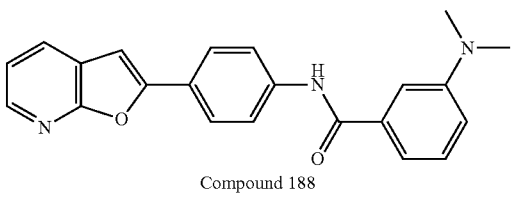
Compound 188
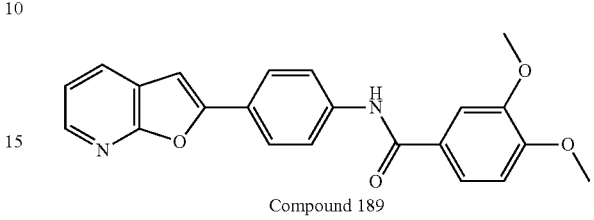
Compound 189
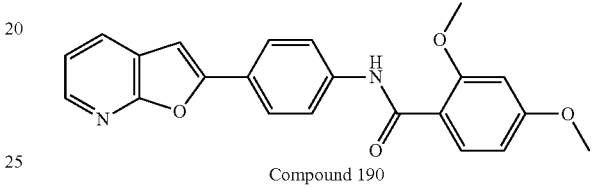
Compound 190
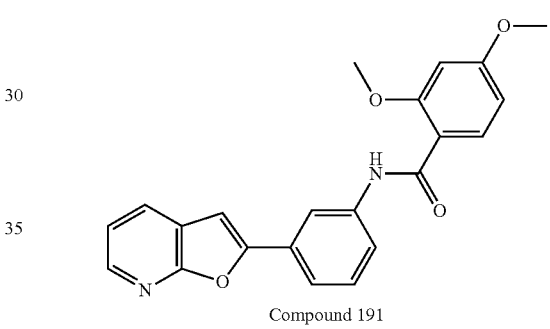
Compound 191
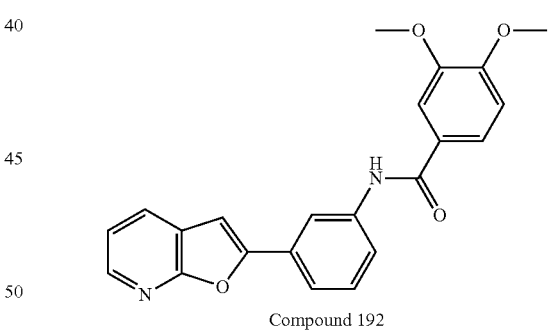
Compound 192
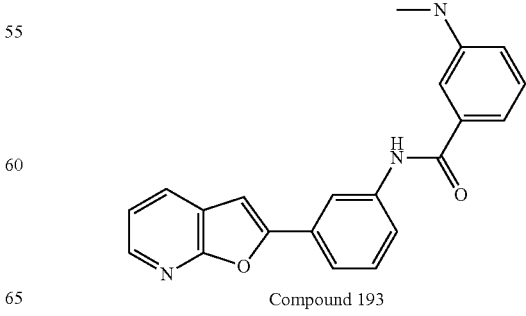
Compound 193

TABLE 1-continued
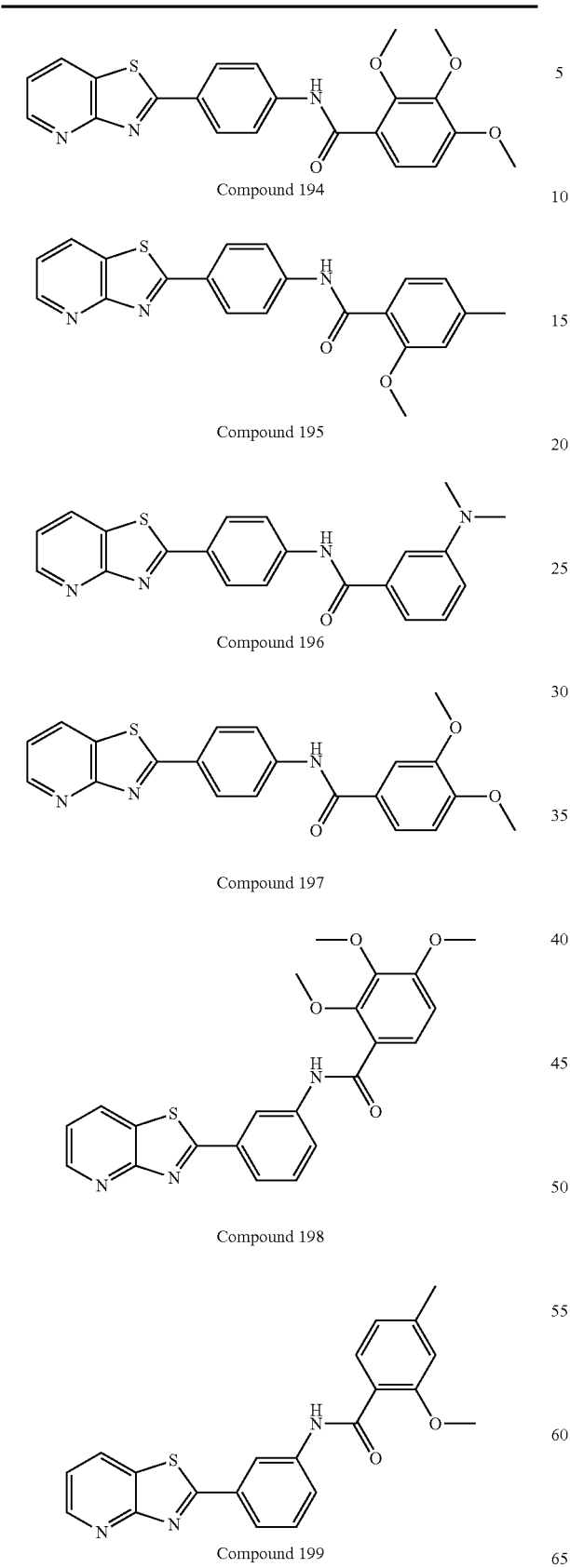
Compound 194
Compound 195
Compound 196
Compound 197
Compound 198
Compound 199
TABLE 1-continued
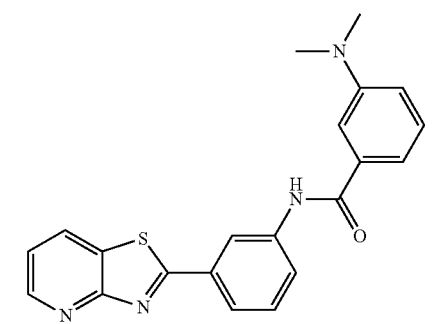 [SMILES: CN(C)c1cccc(C(=O)Nc2cccc(-c3nc4ncccc4s3)c2)c1]
Compound 200
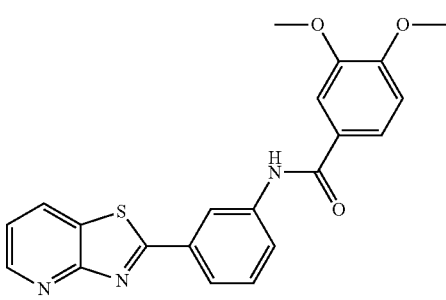 [SMILES: COc1ccc(C(=O)Nc2cccc(-c3nc4ncccc4s3)c2)cc1OC]
Compound 201
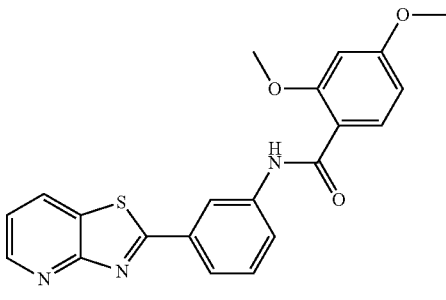 [SMILES: COc1ccc(C(=O)Nc2cccc(-c3nc4ncccc4s3)c2)c(OC)c1]
Compound 202
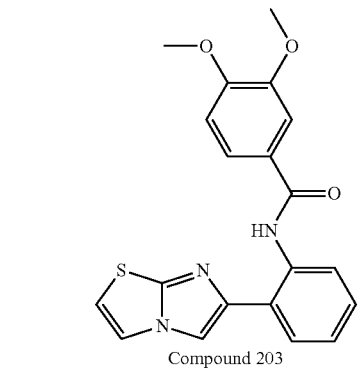
Compound 203

TABLE 1-continued
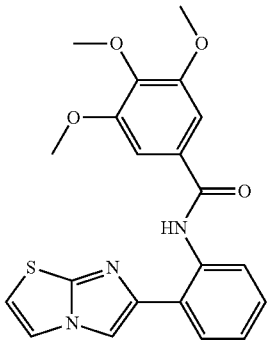 [SMILES: COc1cc(C(=O)Nc2ccccc2-c2cn3ccsc3n2)cc(OC)c1OC]
Compound 204
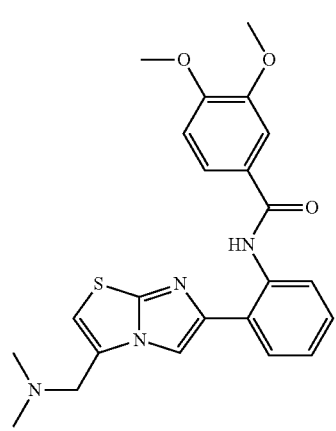 [SMILES: COc1ccc(C(=O)Nc2ccccc2-c2cn3c(CN(C)C)csc3n2)cc1OC]
Compound 205
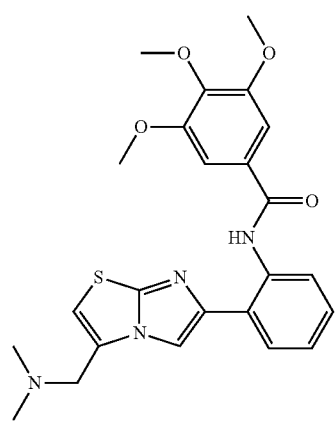 [SMILES: COc1cc(C(=O)Nc2ccccc2-c2cn3c(CN(C)C)csc3n2)cc(OC)c1OC]
Compound 206
TABLE 1-continued
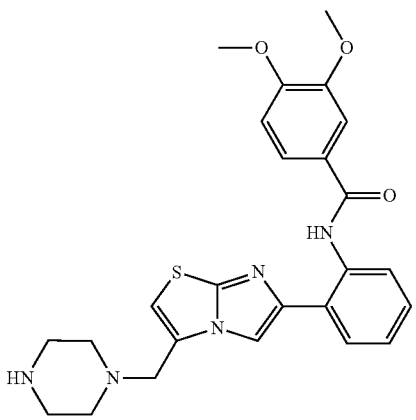 [SMILES: COc1ccc(C(=O)Nc2ccccc2-c2cn3c(CN4CCNCC4)csc3n2)cc1OC]
Compound 207
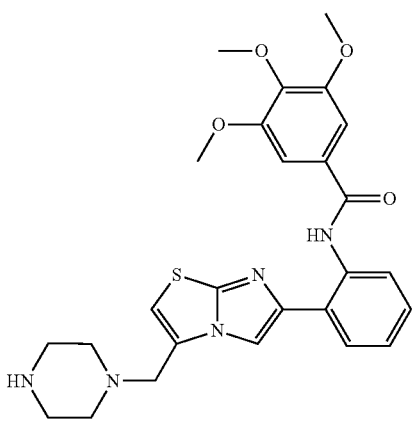 [SMILES: COc1cc(C(=O)Nc2ccccc2-c2cn3c(CN4CCNCC4)csc3n2)cc(OC)c1OC]
Compound 208
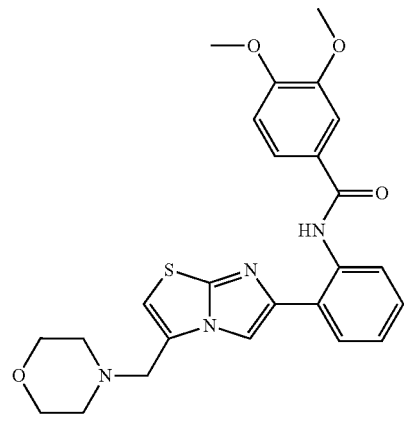 [SMILES: COc1ccc(C(=O)Nc2ccccc2-c2cn3c(CN4CCOCC4)csc3n2)cc1OC]
Compound 209

TABLE 1-continued
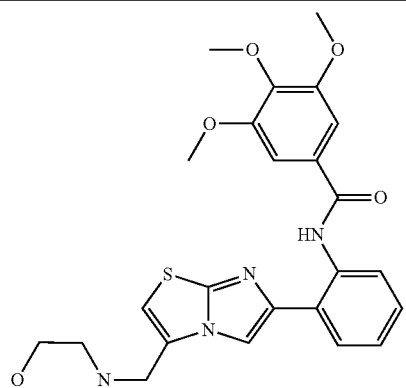
Compound 210
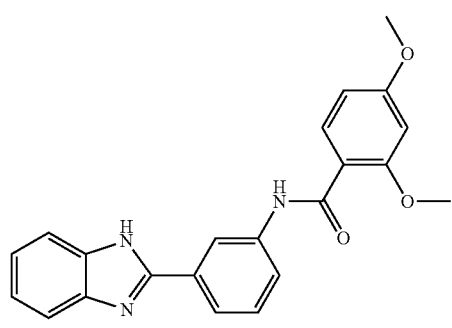 [SMILES: COc1ccc(C(=O)Nc2cccc(-c3nc4ccccc4[nH]3)c2)c(OC)c1]
Compound 211
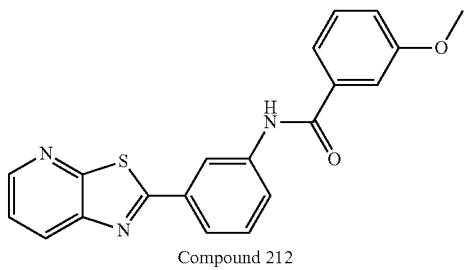
Compound 212
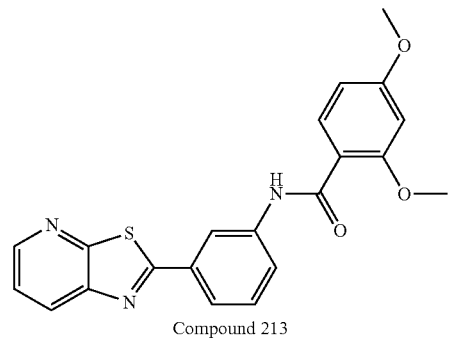
Compound 213
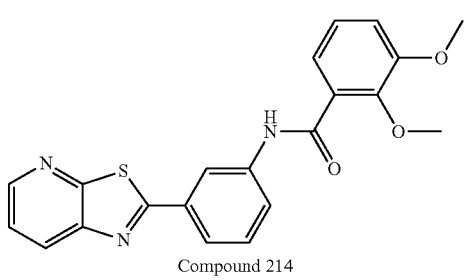
Compound 214
TABLE 1-continued
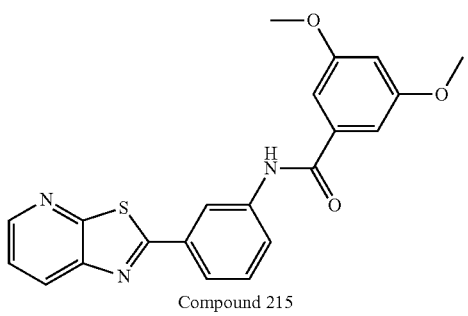
Compound 215
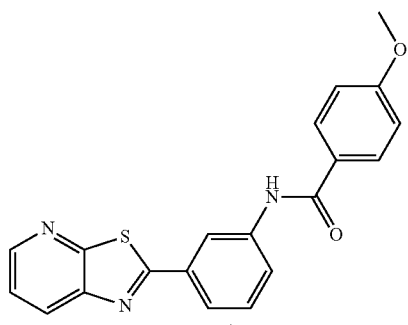 [SMILES: COc1ccc(C(=O)Nc2cccc(-c3nc4cccnc4s3)c2)cc1]
Compound 216
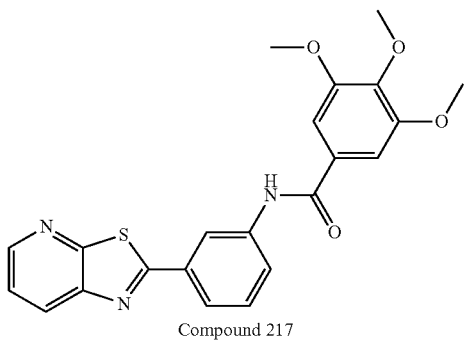
Compound 217
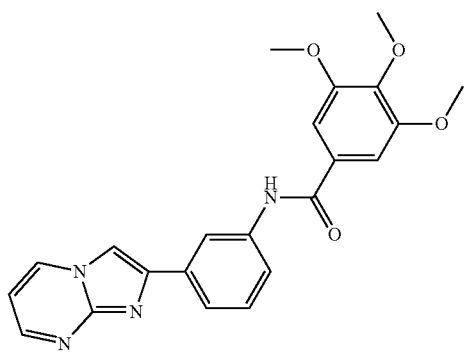 [SMILES: COc1cc(C(=O)Nc2cccc(-c3cn4cccnc4n3)c2)cc(OC)c1OC]
Compound 218

TABLE 1-continued
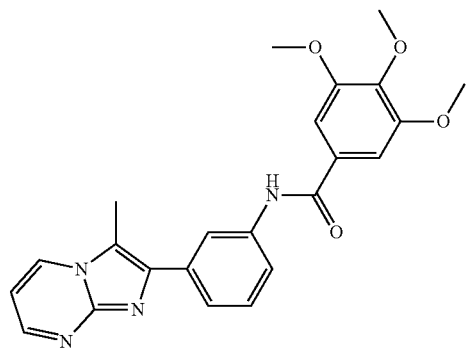 [SMILES: COc1cc(C(=O)Nc2cccc(-c3nc4ncccn4c3C)c2)cc(OC)c1OC]
Compound 219
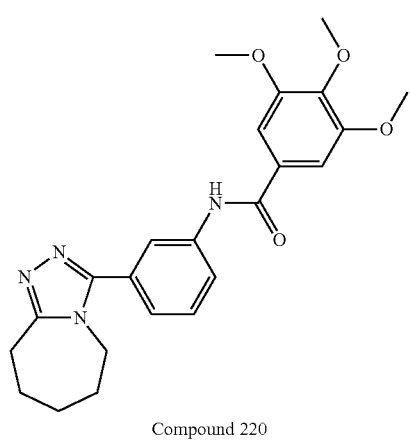
Compound 220
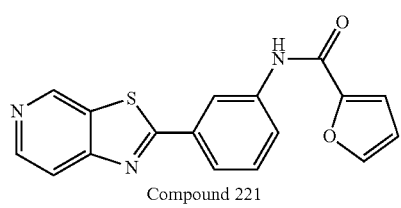
Compound 221
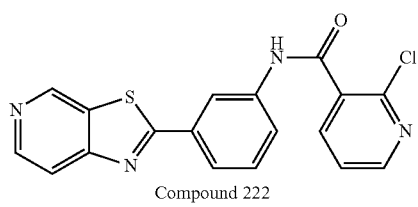
Compound 222
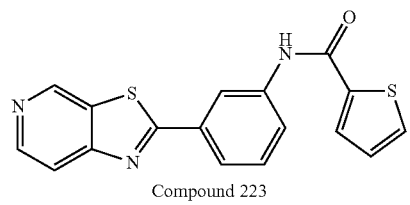
Compound 223
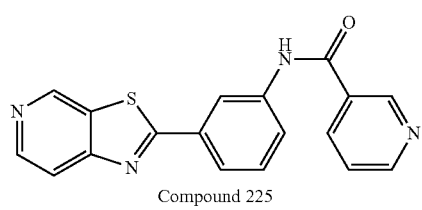
Compound 225
TABLE 1-continued
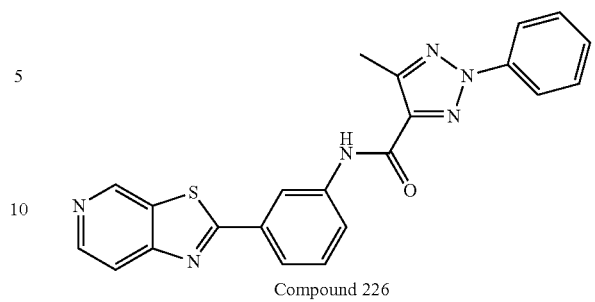
Compound 226
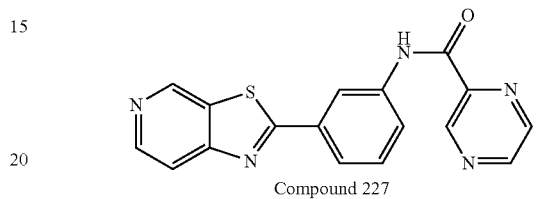
Compound 227
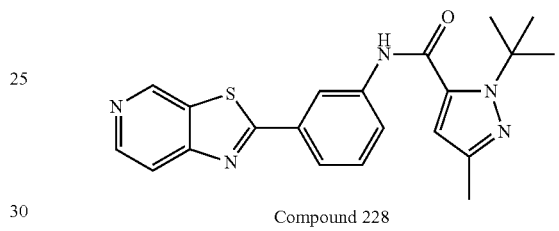
Compound 228
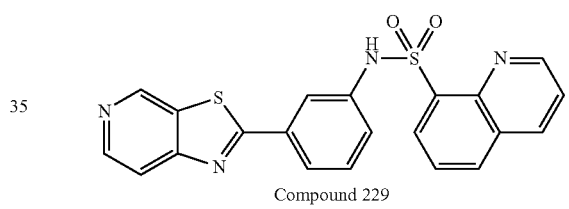
Compound 229
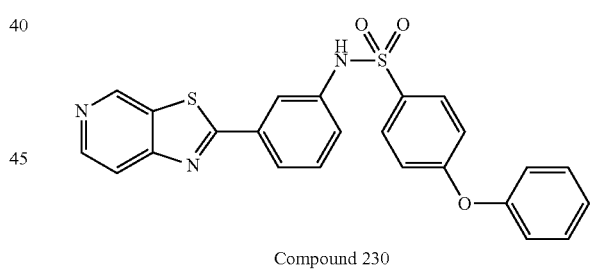
Compound 230
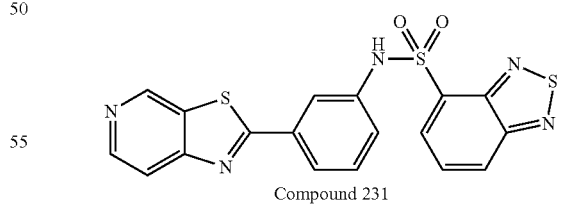
Compound 231
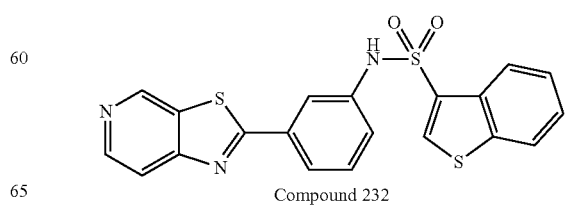
Compound 232

TABLE 1-continued
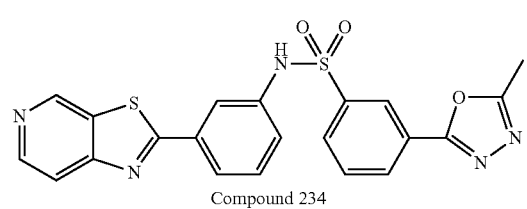
Compound 234
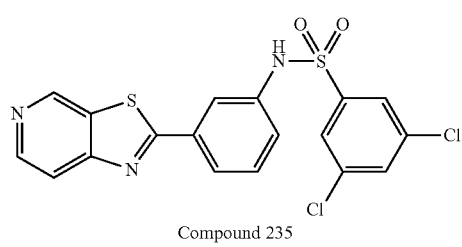
Compound 235
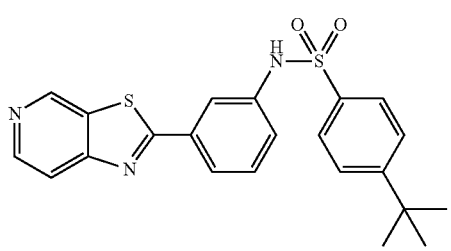 [SMILES: CC(C)(C)c1ccc(S(=O)(=O)Nc2cccc(-c3nc4ccncc4s3)c2)cc1]
Compound 236
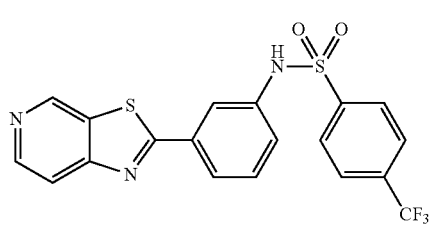 [SMILES: O=S(=O)(Nc1cccc(-c2nc3ccncc3s2)c1)c1ccc(C(F)(F)F)cc1]
Compound 237
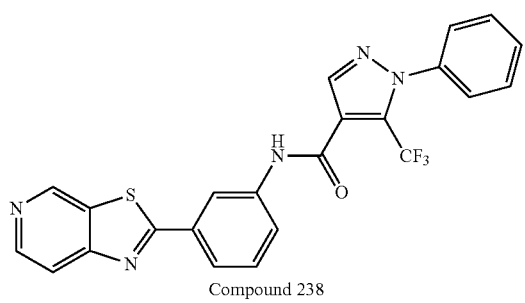
Compound 238
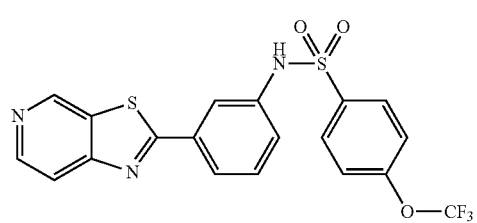 [SMILES: O=S(=O)(Nc1cccc(-c2nc3ccncc3s2)c1)c1ccc(OC(F)(F)F)cc1]
Compound 239
TABLE 1-continued
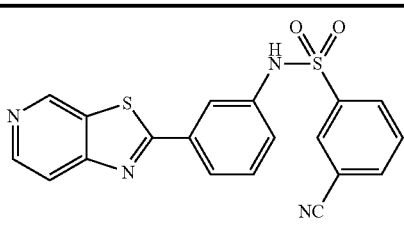
Compound 240
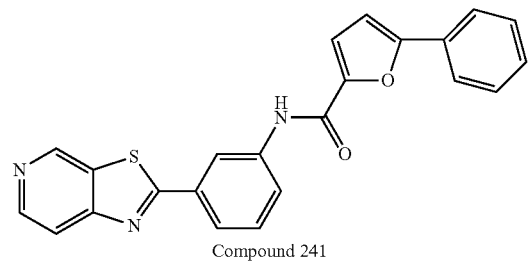
Compound 241
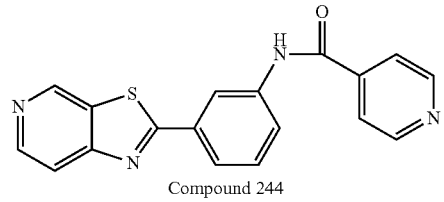
Compound 244
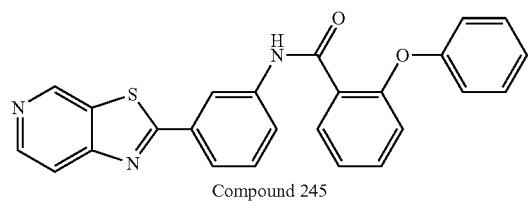
Compound 245
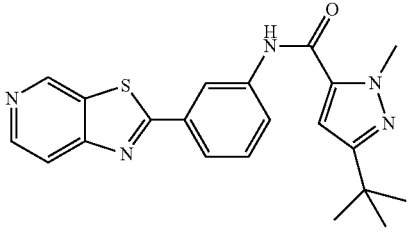 [SMILES: Cn1nc(C(C)(C)C)cc1C(=O)Nc1cccc(-c2nc3ccncc3s2)c1]
Compound 246
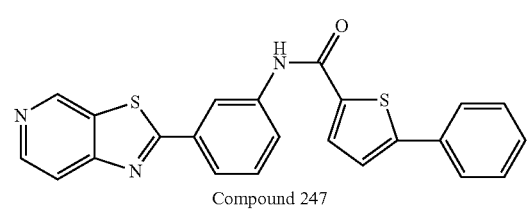
Compound 247
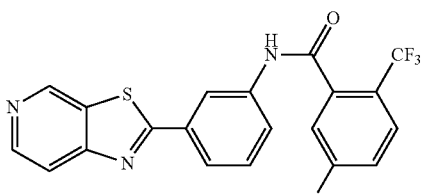
Compound 248

TABLE 1-continued
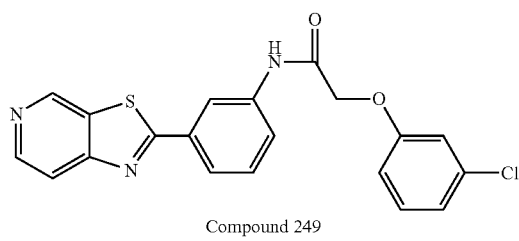
Compound 249
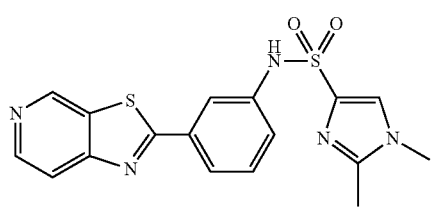 [SMILES: Cc1nc(S(=O)(=O)Nc2cccc(-c3nc4ccncc4s3)c2)cn1C]
Compound 250
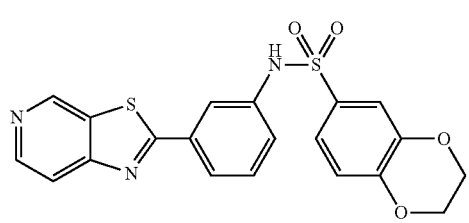 [SMILES: O=S(=O)(Nc1cccc(-c2nc3ccncc3s2)c1)c1ccc2c(c1)OCCO2]
Compound 251
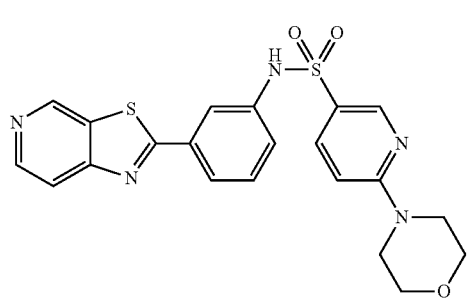 [SMILES: O=S(=O)(Nc1cccc(-c2nc3ccncc3s2)c1)c1ccc(N2CCOCC2)nc1]
Compound 252
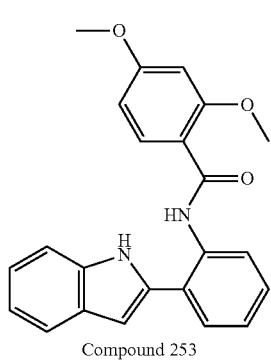
Compound 253
TABLE 1-continued
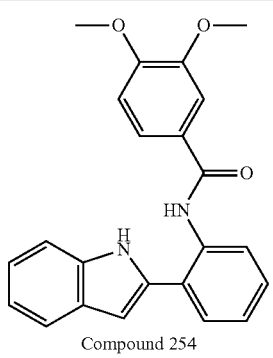
Compound 254
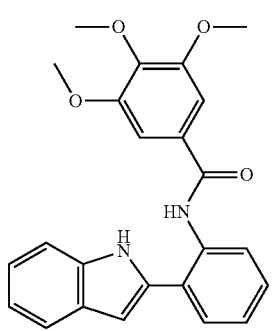 [SMILES: COc1cc(C(=O)Nc2ccccc2-c2cc3ccccc3[nH]2)cc(OC)c1OC]
Compound 255
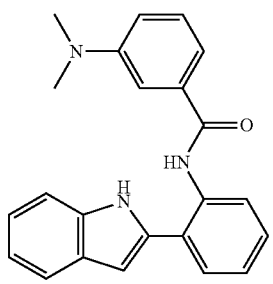 [SMILES: CN(C)c1cccc(C(=O)Nc2ccccc2-c2cc3ccccc3[nH]2)c1]
Compound 256
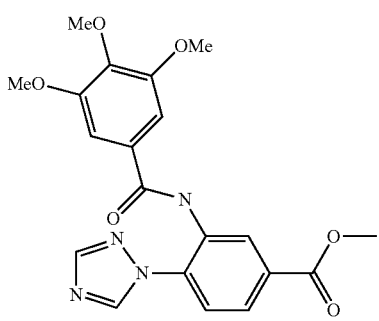 [SMILES: COC(=O)c1ccc(-n2cncn2)c(NC(=O)c2cc(OC)c(OC)c(OC)c2)c1]
Compound 257

TABLE 1-continued
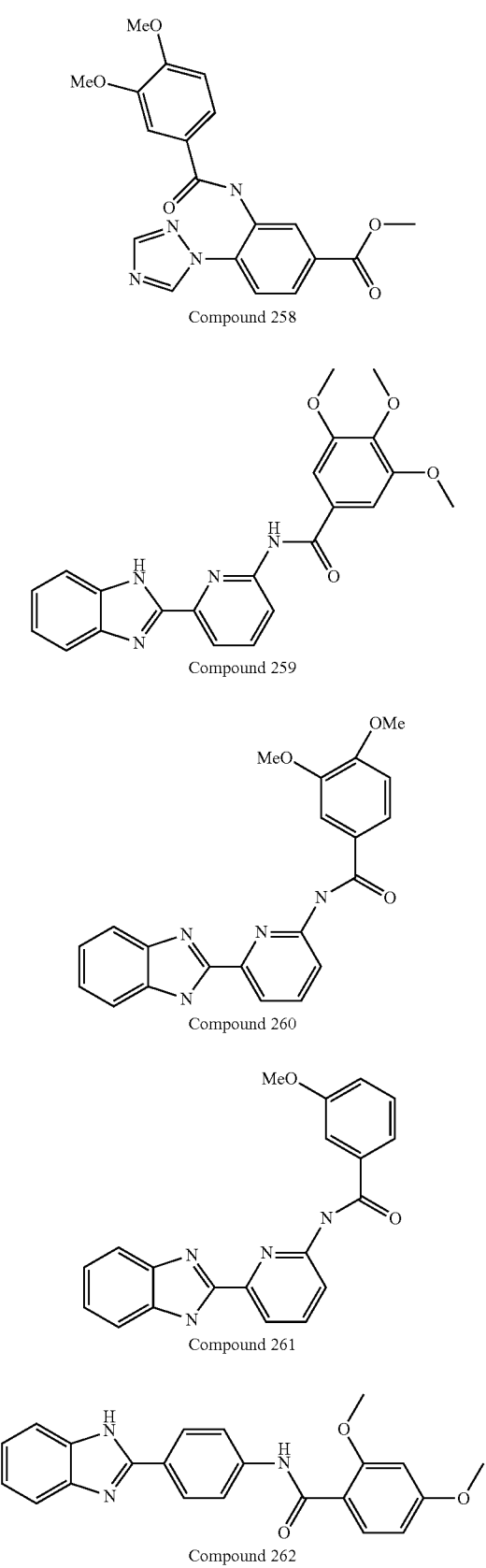
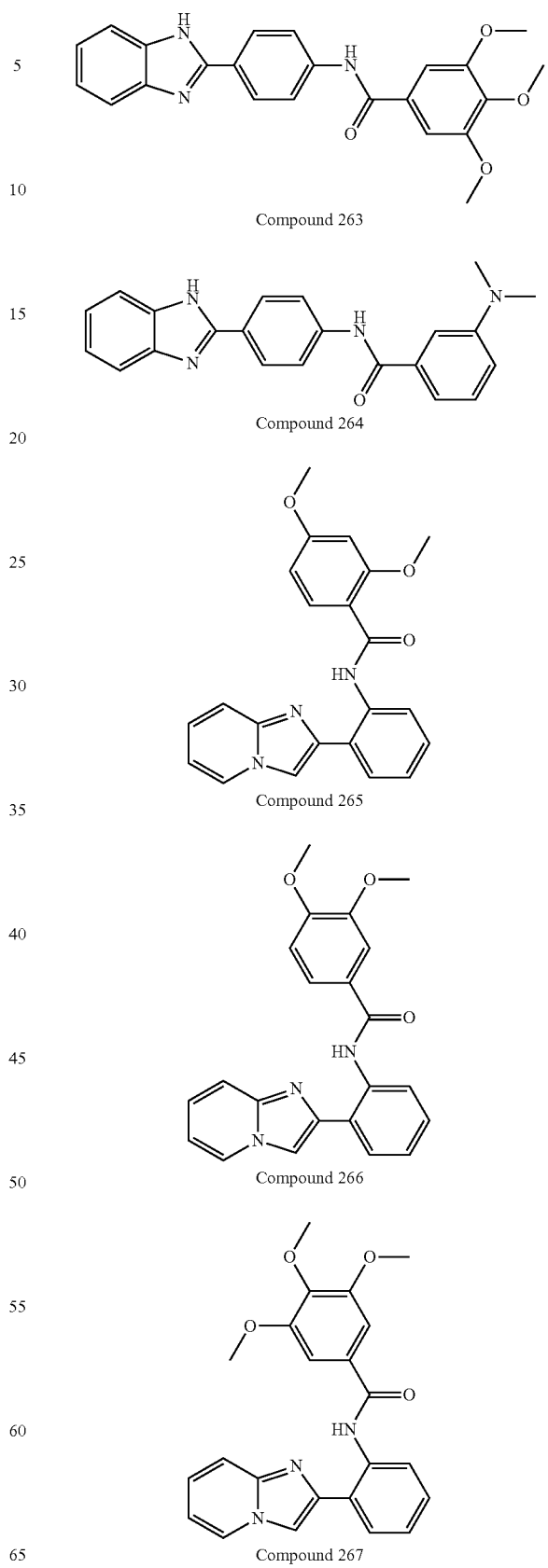

TABLE 1-continued
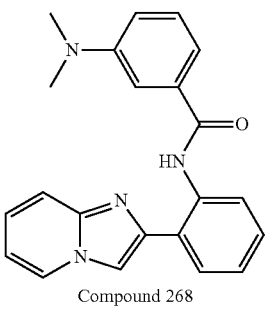
Compound 268
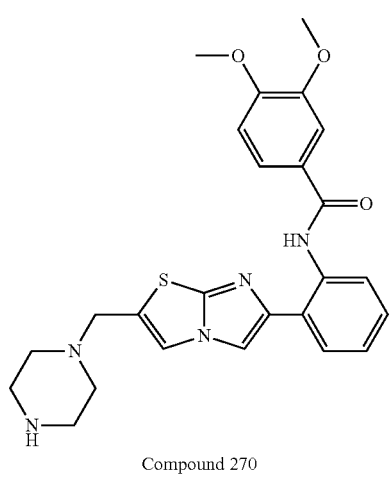
Compound 270
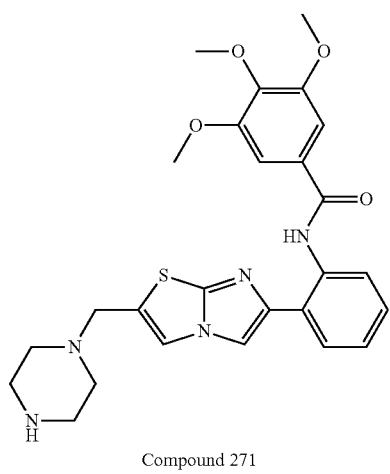
Compound 271
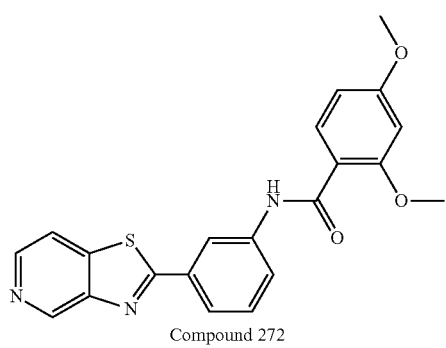
Compound 272
TABLE 1-continued
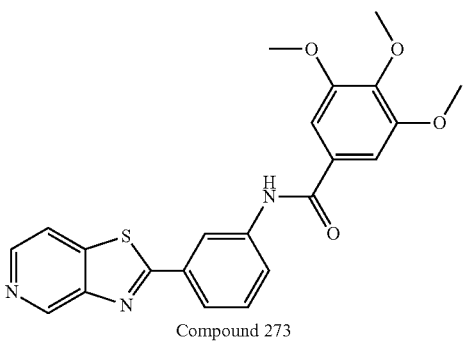
Compound 273
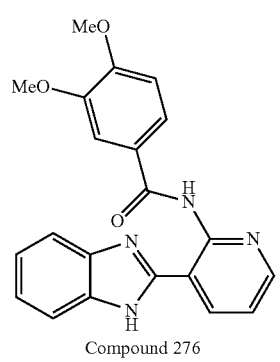
Compound 276
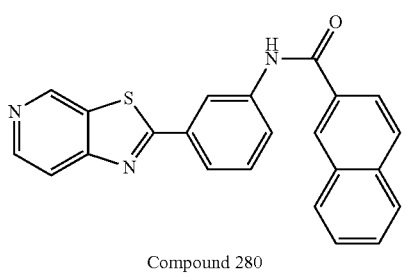
Compound 280
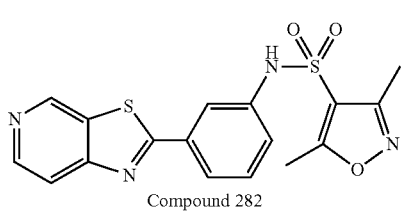
Compound 282
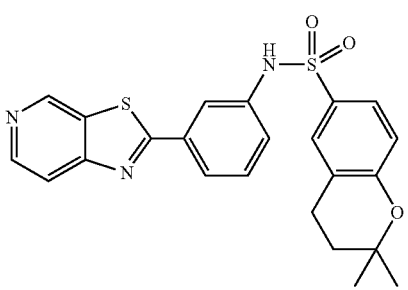 [SMILES: CC1(C)CCc2cc(S(=O)(=O)Nc3cccc(-c4nc5ccncc5s4)c3)ccc2O1]
Compound 283

TABLE 1-continued
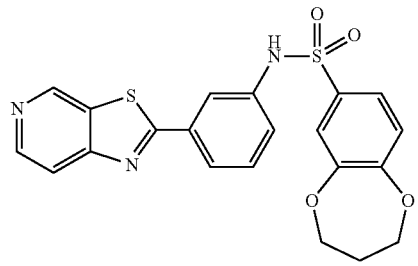 [SMILES: O=S(=O)(Nc1cccc(-c2nc3ccncc3s2)c1)c1ccc2c(c1)OCCCO2]
Compound 284
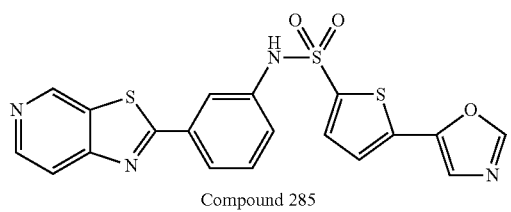
Compound 285
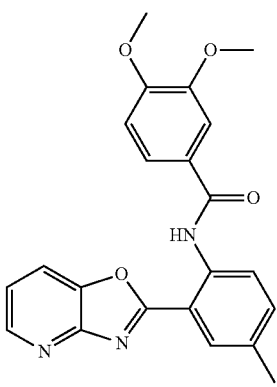 [SMILES: COc1ccc(C(=O)Nc2ccc(C)cc2-c2nc3ncccc3o2)cc1OC]
Compound 286
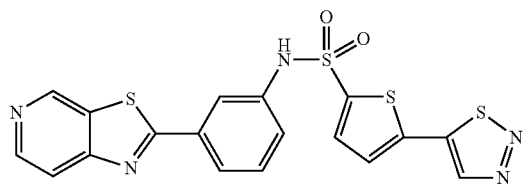 [SMILES: O=S(=O)(Nc1cccc(-c2nc3ccncc3s2)c1)c1ccc(-c2cnns2)s1]
Compound 287
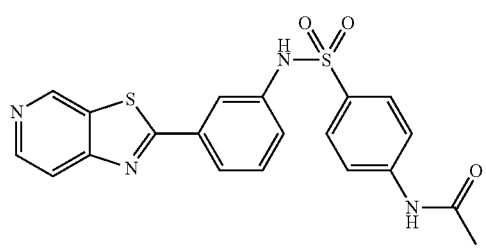 [SMILES: CC(=O)Nc1ccc(S(=O)(=O)Nc2cccc(-c3nc4ccncc4s3)c2)cc1]
Compound 288
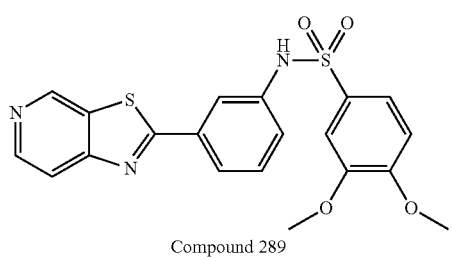
Compound 289
TABLE 1-continued
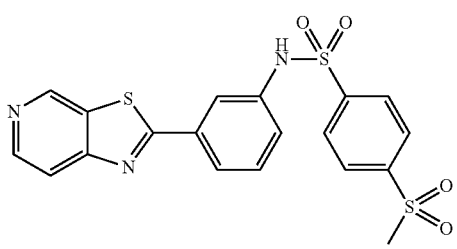 [SMILES: CS(=O)(=O)c1ccc(S(=O)(=O)Nc2cccc(-c3nc4ccncc4s3)c2)cc1]
Compound 290
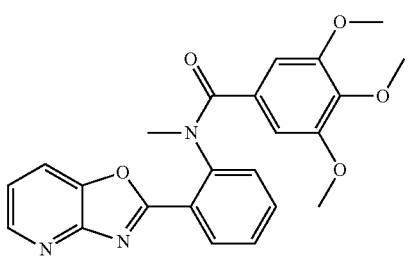 [SMILES: COc1cc(C(=O)N(C)c2ccccc2-c2nc3ncccc3o2)cc(OC)c1OC]
Compound 292
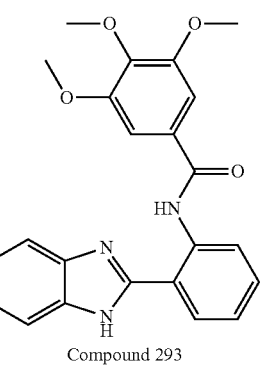
Compound 293
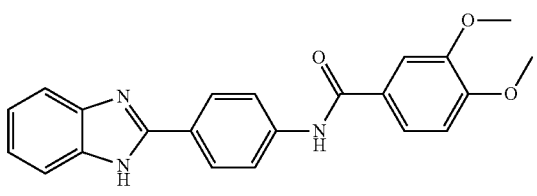 [SMILES: COc1ccc(C(=O)Nc2ccc(-c3nc4ccccc4[nH]3)cc2)cc1OC]
Compound 294
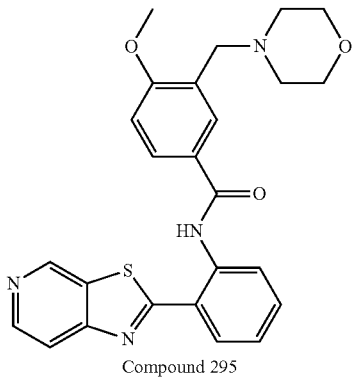
Compound 295

TABLE 1-continued
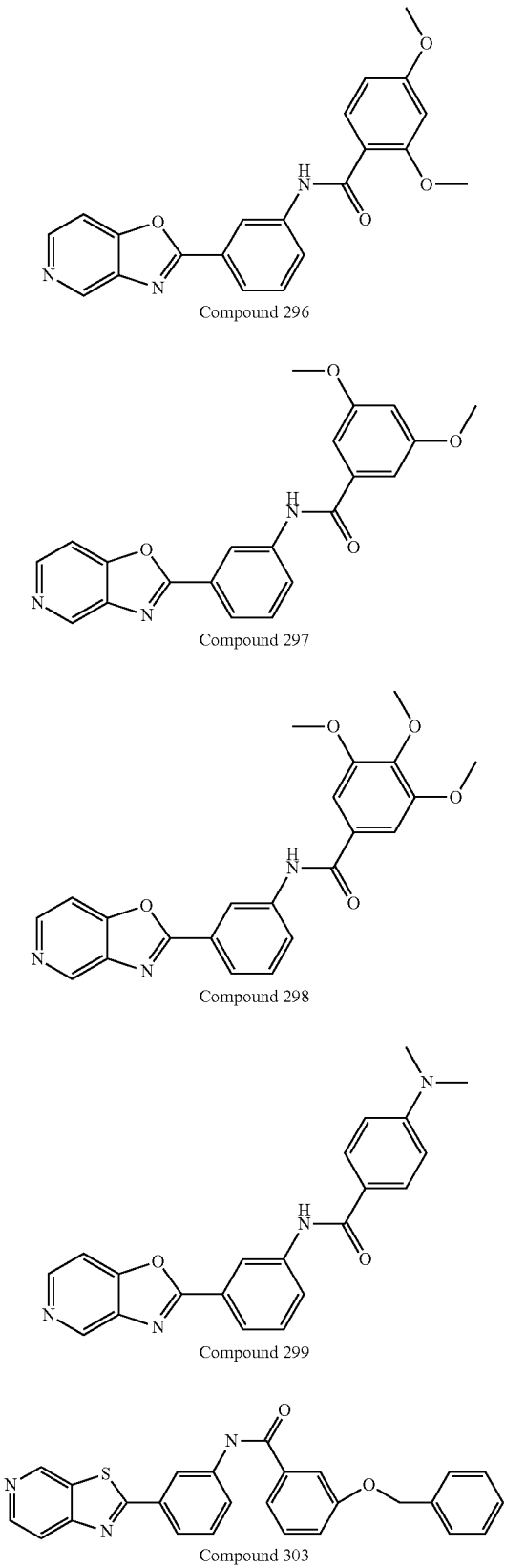
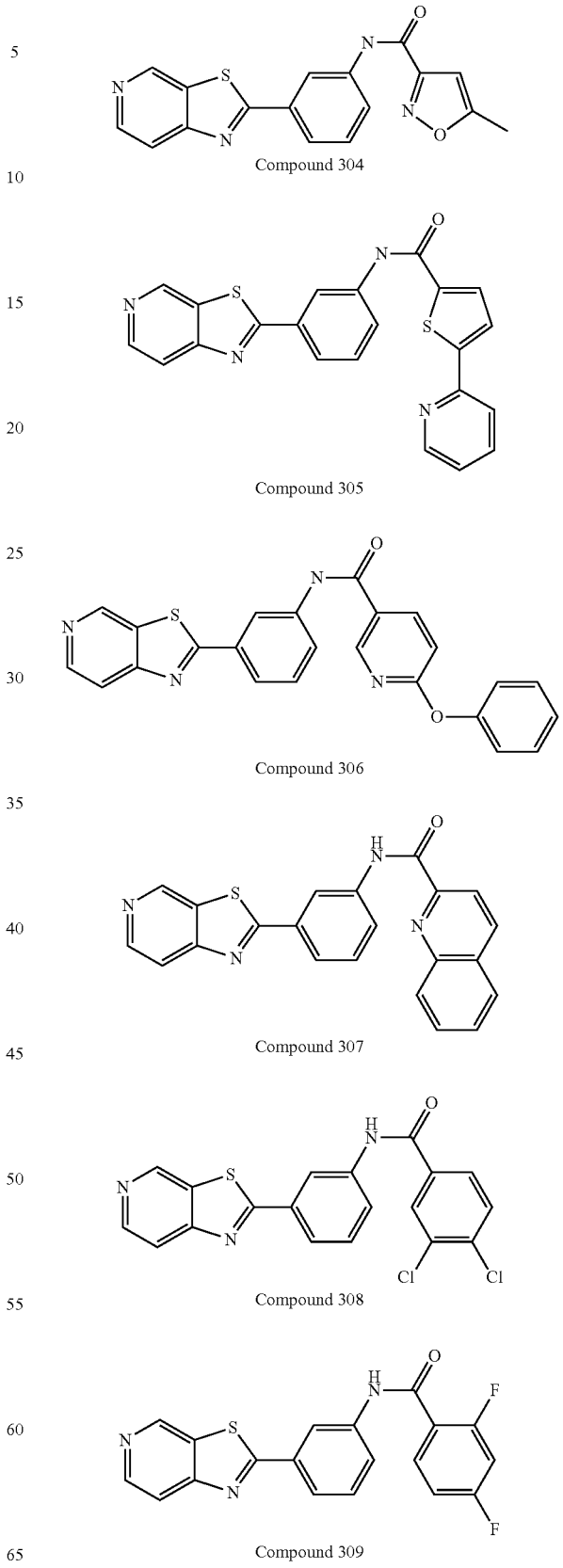

TABLE 1-continued
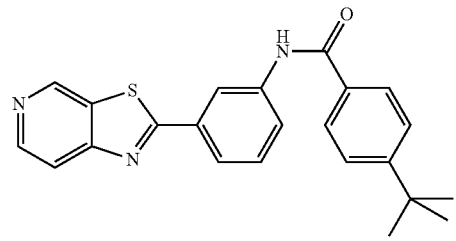 [SMILES: CC(C)(C)c1ccc(C(=O)Nc2cccc(-c3nc4ccncc4s3)c2)cc1]
Compound 310
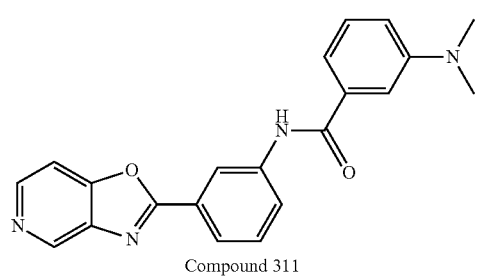
Compound 311
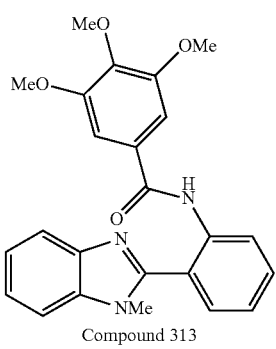
Compound 313
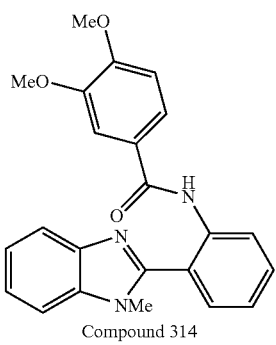
Compound 314
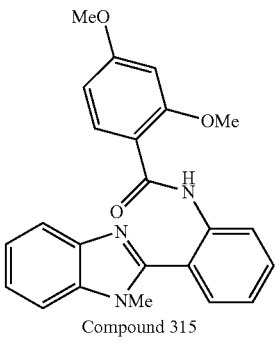
Compound 315
TABLE 1-continued
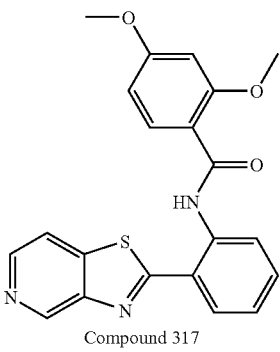
Compound 317
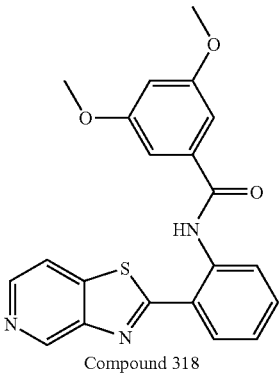
Compound 318
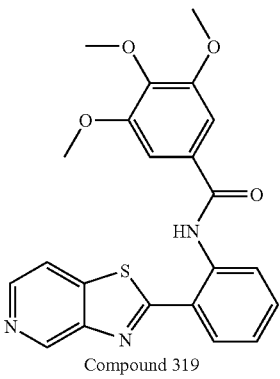
Compound 319
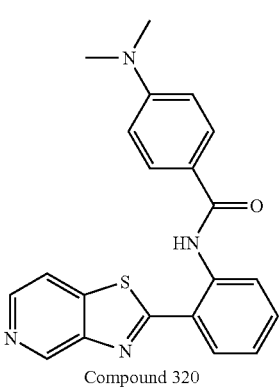
Compound 320

TABLE 1-continued
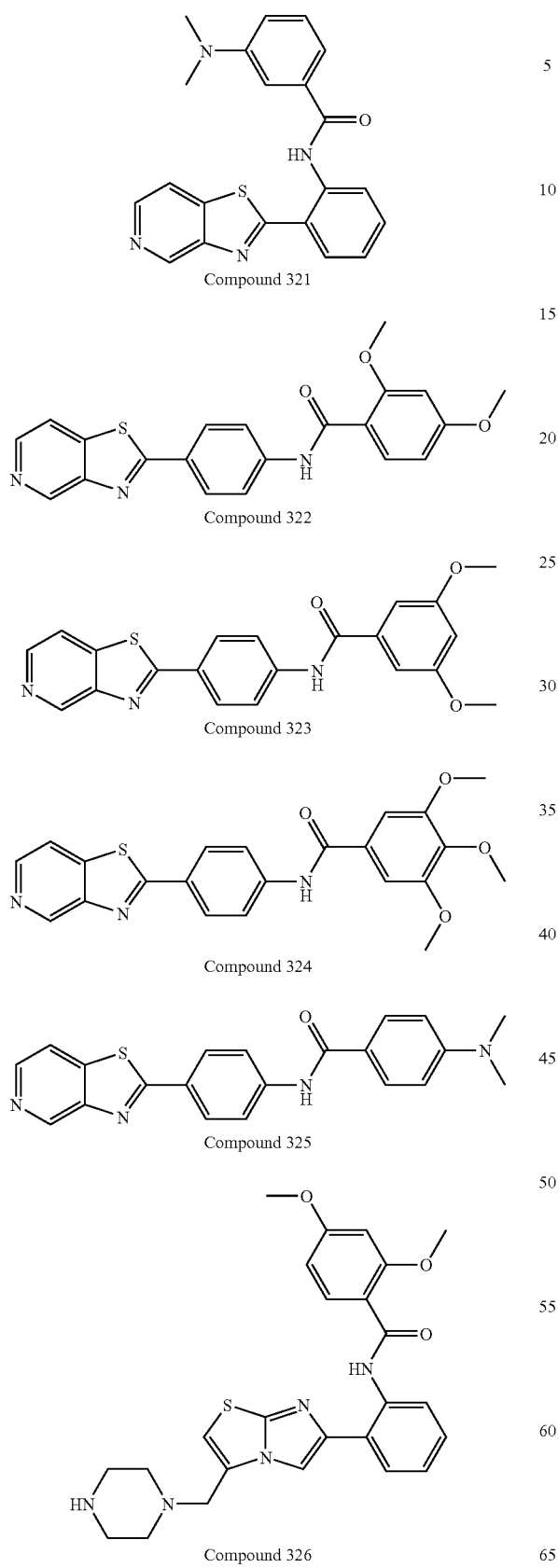
Compound 321
Compound 322
Compound 323
Compound 324
Compound 325
Compound 326
TABLE 1-continued
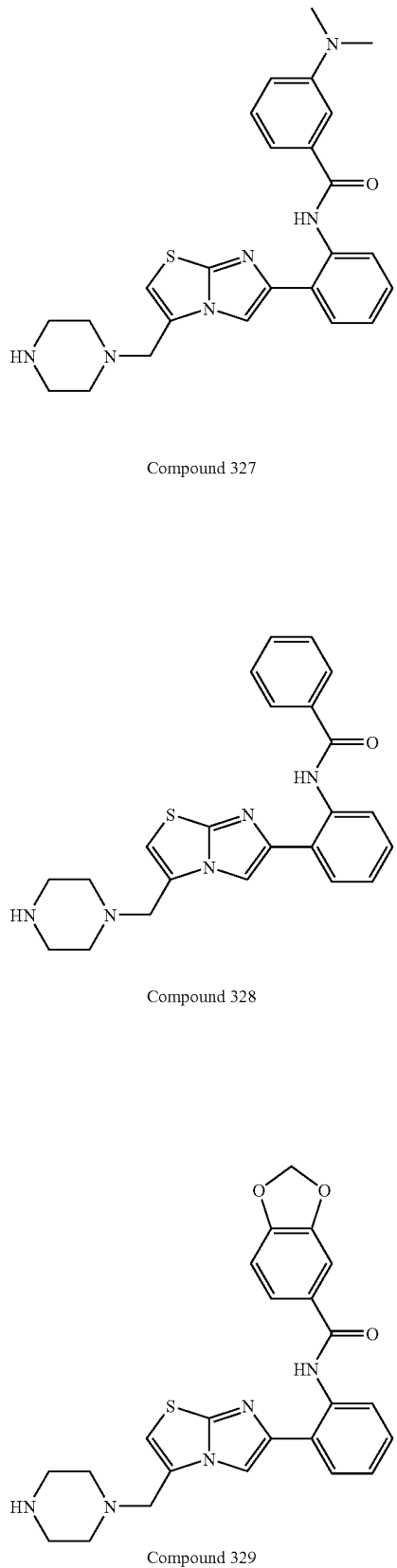
Compound 327
Compound 328
Compound 329

TABLE 1-continued
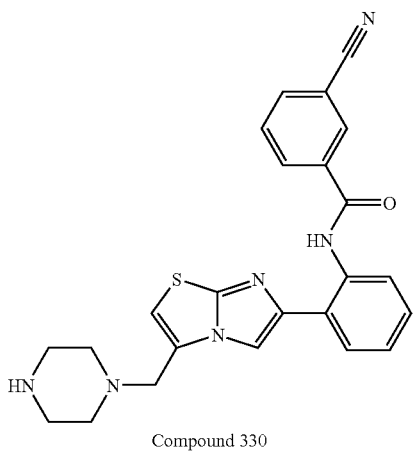
Compound 330
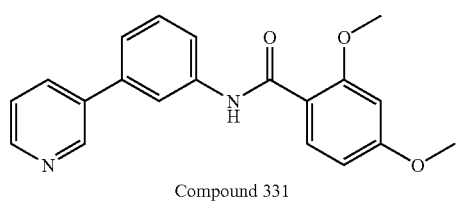
Compound 331
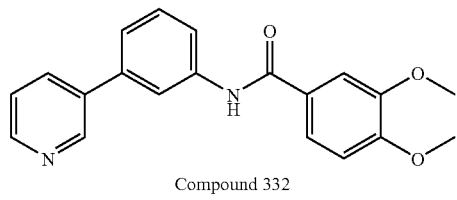
Compound 332
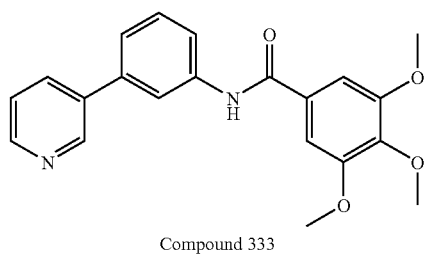
Compound 333
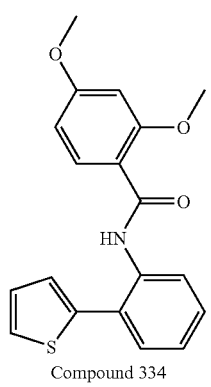
Compound 334
TABLE 1-continued
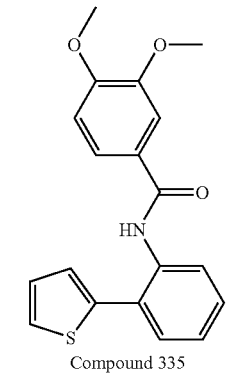
Compound 335
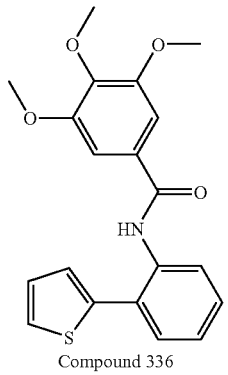
Compound 336
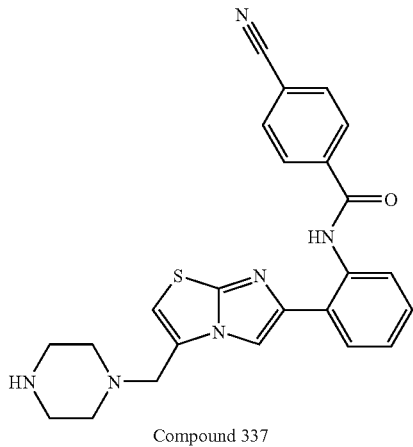
Compound 337
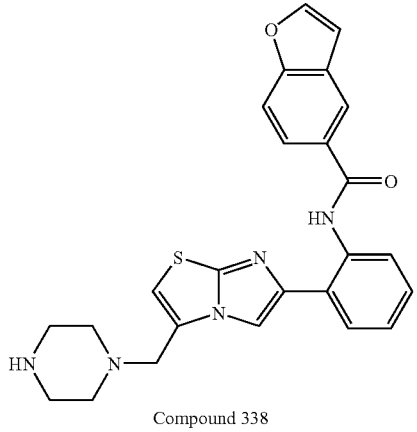
Compound 338

TABLE 1-continued
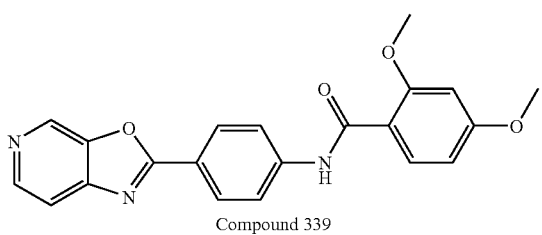
Compound 339
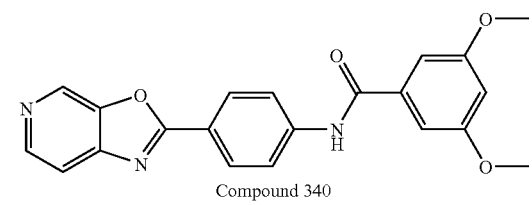
Compound 340
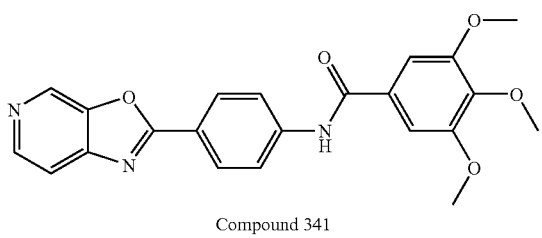
Compound 341
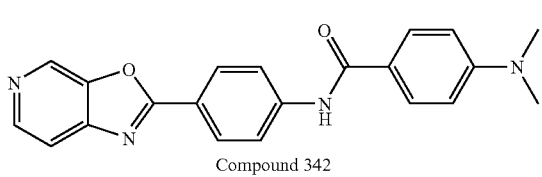
Compound 342
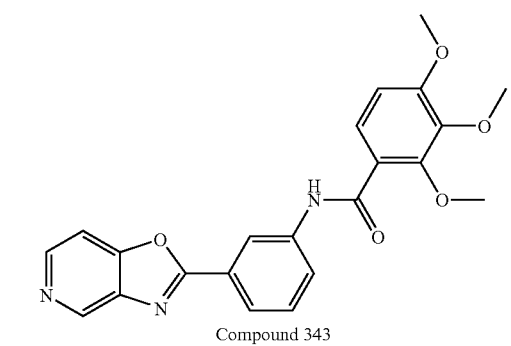
Compound 343
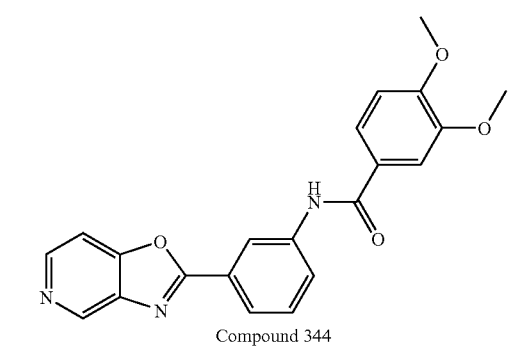
Compound 344
TABLE 1-continued
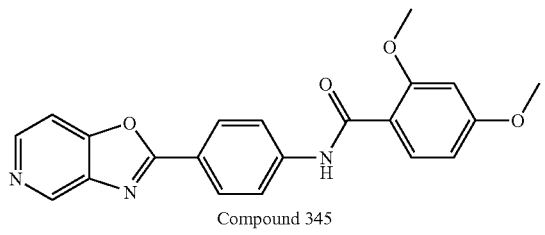
Compound 345
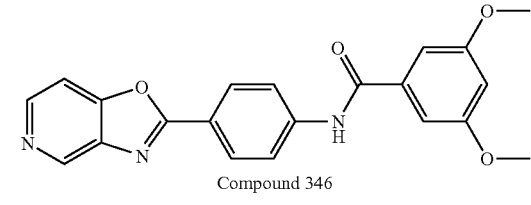
Compound 346
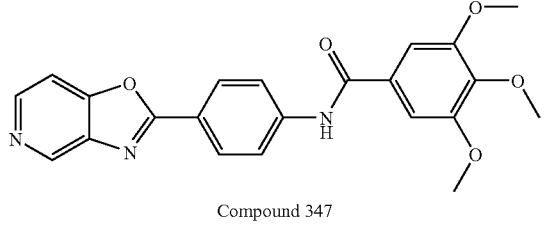
Compound 347
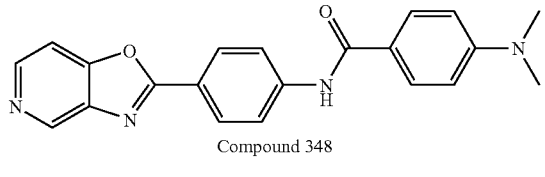
Compound 348
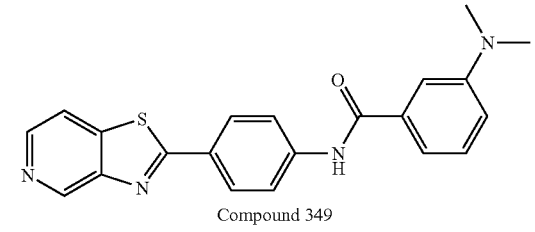
Compound 349
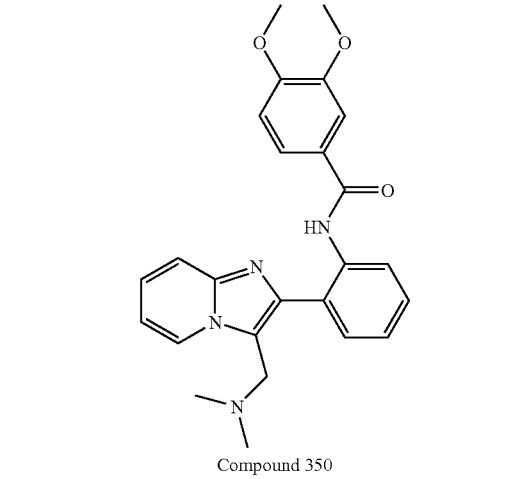
Compound 350

TABLE 1-continued
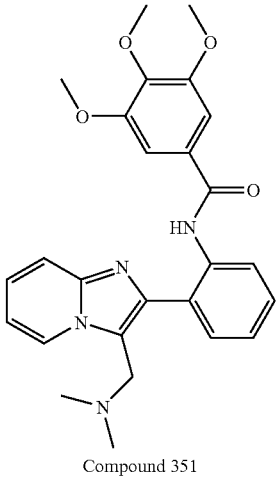
Compound 351
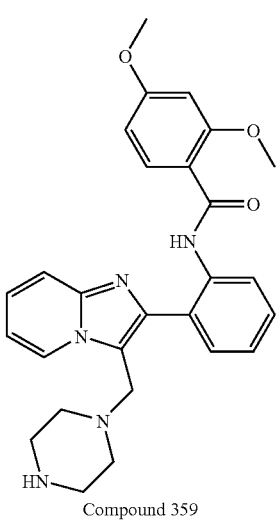
Compound 359
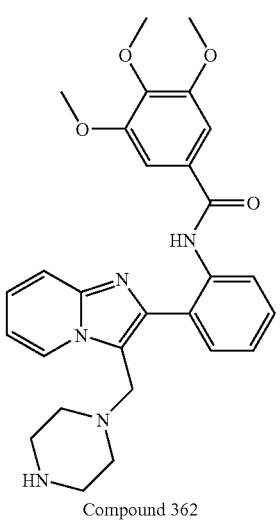
Compound 362
TABLE 1-continued
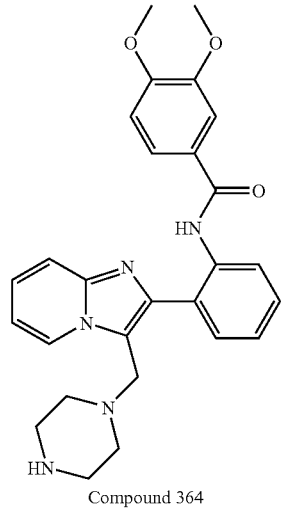
Compound 364
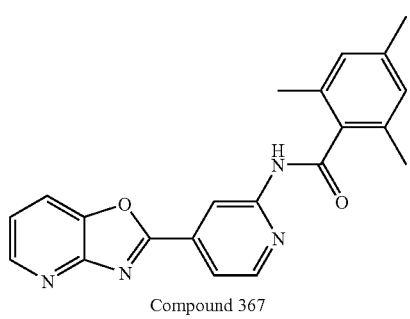
Compound 367
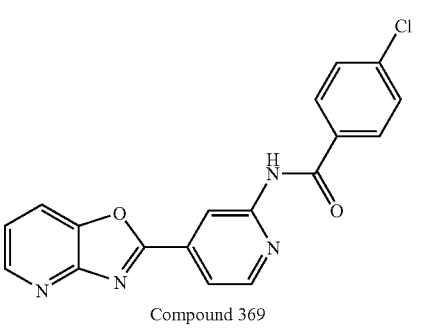
Compound 369
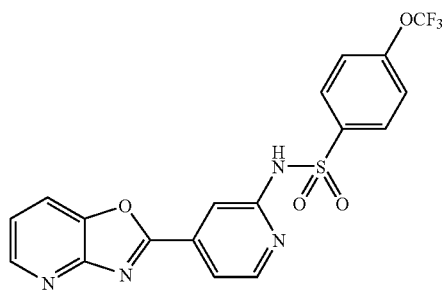 [SMILES: O=S(=O)(Nc1cc(-c2nc3ncccc3o2)ccn1)c1ccc(OC(F)(F)F)cc1]
Compound 370

TABLE 1-continued
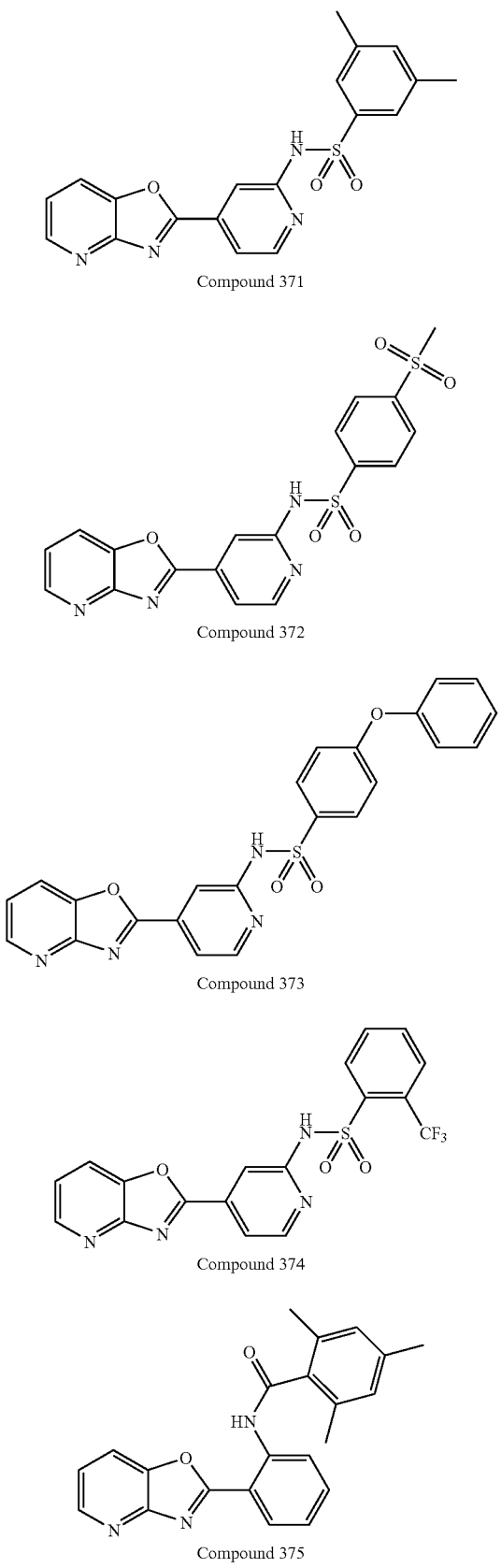
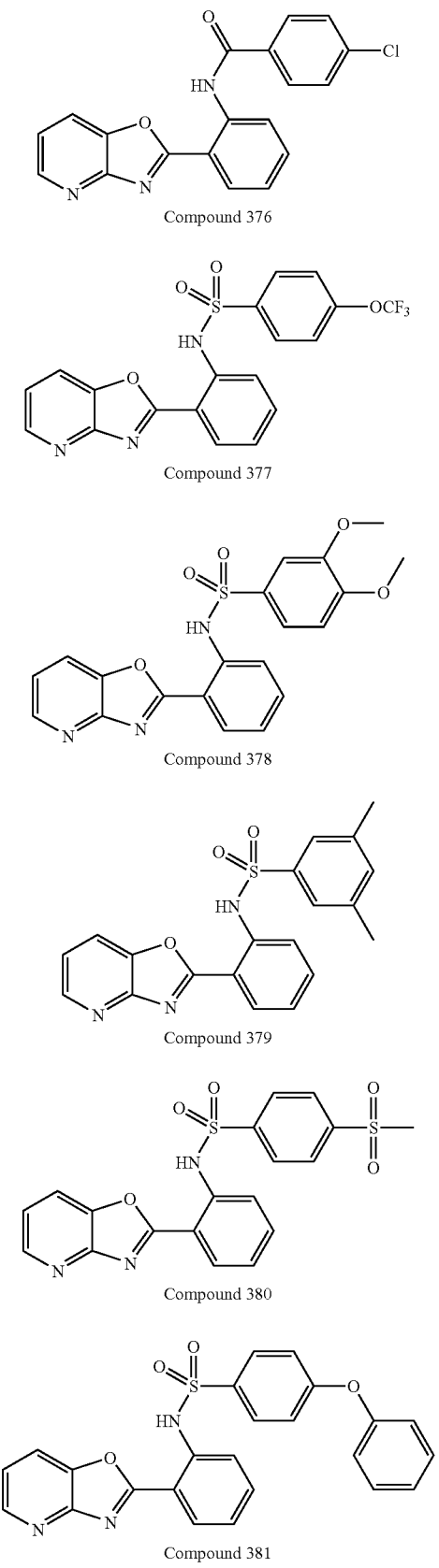

TABLE 1-continued
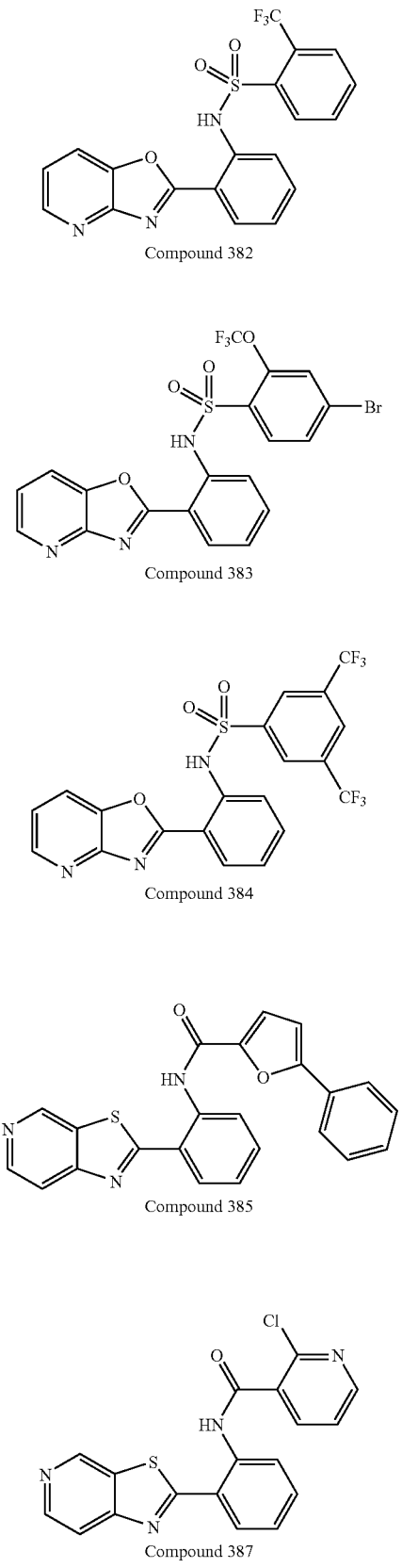
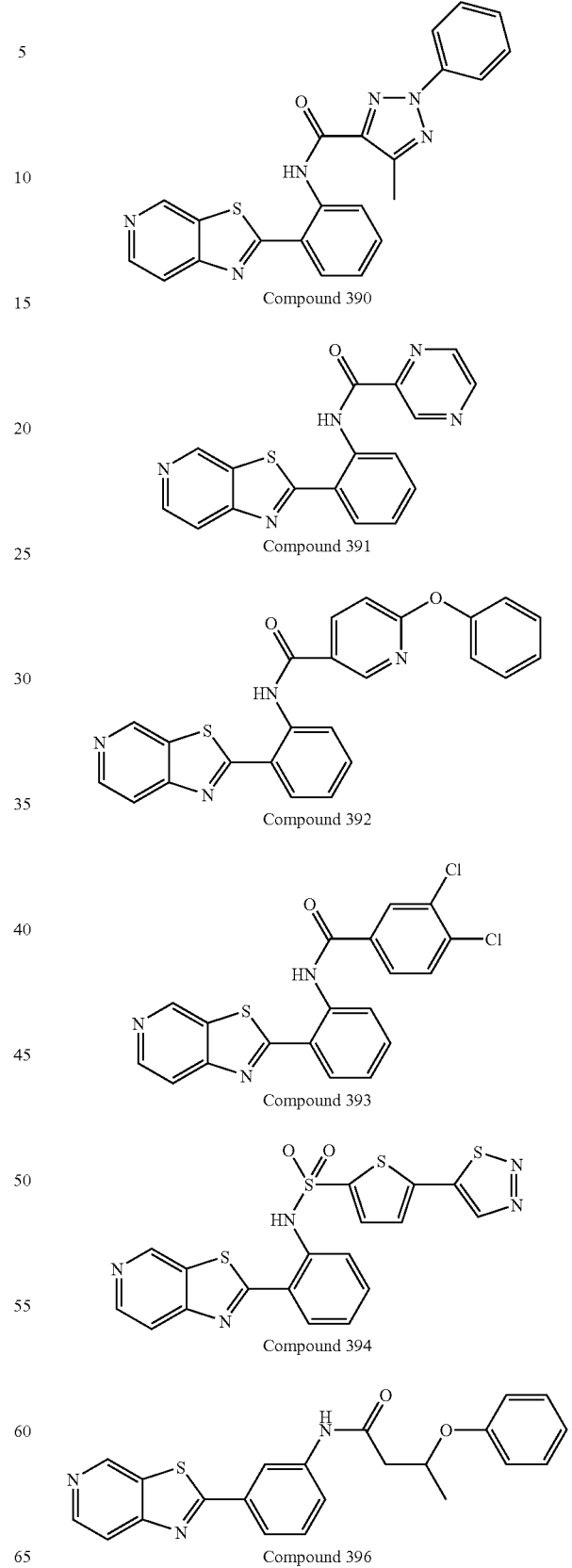

TABLE 1-continued
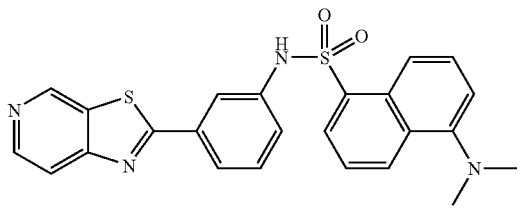 [SMILES: CN(C)c1cccc2c(S(=O)(=O)Nc3cccc(-c4nc5ccncc5s4)c3)cccc12]
Compound 398
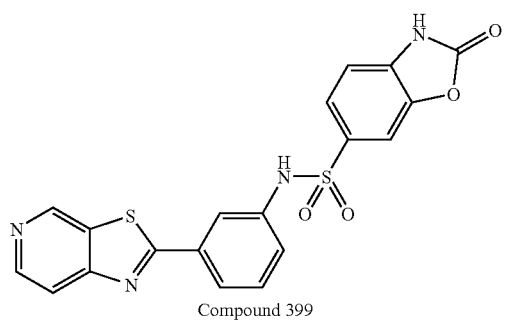
Compound 399
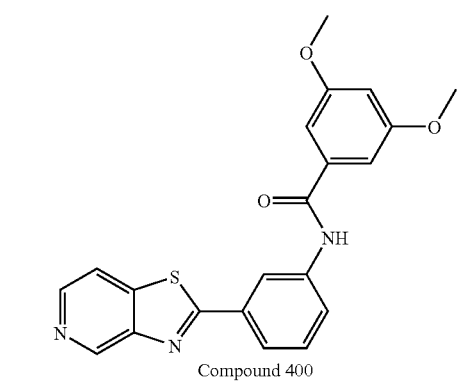
Compound 400
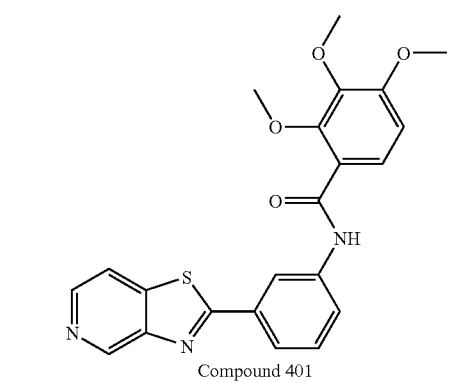
Compound 401
TABLE 1-continued
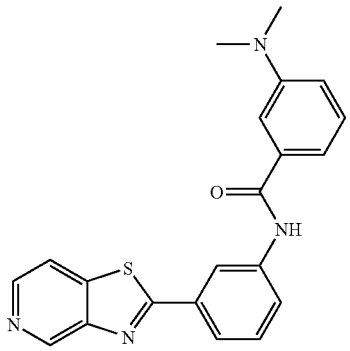 [SMILES: CN(C)c1cccc(C(=O)Nc2cccc(-c3nc4cnccc4s3)c2)c1]
Compound 402
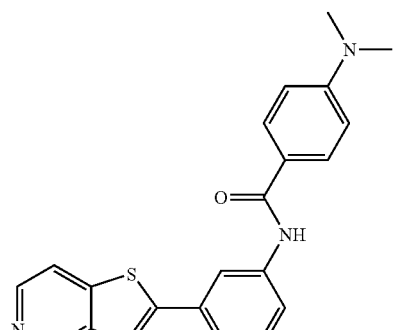
Compound 403
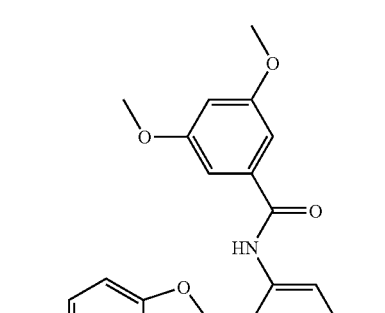
Compound 404
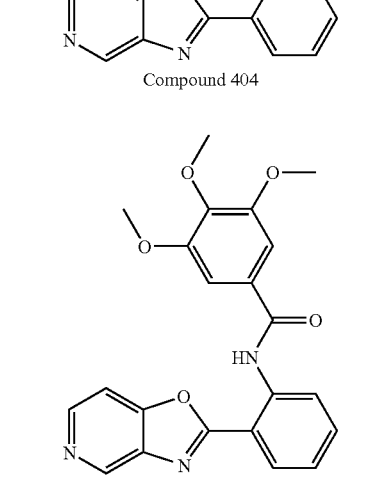
Compound 405

TABLE 1-continued
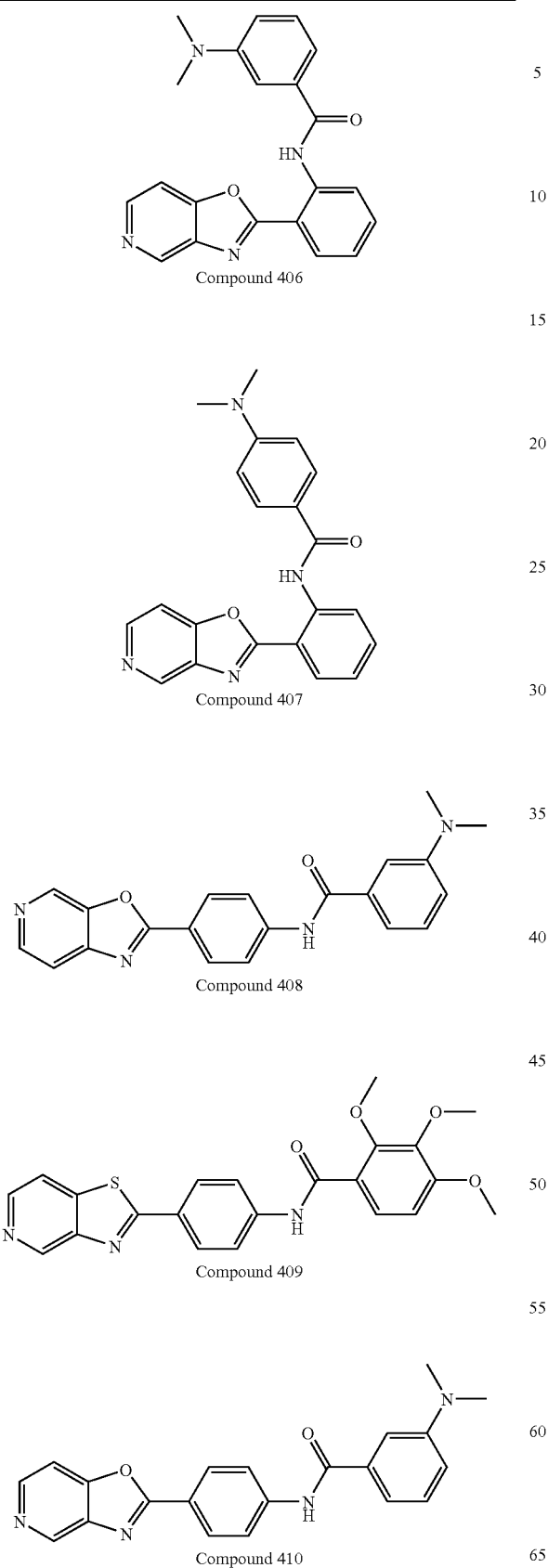
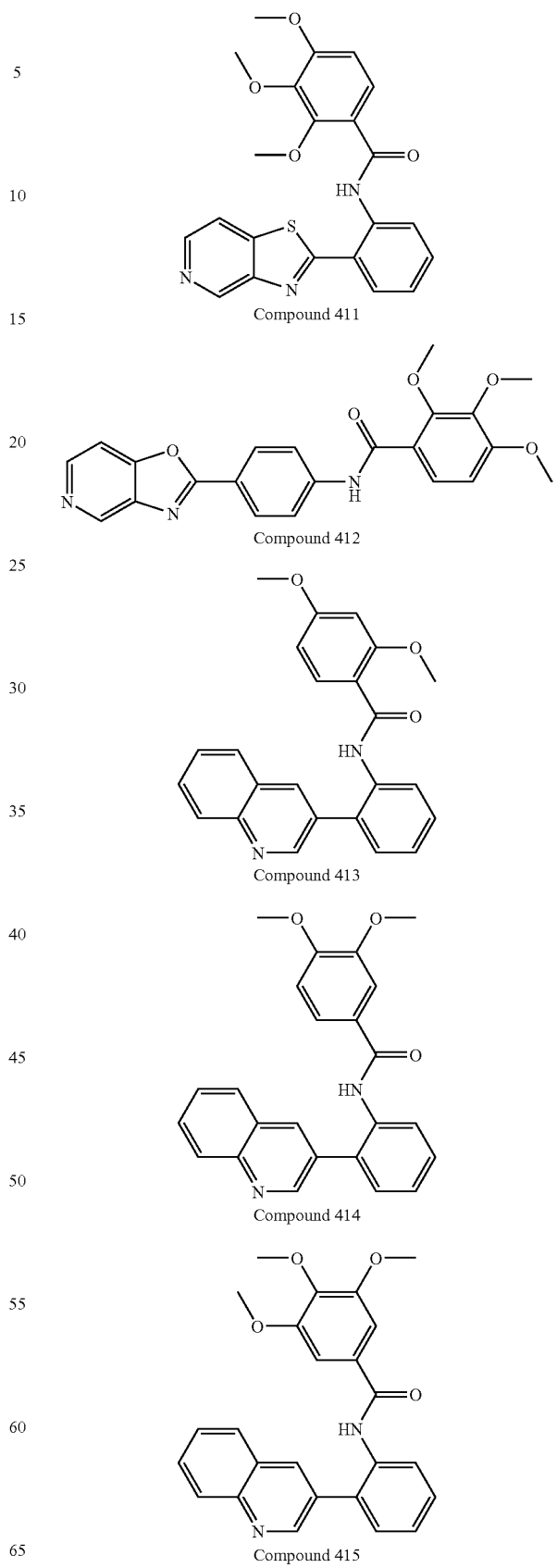

TABLE 1-continued
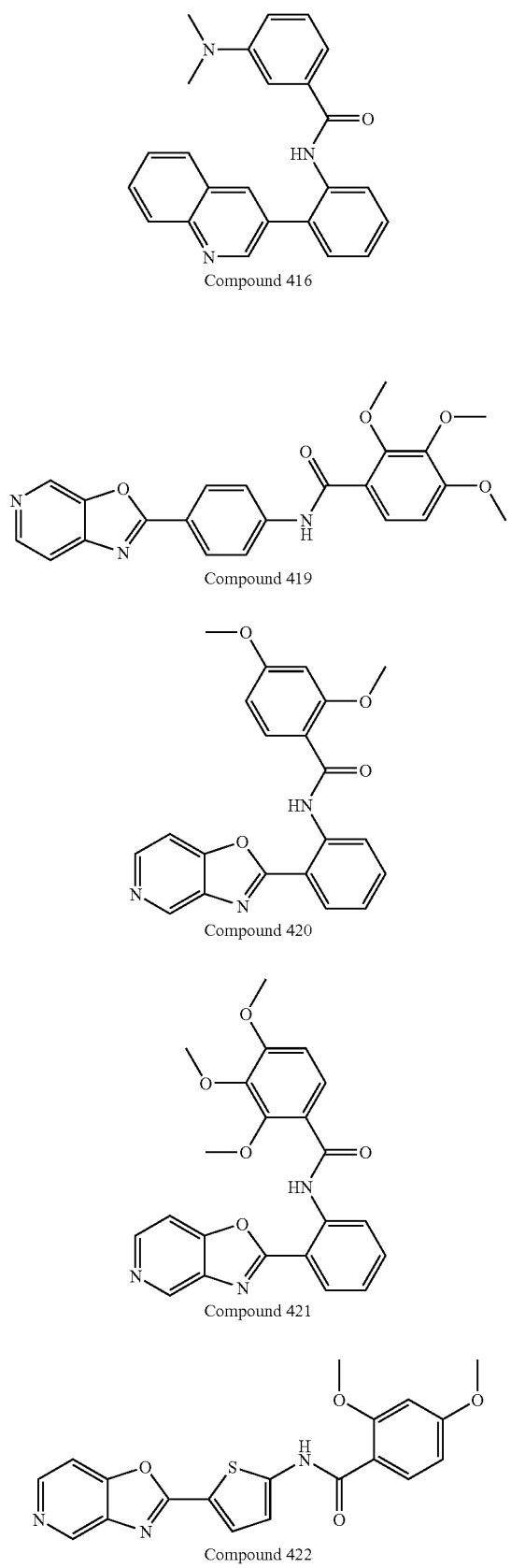
Compound 416
Compound 419
Compound 420
Compound 421
Compound 422
TABLE 1-continued
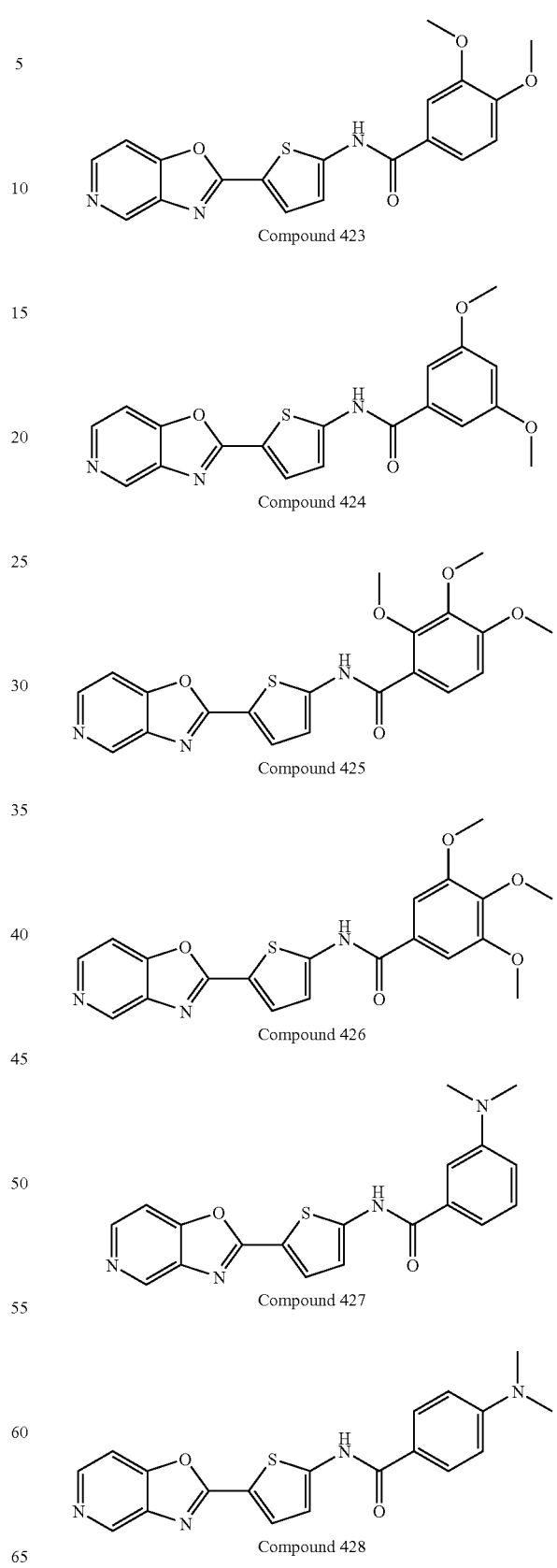
Compound 423
Compound 424
Compound 425
Compound 426
Compound 427
Compound 428

TABLE 1-continued
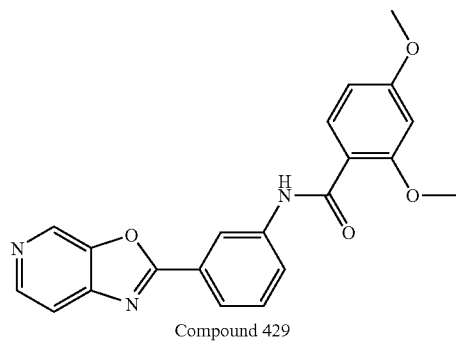
Compound 429
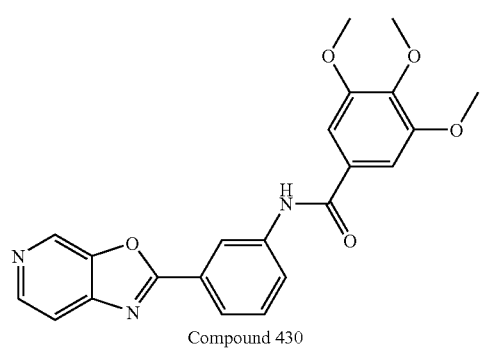
Compound 430
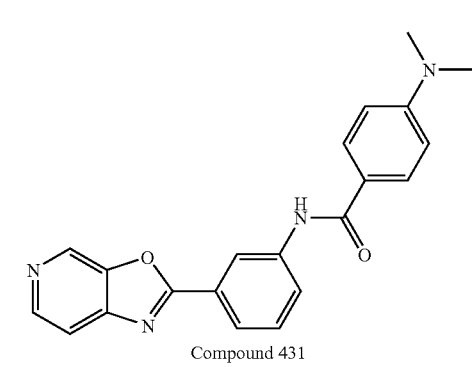
Compound 431
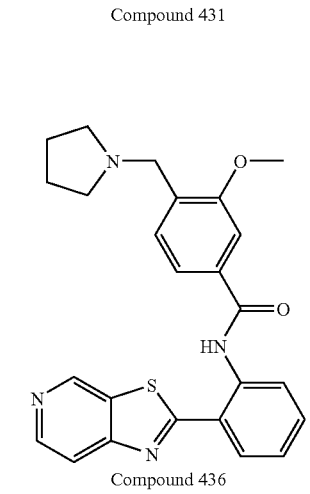
Compound 436
TABLE 1-continued
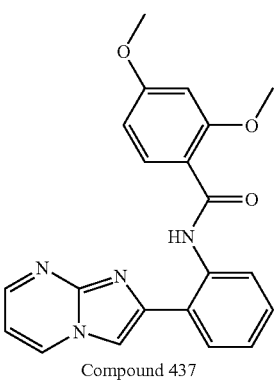
Compound 437
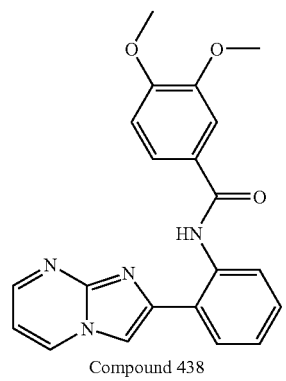
Compound 438
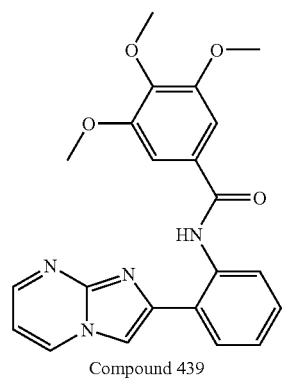
Compound 439
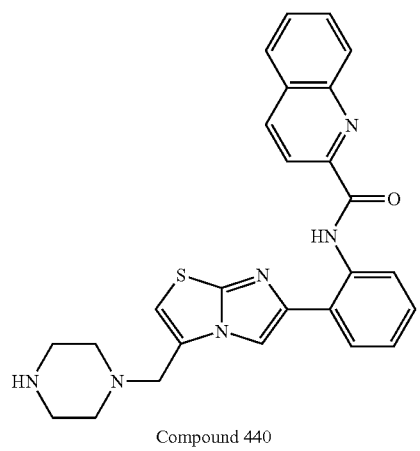
Compound 440

TABLE 1-continued
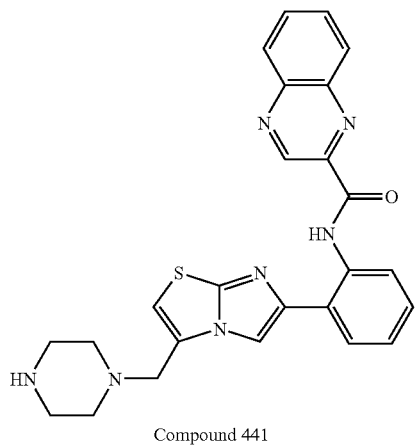
Compound 441
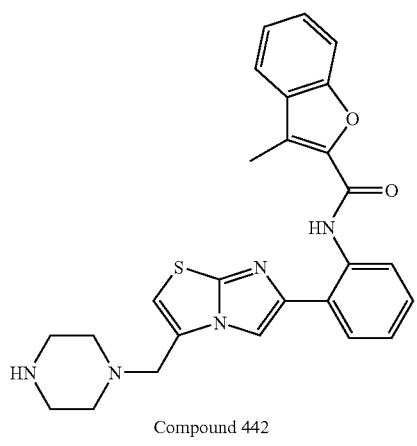
Compound 442
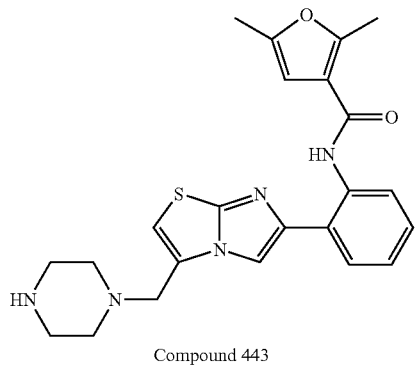
Compound 443
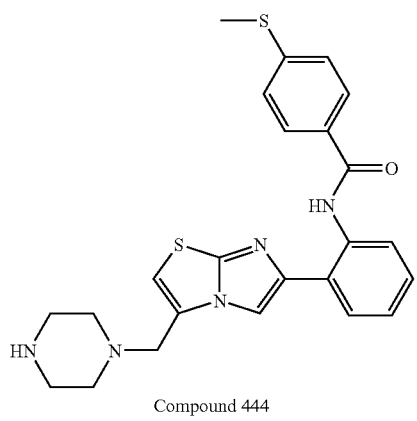
Compound 444
TABLE 1-continued
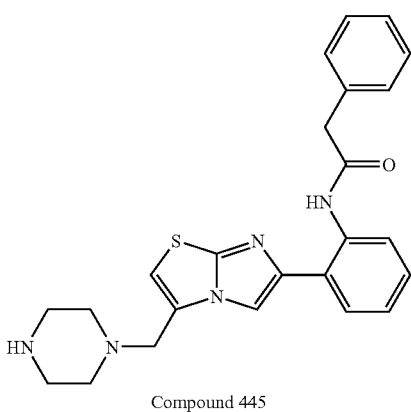
Compound 445
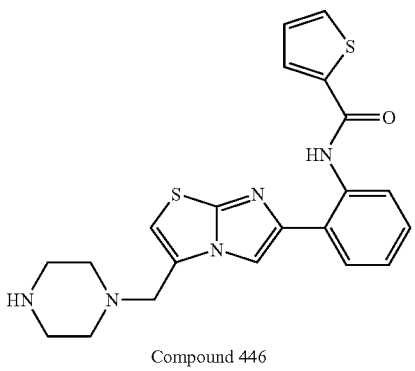
Compound 446
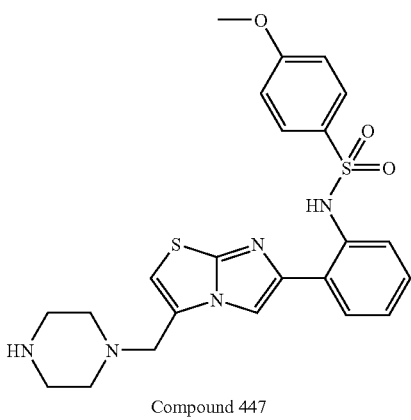
Compound 447
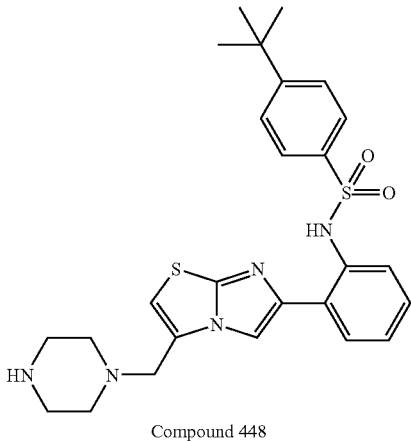
Compound 448

TABLE 1-continued
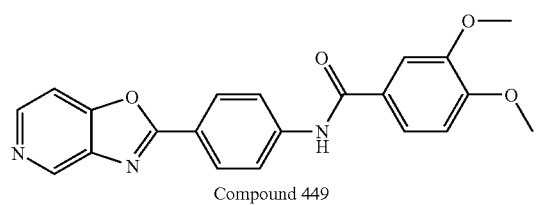
Compound 449
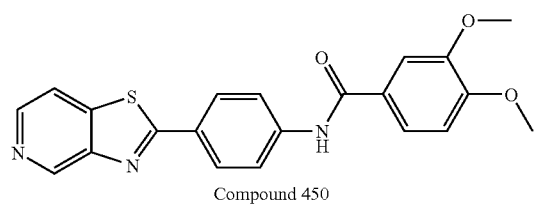
Compound 450
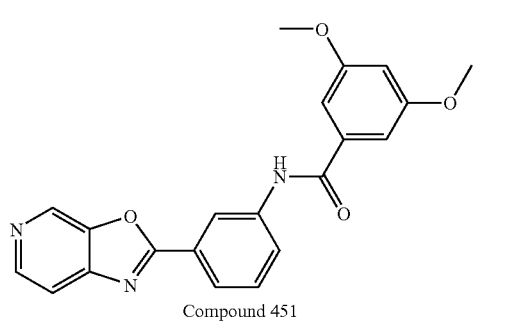
Compound 451
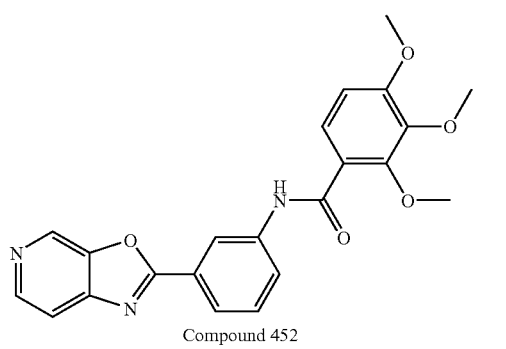
Compound 452
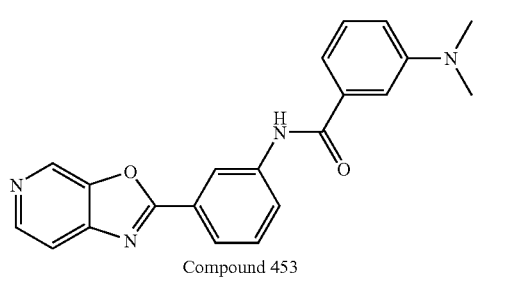
Compound 453
TABLE 1-continued
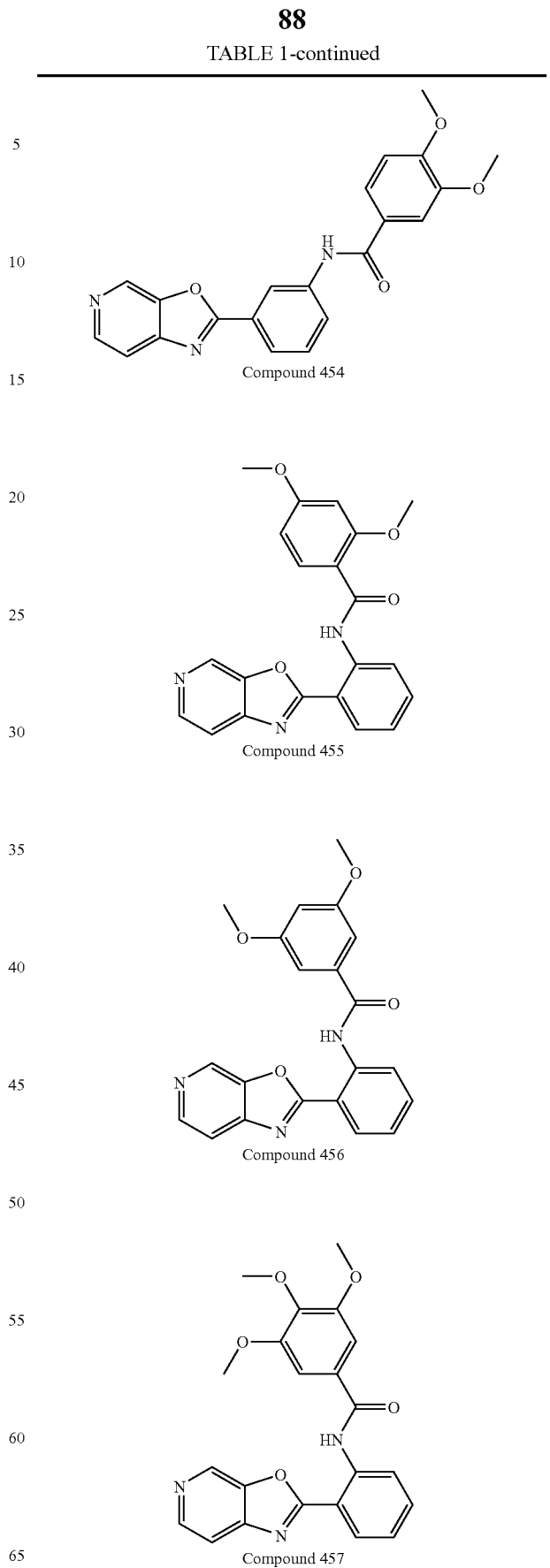

TABLE 1-continued
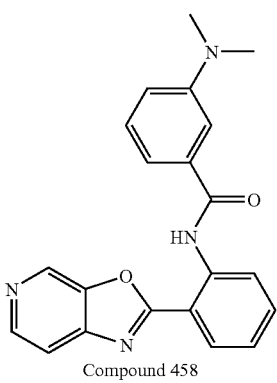
Compound 458
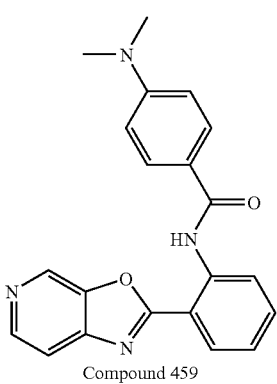
Compound 459
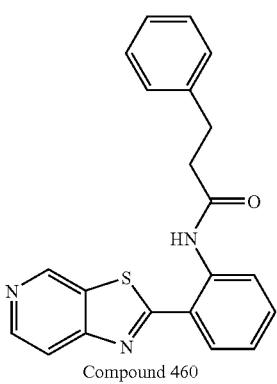
Compound 460
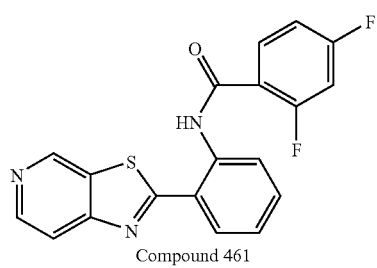
Compound 461
TABLE 1-continued
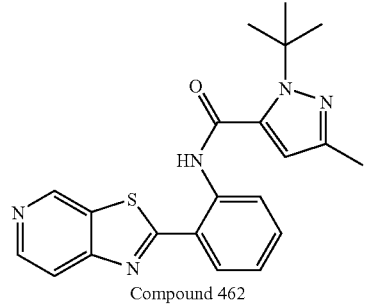
Compound 462
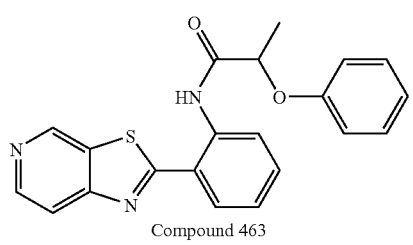
Compound 463
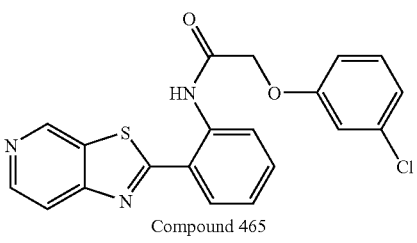
Compound 465
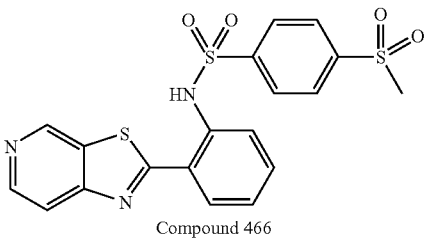
Compound 466
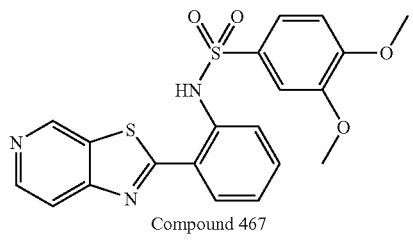
Compound 467
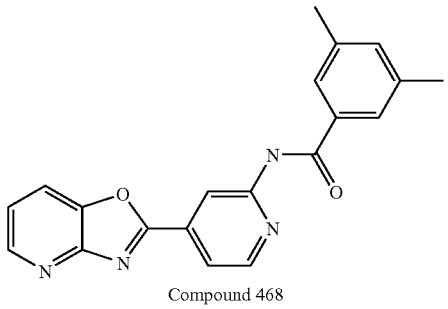
Compound 468

TABLE 1-continued
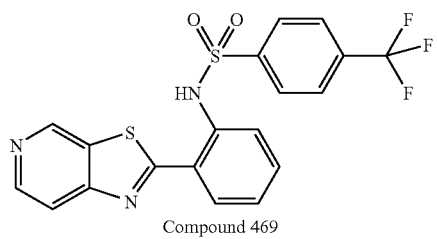
Compound 469
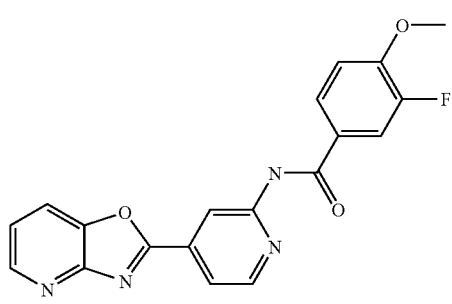 [SMILES: COc1ccc(C(=O)Nc2cc(-c3nc4ncccc4o3)ccn2)cc1F]
Compound 470
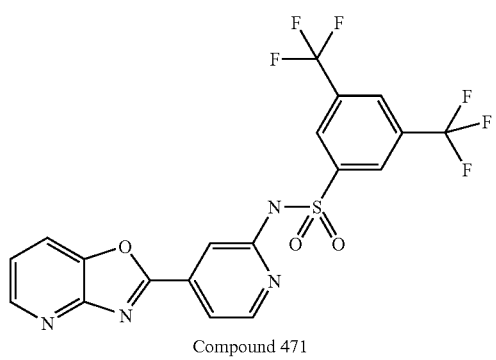
Compound 471
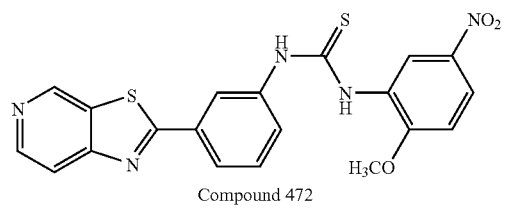
Compound 472
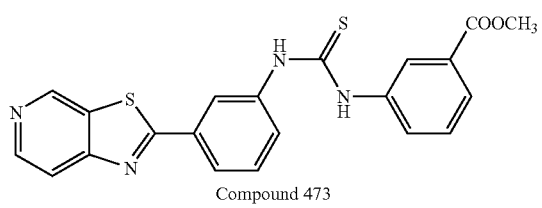
Compound 473
TABLE 1-continued
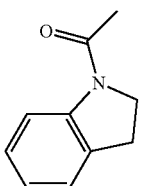
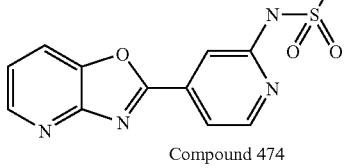
Compound 474
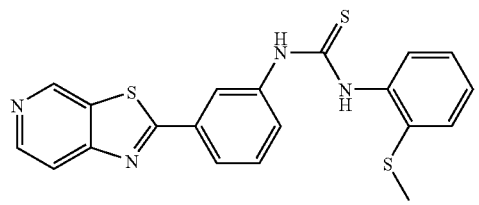 [SMILES: CSc1ccccc1NC(=S)Nc1cccc(-c2nc3ccncc3s2)c1]
Compound 475
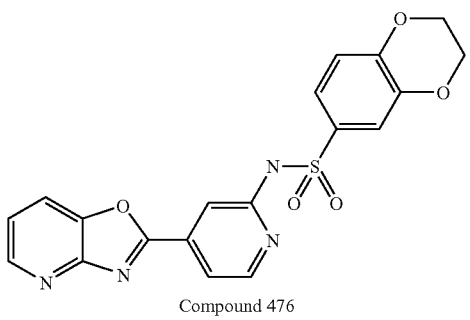
Compound 476
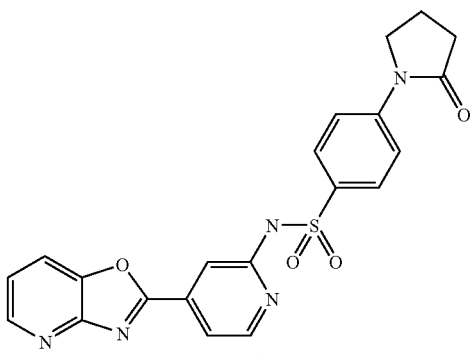 [SMILES: O=C1CCCN1c1ccc(S(=O)(=O)Nc2cc(-c3nc4ncccc4o3)ccn2)cc1]
Compound 477
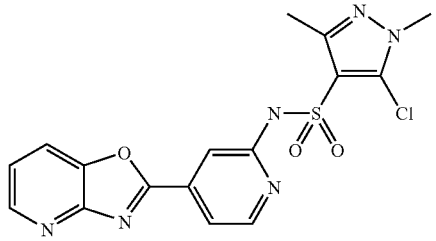 [SMILES: Cc1nn(C)c(Cl)c1S(=O)(=O)Nc1cc(-c2nc3ncccc3o2)ccn1]
Compound 478

TABLE 1-continued
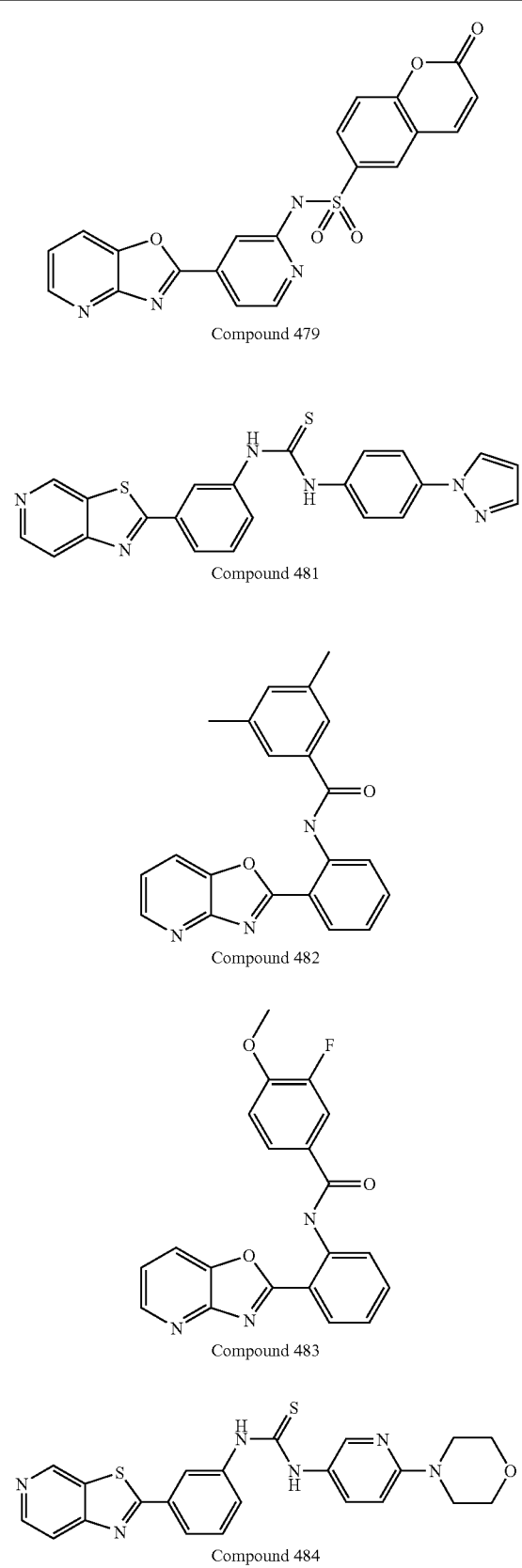
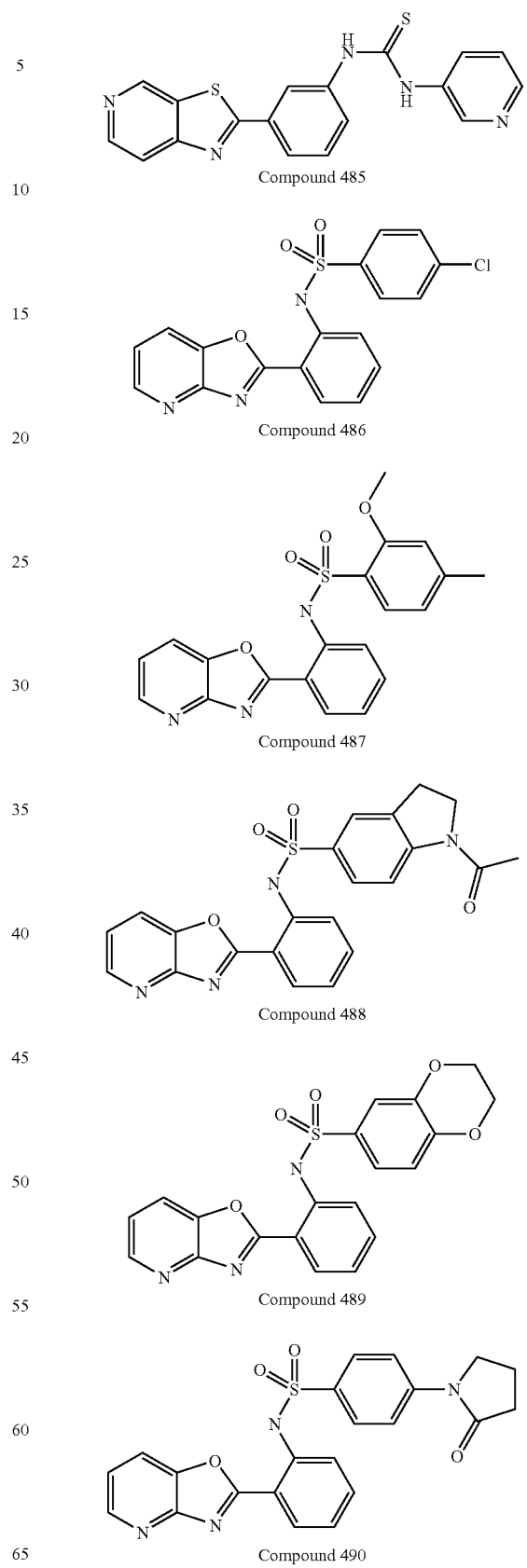

TABLE 1-continued
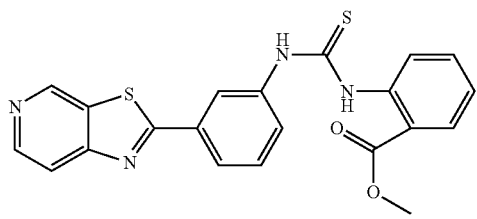 [SMILES: COC(=O)c1ccccc1NC(=S)Nc1cccc(-c2nc3ccncc3s2)c1]
Compound 491
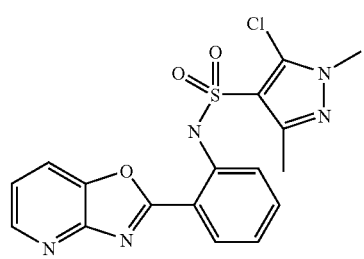 [SMILES: Cc1nn(C)c(Cl)c1S(=O)(=O)Nc1ccccc1-c1nc2ncccc2o1]
Compound 492
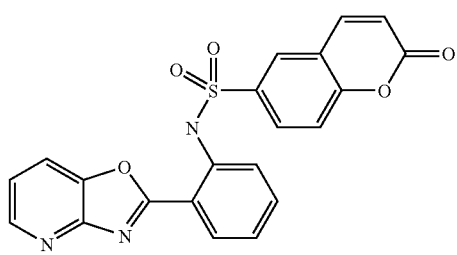 [SMILES: O=c1ccc2cc(S(=O)(=O)Nc3ccccc3-c3nc4ncccc4o3)ccc2o1]
Compound 493
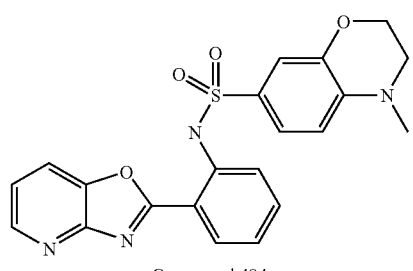
Compound 494
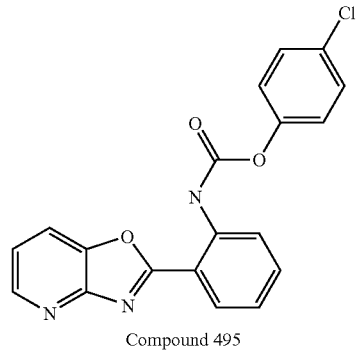
Compound 495
TABLE 1-continued
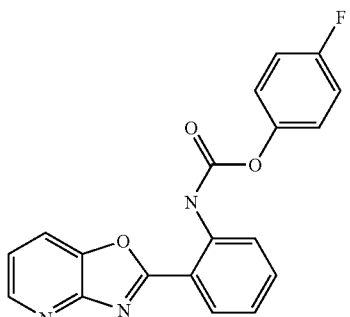
Compound 496
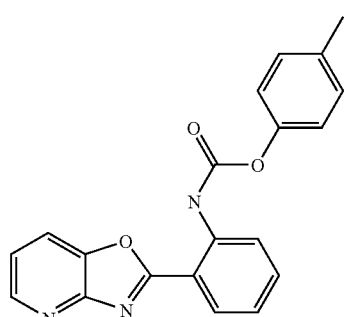
Compound 497
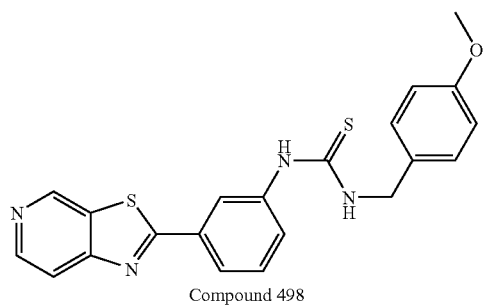
Compound 498
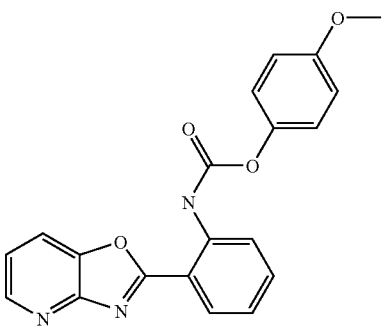 [SMILES: COc1ccc(OC(=O)Nc2ccccc2-c2nc3ncccc3o2)cc1]
Compound 499
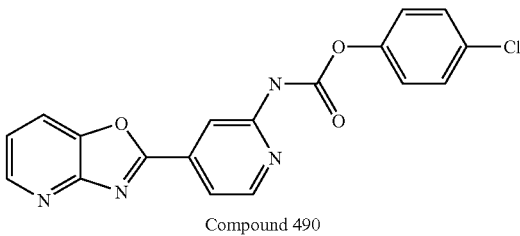
Compound 490

TABLE 1-continued
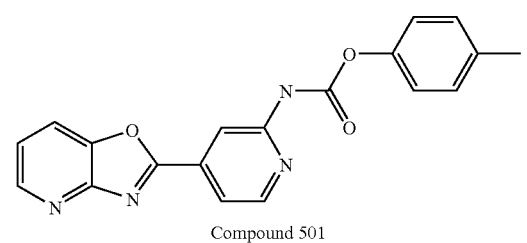
Compound 501
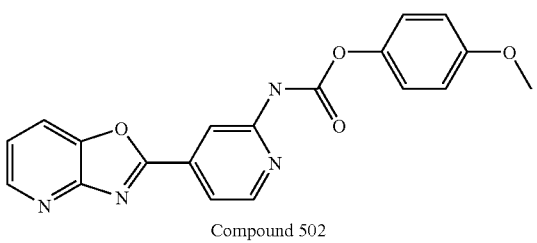
Compound 502
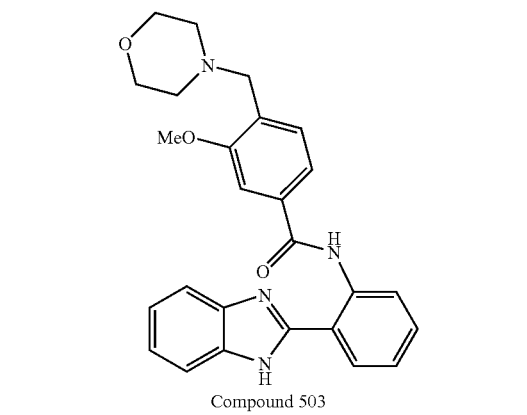
Compound 503
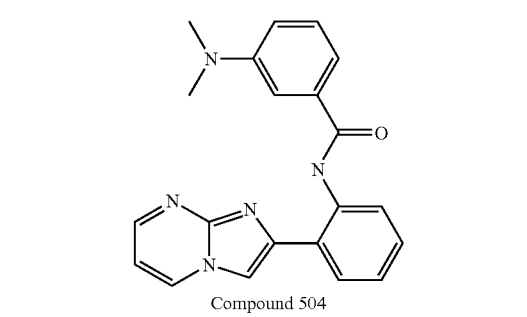
Compound 504
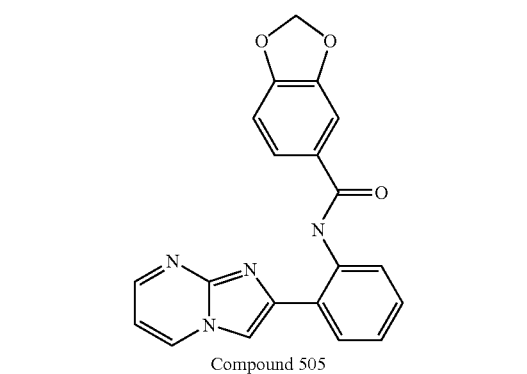
Compound 505
TABLE 1-continued
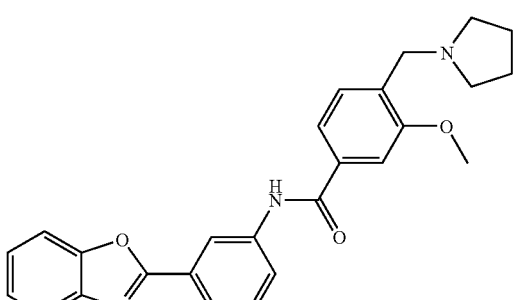
Compound 506
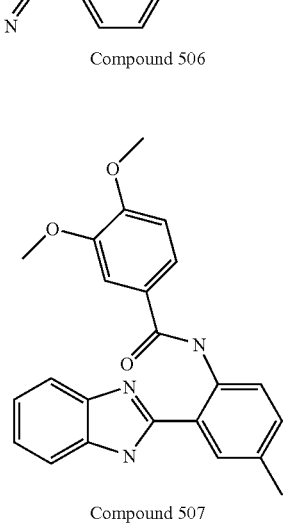
Compound 507
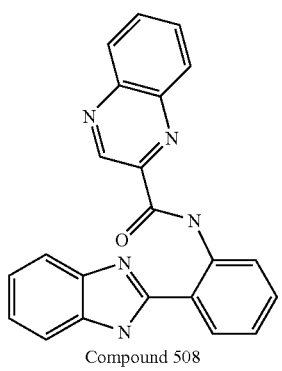
Compound 508
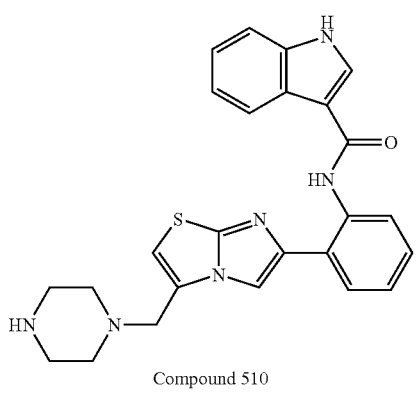
Compound 510

TABLE 1-continued
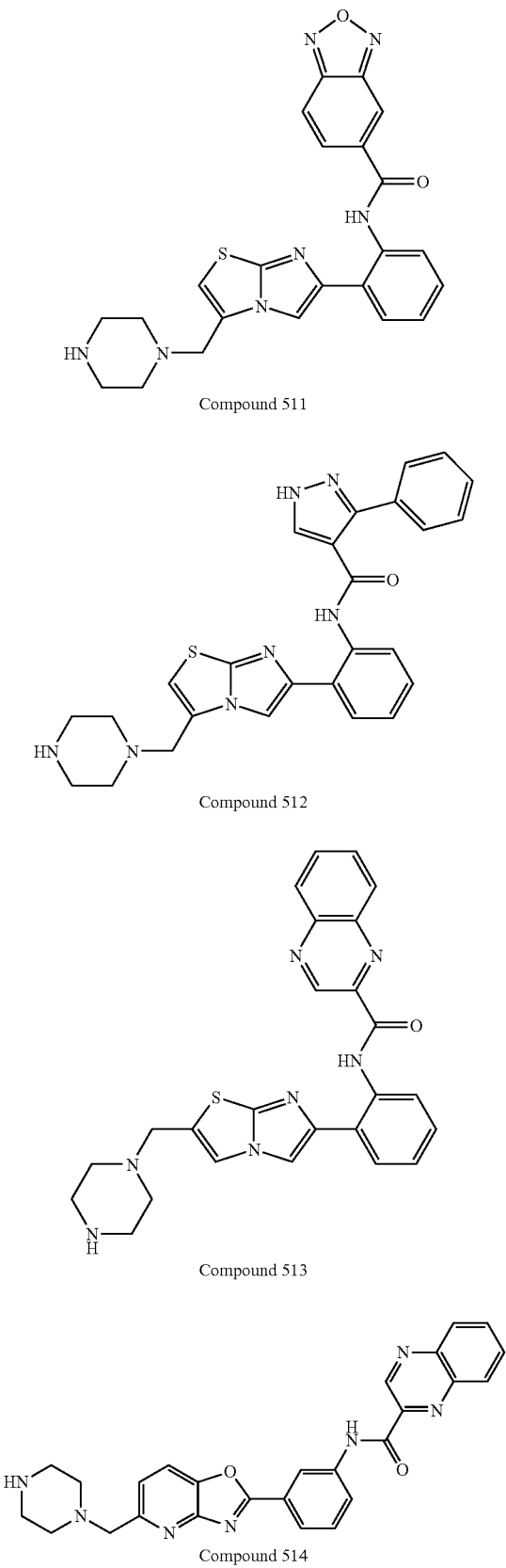
Compound 511
Compound 512
Compound 513
Compound 514
TABLE 1-continued
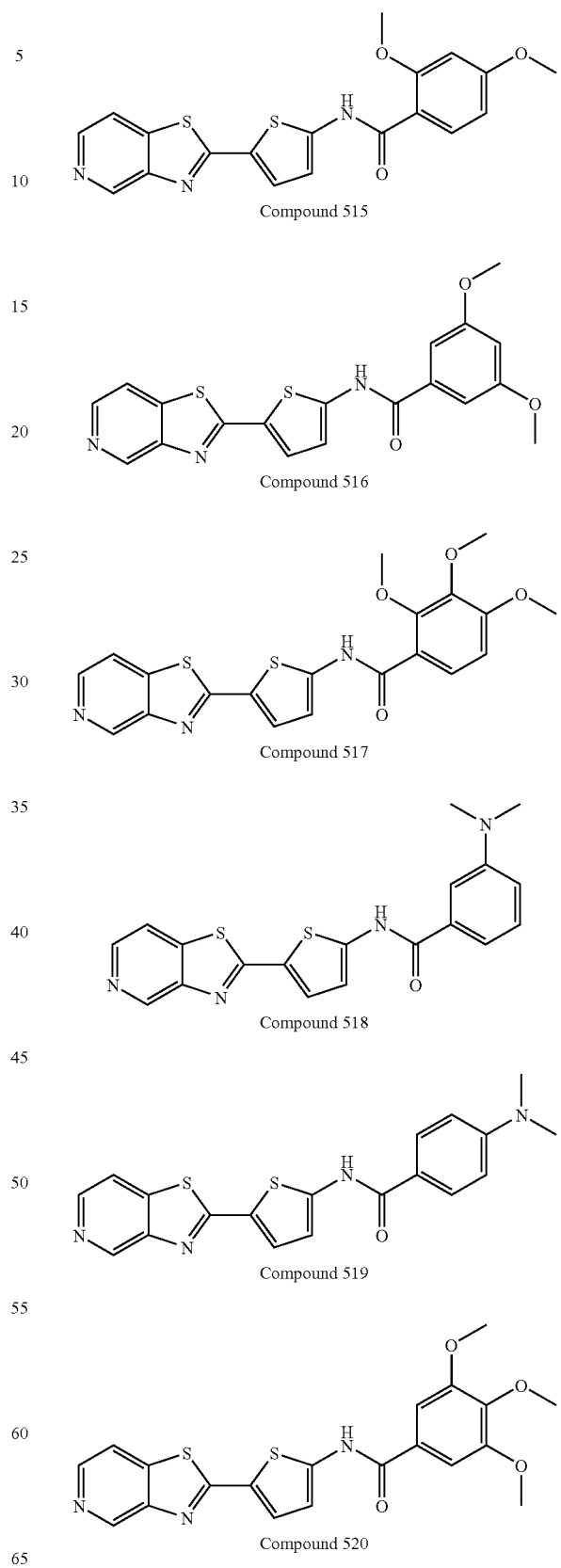
Compound 515
Compound 516
Compound 517
Compound 518
Compound 519
Compound 520

TABLE 1-continued
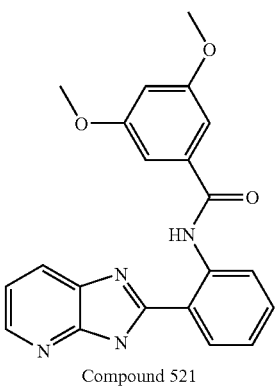
Compound 521
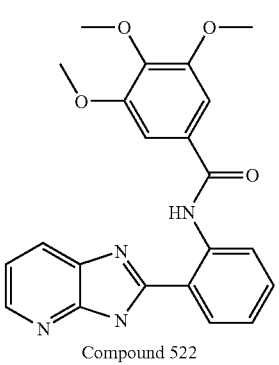
Compound 522
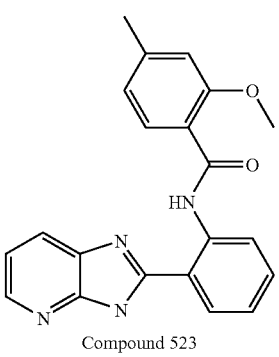
Compound 523
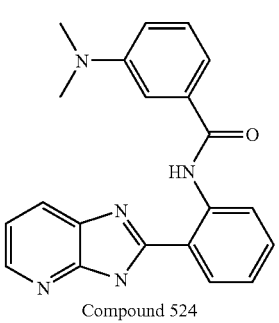
Compound 524
TABLE 1-continued
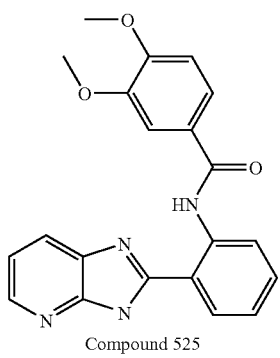
Compound 525
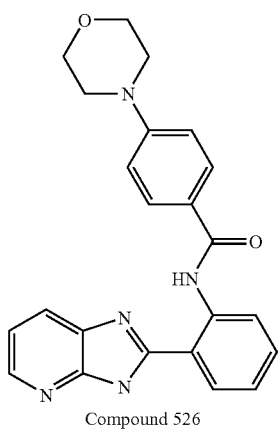
Compound 526
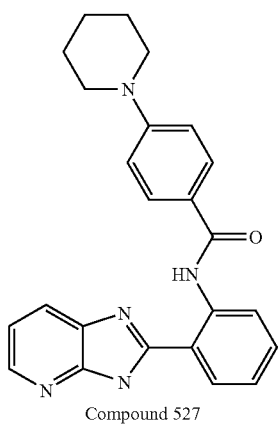
Compound 527
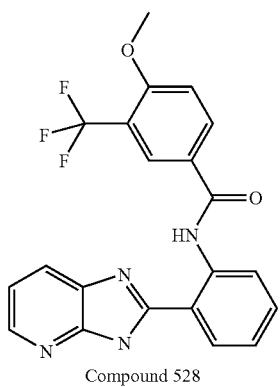
Compound 528

TABLE 1-continued
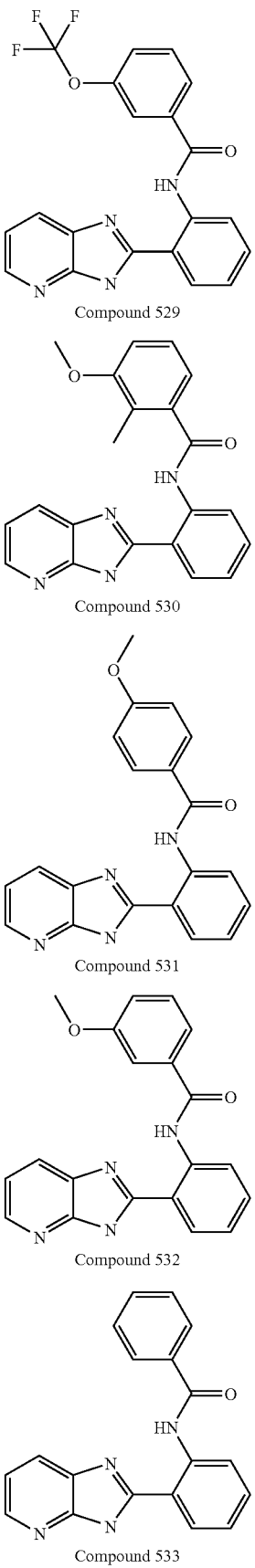
Compound 529
Compound 530
Compound 531
Compound 532
Compound 533
TABLE 1-continued
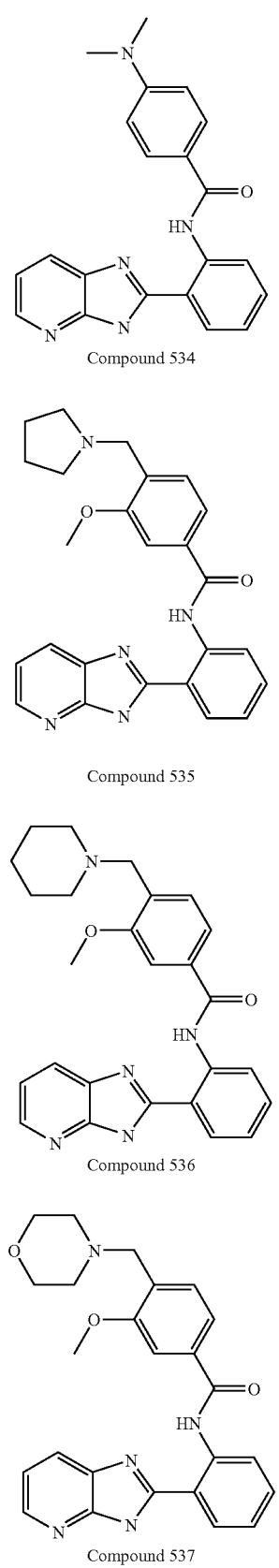
Compound 534
Compound 535
Compound 536
Compound 537

TABLE 1-continued
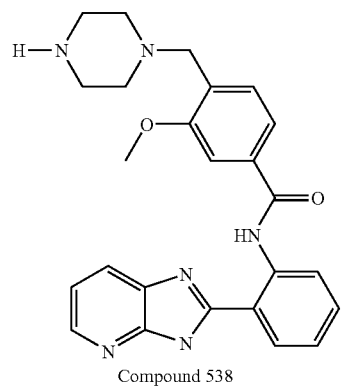
Compound 538
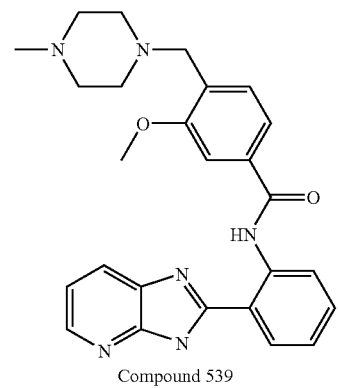
Compound 539
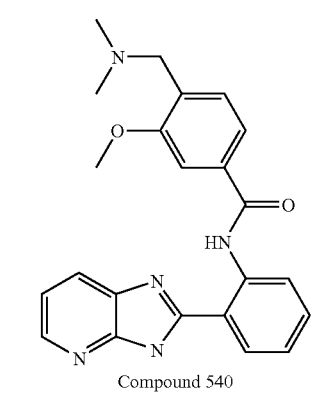
Compound 540
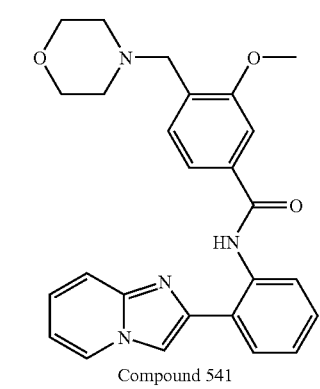
Compound 541
TABLE 1-continued
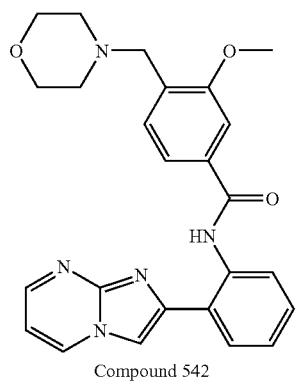
Compound 542
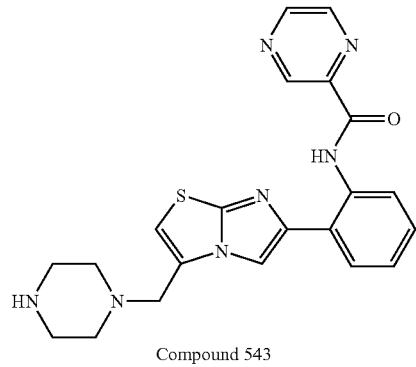
Compound 543
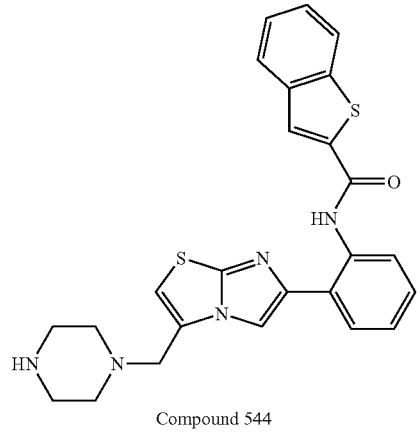
Compound 544
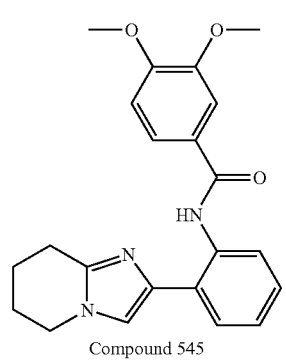
Compound 545

TABLE 1-continued
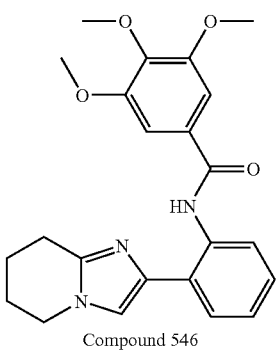
Compound 546
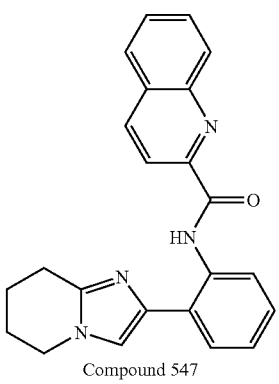
Compound 547
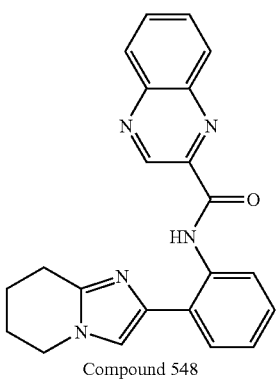
Compound 548
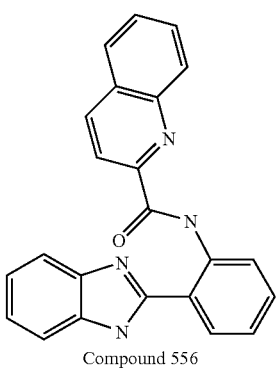
Compound 556
TABLE 1-continued
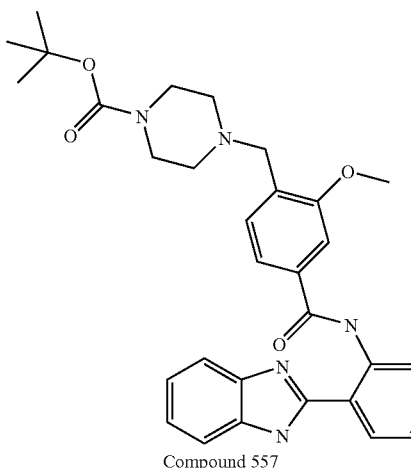
Compound 557
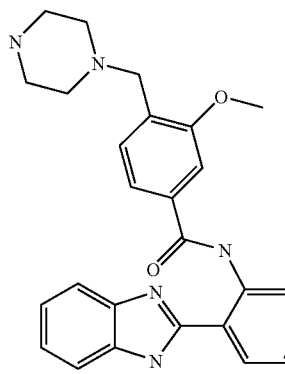
Compound 558
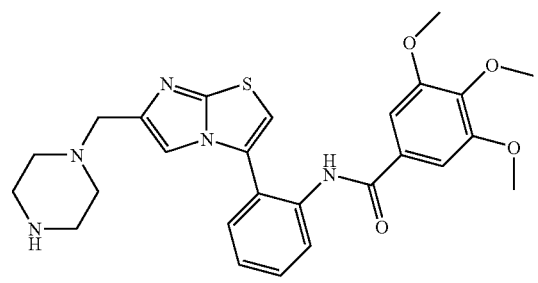 [SMILES: COc1cc(C(=O)Nc2ccccc2-c2csc3nc(CN4CCNCC4)cn23)cc(OC)c1OC]
Compound 559
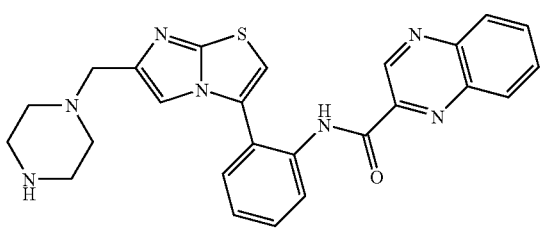 [SMILES: O=C(Nc1ccccc1-c1csc2nc(CN3CCNCC3)cn12)c1cnc2ccccc2n1]
Compound 560
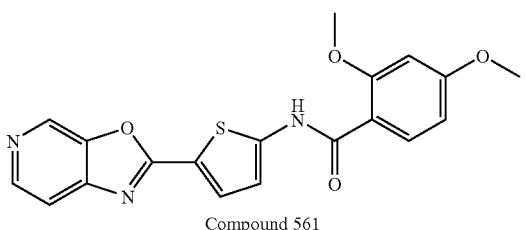
Compound 561

TABLE 1-continued
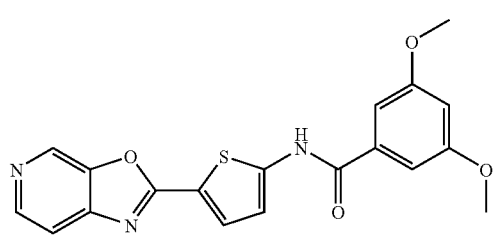 [SMILES: COc1cc(OC)cc(C(=O)Nc2ccc(-c3nc4ccncc4o3)s2)c1]
Compound 562
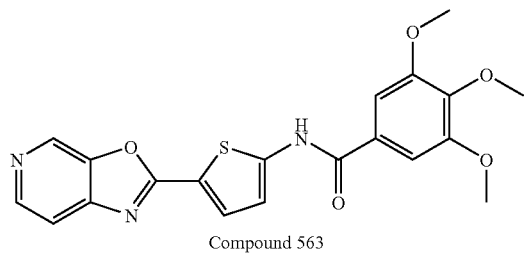
Compound 563
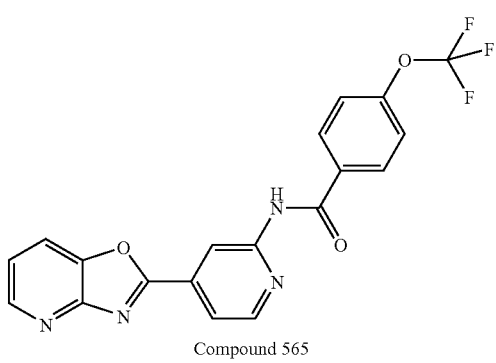
Compound 565
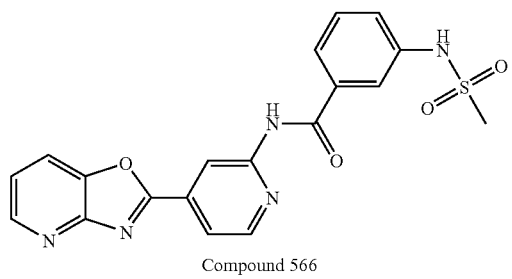
Compound 566
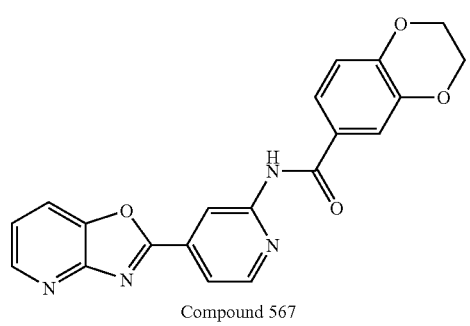
Compound 567
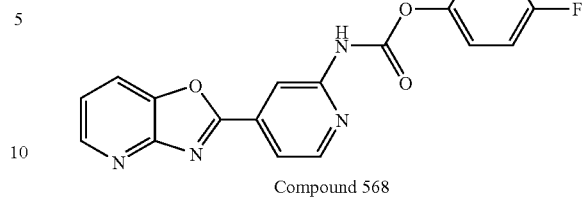
Compound 568
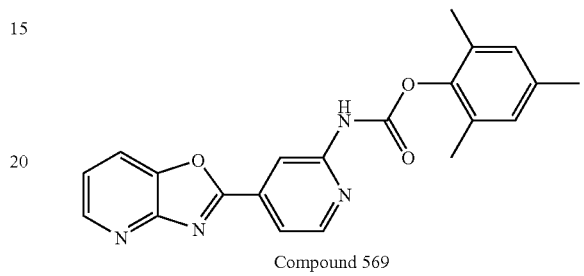
Compound 569
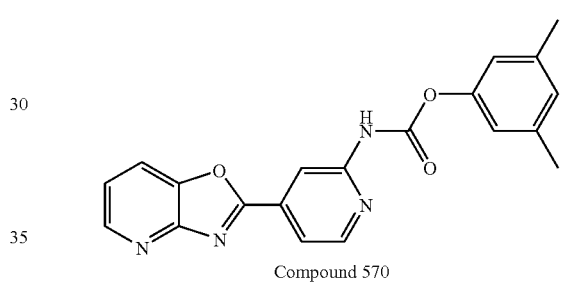
Compound 570
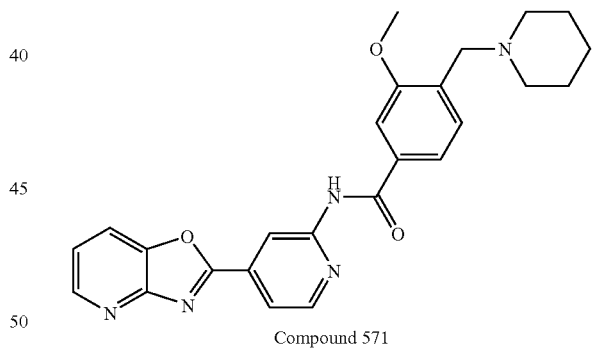
Compound 571
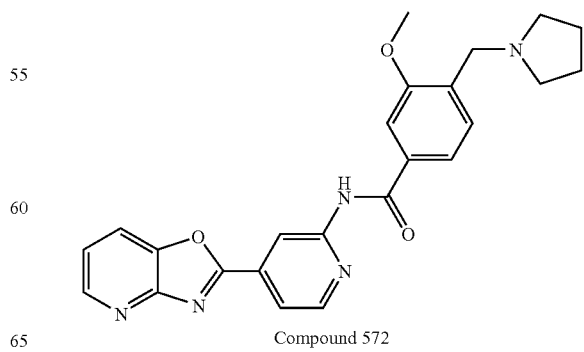
Compound 572

TABLE 1-continued
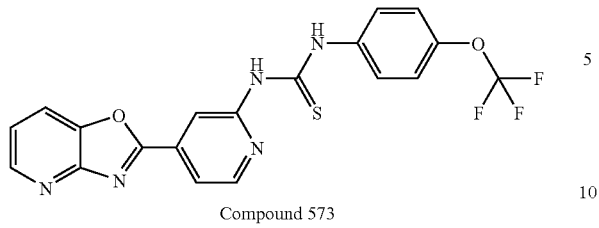
Compound 573
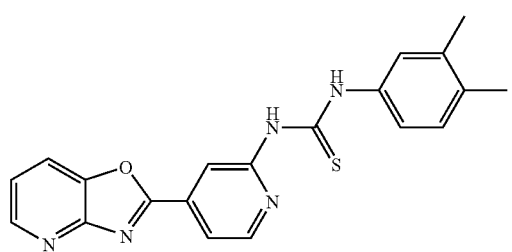 [SMILES: Cc1ccc(NC(=S)Nc2cc(-c3nc4ncccc4o3)ccn2)cc1C]
Compound 574
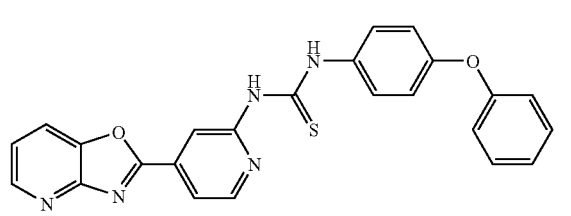 [SMILES: S=C(Nc1ccc(Oc2ccccc2)cc1)Nc1cc(-c2nc3ncccc3o2)ccn1]
Compound 575
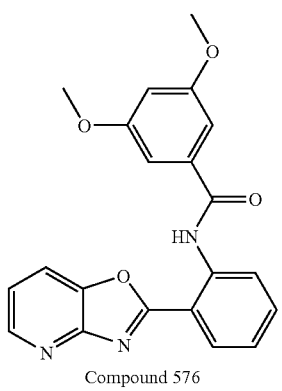
Compound 576
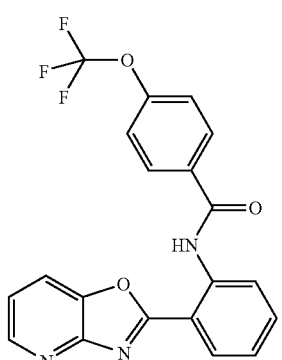
Compound 577
TABLE 1-continued
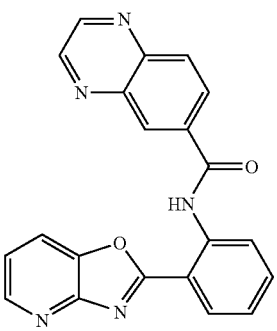 [SMILES: O=C(Nc1ccccc1-c1nc2ncccc2o1)c1ccc2nccnc2c1]
Compound 578
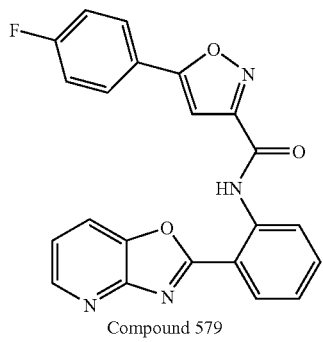
Compound 579
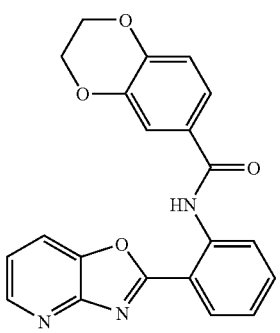 [SMILES: O=C(Nc1ccccc1-c1nc2ncccc2o1)c1ccc2c(c1)OCCO2]
Compound 580
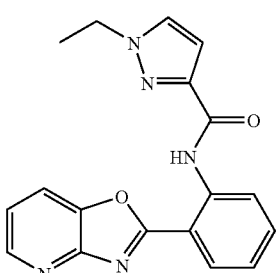
Compound 581

TABLE 1-continued
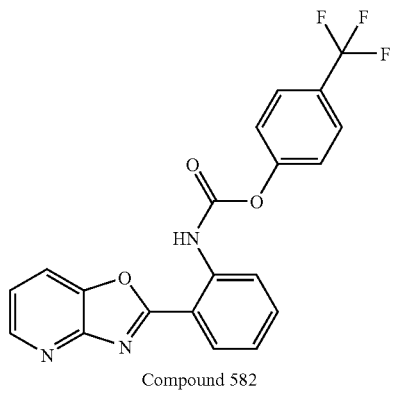
Compound 582
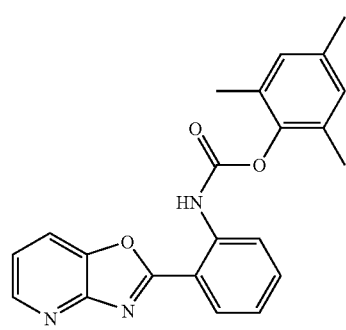 [SMILES: Cc1cc(C)c(OC(=O)Nc2ccccc2-c2nc3ncccc3o2)c(C)c1]
Compound 583
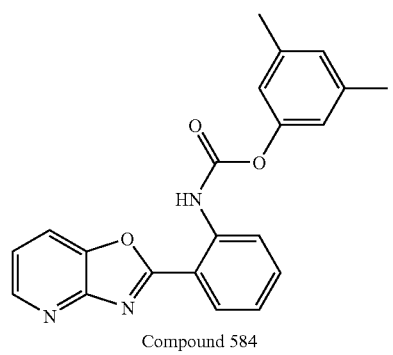
Compound 584
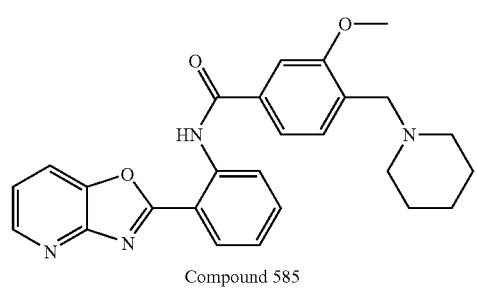
Compound 585
TABLE 1-continued
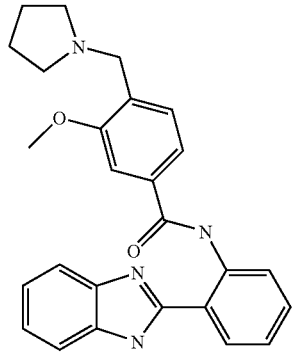 [SMILES: COc1cc(C(=O)Nc2ccccc2-c2nc3ccccc3[nH]2)ccc1CN1CCCC1]
Compound 587
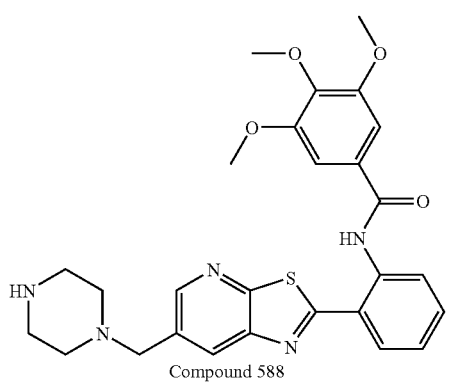
Compound 588
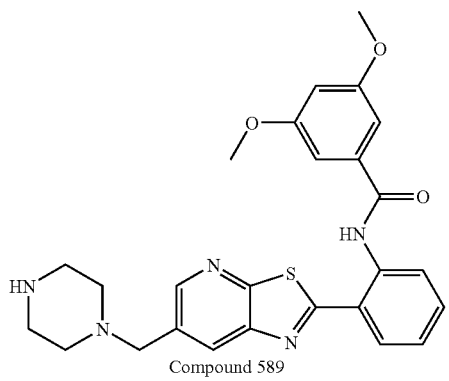
Compound 589
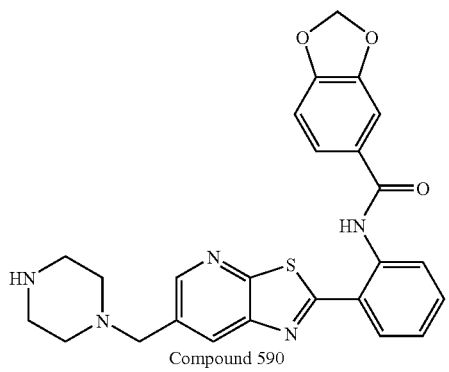
Compound 590

TABLE 1-continued
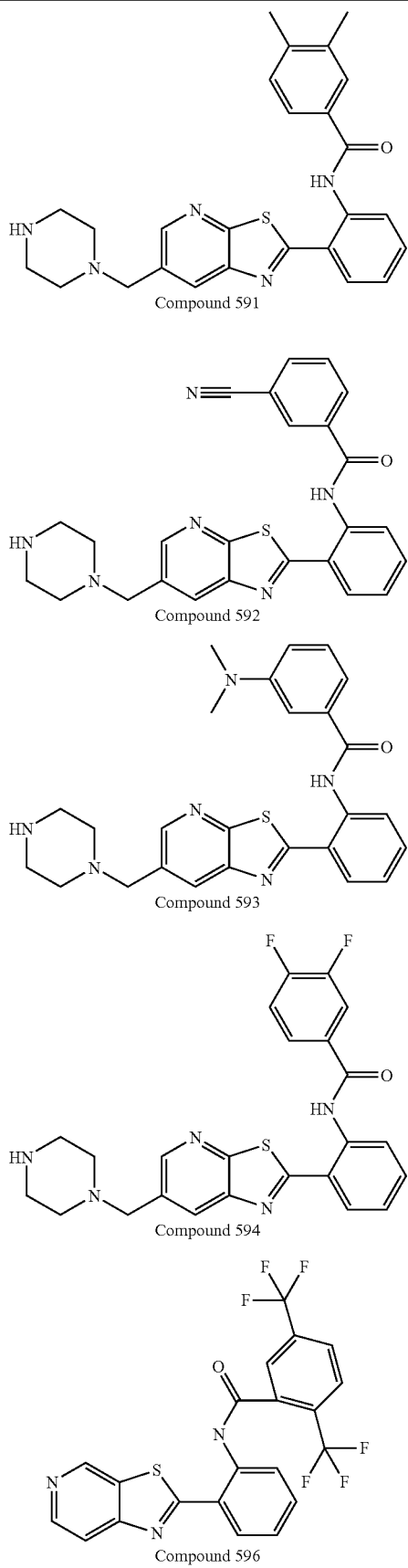
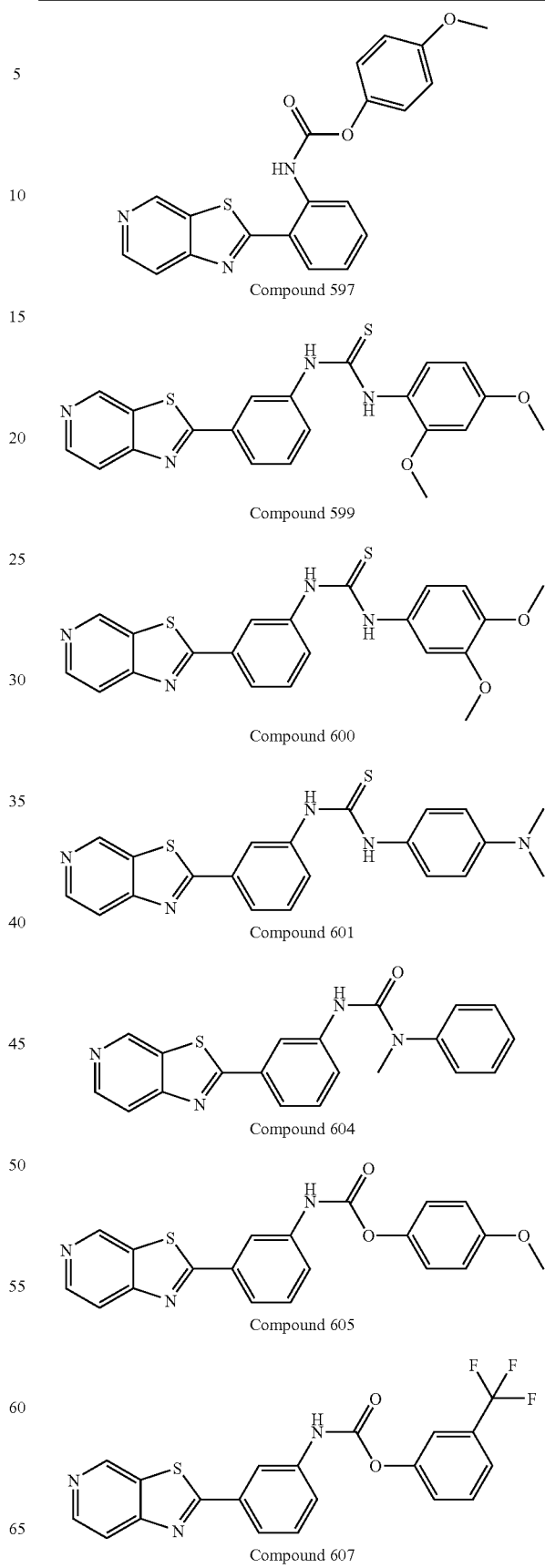

TABLE 1-continued
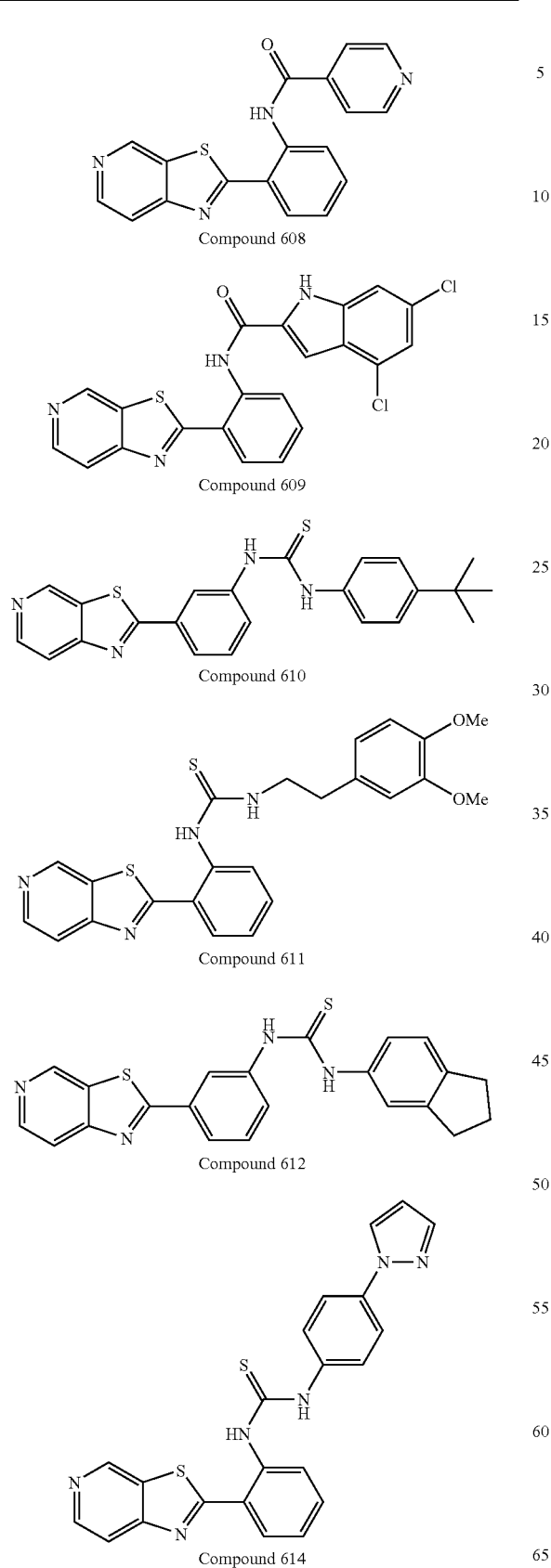
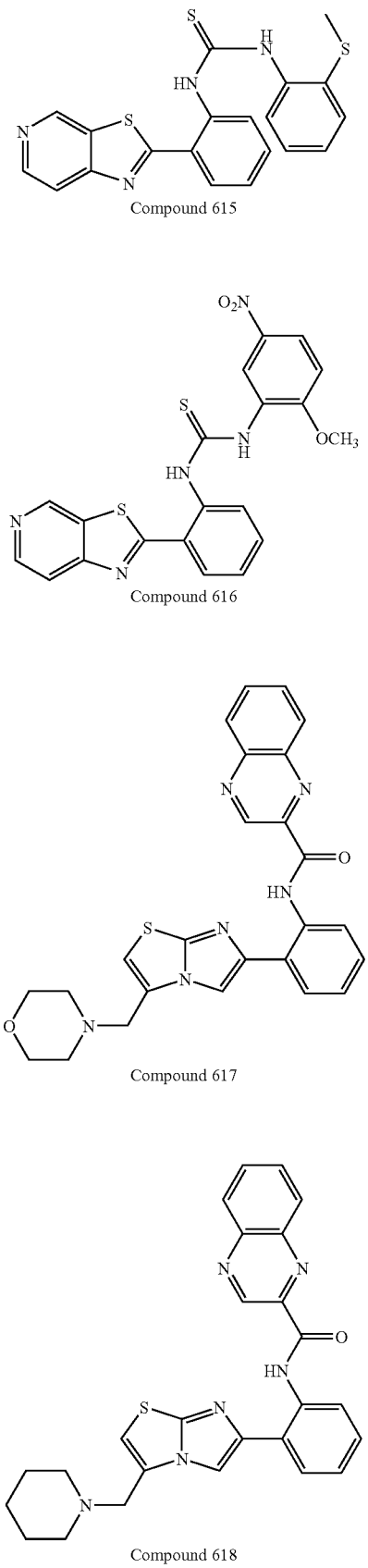

TABLE 1-continued
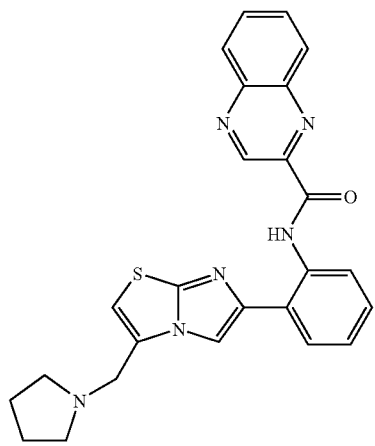 [SMILES: O=C(Nc1ccccc1-c1cn2c(CN3CCCC3)csc2n1)c1cnc2ccccc2n1]
Compound 619
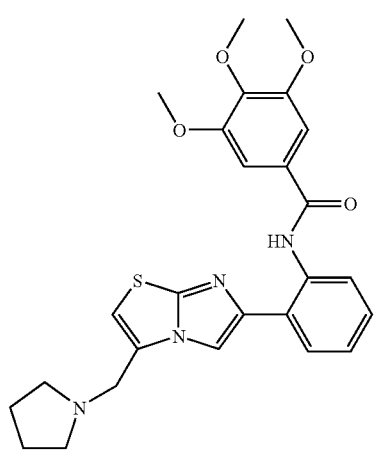 [SMILES: COc1cc(C(=O)Nc2ccccc2-c2cn3c(CN4CCCC4)csc3n2)cc(OC)c1OC]
Compound 620
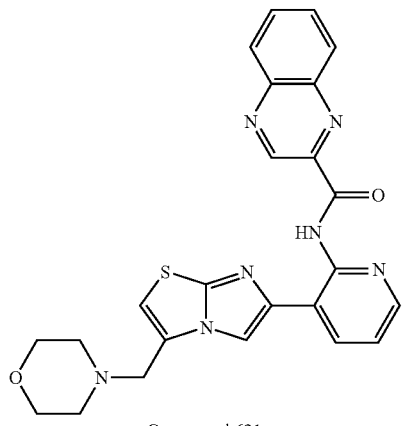
Compound 621
TABLE 1-continued
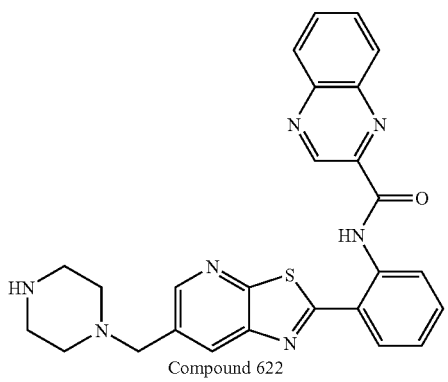
Compound 622
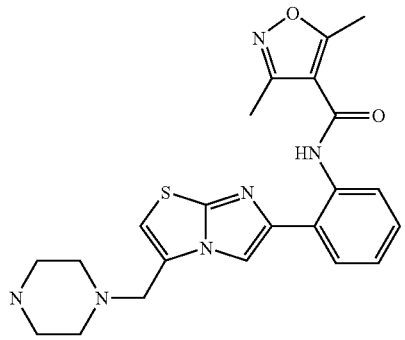 [SMILES: Cc1noc(C)c1C(=O)Nc1ccccc1-c1cn2c(CN3CCNCC3)csc2n1]
Compound 623
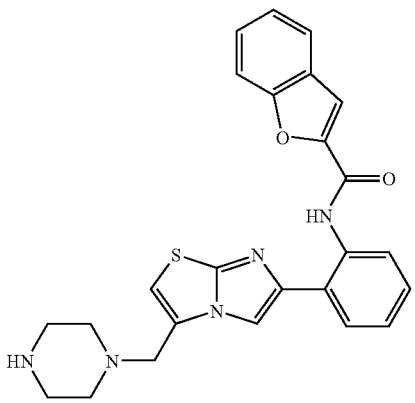 [SMILES: O=C(Nc1ccccc1-c1cn2c(CN3CCNCC3)csc2n1)c1cc2ccccc2o1]
Compound 624
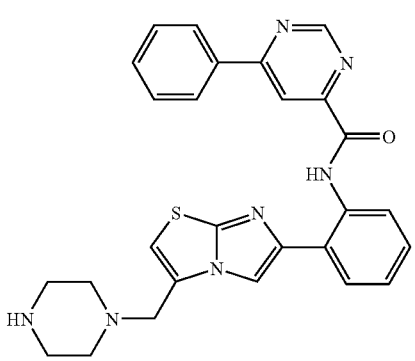 [SMILES: O=C(Nc1ccccc1-c1cn2c(CN3CCNCC3)csc2n1)c1cc(-c2ccccc2)ncn1]
Compound 625

TABLE 1-continued
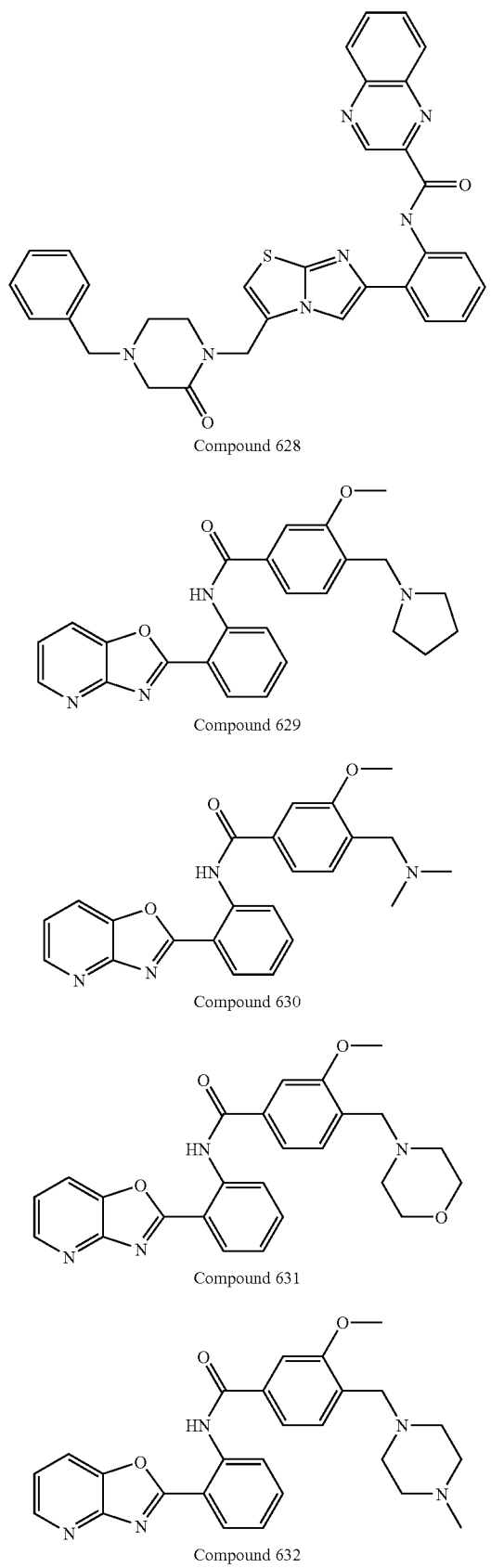
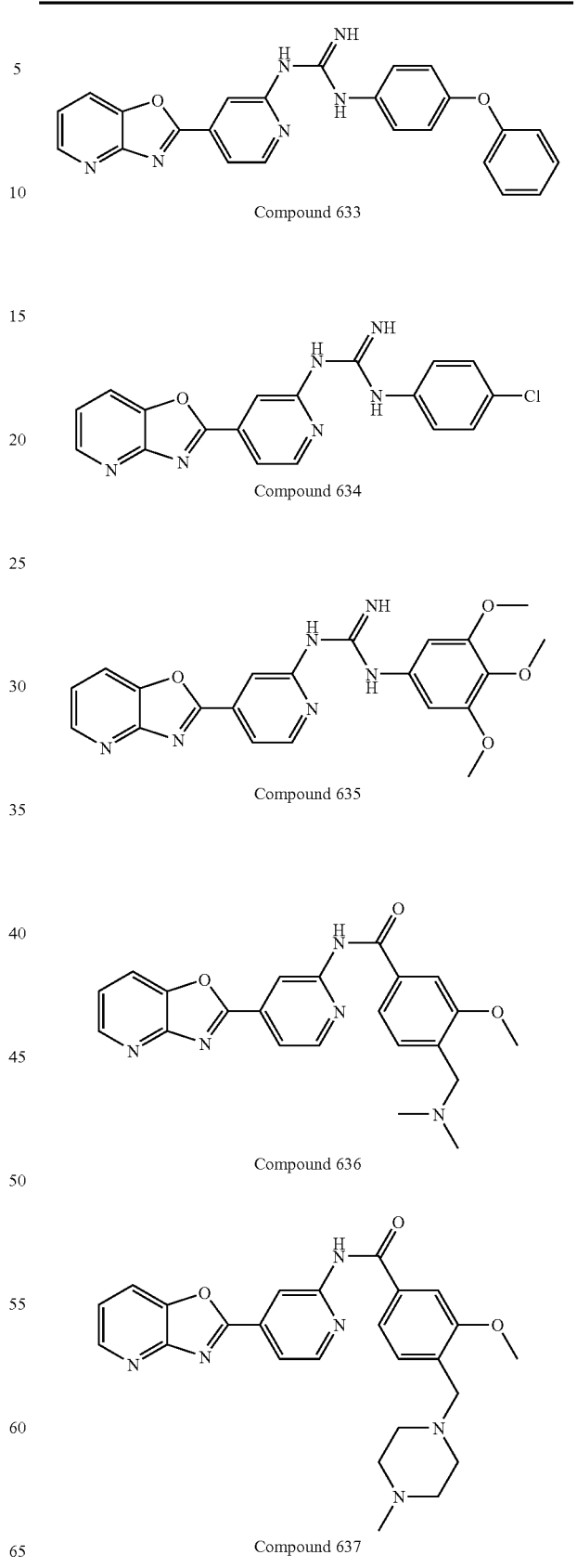

TABLE 1-continued
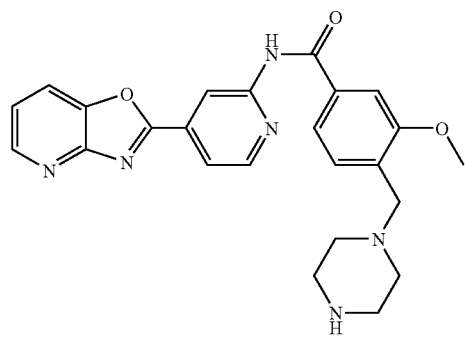
Compound 638
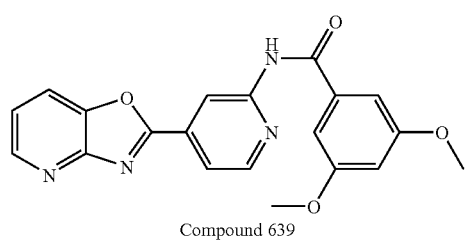
Compound 639
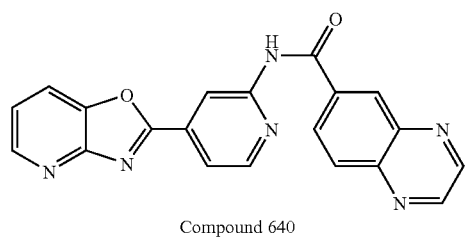
Compound 640
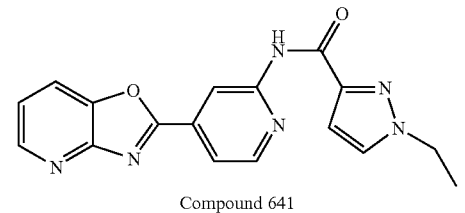
Compound 641
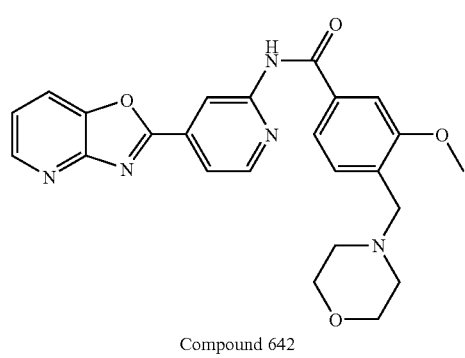 [SMILES: COc1cc(C(=O)Nc2cc(-c3nc4ncccc4o3)ccn2)ccc1CN1CCN(C)CC1]
Compound 642
TABLE 1-continued
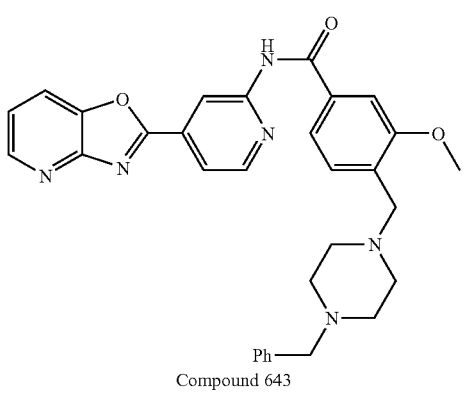
Compound 643
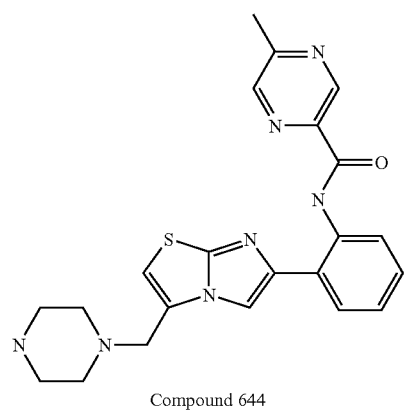
Compound 644
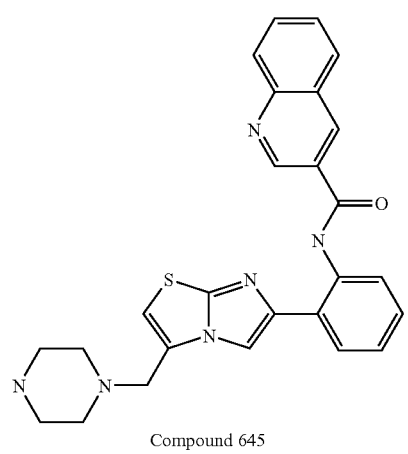
Compound 645
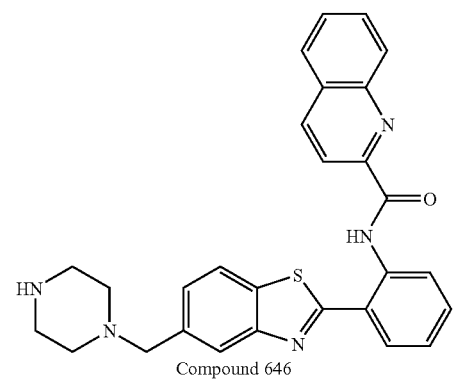
Compound 646

TABLE 1-continued
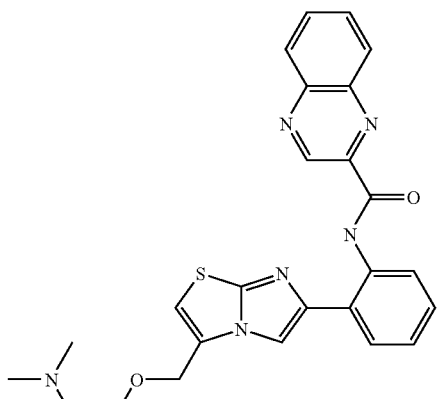
Compound 647
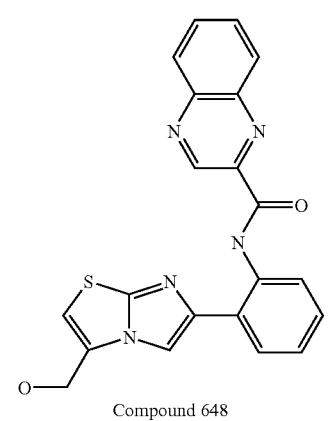
Compound 648
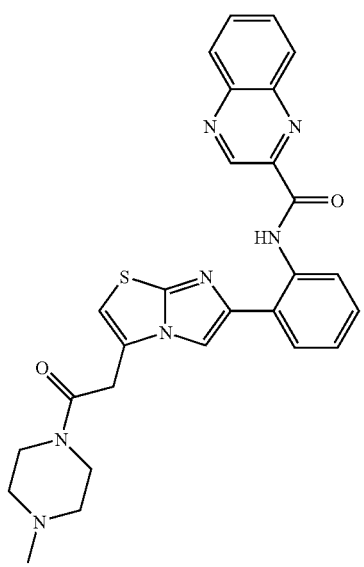 [SMILES: CN1CCN(C(=O)Cc2csc3nc(-c4ccccc4NC(=O)c4cnc5ccccc5n4)cn23)CC1]
Compound 649
TABLE 1-continued
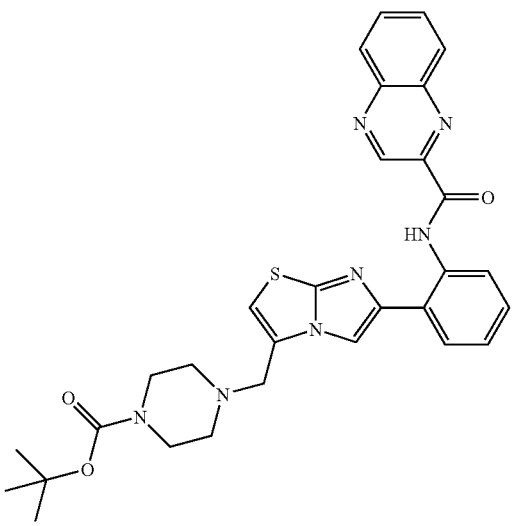 [SMILES: CC(C)(C)OC(=O)N1CCN(Cc2csc3nc(-c4ccccc4NC(=O)c4cnc5ccccc5n4)cn23)CC1]
Compound 650
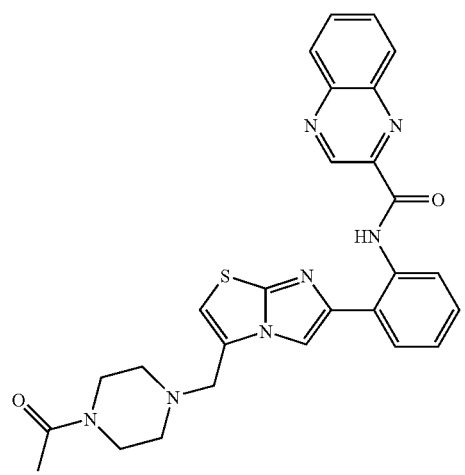 [SMILES: CC(=O)N1CCN(Cc2csc3nc(-c4ccccc4NC(=O)c4cnc5ccccc5n4)cn23)CC1]
Compound 651
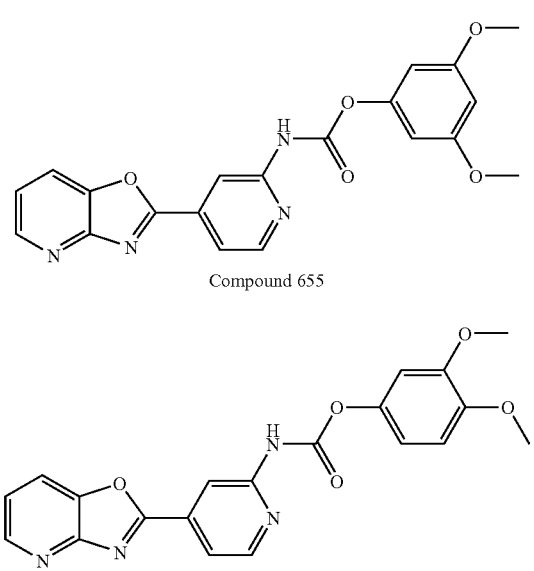
Compound 655
Compound 656

TABLE 1-continued
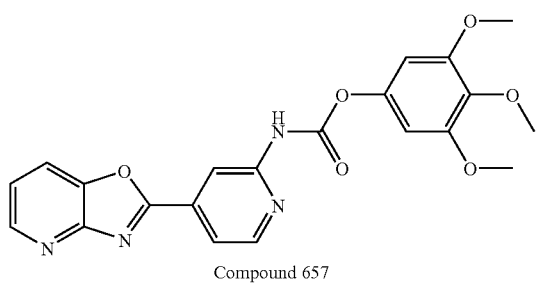
Compound 657
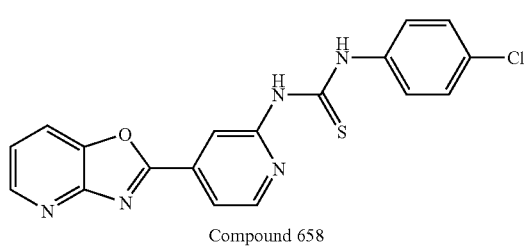
Compound 658
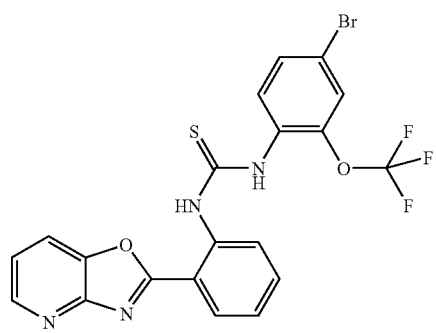 [SMILES: FC(F)(F)Oc1cc(Br)ccc1NC(=S)Nc1ccccc1-c1nc2ncccc2o1]
Compound 659
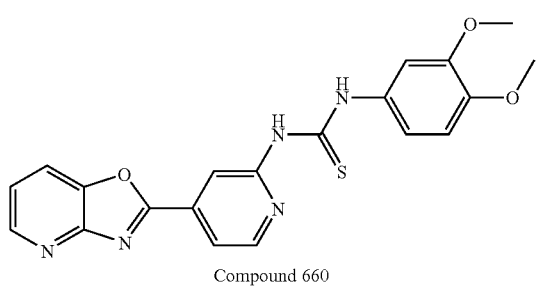
Compound 660
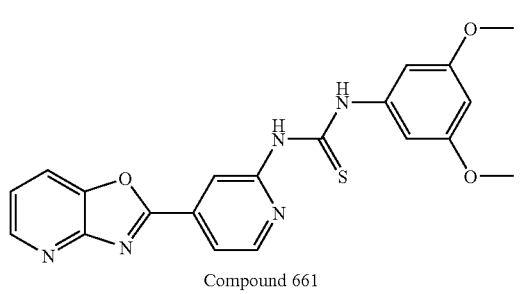
Compound 661
TABLE 1-continued
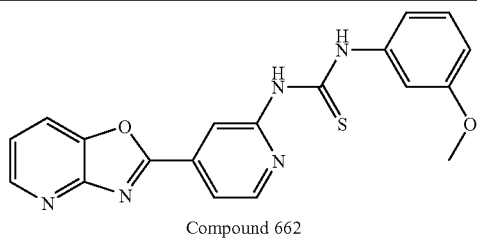
Compound 662
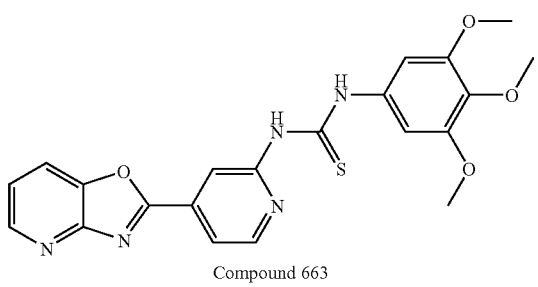
Compound 663
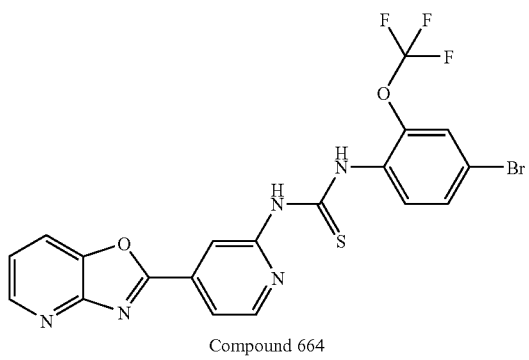
Compound 664
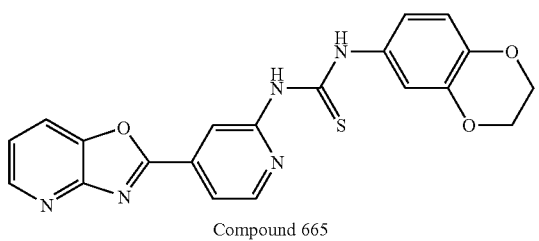
Compound 665
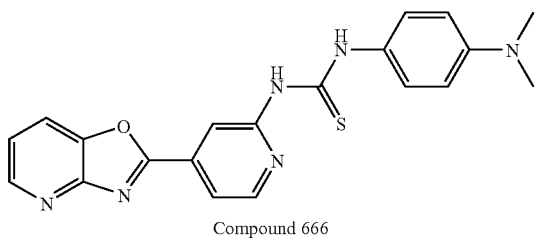
Compound 666
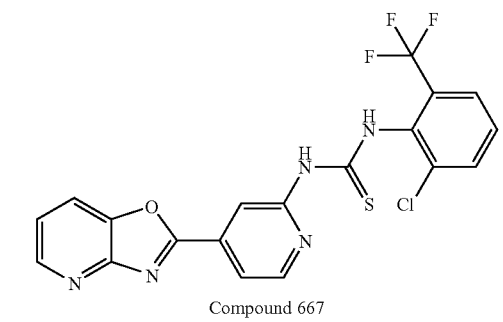
Compound 667

TABLE 1-continued
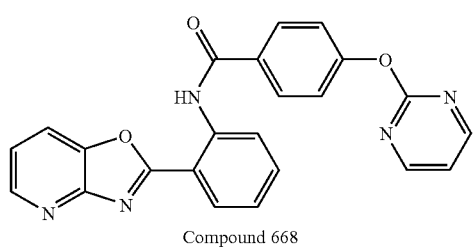
Compound 668
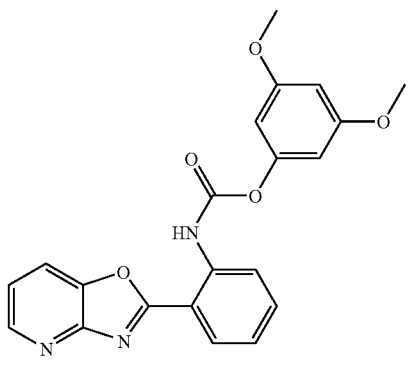 [SMILES: COc1cc(OC)cc(OC(=O)Nc2ccccc2-c2nc3ncccc3o2)c1]
Compound 669
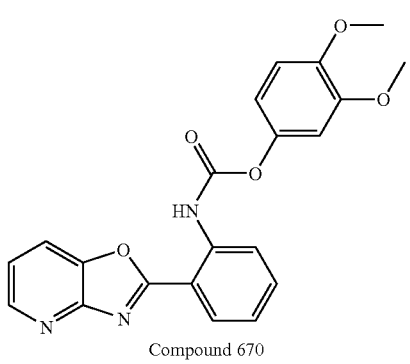
Compound 670
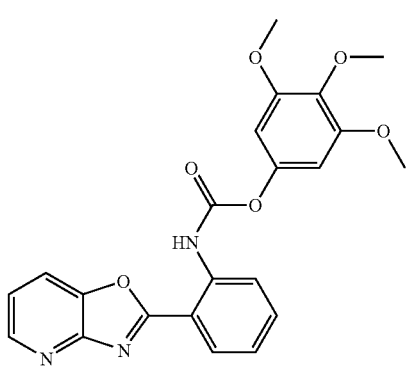 [SMILES: COc1cc(OC(=O)Nc2ccccc2-c2nc3ncccc3o2)cc(OC)c1OC]
Compound 671
TABLE 1-continued
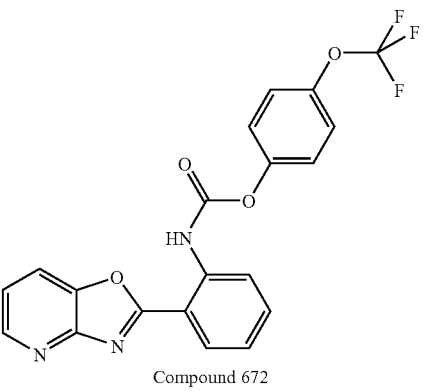
Compound 672
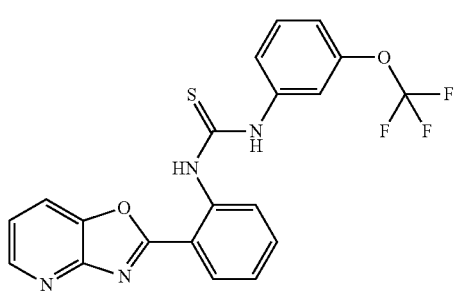 [SMILES: FC(F)(F)Oc1cccc(NC(=S)Nc2ccccc2-c2nc3ncccc3o2)c1]
Compound 673
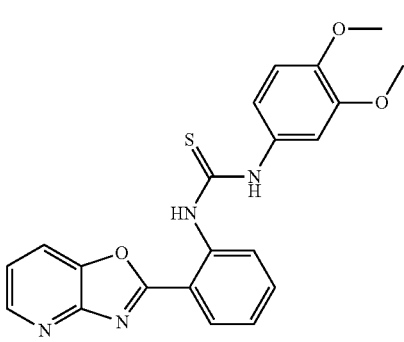 [SMILES: COc1ccc(NC(=S)Nc2ccccc2-c2nc3ncccc3o2)cc1OC]
Compound 674
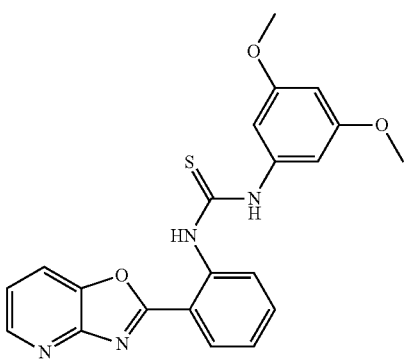 [SMILES: COc1cc(NC(=S)Nc2ccccc2-c2nc3ncccc3o2)cc(OC)c1]
Compound 675

TABLE 1-continued
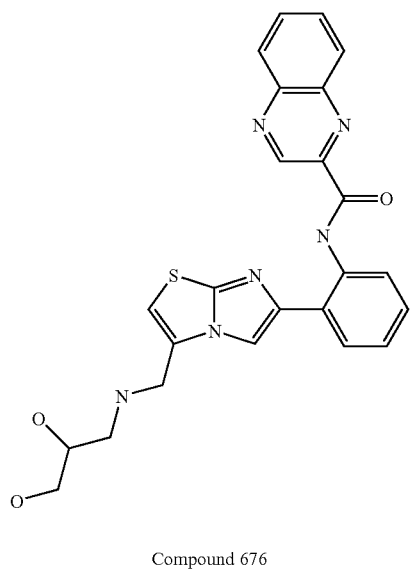
Compound 676
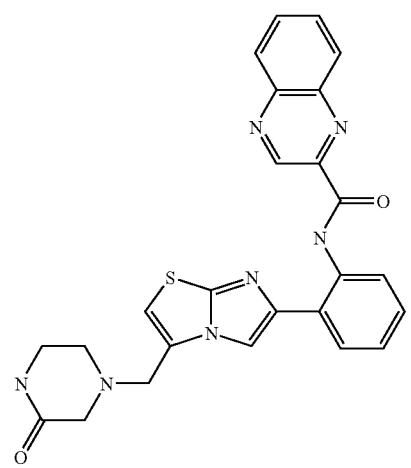 [SMILES: O=C1CN(Cc2csc3nc(-c4ccccc4NC(=O)c4cnc5ccccc5n4)cn23)CCN1]
Compound 677
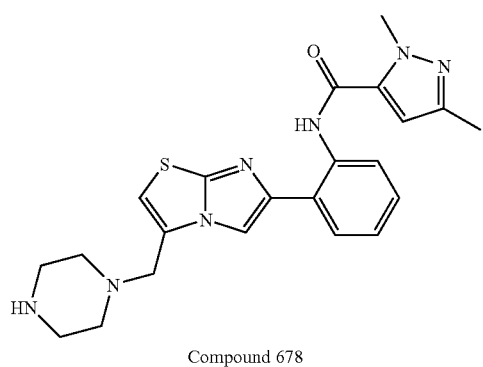
Compound 678
TABLE 1-continued
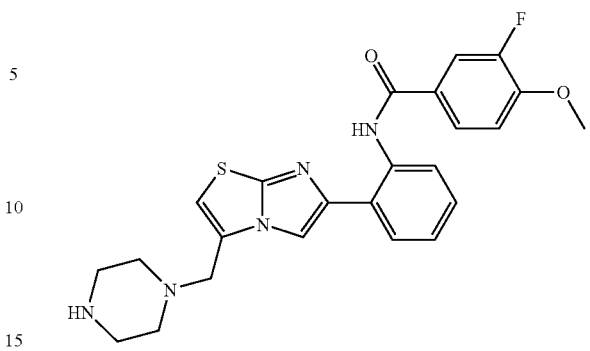
Compound 679
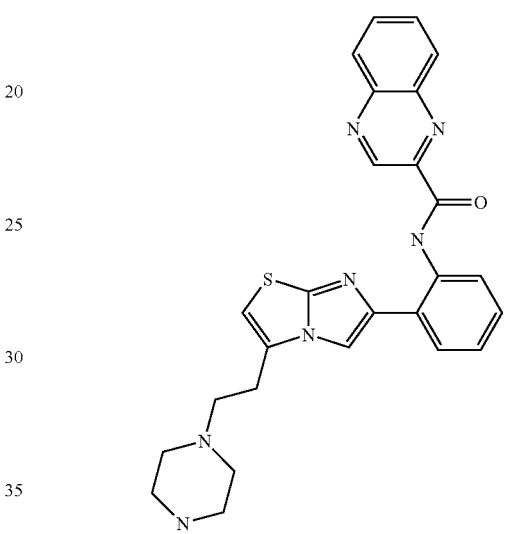
Compound 680
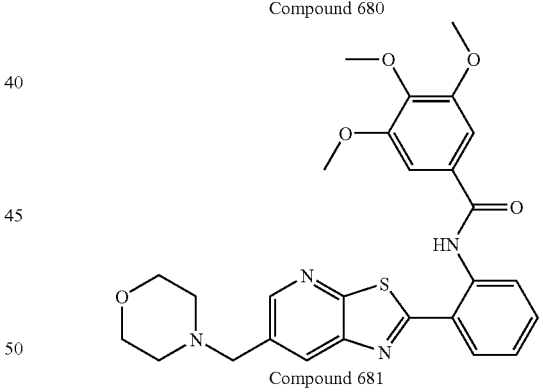
Compound 681
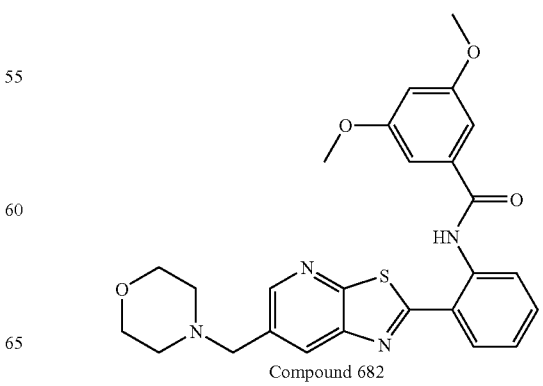
Compound 682

TABLE 1-continued
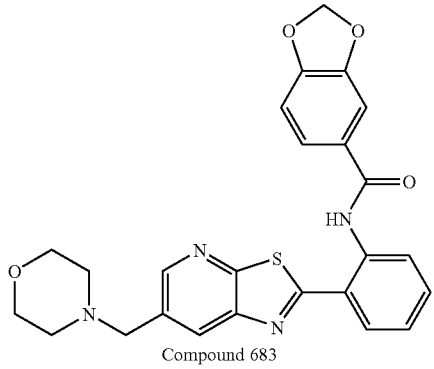
Compound 683
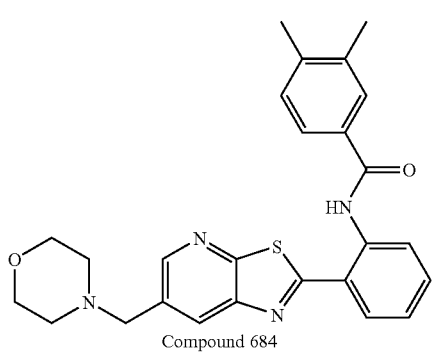
Compound 684
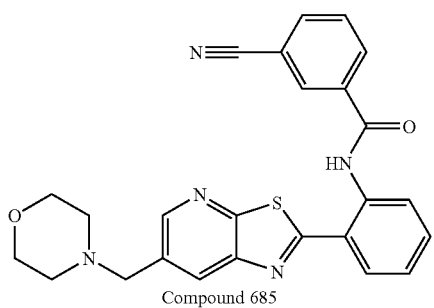
Compound 685
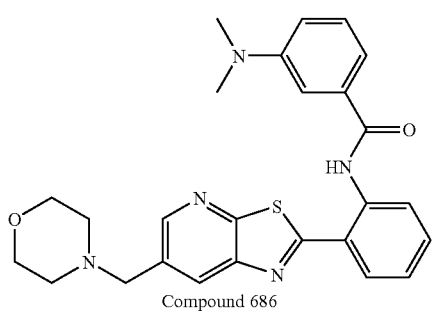
Compound 686
TABLE 1-continued
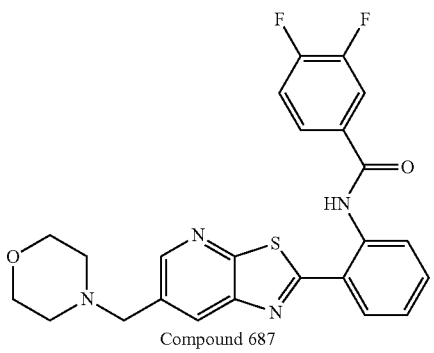
Compound 687
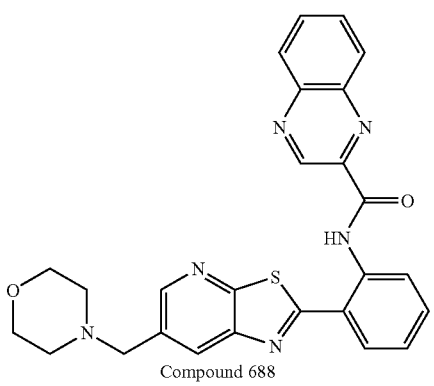
Compound 688
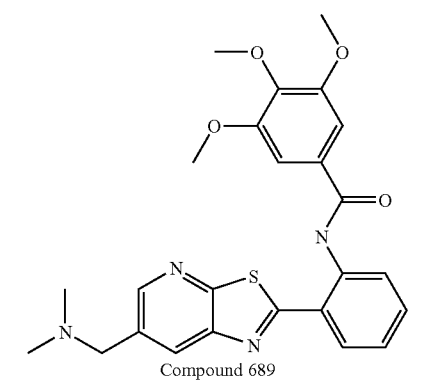
Compound 689
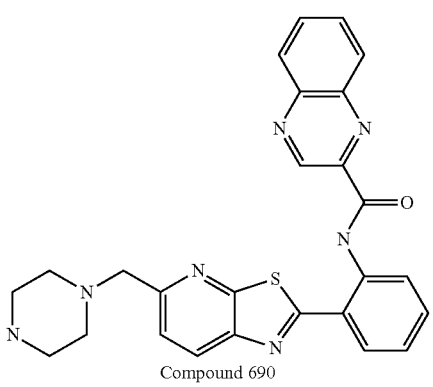
Compound 690

TABLE 1-continued
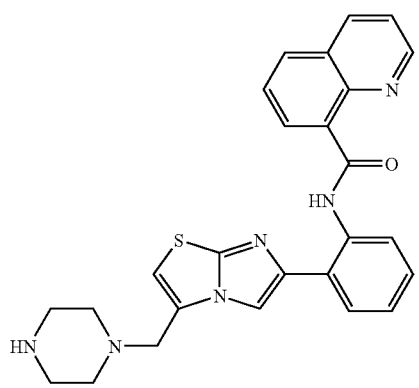 [SMILES: O=C(Nc1ccccc1-c1cn2c(CN3CCNCC3)csc2n1)c1cccc2cccnc12]
Compound 692
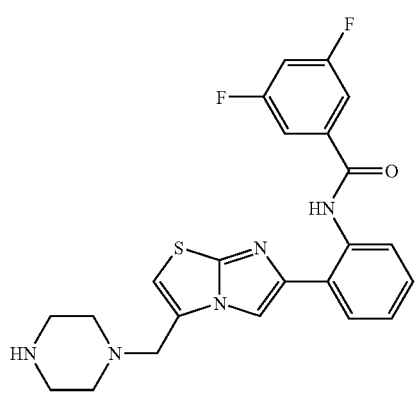 [SMILES: O=C(Nc1ccccc1-c1cn2c(CN3CCNCC3)csc2n1)c1cc(F)cc(F)c1]
Compound 695
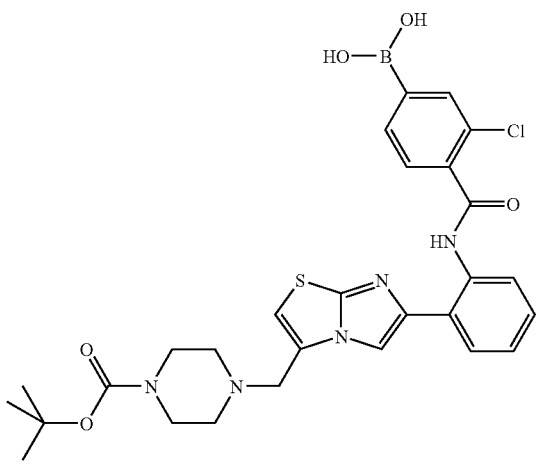 [SMILES: CC(C)(C)OC(=O)N1CCN(Cc2csc3nc(-c4ccccc4NC(=O)c4ccc(B(O)O)cc4Cl)cn23)CC1]
Compound 697
TABLE 1-continued
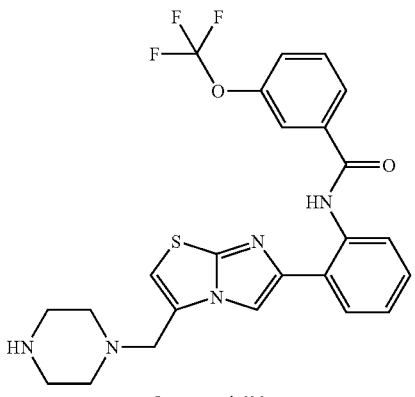
Compound 698
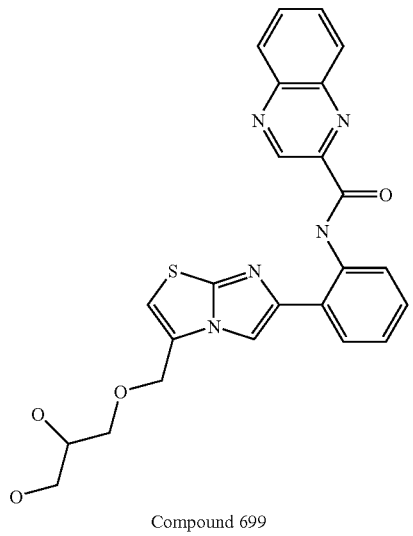
Compound 699
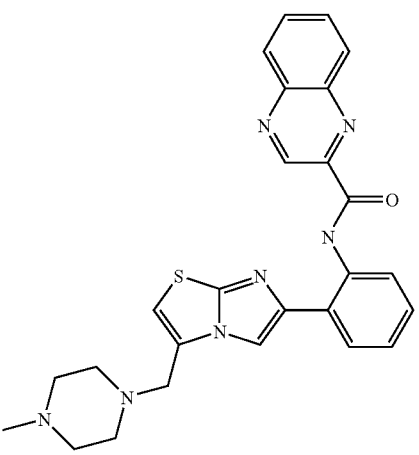 [SMILES: CN1CCN(Cc2csc3nc(-c4ccccc4NC(=O)c4cnc5ccccc5n4)cn23)CC1]
Compound 700

TABLE 1-continued
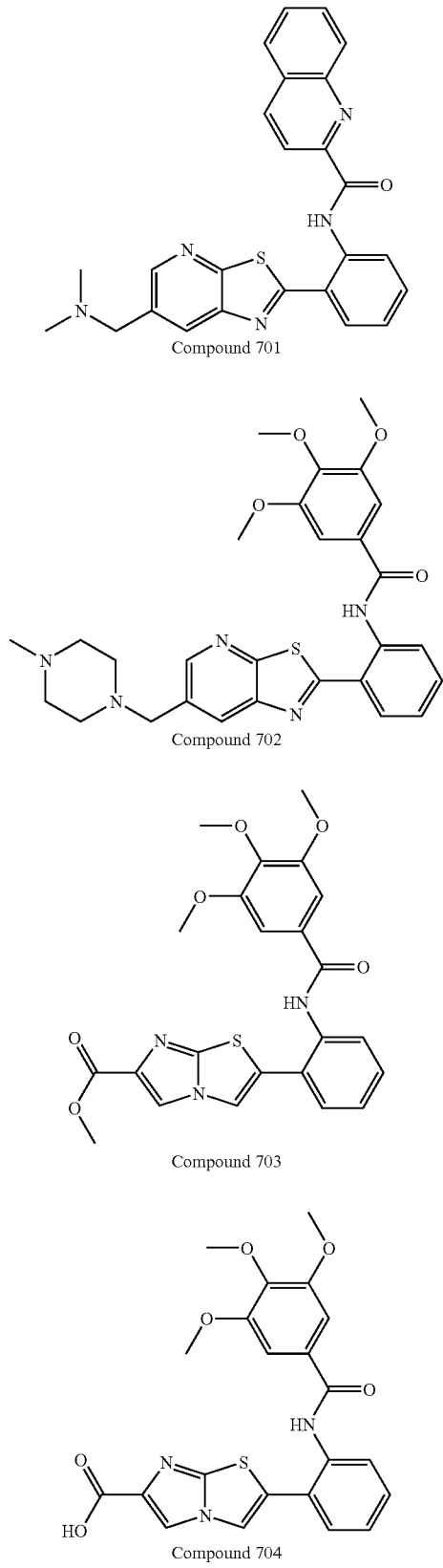
Compound 701
Compound 702
Compound 703
Compound 704
TABLE 1-continued
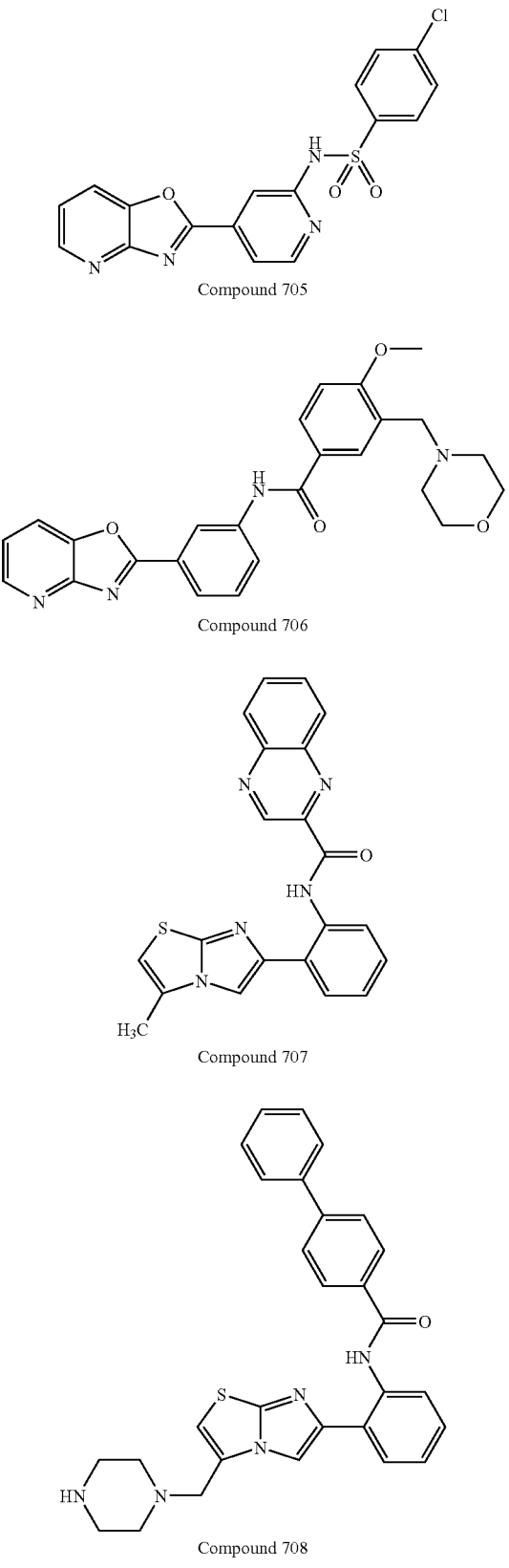
Compound 705
Compound 706
Compound 707
Compound 708

TABLE 1-continued
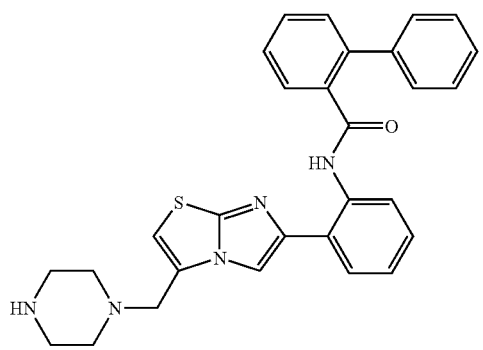 [SMILES: O=C(Nc1ccccc1-c1cn2c(CN3CCNCC3)csc2n1)c1ccccc1-c1ccccc1]
Compound 709
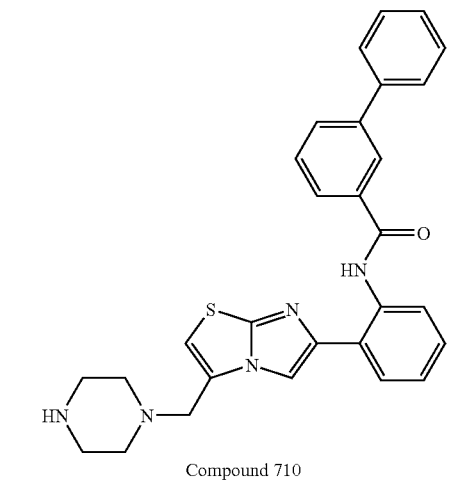
Compound 710
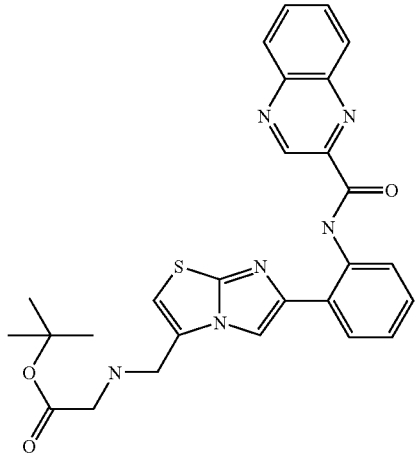 [SMILES: CC(C)(C)OC(=O)CNCc1csc2nc(-c3ccccc3NC(=O)c3cnc4ccccc4n3)cn12]
Compound 711
TABLE 1-continued
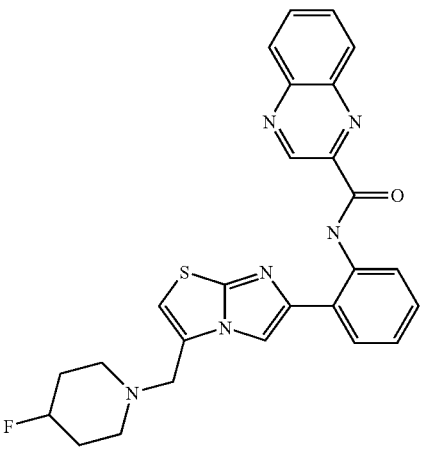 [SMILES: O=C(Nc1ccccc1-c1cn2c(CN3CCC(F)CC3)csc2n1)c1cnc2ccccc2n1]
Compound 714
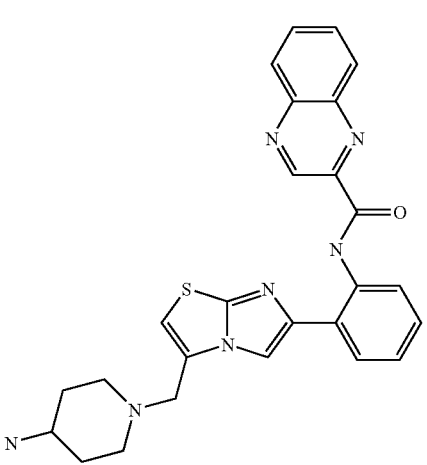 [SMILES: NC1CCN(Cc2csc3nc(-c4ccccc4NC(=O)c4cnc5ccccc5n4)cn23)CC1]
Compound 715
Compound 716

TABLE 1-continued
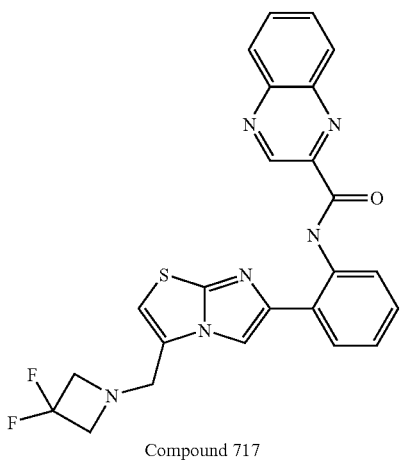
Compound 717
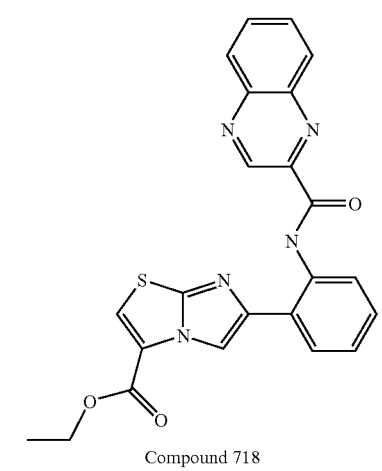
Compound 718
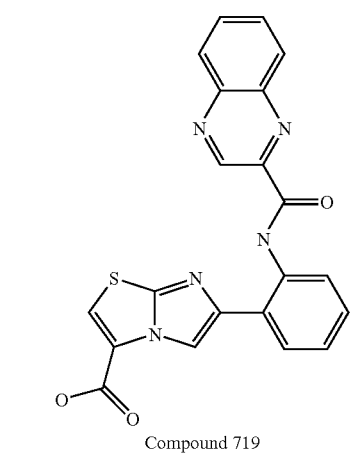
Compound 719
TABLE 1-continued
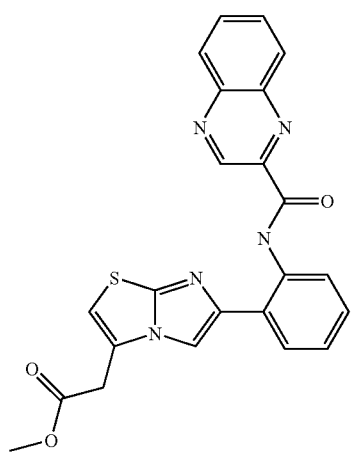 [SMILES: COC(=O)Cc1csc2nc(-c3ccccc3NC(=O)c3cnc4ccccc4n3)cn12]
Compound 720
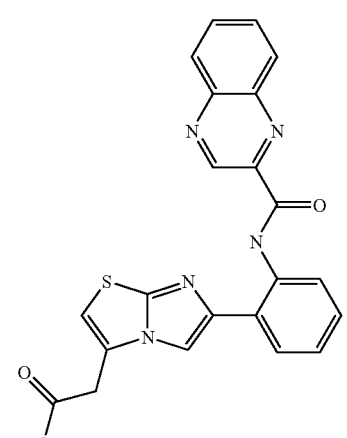
Compound 721
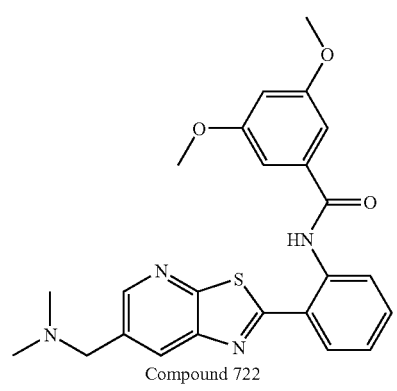
Compound 722

TABLE 1-continued
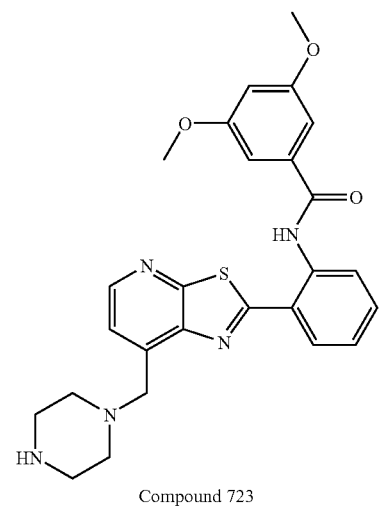
Compound 723
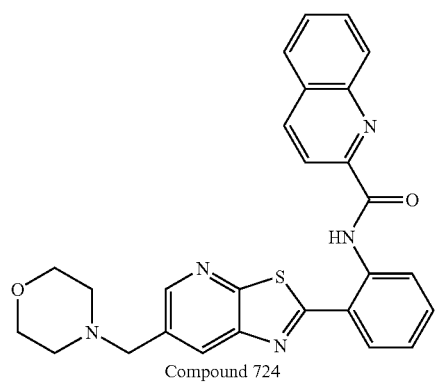
Compound 724
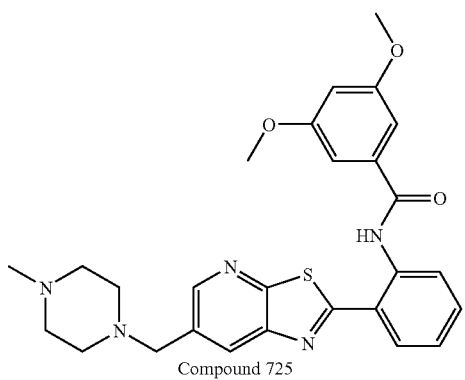
Compound 725
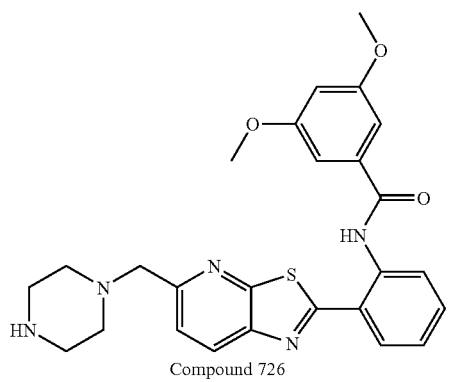
Compound 726
TABLE 1-continued
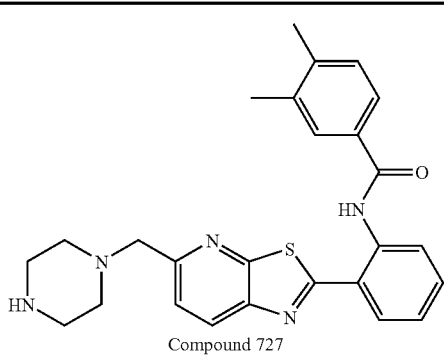
Compound 727
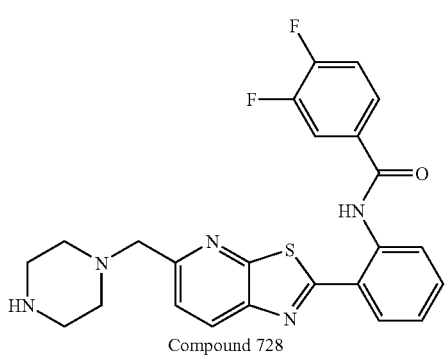
Compound 728
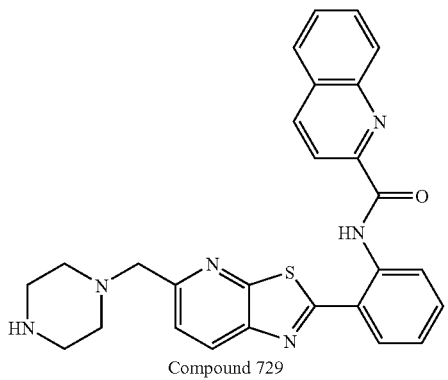
Compound 729
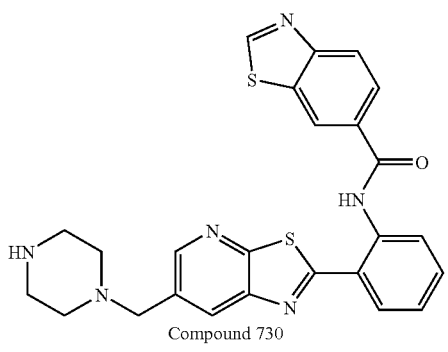
Compound 730

TABLE 1-continued
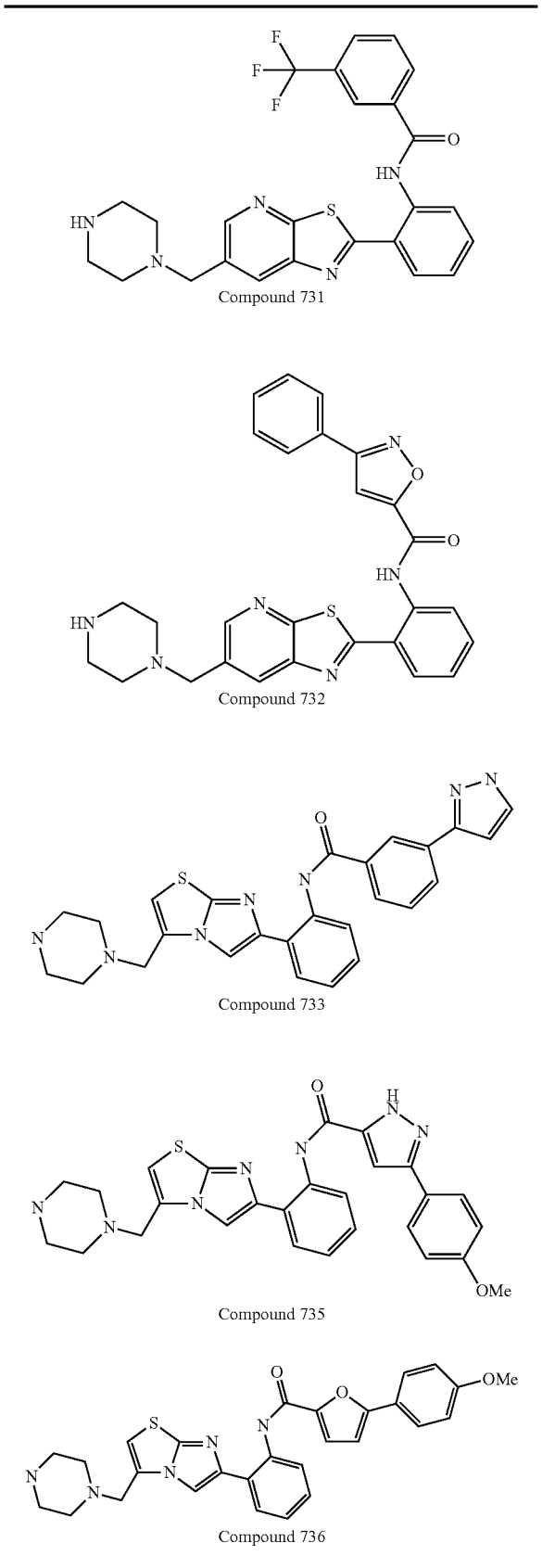
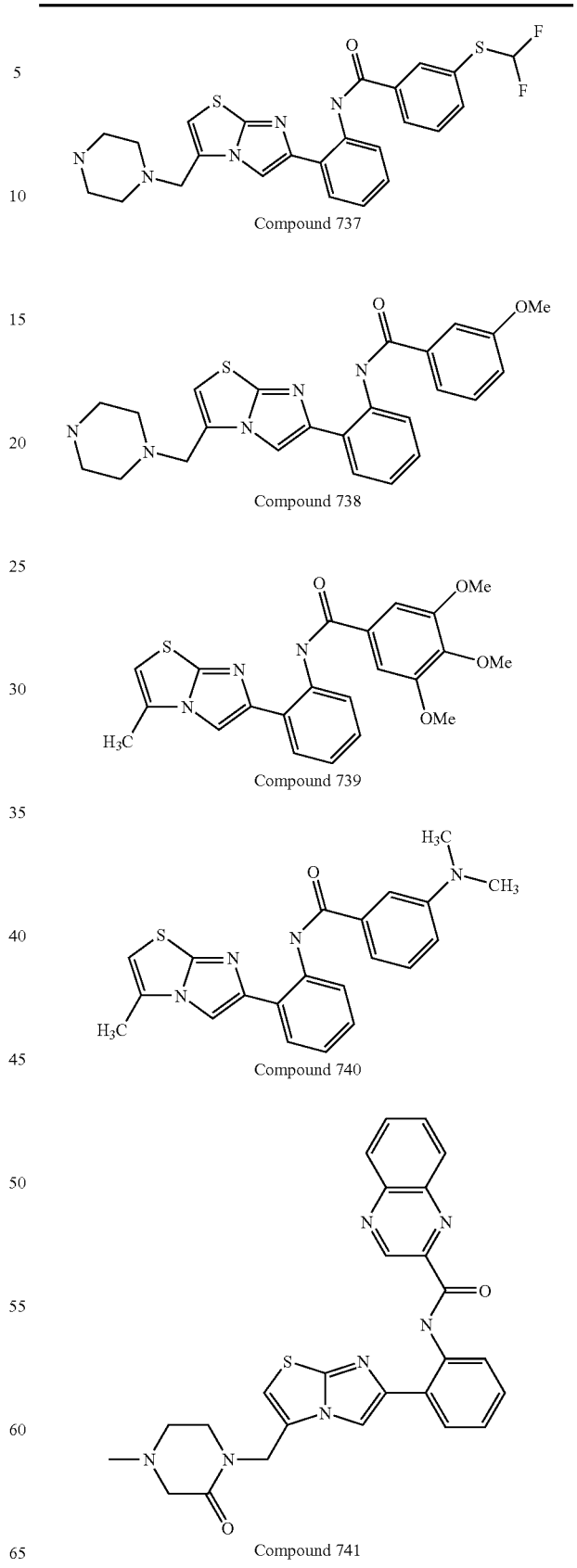

TABLE 1-continued
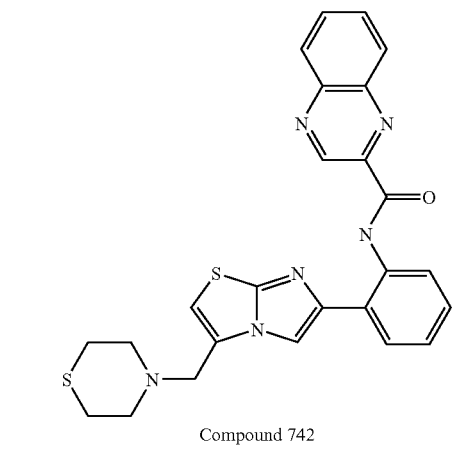
Compound 742
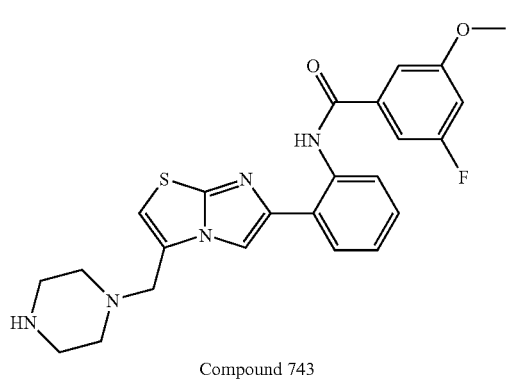
Compound 743
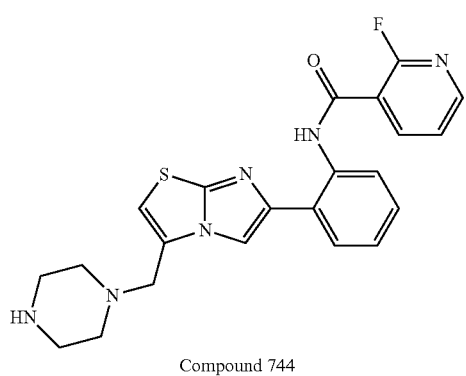
Compound 744
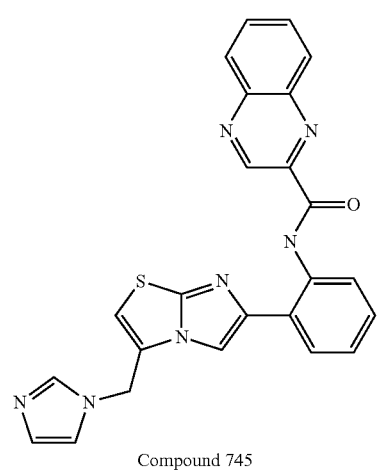
Compound 745
Non-limiting examples of suitable SIRT1 activators include, e.g.,
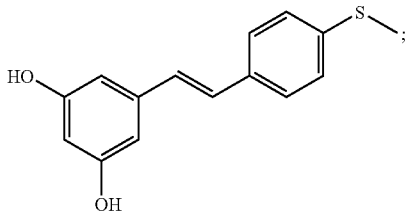
BML-230
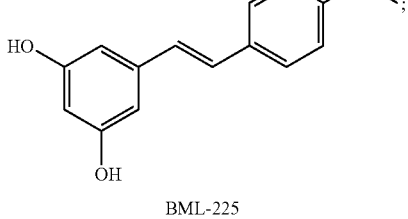
BML-225
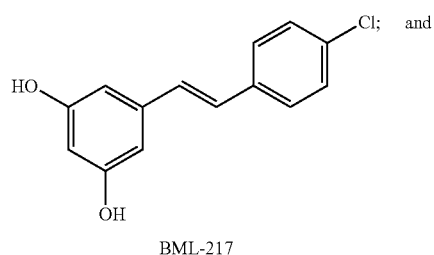
BML-217
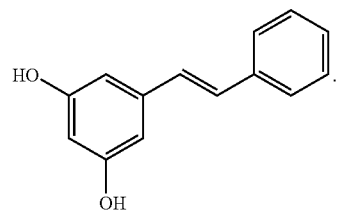
Pinosylvin
Other suitable SIRT1 activators include, e.g.,
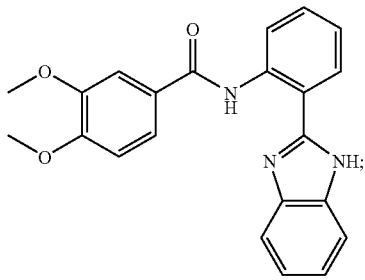

SR1460

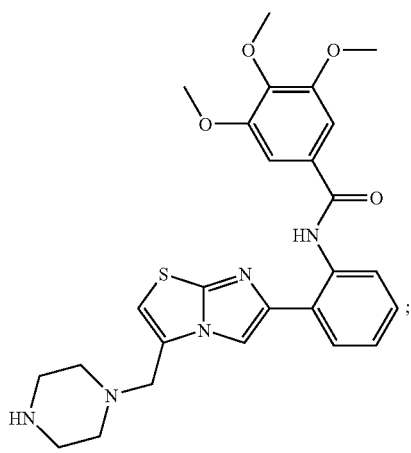

SR1720

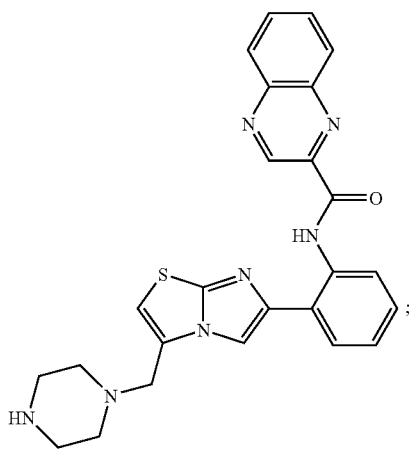   and

SRT-2183

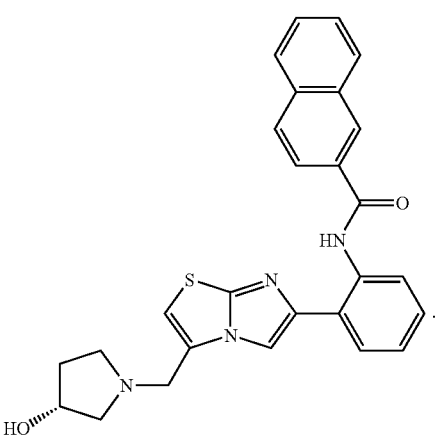

SRT1720, SRT1460, and SRT2183 are selective SIRT1 activators. See, e.g., Milne et al. (2007) *Nature* 450:712.

Also suitable for use are SIRT1 activators that are quinoxaline compounds. Suitable quinoxaline SIRT1 activators include, e.g., 3-benzenesulfonyl-1-(4-fluoro-phenyl)-1H-pyrrolo[2,3-b]-quinoxalin-2-ylamine; 2-amino-1-(2-ethyl-phenyl)-1H-pyrrolo[2,3-b]quinoxaline-3-carboxylic acid (tetrahydro-furan-2-ylmethyl)-amine; 2-amino-1-(3-methoxy-propyl)-1H-pyrrolo[2,3-b]quinoxaline-3-carboxylic acid cyclopentylamide. See, e.g., Nayagam et al. (2006) *J. Biolmolec. Screening* 11:959.

Other suitable SIRT1 activators include, e.g., stilbene compounds, e.g., ester analogs of resveratrol, e.g., as described in U.S. Patent Publication No. 2008/0255382. For example, suitable SIRT1 activators include, e.g., ester analogs of 3,5,4'-trihydroxy-trans-stilbene.

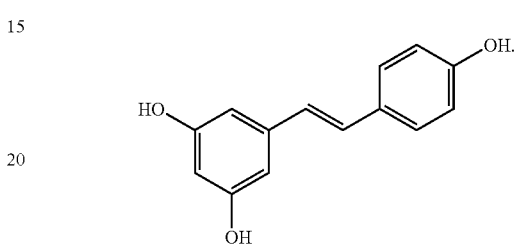

(resveratrol)

Ester analogs include compounds of the formula:

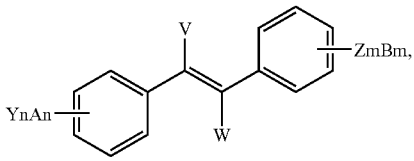

where each Y and each Z is independently —O (ethers), —O—C=O; —C=O—O (esters); —O—C=O—O (carbonates); —O—C=O—NH; —O=O—NR; —NH—C=O—O; —NR—C=O—O (carbamates); —NH—C=P; —NR—C=O; —C=O—NH; —C=O—NR (primary and secondary amides)-NH; —NR (primary and secondary amines); —N (heterocyclic rings); —S (thiol ethers); and halogen;

where each n and each m is independently 1, 2, 3, 4, or 5;

where each A and each B is independently H, R, or absent;

where each V and each W is independently H, straight or branched alkyl of from 1 to 6 carbon atoms, cycloalkyl of from 3 to 8 carbon atoms, alkoxy, phenyl, benzyl, or halogen, and where R is an alkyl with at least one carbon atom, an aryl, or an aralkyl.

Suitable SIRT1 activators include, e.g., 4'-acetoxy-3,5-bis(methoxymethoxy)stilbene; 4'-acetoxy-3,5-dihydroxystilbene; 3,5-diacetoxy-4'-chloroacetoxy stilbene; 3,5-diacetoxy-4'-hydroxy stilbene; 3,4'-diacetoxy-5-hydroxystilbene; 3-acetoxy-4'5-dihydroxystilbene; and 3,4,5'-triacetoxystilbene.

Suitable SIRT1 activators include compounds of any one of Formulas I-VI as described in U.S. Patent Publication No. 2009/0012080. For example, a suitable SIRT1 activator is a compound of the formula:

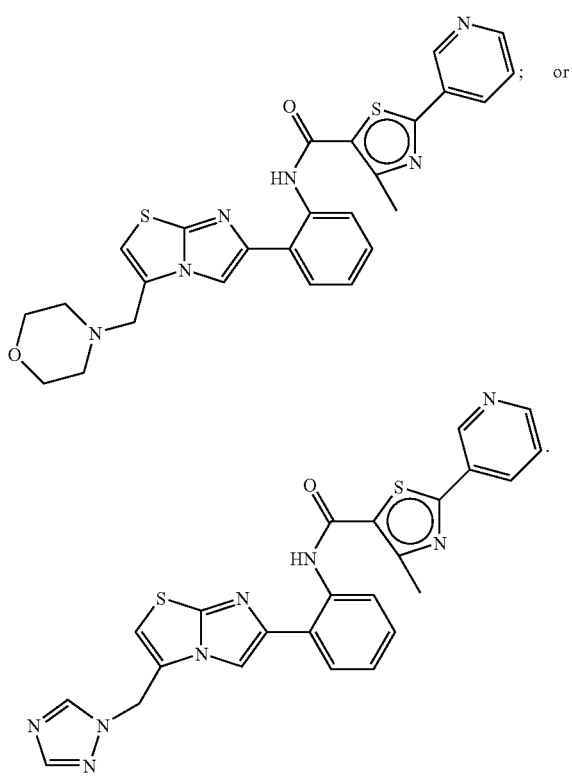

For example, a suitable SIRT1 activator is 4-methyl-N-(2 (3-morpholinomethyl)imidazo[2,1-b]thiazol-6-yl)phenyl)-2-(pyridin-3-yl)thiazol-5-carboxamide, or a pharmaceutically acceptable salt thereof.

Methods of Modulating Activation and Differentiation of a CD4+ T Cell

The present disclosure provides a method of modulating activation and differentiation of a CD4+ T cell, the method generally involving contacting the CD4+ T cell (in vitro, ex vivo, or in vivo) with a SIRT1 inhibitor. In some embodiments, the CD4+ T cell is a helper T cell (e.g., a Th1, Th2, or Th17 cell), and the SIRT1 inhibitor inhibits deacetylation of NF-κB in the CD4+ T cell, thereby increasing CD4+ T helper T cell activity and/or numbers. In other embodiments, the CD4+ T cell is a CD4+/CD25+/FoxP3+ Treg cell, and the SIRT1 inhibitor reduces deacetylation of FoxP3 in the CD4+/CD25+/FoxP3+ Treg cell, thereby increasing Treg activity and/or numbers.

Increasing CD4+ T Helper Cell Activity and/or Numbers

In some embodiments, the CD4+ T cell is a helper T cell (e.g., a Th1, a Th2, or a Th17 cell), and the SIRT1 inhibitor inhibits deacetylation of NF-κB in the CD4+ T cell, thereby increasing CD4+ T helper cell activity and/or numbers. CD4+ T helper cell activity and/or numbers can be increased in vitro, in vivo, or ex vivo. Increasing CD4+ T helper cell activity and/or numbers is useful for increasing an immune response, e.g., increasing an immune response to an antigen. Thus, the present disclosure provides a method of increasing an immune response in an individual, the method involving administering to an individual in need thereof an effective amount of an inhibitor of SIRT1. The method can also be carried out ex vivo, e.g., by (a) contacting CD4+ T helper cells obtained from a donor individual with a SIRT1 inhibitor ex vivo, thereby increasing the activity and/or numbers of CD4+ T helper cells, and (b) returning the CD4+ T helper cells from step (a) to the donor individual or to a recipient individual other than the donor.

In some embodiments, an effective amount of a SIRT1 inhibitor is an amount that, when contacted with a starting population of CD4+ T helper cells, increases the number of CD4+ T helper cells by at least about 10%, at least about 15%, at least about 20%, at least about 25%, at least about 30%, at least about 35%, at least about 40%, at least about 50%, at least about 2-fold, at least about 2.5-fold, at least about 5-fold, at least about 10-fold, at least about 25-fold, at least about 50-fold, at least about 100-fold, at least about 500-fold, or at least about 1000-fold, or more, compared to the number of CD4+ T helper cells in the starting population before contacting with the SIRT1 inhibitor. As noted above, in some embodiments, the contacting occurs in vitro. In other embodiments, the contacting occurs ex vivo. In other embodiments, the contacting occurs in vivo.

In some embodiments, an effective amount of a SIRT1 inhibitor is an amount that is effective to reduce deacetylation of NF-κB in a CD4+ T helper cell by at least about 10%, at least about 15%, at least about 20%, at least about 25%, at least about 30%, at least about 35%, at least about 40%, at least about 50%, at least about 60%, at least about 70%, at least about 80%, or more than 80%, compared to the level of deacetylation of NF-κB in the CD4+ T helper cell in the absence of the SIRT1 inhibitor.

In some embodiments, an effective amount of a SIRT1 inhibitor is an amount that, when administered to an individual, increases an immune response in the individual by at least about 10%, at least about 15%, at least about 20%, at least about 25%, at least about 30%, at least about 35%, at least about 40%, at least about 50%, at least about 2-fold, at least about 2.5-fold, at least about 5-fold, at least about 10-fold, at least about 25-fold, at least about 50-fold, or at least about 100-fold, compared to the immune response in the absence of treatment with the SIRT1 inhibitor.

In some embodiments, an effective amount of a SIRT1 inhibitor is an amount that increases the number of CD4+ cells in an individual by at least about 10%, at least about 15%, at least about 20%, at least about 25%, at least about 30%, at least about 35%, at least about 40%, at least about 50%, at least about 2-fold, at least about 2.5-fold, at least about 5-fold, at least about 10-fold, at least about 25-fold, at least about 50-fold, or at least about 100-fold, compared to the number of CD4+ T cells in the individual in the absence of treatment with the SIRT1 inhibitor.

In some embodiments, an effective amount of a SIRT1 inhibitor is an amount that increases the number of cytotoxic T cells in an individual by at least about 10%, at least about 15%, at least about 20%, at least about 25%, at least about 30%, at least about 35%, at least about 40%, at least about 50%, at least about 2-fold, at least about 2.5-fold, at least about 5-fold, at least about 10-fold, at least about 25-fold, at least about 50-fold, or at least about 100-fold, compared to the number of cytotoxic T cells in the individual in the absence of treatment with the SIRT1 inhibitor.

In some embodiments, an effective amount of a SIRT1 inhibitor is an amount that is effective to reduce the number of cancer cells and/or to reduce the volume of a tumor in an individual by at least about 10%, at least about 15%, at least about 20%, at least about 25%, at least about 30%, at least about 35%, at least about 40%, at least about 50%, at least about 60%, at least about 70%, at least about 80%, at least about 90%, or more than 90%, compared to the number of cancer cells or compared to the tumor volume in the individual in the absence of treatment with the SIRT1 inhibitor. In some embodiment, a SIRT1 inhibitor is administered in conjunction with administration of a tumor-specific antigen.

In some embodiments, a SIRT1 inhibitor is administered in conjunction with administration of an antigen that induces an immune response to a pathological microorganism. In some embodiments, an effective amount of a SIRT1 inhibitor is an amount that is effective to reduce the number of pathological microorganisms in an individual by at least about 10%, at least about 15%, at least about 20%, at least about 25%, at least about 30%, at least about 35%, at least about 40%, at least about 50%, at least about 60%, at least about 70%, at least about 80%, at least about 90%, or more than 90%, compared to the number of pathological microorganisms in the individual in the absence of treatment with the SIRT1 inhibitor. In some embodiment, a SIRT1 inhibitor is administered in conjunction with administration of an antigen that induces an immune response to a pathological microorganism.

In some embodiments, an effective amount of a SIRT1 inhibitor is an amount that increases the level of one or more antigen-specific antibodies in an individual by at least about 10%, at least about 15%, at least about 20%, at least about 25%, at least about 30%, at least about 35%, at least about 40%, at least about 50%, at least about 2-fold, at least about 2.5-fold, at least about 5-fold, at least about 10-fold, at least about 25-fold, at least about 50-fold, or at least about 100-fold, compared to the level of the one or more antigen-specific antibodies in the individual in the absence of treatment with the SIRT1 inhibitor.

Analysis (both qualitative and quantitative) an immune response can be by any method known in the art, including, but not limited to, measuring antigen-specific antibody production, activation of specific populations of lymphocytes such as $CD4^+$ T cells or NK cells, and/or production of cytokines such as IFN, IL-2, IL-4, or IL-12. Methods for measuring specific antibody responses include enzyme-linked immunosorbent assay (ELISA) and are well known in the art. Measurement of numbers of specific types of lymphocytes such as $CD4^+$ T cells can be achieved, for example, with fluorescence-activated cell sorting (FACS). Cytotoxicity assays can be performed for instance as described in Raz et al. (1994) Proc. Natl. Acad. Sci. USA 91: 9519-9523. Serum concentrations of cytokines can be measured, for example, by ELISA. These and other assays to evaluate the immune response are well known in the art. In some embodiments, a Th1-type immune response is increased.

A subject method of increasing an immune response in an individual is useful for treating various disorders including, e.g., treating an infectious disease (e.g., a disease caused by a pathological microorganism such as a virus, a bacterium, etc.); increasing an immune response to a cancer cell in an individual; enhancing an immune response in an individual who is immunodeficient or immunocompromised; etc.

Thus, for example, a subject method can be used to increase an immune response for treating:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, and *Bordetella*;

(c) other infectious diseases, such Chlamydia infection, fungal diseases including but not limited to candidiasis, aspergillosis, histoplasmosis, cryptococcal meningitis, and parasitic diseases including but not limited to malaria, *Pneumocystis carinii* pneumonia, leishmaniasis, cryptosporidiosis, toxoplasmosis, and trypanosome infection; and (d) neoplastic diseases, such as, for example, intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers.

Increasing Treg Activity and/or Numbers

In other embodiments, the $CD4^+$ T cell is a $CD4^+/CD25^+/FoxP3^+$ Treg cell, and the SIRT1 inhibitor reduces deacetylation of FoxP3 in the $CD4^+/CD25^+/FoxP3^+$ Treg cell, thereby increasing Treg activity and/or numbers. Thus, in some embodiments, the present disclosure provides a method of increasing Treg activity and/or numbers, the method generally involving contacting a naïve $CD4^+$ T cell and/or a Treg cell (a $CD4^+/CD25^+/FoxP3^+$ T cell) with a SIRT1 modulator, where the contacting can take place in vitro, ex vivo, or in vivo.

Increasing Treg activity and/or numbers is useful for reducing an undesirable immune response such as an autoimmune response, an allergic response, graft rejection, or a graft-versus-host response. Thus, in some embodiments, the present disclosure provides a method of treating an autoimmune disorder, a method of treating an allergic disorder, a method of reducing graft rejection, and a method of reducing graft-versus-host disease, in an individual, the methods generally involving administering to an individual in need thereof (e.g., an individual having an autoimmune disorder, an individual having an allergic disorder, a graft recipient) an effective amount of an SIRT1 inhibitor.

In some embodiments, an autoimmune response, an allergic response, graft rejection, or a graft-versus-host response, can be reduced by contacting naïve $CD4^+$ T cells and/or Treg cells obtained from an individual (e.g., an individual having an autoimmune disorder, an individual having an allergic disorder, a graft recipient) with an SIRT1 inhibitor ex vivo, and returning the Treg cells to the individual. For example, an ex vivo method can involve: (a) contacting naïve $CD4^+$ T cells and/or Tregs obtained from a donor individual with a SIRT1 inhibitor ex vivo, thereby increasing the activity and/or numbers of Tregs, and (b) returning the Tregs from step (a) to the donor individual or to a recipient individual other than the donor.

In some embodiments, an effective amount of a SIRT1 inhibitor is an amount that, when contacted with a starting population of Tregs (or a starting population that is a mixture of naïve CDC T cells and Tregs), increases the number of Tregs by at least about 10%, at least about 15%, at least about 20%, at least about 25%, at least about 30%, at least about 35%, at least about 40%, at least about 50%, at least about 2-fold, at least about 2.5-fold, at least about 5-fold, at least about 10-fold, at least about 25-fold, at least about 50-fold, at least about 100-fold, at least about 500-fold, or at least about 1000-fold, or more, compared to the number of Tregs in the starting population before contacting with the SIRT1 inhibitor. As noted above, in some embodiments, the contacting occurs in vitro. In other embodiments, the contacting occurs ex vivo. In other embodiments, the contacting occurs in vivo.

In some embodiments, an effective amount of a SIRT1 inhibitor is an amount that is effective to reduce deacetylation of FoxP3 in a Treg by at least about 10%, at least about 15%, at least about 20%, at least about 25%, at least about 30%, at least about 35%, at least about 40%, at least about 50%, at least about 60%, at least about 70%, at least about 80%, or more than 80%, compared to the level of deacetylation of FoxP3 in the Treg in the absence of the SIRT1 inhibitor. For example, in some embodiments, an effective amount of a SIRT1 inhibitor is an amount that is effective to reduce deacetylation of K31, K263, and K268 (or an equivalent lysine residue) in a FoxP3 polypeptide in a Treg cell by at least about 10%, at least about 15%, at least about 20%, at least about 25%, at least about 30%, at least about 35%, at least about 40%, at least about 50%, at least about 60%, at least about 70%, at least about 80%, or more than 80%, compared to the level of deacetylation of K31, K263, and K268 residues in FoxP3 in the Treg in the absence of the SIRT1 inhibitor.

Amino acid sequences of FoxP3 polypeptides are known in the art. Examples of FoxP3 amino acid sequences are presented in FIG. 13, which shows an alignment of human, mouse, and bovine FoxP3, and which shows the K31, K263, and K268 residues. A FoxP3 polypeptide can comprise an amino acid sequence having at least about 70%, at least about 80%, at least about 90%, at least about 95%, at least about 98%, at least about 99%, or 100%, with the human FoxP3 amino acid sequence depicted in FIG. 13.

In some embodiments, an "effective amount" of a SIRT1 inhibitor is an amount that achieves a degree of immunosuppression sufficient to delay, inhibit, suppress or moderate tissue transplant rejection and/or delay, inhibit, suppress or moderate one or more symptoms of an autoimmune disease and/or delay, inhibit, suppress or moderate an undesired immune response to a foreign antigen such as a therapeutic protein, a viral vector, an allergen, a venom and the like.

In some embodiments, an "effective amount" of a SIRT1 inhibitor is an amount that reduces an undesired immune response (e.g., an autoimmune response, an allergic response, a graft-versus-host response, a graft rejection) by at least about 10%, at least about 20%, at least about 30%, at least about 40%, at least about 50%, at least about 60%, at least about 70%, at least about 80%, or more than 80%, compared to the degree of the undesired immune response in the absence of treatment with the SIRT1 inhibitor. Whether an SIRT1 inhibitor is effective in reducing an undesired immune response (e.g., an autoimmune response, an allergic response, a graft-versus-host response, a graft rejection) can be determined by measuring one or more well-known parameters associated with the undesired immune response (e.g., the level of autoantibody; the level of auto-reactive T cells; the level of allergen-specific IgE; a symptom of allergy; the level of antibody specific for a graft tissue; etc.).

In some embodiments, a subject method is effective to reduce the number and/or activity of an autoreactive cell in an individual by at least about 5%, at least about 10%, at least about 25%, at least about 30%, at least about 40%, at least about 50%, at least about 60%, at least about 70%, at least about 80%, or at least about 90%, or more, when compared to the number and/or level of autoreactive cells in the individual not treated with a SIRT1 inhibitor.

Whether administration of a SIRT1 inhibitor is effective to reduce the number and/or activity of an autoreactive T lymphocyte in an individual is readily determined using known assays. For example, where the autoreactive T lymphocytes are specific for an autoantigen, the number and activity level of autoantigen-specific T lymphocytes is determined using, e.g., a mixed lymphocyte reaction in which irradiated cells comprising a detectable label in the cytoplasm and displaying the autoantigen are mixed with lymphocytes from the individual. Release of detectable label from the cytoplasm of the autoantigen-displaying cells indicates the presence in the individual of autoreactive lymphocytes. Methods of detecting autoreactive T lymphocytes associated with Type 1 diabetes are known in the art; and any such methods can be used. See, e.g., U.S. Pat. No. 6,022,697 for a discussion of a method of detecting autoreactive T lymphocytes associated with Type 1 diabetes.

A subject method is useful for treating an autoimmune disease, e.g., for reducing or ameliorating at least one symptom of an autoimmune disease in an individual having an autoimmune disease (e.g., an individual who has been diagnosed as having an autoimmune diseases). Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus).

A subject method can be used to increase transplantation tolerance in a subject (e.g., to reduce the likelihood of rejection of the transplant by the transplant recipient). In some embodiments, the subject is a recipient of an allogeneic transplant (e.g., the graft is an allograft). Cells, tissues or organs (or parts thereof) that can be transplanted between members of the same species include, but are not limited, to heart, lung, kidney, liver, pancreas, pancreatic islets, brain tissue, cornea, stomach, bone, bone marrow, muscle, intestine, bladder, skin and stem cells. Optionally, the transplanted tissue or organ is bio-engineered, e.g., when the transplanted tissue or organ is grown from a stem cell or other type of precursor cell(s). Bio-engineered tissue or organ can be grown outside of the body and transplanted directly into the host. Alternatively, the precursor cells or immature organ or tissue is transplanted into the host to grow and mature.

The transplanted organ, tissue or cell(s) can also be a xenograft, i.e., the donor is a member of a species different than the recipient. Xenografts are advantageously used with a bio-engineered tissue or organ, which, instead of being transplanted directly into the recipient in need of the tissue or organ, can be transplanted into a surrogate host such as non-human mammal until a suitable human recipient in need of the bio-engineered tissue or organ is identified. Alternatively, the tissue or organ can be transplanted into the surrogate to allow the bio-engineered tissue or organ to mature. Use of surrogate hosts may be preferred in instances where further development of the tissue or organ is required before transplantation into a human recipient. In another alternative, a xenograft is used when a suitable allograft donor is unavailable. When a transplanting into a different a species, it is desirable to select a host such that the size of the organs in the host and donor are similar. In addition, the host is selected to minimize transmission of communicable diseases.

In some embodiments, a subject method can be used to reduce the incidence and/or severity of an allergic reaction in an individual. Thus, a subject method can be used to reduce adverse reaction in an individual to an allergen. Allergens of interest include antigens found in food, such as strawberries, peanuts, milk polypeptides, egg whites, etc. Other allergens of interest include various airborne antigens, such as grass pollens, animal danders, house mite feces, etc. Molecularly cloned allergens include *Dermatophagoides pteryonyssinus* (Der P1); Lol pl-V from rye grass pollen; a number of insect venoms, including venom from jumper ant *Myrmecia pilosula*; *Apis mellifera* bee venom phospholipase A2 (PLA$_2$ and antigen 5S; phospholipases from the yellow jacket *Vespula maculifrons* and white faced hornet *Dolichovespula maculata*; a large number of pollen polypeptides, including birch pollen, ragweed pollen, Parol (the major allergen of *Parietaria officinalis*) and the cross-reactive allergen NO (from *Parietaria judaica*), and other atmospheric pollens including *Olea europaea, Artemisia* sp., gramineae, etc. Other allergens of interest are those responsible for allergic dermatitis caused by blood sucking arthropods, e.g. Diptera, including mosquitos (*Anopheles* sp., *Aedes* sp., *Culiseta* sp., *Culex* sp.); flies (*Phlebotomus* sp., *Culicoides* sp.) particularly black flies, deer flies and biting midges; ticks (*Dermacenter* sp., *Ornithodoros* sp., *Otobius* sp.); fleas, e.g. the order *Siphonaptera*, including the genera *Xenopsylla, Pulex* and *Ctenocephalides felis*. Other allergens of interest include drug allergens.

SIRT1 Inhibitors

SIRT1 inhibitors that are suitable for use in a subject method include, but are not limited to, sirtinol (2-[(2-hydroxynaphthalen-1-ylmethylene)amino]-N-(1-phenyl-ethyl)benzamide); a compound as described in U.S. Pat. No. 7,345,178, provided the compound is an SIRT1 inhibitor, e.g., a compound as shown in Table 5 of U.S. Pat. No. 7,345,178; a compound as described in U.S. Patent Publication No. 2008/0255382; and the like; or a pharmaceutically acceptable salt of any of the foregoing compounds.

Suitable SIRT1 inhibitors include, e.g., (Ex-527)

Ex-527 is 6-chloro-2,3,4,9-tetrahydro-1H-carbazole-1-carboxamide. Ex-527 is a selective SIRT1 inhibitor. See, e.g., Napper et al. (2005) J. Med. Chem. 48:8045.

Suitable SIRT1 inhibitors include, e.g., compounds of Table 5 of U.S. Pat. No. 7,345,178, e.g.:

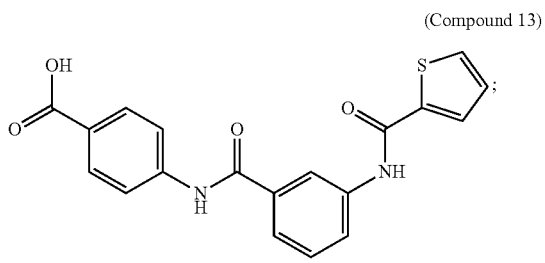
(Compound 13)

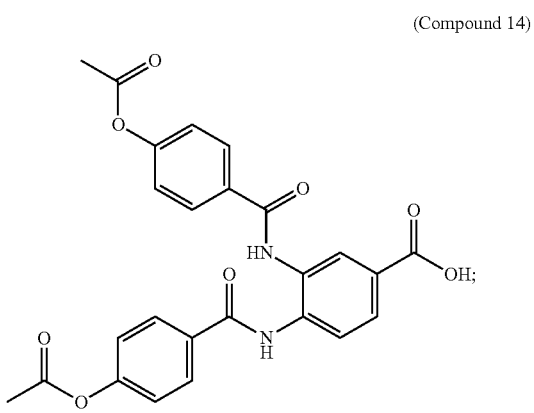
(Compound 14)

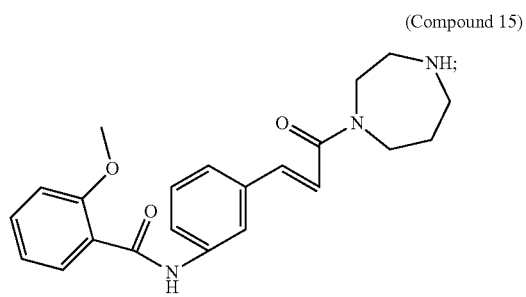
(Compound 15)

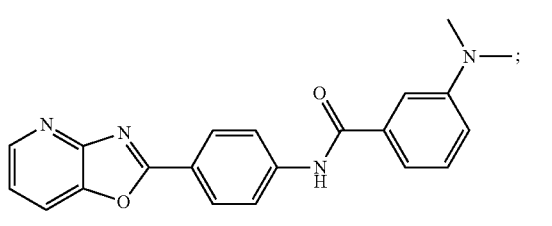
(Compound 23)

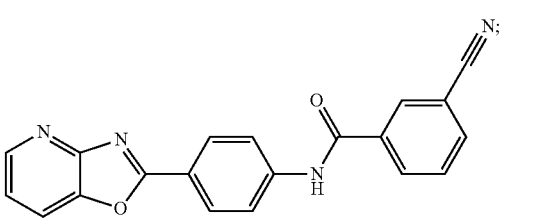
(Compound 25)

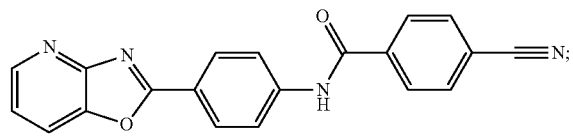
(Compound 26)

(Compound 28)

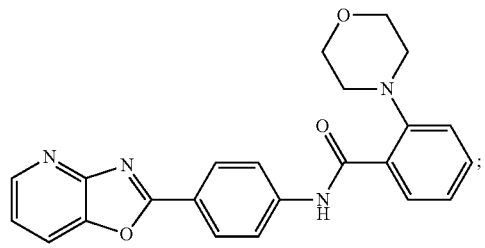

(Compound 30)

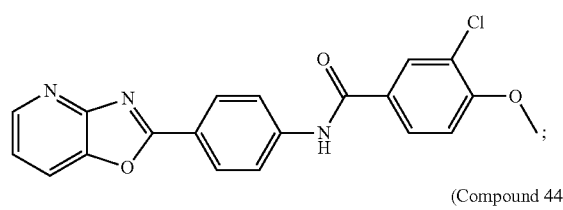

(Compound 44)

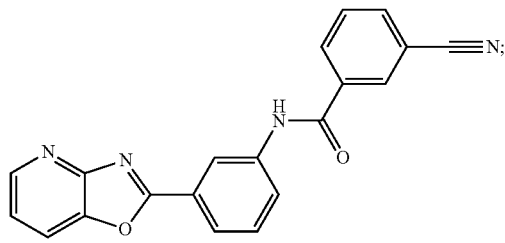

(Compound 47)

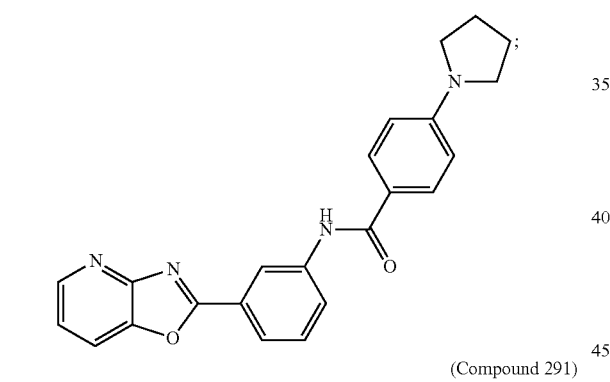

(Compound 291)

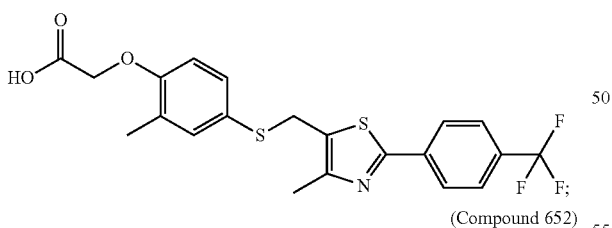

(Compound 652)

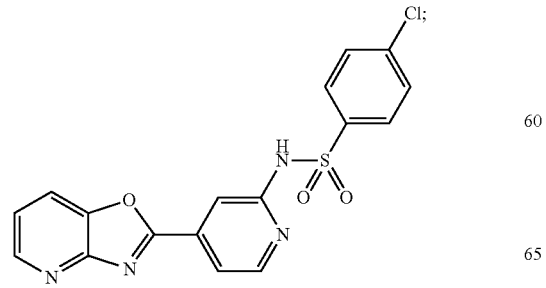

(Compound 653)

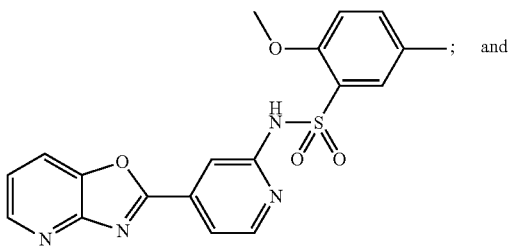

(Compound 654)

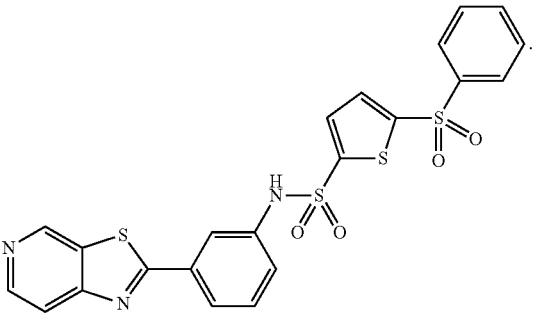

Suitable SIRT1 inhibitors include a compound as disclosed in U.S. Patent Publication No. 20008/0214800, or a pharmaceutically acceptable salt of such a compound. Examples of suitable SIRT1 inhibitors include, e.g.:

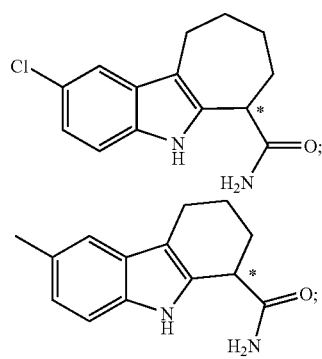

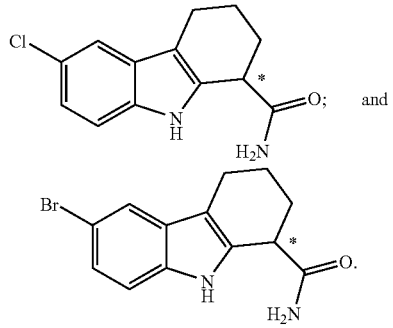

Suitable SIRT1 inhibitors include, e.g., 7-chloro-1,2,3,4-tetrahydro-cyclopenta[b]indole-3-carboxylic acid amide; 6-bromo-2,3,4,9-tetrahydro-1H-carbazole-2-carboxylic acid amide; 1,2,3,4-tetrahydro-cyclopenta[b]indole-3-carboxylic acid amide; and 6-chloro-2,3,4,9-tetrahydro-1H-carbazole-1-carboxylic acid(5-chloro-pyridin-2-yl)-amide.

Combination Therapy

In some embodiments, a subject treatment method comprises administering to an individual in need thereof an effective amount of a SIRT1 inhibitor or a SIRT1 activator, and at least one additional therapeutic agent.

HIV-associated Immune Hyperactivation

In some embodiments, as discussed above, a subject method provides for treating immune hyperactivation that is associated with an immunodeficiency virus infection. In some embodiments, a subject method for reducing immunodeficiency virus infection-associated immune hyperactivation involves administering a SIRT1 activator alone, e.g., as monotherapy. In other embodiments, a subject method for reducing immunodeficiency virus infection-associated immune hyperactivation involves administering a SIRT1 activator, and at least one additional therapeutic agent, in combination therapy.

Suitable additional therapeutic agents include, e.g., therapeutic agents for the treatment of an immunodeficiency virus infection, or for the treatment of a disorder that may accompany an immunodeficiency virus infection (e.g., a bacterial infection, a fungal infection, and the like). Suitable additional therapeutic agents include, e.g., beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof.

Increasing an Immune Response

In some embodiments, a subject method of increasing an immune response comprises administering to an individual in need thereof a SIRT1 inhibitor and at least one additional therapeutic agent in combined effective amounts to increase an immune response in the individual. In some embodiments, a subject method of increasing an immune response comprises administering to an individual in need thereof a SIRT1 inhibitor and an antigen in combined effective amounts to increase an immune response to the antigen in the individual. In some embodiments, a subject method of increasing an immune response comprises administering to an individual in need thereof a SIRT1 inhibitor and at least one additional therapeutic agent in combined effective amounts to increase an immune response in the individual; and administering an antigen to the individual, where an immune response to the antigen is increased.

Suitable additional therapeutic agents include, e.g., immunostimulatory polynucleotides ("ISS"; see, e.g., U.S. Pat. No. 7,479,285); an ISS conjugated to an antigen (see, e.g., U.S. Pat. No. 6,610,661); a Toll-like receptor agonist (see, e.g., U.S. Pat. No. 7,387,271); an immunostimulatory cytokine (e.g., IL-2); and the like. Suitable ISS include polynucleotides that include an unmethylated 5'-CG-3' sequence. ISS can be from about 6 nucleotides in length to about 200 nucleotides in length, or longer than 200 nucleotides in length. An ISS can comprise a phosphate backbone modification, where backbone phosphate group modifications include, e.g., methylphosphonate, phosphorothioate, phosphoroamidate and phosphorodithioate internucleotide linkages TLR agonists include, e.g., TLR1, TLR2, TLR3, TLR4, TLR5, TLR6, TLR7, TLR8 and TLR9 agonists. Suitable TLR agonists include, e.g., an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, and a thiazolonaphthyridine amine.

Reducing an Undesired Immune Response

In some embodiments, a subject method of reducing an undesired immune response (e.g., an autoimmune response; an allergic response; a graft-versus-host response; rejection of a transplanted organ, tissue, or cell) involves administering a SIRT1 inhibitor alone, e.g., as monotherapy. In other embodiments, a subject method of reducing an undesired immune response (e.g., an autoimmune response; an allergic response; a graft-versus-host response; rejection of a transplanted organ, tissue, or cell) involves administering a SIRT1 inhibitor in combination therapy with one or more additional therapeutic agents.

For the treatment of autoimmune disorders, a SIRT1 inhibitor can be administered in combination therapy with one or more agents for treating an autoimmune disorder. Those skilled in the art are aware of agents that are suitable for treating autoimmune disorders. For example, agents that are suitable for treating Type 1 diabetes include insulin, including naturally occurring insulin, insulin analogs, and the like. Interferon-alpha is an agent that is currently in use for treating multiple sclerosis, and can be used in combination therapy with a SIRT1 inhibitor. Other agents that are currently in use for treating autoimmune disorders include corticosteroid drugs; non-steroidal anti-inflammatory drugs (NSAIDs); and immunosuppressant drugs such as cyclophosphamide, methotrexate, and azathioprine.

For the treatment of allergies, a SIRT1 inhibitor can be administered in combination therapy with one or more agents for treating an allergic disorder. Suitable agents include, but are not limited to, antihistamines such as diphenhydramine (Benadryl); epinephrine; decongestants; and the like.

For reduction of graft rejection or for reduction of GVHD, a SIRT1 inhibitor can be administered in combination therapy with one or more agents for reducing graft rejection or GVHD. Agents suitable for reducing graft rejection or GVHD include, but are not limited to, glucocorticoids (e.g., cortisol; dexamethasone; etc.); cytostatic agents (e.g., cyclophosphamide; nitrosoureas; platinum compounds; methotrexate; azathioprine; mercaptopurine; dactinomycin; anthracyclines; mitomycin C; bleomycin; mitramycin; etc.); an anti-CD20 monoclonal antibody; cyclosporin; tacrolimus; voclosporin; sirolimus; and the like.

Formulations, Dosages, Routes of Administration

A SIRT1 activator or a SIRT1 inhibitor can be formulated with one or more pharmaceutically acceptable excipients. SIRT1 activators and SIRT1 inhibitors are referred to collectively below as "active agent" or "drug." A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The term "unit dosage form," as used herein, refers to physically discrete units suitable as unitary dosages for human and animal subjects, each unit containing a predetermined quantity of a subject active agent calculated in an amount sufficient to produce the desired effect in association with a pharmaceutically acceptable diluent, carrier or vehicle. The specifications for an active agent depend on the particular compound employed and the effect to be achieved, and the pharmacodynamics associated with each compound in the host.

In the subject methods, a SIRT1 activator or a SIRT1 inhibitor may be administered to the host using any convenient means capable of resulting in the desired outcome, e.g., reduction of disease, reduction of a symptom of a disease, etc. Thus, a SIRT1 activator or a SIRT1 inhibitor can be incorporated into a variety of formulations for therapeutic administration. More particularly, a SIRT1 activator or a SIRT1 inhibitor can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

In pharmaceutical dosage forms, a SIRT1 activator or a SIRT1 inhibitor ("active agent") may be administered in the form of its pharmaceutically acceptable salts, or an active agent may be used alone or in appropriate association, as well as in combination, with other pharmaceutically active compounds. The following methods and excipients are merely exemplary and are in no way limiting.

For oral preparations, an active agent (a SIRT1 activator or a SIRT1 inhibitor) can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. An active agent can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycol monomethyl ethers, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the subject active agent. Similarly, unit dosage forms for injection or intravenous administration may comprise a subject active agent in a composition as a solution in sterile water, normal saline or another pharmaceutically acceptable carrier.

An active agent can be formulated for administration by injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, an active agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of active agent can be accomplished using any of a variety of refillable, pump systems. Pumps provide consistent, controlled release over time. In some embodiments, the active agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug ("active agent") is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (a SIRT1 activator or a SIRT1 inhibitor) is delivered using an implantable drug delivery system, e.g., a system that is programmable to provide for administration of an active agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of an active agent adequate to achieve the desired state in the subject being treated.

Oral Formulations

In some embodiments, an active agent (a SIRT1 activator or a SIRT1 inhibitor) is formulated for oral delivery to an individual in need of such an agent.

For oral delivery, a formulation comprising an active agent will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, an active agent is formulated with one or more pharmaceutical excipients and coated with an enteric coating, as described in U.S. Pat. No. 6,346,269. For example, a solution comprising an active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for an active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate(HPMCP), cellulose acetate phthalate (CAP), polyvinyl phthalic acetate (PVPA), Eudragit™ and shellac.

Suitable oral formulations also include an active agent formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) *Biomaterials* 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly (lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B. V.).

Suitable oral formulations also include an active agent with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Trilayer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent, and an active agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Inhalational Formulations

An active agent (a SIRT1 activator or a SIRT1 inhibitor) will in some embodiments be administered to a patient by means of a pharmaceutical delivery system for the inhalation route. An active agent can be formulated in a form suitable for administration by inhalation. The inhalational route of administration provides the advantage that the inhaled drug can bypass the blood-brain barrier. The pharmaceutical delivery system is one that is suitable for respiratory therapy by delivery of an active agent to mucosal linings of the bronchi. This invention can utilize a system that depends on the power of a compressed gas to expel the active agent from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains an active agent, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An active agent can also be formulated for delivery with a nebulizer, which is an instrument that generates very fine liquid particles of substantially uniform size in a gas. For example, a liquid containing the active agent is dispersed as droplets. The small droplets can be carried by a current of air through an outlet tube of the nebulizer. The resulting mist penetrates into the respiratory tract of the patient.

A powder composition containing an active agent, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present invention. An active agent can be formulated in basically three different types of formulations for inhalation. First, an active agent can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, an active agent can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

An active agent can be formulated into dry powder formulations. Such formulations can be administered by simply inhaling the dry powder formulation after creating an aerosol mist of the powder. Technology for carrying such out is described within U.S. Pat. Nos. 5,775,320 and 5,740,794.

Dosages and Dosing

Depending on the subject and condition being treated and on the administration route, an active agent can be administered in dosages of, for example, 0.1 µg to 500 mg/kg body weight per day, e.g., from about 0.1 µg/kg body weight per day to about 1 µg/kg body weight per day, from about 1 µg/kg body weight per day to about 25 µg/kg body weight per day, from about 25 µg/kg body weight per day to about 50 µg/kg body weight per day, from about 50 µg/kg body weight per day to about 100 µg/kg body weight per day, from about 100 µg/kg body weight per day to about 500 µg/kg body weight per day, from about 500 µg/kg body weight per day to about 1 mg/kg body weight per day, from about 1 mg/kg body weight per day to about 25 mg/kg body weight per day, from about 25 mg/kg body weight per day to about 50 mg/kg body weight per day, from about 50 mg/kg body weight per day to about 100 mg/kg body weight per day, from about 100 mg/kg body weight per day to about 250 mg/kg body weight per day, or from about 250 mg/kg body weight per day to about 500 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

For example, an active agent can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

An exemplary dosage may be a solution suitable for intravenous administration; a tablet taken from two to six times daily, or one time-release capsule or tablet taken once a day and containing a proportionally higher content of active agent, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is in some embodiments one which provides up to about 1 µg to about 1,000 µg or about 10,000 µg of active agent in a blood sample taken from the individual being treated, about 24 hours after administration of the active agent to the individual.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

In some embodiments, multiple doses of an active agent are administered. The frequency of administration of an active agent can vary depending on any of a variety of factors, e.g., severity of the symptoms, etc. For example, in some embodiments, an active agent is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in some embodiments, an active agent is administered continuously.

The duration of administration of an active agent, e.g., the period of time over which an active agent is administered, can vary, depending on any of a variety of factors, e.g., patient response, etc. For example, an active agent can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, an active agent is administered for the lifetime of the individual.

Routes of Administration

An active agent is administered to an individual using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g, administration for longer than one week, e.g., administration over a period of time of from about 2 weeks to about one month, from about one month to about 3 months, from about 3 months to about 6 months, from about 6 months to about 1 year, or longer than one year).

Conventional and pharmaceutically acceptable routes of administration include intranasal, intramuscular, intratracheal, subcutaneous, intradermal, transdermal, sublingual, topical application, intravenous, ocular (e.g., topically to the eye, intravitreal, etc.), rectal, nasal, oral, and other enteral and parenteral routes of administration. Routes of administration may be combined, if desired, or adjusted depending upon the agent and/or the desired effect. The active agent can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, ocular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent can also be delivered to the subject by enteral administration. Enteral routes of administration include, but are not necessarily limited to, oral and rectal (e.g., using a suppository) delivery.

Methods of administration of an active agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Subjects Suitable for Treatment

Subjects suitable for treatment with a subject method include individuals in need of such treatment.

Methods of Reducing Chronic Immune Hyperactivity

Subjects suitable for treatment with a subject method of reducing chronic immune hyperactivity include individuals who have chronic immune hyperactivity due to an infection with an immunodeficiency virus, e.g., human immunodeficiency virus-1, human immunodeficiency virus-2.

Methods of Increasing an Immune Response

Subjects suitable for treatment a subject method of increasing an immune response include an individual who has been infected with a pathogenic microorganism; an individual who is susceptible to infection by a pathogenic microorganism, but who has not yet been infected; and an individual who has cancer.

Subjects suitable for treatment with a subject method of increasing an immune response include pediatric target populations, e.g., individuals between about 1 year of age and about 17 years of age, including infants (e.g., from about 1 month old to about 1 year old); children (e.g., from about 1 year old to about 12 years old); and adolescents (e.g., from about 13 years old to about 17 years old). Subjects suitable for treatment with a subject method of increasing an immune response include adult individuals.

Subjects suitable for treatment with a subject method of increasing an immune response include immunodeficient individuals, e.g., individuals with an acquired immunodeficiency, e.g., as a results of radiation therapy for cancer, as a result of corticosteroid treatment, as a result of cancer chemotherapy, etc. Also suitable for treatment with a subject method of increasing an immune response are individuals who have undergone bone marrow transplantation or any other organ transplantation, e.g., immunosuppressed individuals.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like. "α" preceding a protein denotes an antibody to that protein; for example, α-p65 is an antibody to p65.

Example 1

Human Immunodeficiency Virus Type 1 Tat Protein Inhibits the SIRT1 Deacetylase and Induces T Cell Hyperactivation Experimental Procedures Cells and Plasmids HeLa, 293, 293T and Jurkat cells were cultured under standard tissue culture conditions. MEF cells derived from SIRT1−/− cells were grown as described (Pagans et al., 2005). Mutant constructs for SIRT1 HDAC domain were prepared by site-directed mutagenesis using FLAG-tagged SIRT1 as a template. The Sir2a deletion constructs were kindly provided by V. Sartorelli, NIH, the 3×-κB luciferase reporter by N. Chirmule, Merck Inc, the IκBα luciferase reporter by K. Yamamoto, UCSF, and the E-selectin luciferase reporter by J. Pober, Yale University.

Infection with Lentiviral Vectors

LTR-GFP and LTR-Tat-GFP are HIV-based vectors derived from the pHR' series, in which GFP alone or Tat (101 aa) and GFP are under the control of the HIV-1 LTR through the use of an internal ribosomal entry site (Jordan et al., 2001). For experiments with mutant Tat, the EF-1α promoter was inserted into the LTR-GFP vector upstream of wild type or mutant Tat (EF1α-Tat-GFP). Each vector was cotransfected into 293T cells together with a packaging construct (pCMV-R8.91) that provides all HIV genes required for production of infective particles and a plasmid encoding the vesicular stomatitis virus envelope G protein (VSV-G) to produce pseudotyped viral particles with broad host range and high infectivity. Viral supernatant containing 1500 ng of p24 was used to infect 18×10$^6$ Jurkat T cells. Infections were carried out in 6-well plates at 2400 rpm in a Beckman-Coulter centrifuge for 2 h at 32° C. in the presence of polybrene (1 µg/ml, Sigma). Jurkat T cells (10$^6$) were stimulated with plate bound α-CD3 (3 µg/ml) and soluble α-CD28 (1 µg/ml) antibodies 36 h after infection as previously described (Ott et al., 1998) or were preincubated with nicotinamide (10 mM, Sigma) for 1 h before treatment with α-CD3/28 antibodies. Flow cytometry analysis of GFP expression (FACSCalibur, BD Bioscience) showed that infection efficiencies ranged from 70-98% GFP cells in individual experiments. Tat expression was visualized by western blotting with polyclonal α-FLAG and α-β-actin (Sigma) antibodies.

Generation of SIRT1- and Tat-expressing MEF Cell Lines

Open reading frames corresponding to Myc-tagged human SIRT1 and T7-tagged HIV-1 Tat (101 aa) were inserted into the murine stem cell virus (MSCV)-based retroviral vectors MSCV-puromycin and MSCV-zeocin, respectively (Clontech). To obtain recombinant virus, 10 µg of each construct or empty control vectors were transfected into BOSC23 cells, a retroviral packaging cell line derived from 293 cells. The supernatants were collected 48 h after transfection and filtered through a 0.45-µm membrane. SIRT1−/− MEF cells (2×10$^5$) were incubated with 2 ml of the supernatant containing SIRT1-expressing retrovirus or control virus together with polybrene (8 µg/ml, Sigma). Cells were selected after 48 h with puromycin (2.5 µg/ml, Invitrogen). Polyclonal puromycin-resistant MEF cells were reinfected with Tat-expressing or empty control retroviruses and selected in the presence of both puromycin (2.5 µg/ml) and zeocin (100 µg/ml, Invitrogen).

RNA Purification, cDNA Synthesis, and Real-time RT-PCR

Total RNA was extracted using RNA STAT-60 reagent (Tel-Test) according to the manufacturer's instruction. The first strand cDNA was generated using 2 µg of total RNA and SuperScript reverse transcriptase (Invitrogen). Human IL-2 and murine E-selectin mRNAs were quantified by QuantiTect gene expression assays (Qiagen). Murine IκBα and murine/human GAPDH mRNA concentrations were determined with SYBR Green I master mix (MCLab). Relative gene expression ratios between stimulated and nonstimulated conditions were calculated by the equation, ratio=$2^{-\Delta\Delta Ct}$, comparative Ct method (Applied Biosystems).

Transfections and Coimmunoprecipitations

Luciferase reporter constructs and protein expression vectors were transiently cotransfected into HeLa cells using Lipofectamine (Invitrogen). 24 h after transfection, cells were lysed and processed for luciferase assays (Promega). P values (paired t-test) were used for statistical analysis.

293 cells grown in 6-well plates at 70% confluency were cotransfected with expression vectors included in the Figure legends. Transfection, cell lysis, immunoprecipitation, and western blotting were previously described (Pagans et al., 2005).

Fluorescent Deacetylase Assay

Full-length human SIRT1 (His-tagged) was purified using Ni-NTA agarose (Qiagen) and Superdex 200 gel filtration. The rate of 1 µM SIRT1 was calculated for 200l µM fluorogenic deacetylase substrate (BioMol) in the presence of twelve concentrations (1, 2, 3, 4, 5, 6, 10, 15, 25, 50, 126, 252 µM) of synthetic Tat (72 aa; Peptide Specialty Laboratory, Heidelberg, Germany).

Radioactive HDAC Assays

Expression plasmids for FLAG-tagged wild type and mutants SIRT1 (1 µg) were transfected in 293 cells with lipofectamine reagent. Equal amounts of whole cell extracts (2 mg) were immunoprecipitated and in vitro HDAC assays were performed as previously described (Pagans et al., 2005).

Recombinant p65 protein prepared from baculovirus-infected Sf9 insect cells (BD Biosciences) was acetylated by immunoprecipitated p300 overexpressed in 293 cells as previously described (Chen et al., 2005). Acetylated p65 protein was incubated with recombinant SIRT1 (1 µg/5U; Biomol) in SIRT1 deacetylase buffer (50 mM Tris-HCl pH 9, 4 mM $MgCl_2$, 0.2 mM DTT) in the presence of NAD (1 mM; Sigma) for 3 h at 37° C. Reactions containing synthetic Tat (0.1 μg) or nicotinamide (10 mM) were preincubated for 15 min at room temperature. Reactions were stopped by the addition of SDS loading buffer, boiled, and after brief centrifugation, analyzed by western blotting with rabbit a-AcK310 p65 (Chen et al., 2005) or mouse α-p65 antibodies (sc-8008, Santa Cruz).

Results

Tat and Nicotinamide Hyperactivate T Cells Via the Same Cellular Pathway

To recapitulate the effect of Tat on immune activation in a manner as close to natural HIV infection as possible, we employed an HIV-based lentiviral vector in which both FLAG-tagged Tat and green fluorescent protein (GFP) are expressed under the control of the HIV promoter in the 5'-LTR. Jurkat T cells were infected with viral particles containing this vector or a control vector expressing only GFP. Infected cultures were stimulated with antibodies specific for the CD3 and CD28 receptors to mimic physiological T-cell activation.

Figure 1B:
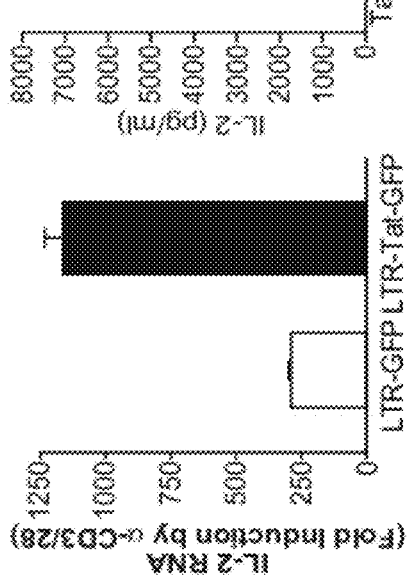
Figure 1C:
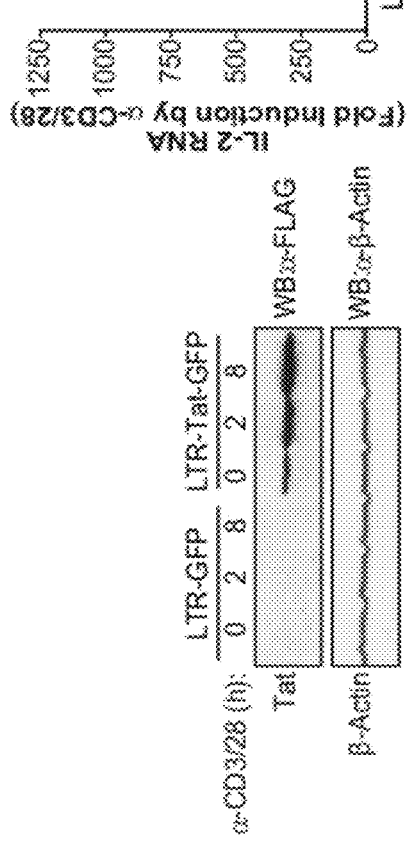

Tat expression was visualized by western blot analysis (FIG. 1A). Treatment with α-CD3/28 slightly increased the levels of Tat due to the stimulatory effect of these antibodies on the viral LTR. In cells expressing Tat, a ~1200-fold induction of IL-2 mRNA was detected by real-time PCR in response to α-CD3/28 treatment, whereas IL-2 expression in control cells was only induced ~250 fold (FIG. 1B). A similar difference was observed when IL-2 protein was measured in the culture supernatant (FIG. 1C). No effect of Tat was observed in nonactivated cultures. These findings recapitulated results previously obtained in peripheral blood lymphocytes and Jurkat T cells infected with infectious HIV and support a model where Tat synergistically stimulates IL-2 production following ligation of the CD3 and CD28 receptors (Fortin et al., 2004; Ott et al., 1997).

Figure 1D:
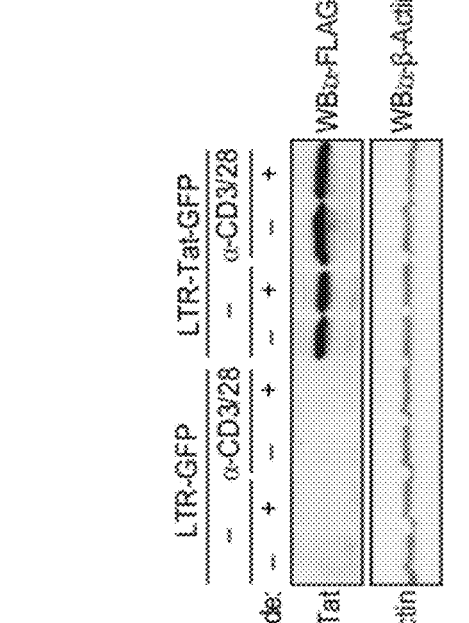
Figure 1E:
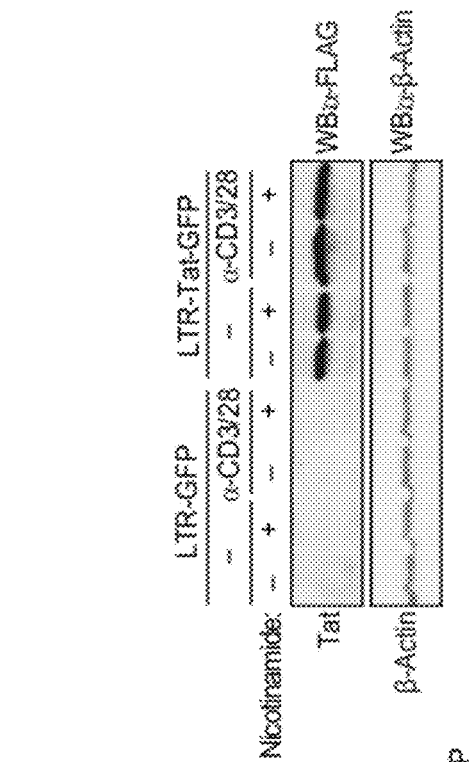
Figure 1F:
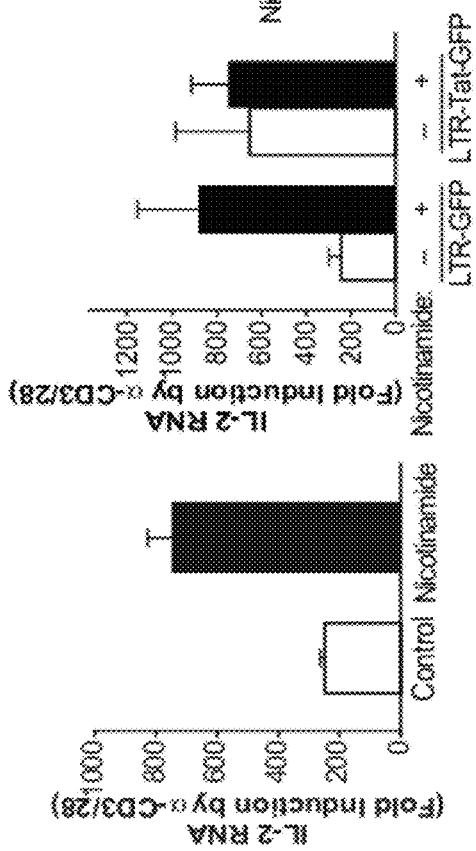

To test the potential regulatory role of SIRT1 in the IL-2 response, we treated Jurkat T cells with nicotinamide, a natural byproduct of the sirtuin deacetylase reaction which functions as a feedback inhibitor of these enzymes (Landry et al., 2000). Treatment with nicotinamide superinduced IL-2 mRNA to similar levels as Tat in α-CD3/28-stimulated cells (FIG. 1D). To test whether Tat and nicotinamide synergize in the hyperactivation of IL-2 expression, we treated Tat- or control-infected Jurkat cultures with nicotinamide before activation. These studies revealed no additive effect of combinations of Tat and nicotinamide on IL-2 expression in α-CD3/28-stimulated T cells (FIG. 1E). Levels of Tat protein were equivalent in infected cultures treated with nicotinamide and control-treated cultures excluding the possibility that nicotinamide suppressed the expression of Tat (FIG. 1F). These results suggest that Tat and nicotinamide may target closely related cellular pathways and raised the interesting possibility that Tat hyperactivation of T cells may involve its known assembly with SIRT1.

FIGS. 1A-F. Tat and nicotinamide cause T-cell hyperactivation (A) Western blot analysis of Tat protein in Jurkat T cells infected with lentiviral vectors expressing LTR-GFP and LTR-Tat-GFP. Infected cultures were activated for 2 h and 8 h with α-CD3/28 antibodies. (B) Real-time RT-PCR analysis of IL-2 mRNA levels in infected cultures 2 h after activation with α-CD3/28. Results are expressed as fold induction by α-CD3/28 treatment. (C) IL-2 protein levels measured by ELISA in the supernatant of infected cultures 8 h after α-CD3/28 treatment. (D) Real-time RT-PCR analysis of IL-2 mRNA levels in noninfected Jurkat T cells after treatment with nicotinamide and activation with α-CD3/28. (E) Real-time RT-PCR analysis of IL-2 mRNA levels in Jurkat T cells infected with lentiviral vectors after treatment with nicotinamide and activation with α-CD3/28 antibodies. (F) Western blot analysis of Tat protein in Jurkat T cells infected with lentiviral vectors after treatment with nicotinamide and activation with α-CD3/28. In B-E averages of three independent experiments (±SEM) are shown.

SIRT1 is Required for the Hyperactivation of NF-κB Target Genes by Tat

T-cell activation is coupled to the stimulation of several transcription factors that regulate the transcriptional status of the IL-2 gene. Efforts were focused on NF-κB since its activity is regulated by SIRT1 (Yeung et al., 2004). It was previously previously reported that Tat enhanced IL-2 promoter activity via the NF-κB binding sites present within the IL-2 promoter (Fortin et al., 2004; Ott et al., 1997; Ott et al., 1998; Westendorp et al., 1994). It was speculated that Tat, like nicotinamide, inhibits the SIRT1 deacetylase activity leading to hyperactivation of NF-κB-responsive genes including IL-2.

This hypothesis was tested in cells derived from SIRT1–/– mice. Mouse embryonic fibroblasts (MEFs) lacking SIRT1 expression were infected with a retroviral vector expressing SIRT1 or the empty vector alone. Polyclonal populations of SIRT1-expressing or SIRT1-negative cells were each infected with retroviral vectors expressing Tat or with the empty vector alone. This protocol generated four polyclonal MEF cultures, allowing the analysis of the effect of Tat in the presence or absence of SIRT1 (FIG. 2A). MEF cell lines were treated with TNFα to induce NF-κB. Since MEF cells do not produce IL-2, we focused instead on the expression of IκBα, a ubiquitous NF-κB-responsive gene product (Sun et al., 1993). We found that Tat expression increased endogenous levels of IκBα mRNA 2 to 4-fold over control-infected cells in response to TNFα (FIG. 2B). Remarkably, this effect was only observed in cultures where SIRT1 expression had been reconstituted. No difference between Tat-expressing and control cells was detected in SIRT1-negative cells, indicating that Tat-mediated superinduction of NF-κB-responsive genes was dependent on SIRT1.

A similar result was observed with E-selectin, another NF-κB-responsive gene that is also superinduced by Tat (Cota-Gomez et al., 2002; Lee et al., 2004). After TNFα treatment, endogenous E-selectin gene expression was enhanced 6-fold by Tat in SIRT1-expressing, but not in SIRT1-negative cells (FIG. 2C). Here, the Tat effect was only observed at 2 h after TNFα treatment. At 8 h, no induction of E-selectin gene expression was evident, consistent with the prior finding that E-selectin mRNA accumulation peaks 2 h after TNFα treatment and then rapidly declines (Edelstein et al., 2005). In contrast to the results with IicBa and E-selectin, Tat had no effect on the constitutive expression of the endogenous glyceraldehyde-3-phosphate dehydrogenase gene (GAPDH) (FIG. 2D).

FIGS. 2A-D. Tat-mediated superinduction of NF-κB-responsive genes requires SIRT1 (A) Western blot analysis of SIRT1, Tat and β-actin in SIRT1–/– MEF cells infected with MSCV-based retroviral particles expressing SIRT1 or Tat. (B-D) Real-time RT-PCR analysis of IκBα (B), E-selectin (C), and GAPDH (D) mRNA levels in the four polyclonal MEF populations described in (A) after incubation with TNFα (20 ng/ml) for 2 h and 8 h. Data are presented relative to values obtained in cells lacking Tat (100%). The mean of three independent experiments (±SEM) is shown.

Tat Neutralizes the Negative Effect of SIRT1 on NF-κB Function

Figure 3A:
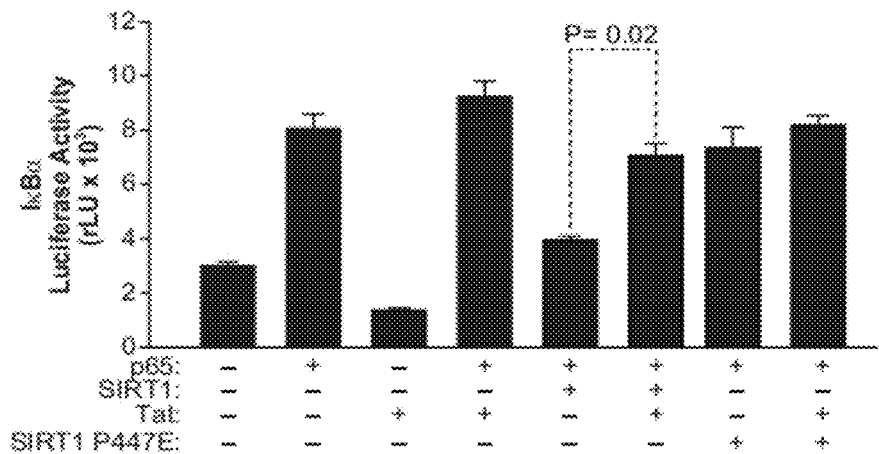
FIGS. 3A-C depicts the effect of Tat on the inhibitory effect of SIRT1 on NK-κ-B-responsive promoters.

Next, we assessed the effect of Tat on the IκBα and E-selectin gene promoters. We transfected an IκBαpromoter luciferase reporter construct together with combinations of expression vectors encoding p65, SIRT1, and Tat into HeLa cells (FIG. 3A). SIRT1 suppressed the activation of the IκBα promoter by p65 in accordance with the previous finding that deacetylation by SIRT1 inactivates p65 activity (Yeung et al., 2004). Coexpression of Tat restored p65 activity, suggesting that Tat interfered with the deacetylation of p65 by SIRT1 (FIG. 3A). No change in expression levels of p65 was observed by western blotting in the presence of SIRT1 or Tat. The suppressive activity of SIRT1 was dependent on its intrinsic deacetylase activity of SIRT1, since a catalytically inactive SIRT1 mutant (P447E; shown in FIG. 4D) did not suppress the activity of p65 and was unresponsive to the action of Tat. Expression of Tat did not affect basal or p65-mediated activity of the IκBα promoter in the absence of SIRT1 expression (FIG. 3A).

Figure 3B:
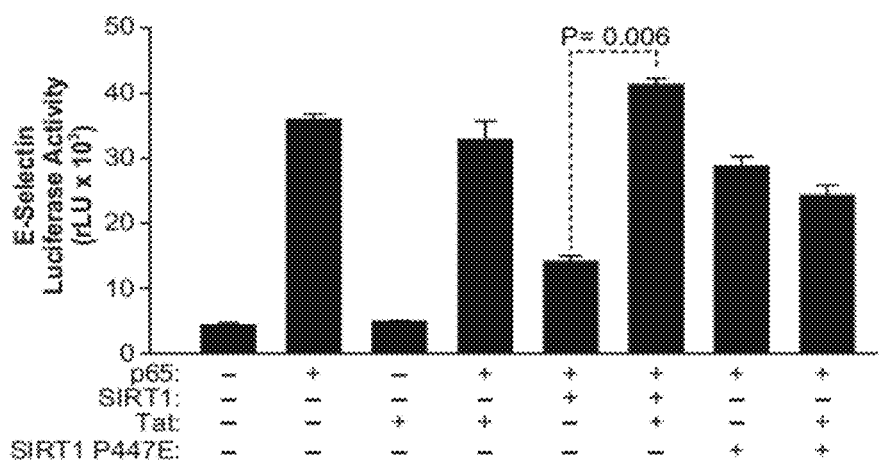

The same results were observed using an E-selectin promoter luciferase construct. Again, SIRT1 reduced p65-activated E-selectin promoter activity, and Tat reversed the negative effect of SIRT1 (FIG. 3B). No reduction was observed with the mutant SIRT1, which was also unresponsive to Tat (FIG. 3B).

Figure 3C:
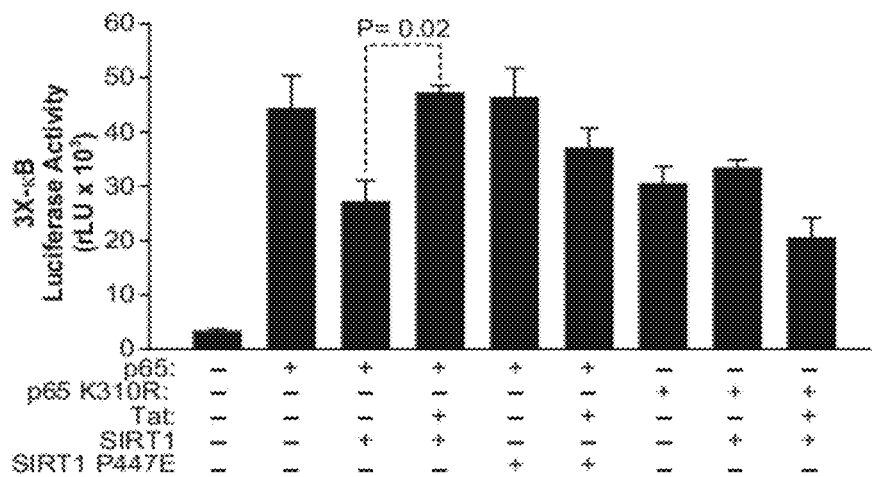

To verify that Tat and SIRT1 modulated the activities of the E-selectin and IκBα promoters through NF-κB, we transfected p65-, Tat-, and SIRT1-expressing constructs together with a 3x-κB luciferase reporter. Expression of SIRT1 reduced p65-mediated activation of the KB reporter, while coexpression of Tat reversed this negative effect (FIG. 3C). Again, expression of the catalytically inactive SIRT1 mutant did not interfere with the activity of p65, and additional Tat expression had no effect in this setting (FIG. 3C). Likewise, overexpression of a p65 mutant (K310R), which lacked the deacetylation site for SIRT1 and showed reduced activation of the NF-κB luciferase construct, was unaffected by SIRT1 and Tat (FIG. 3C). These results demonstrate that Tat targets the SIRT1 deacetylase activity to hyperactivate NF-κB function.

FIGS. 3A-C. Tat neutralizes the inhibitory effect of SIRT1 on NF-κB-responsive promoters. Promoter reporter assays using (A) the IκBα, (B) the E-selectin, and (C) the 3x-KB luciferase reporter construct. Luciferase constructs (0.2 µg) were transiently cotransfected with expression vectors for p65 or p65 K310R (1 ng), SIRT1 or SIRT1 P447E (0.2 µg), and Tat (50 ng) into HeLa cells. The mean of three independent experiments (±SEM) is shown.

Tat Binds the Deacetylase Domain of SIRT1

We showed previously that Tat and SIRT1 interact in cells (Pagans et al., 2005). To map the Tat-interacting domain in SIRT1, we used deletion mutants of the murine SIRT1 protein (Sir2a) (Fulco et al., 2003). Progressive N-terminal deletions at amino acids 120, 236, or 341 did not affect coimmunoprecipitation of SIRT1 with Tat (FIG. 4A, lanes 1-3). However, deletion of the first 512 amino acids abrogated binding to Tat, indicating that the Tat-interaction domain lies between amino acids 341 and 512 of SIRT1 (FIG. 4A, lane 4). In agreement with this conclusion, expression of amino acids 236 to 510 of SIRT1 proved sufficient to support interaction with Tat (FIG. 4A, lane 5). The results of the coimmunoprecipitation studies are summarized in FIG. 4B.

The region spanning amino acids 341-512 contains the catalytic domain of SIRT1, which is shared among all sirtuins. It is 98% conserved in the murine and human SIRT1 proteins and consists of two distinct domains: a large Rossmann fold domain characteristic of NAD$^+$-binding proteins and a smaller domain containing a structural zinc ion. The NAD and acetyl-lysine substrate bind in the active site cleft between the two domains (Avalos et al., 2002). To determine whether Tat interacts with the catalytic domain of SIRT1, point mutations were introduced into human SIRT1 expression construct to disrupt NAD$^+$-binding (R274A, N346A) or acetyl-lysine binding (F414D, E416A, V445E, P447E) (FIG. 4C). In addition, we mutated two conserved cysteines (C371/374G) located in a zinc-bound domain predicted to serve as a protein-protein interaction domain (Min et al., 2001).

Prior to analyzing their interaction with Tat, the catalytic activities of these mutants were measured using an in vitro HDAC assay and radioactive acetylated histone peptides as substrates. We transfected wildtype and mutant SIRT1 proteins into 293 cells and immunoprecipitated the FLAG-tagged proteins (FIG. 4D). The immunoprecipitated material was tested for enzymatic activity. Incubation with wildtype SIRT1 or the R274A mutant resulted in deacetylation of the histone peptide in the presence of NAD (FIG. 4D). The deacetylase activity of the F414D, E416A, and V445E mutants was severely impaired, while no activity was measured for N346A, C371/374G, and P447E mutants.

Next, we cotransfected wildtype and SIRT1 mutants together with T7-tagged Tat. Wildtype and mutant SIRT1 proteins were expressed at similar levels (FIG. 4E, upper panel). After pulldown with T7-agarose, immunoprecipitated complexes were analyzed for the presence of SIRT1 (FIG. 4E, lower panels). While binding to Tat was preserved in SIRT1 R274A, N346A, C371/374G, and E416A, no binding to Tat was observed with any of the SIRT1 mutants carrying a mutation within the acetyl-lysine-binding domain (F414D, V445E, P447E). The same results were obtained when SIRT1 proteins were immunoprecipitated, and coimmunoprecipitation of Tat was determined. These data demonstrate that Tat interacts with the substrate-binding domain of SIRT1.

FIGS. 4A-E. Tat binds to the acetyl lysine-binding site in SIRT1 (A) Communoprecipitation assay of Tat and SIRT1 deletion mutants. Expression vectors for Myc-tagged murine Sir2a deletion mutants or full length human SIRT1 (each 1 µg) were transiently cotransfected with constructs expressing FLAG-tagged Tat (1 µg) in 293 cells Immunoprecipitations were performed with α-FLAG agarose and western blotting with a-Myc and α-FLAG antibodies. (B) Schematic summary of Tat binding to murine Sir2a deletion mutants. The relative localization of the human SIRT1 HDAC domain is shown at the bottom. (C) Schematic representation of the human SIRT1 HDAC domain with point mutations. (D) In vitro HDAC assays of immunoprecipitated human SIRT1 mutants with and without NAD$^+$. (E) Communoprecipitation of SIRT1 mutants and Tat in 293 cells. Cell extracts were immunoprecipitated with α-T7 agarose followed by western blotting with α-FLAG and α-T7 antibodies.

Tat Inhibits the SIRT1 Deacetylase activity and Induces Hyperacetylation of NF-κB Since an intact acetyl-lysine binding function is critical for the deacetylase activity of SIRT1, we tested whether Tat binding affected the enzymatic activity of SIRT1. We performed fluorescent deacetylation assays using purified full-length SIRT1 and acetylated p53 peptides (aa 379-382). Addition of synthetic Tat (aa 1-72) inhibited deacetylation of p53 by SIRT1 in a dose-dependent manner (FIG. 5A). The Tat concentration required for half maximal inhibition (IC$_{50}$) of SIRT1 was 3.5±0.5 µM. In contrast, the IC$_{50}$ for nicotinamide in the same experiments was 208±21 µM (data not shown). This result indicates that Tat is a very potent inhibitor of the SIRT1 deacetylase activity.

Next, we examined the effect of Tat on deacetylation of p65. In vitro acetylated recombinant p65 protein was incubated with recombinant SIRT1 and synthetic Tat proteins. The extent of deacetylation was determined by western blotting with antibody specific for acetylated K310 in p65 ($\alpha$-AcK310 p65). SIRT1 deacetylated p65 in the absence of Tat (FIG. 5B, lane 2). In the presence of Tat, deacetylation of p65 by SIRT1 was suppressed, confirming that direct interaction between Tat and SIRT1 inhibits the deacetylase activity of SIRT1 (FIG. 5B, lane 3). The same inhibition of p65 deacetylation by SIRT1 was observed with nicotinamide (FIG. 5B, lane 4).

To test the effect of Tat on p65 acetylation in cells, we transfected expression vectors for p65, p300, SIRT1 and Tat into 293 cells. Overexpressed p65 translocates spontaneously into the cell nucleus because of limiting amounts of cellular I$\kappa$B$\alpha$. To induce efficient p65 acetylation, we coexpressed the acetyltransferase p300 (FIG. 5C, lane 2). Coexpression of SIRT1 reduced acetylation of p65 at K310 caused by p300 as expected (FIG. 5C, lane 3). Introduction of Tat restored p65 acetylation in a dose-response manner (FIG. 5C, lane 4-6). These results demonstrate that Tat reverts deacetylation of p65 by SIRT1 in cells and induces relative hyperacetylation of p65 in the presence of SIRT1.

We also examined the acetylation status of endogenous p65 in Tat-expressing cells. 293 cells were tranfected with the Tat expression vector and treated with TNF$\alpha$ to induce nuclear translocation of endogenous p65. Acetylation of endogenous p65 was slightly increased in the presence of Tat (FIG. 5D, lanes 1 and 2). Coexpression of p300 with Tat strongly induced hyperacetylation of p65, consistent with the model that Tat inhibits physiological deacetylation of NF-$\kappa$B by SIRT1 (FIG. 5D, lanes 3 and 4).

FIGS. 5A-D. Tat inhibits the SIRT1 deacetylase activity (A) In vitro deacetylation assay of recombinant SIRT1 in the presence of synthetic Tat (aa 1-72). The rate of 1 $\mu$M SIRT1 was calculated for 200 $\mu$M fluorogenic deacetylase substrate (aa 379-382 of p53) in the presence of twelve concentrations of synthetic Tat. The data were plotted in Prism with X equal to $\text{Log}_{10}$[Tat] and Y equal to rate. A nonlinear regression was done using the one-site competitive binding equation to determine the $\text{IC}_{50}$. (B) In vitro deacetylase assay of recombinant SIRT1 and recombinant acetylated p65 in the presence of synthetic Tat or nicotinamide Western blotting was performed with $\alpha$-AcK310 p65 and $\alpha$-p65 antibodies. (C) In vivo acetylation assay of overexpressed p65. Expression vectors encoding T7-tagged p65 (0.5 $\mu$g), p300 (2 $\mu$g), SIRT1 (1 $\mu$g), and Tat (0.1, 0.25, and 0.5 $\mu$g) were transiently cotransfected in 293 cells as indicated. Total cell lysates were analyzed by western blotting with $\alpha$-AcK310 p65 or $\alpha$-T7 antibodies. (D) In vivo acetylation assay of endogenous p65. 293 cells were cotransfected with expression vectors encoding Tat (0.5 $\mu$g) and p300 (10 $\mu$g) as indicated and treated with TNF$\alpha$ (20 ng/ml) and trichostatin (TSA; 400 nM) over night. TSA is an inhibitor of class I and II HDACs, but not sirtuins and was added to prolong nuclear retention of p65 through hyperacetylation of K218 and K220. Endogenous p65 was immunoprecipitated using $\alpha$-p65 antibody and subjected to western blotting with $\alpha$-AcK310 p65 or $\alpha$-p65 antibodies.

Tat Induces T-cell Hyperactivation Through Hyperacetylation of NF-$\kappa$B

Figure 6A:
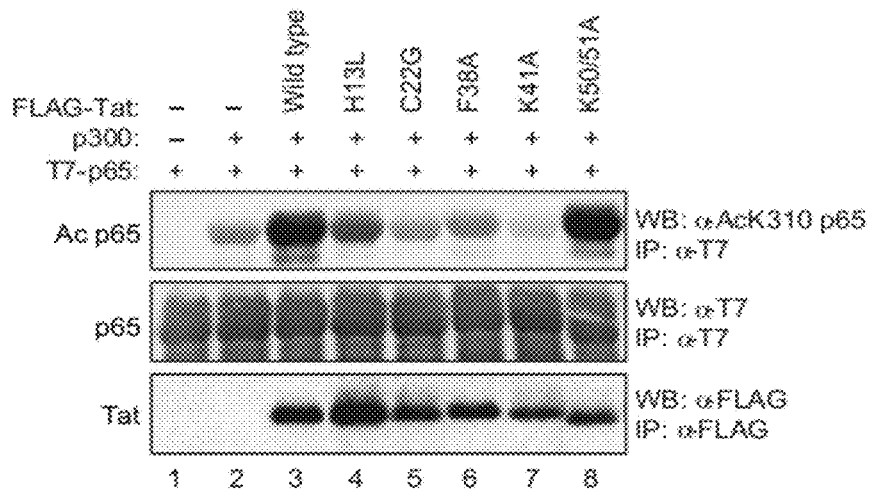
FIGS. 6A-C depict the effect of hyperacetylation of p65 by Tat on T-cell hyperactivation.

To examine whether the functions of Tat in SIRT1 inhibition and T-cell hyperactivation are linked, we searched for Tat mutants deficient in the induction of p65 hyperacetylation. We screened a series of Tat proteins carrying point mutations in different protein domains of Tat. These point mutants were expressed in 293 cells together with p65 and the p300 acetyltransferase. Expression of p300 induced acetylation of K310 in p65, and wild type Tat (two-exon, 101 aa) proteins further enhanced this acetylation (FIG. 6A, lanes 1-3). Mutations within the so-called cysteine-rich and core domains of Tat (aa 22-31 and aa 38-48) markedly decreased hyperacetylation of p65 induced by Tat, while a point mutation introduced into the N-terminal acidic domain (aa 1-21) still hyperacetylated p65 albeit to a lesser extent (FIG. 6A, lanes 4-7). A Tat mutant containing two point mutations within the RNA-binding domain (aa 49-59) induced p65 hyperacetylation as efficiently as the wild type protein (FIG. 6A, lane 8). Western blotting with FLAG antibody showed that wild type and H13L Tat were equally expressed while the other Tat mutants were slightly less expressed (FIG. 6A, lower panel). Of note, expression levels of K41A and K50/51A Tat were equivalent, and these mutants were chosen for further analysis.

Figure 6B:
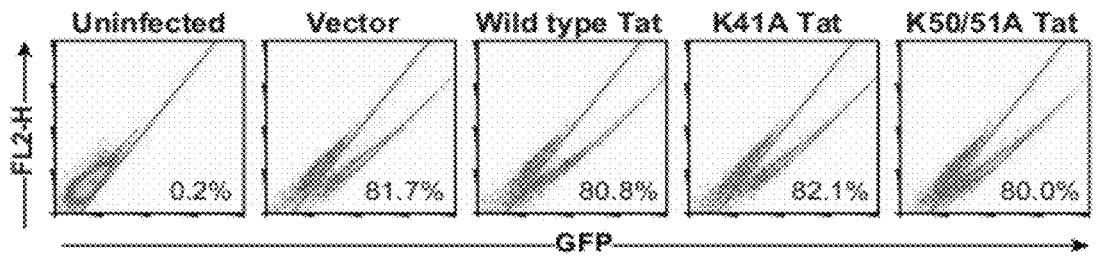
Figure 6C:
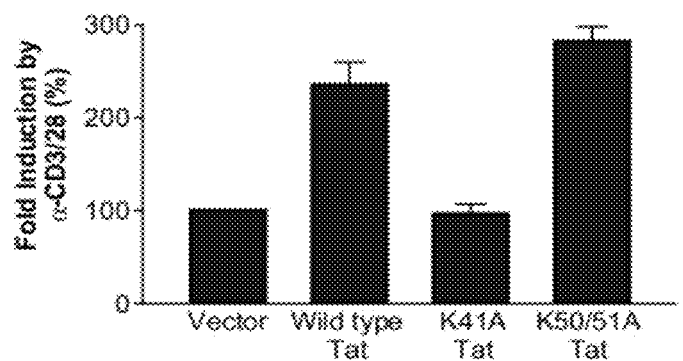

To study the effect of Tat mutations on T-cell activation, we generated lentiviral vectors expressing wild type or mutant Tat proteins (K41A and K50/51A Tat). Because both Tat mutants have reduced transcriptional activities on the HIV LTR, we chose a lentiviral construct, which contained the heterologous elongation factor 1$\alpha$ (EF-1$\alpha$) promoter driving Tat and GFP expression instead of the HIV LTR. High titer viral stocks were produced and used to infect Jurkat T cells. Flow cytometry of GFP showed equivalent infection with wild type or mutant Tat-expressing viruses (FIG. 6B). Following treatment with $\alpha$-CD3/28 antibodies, IL-2 mRNA levels were superinduced 2-3 fold by wild type Tat (FIG. 6C). No superinduction was observed with K41A Tat while K50/51A Tat superinduced IL-2 mRNA levels as efficiently as wild type Tat (FIG. 6C). These results collectively demonstrate that Tat expressed in the context of lentiviral infection hyperactivates T cells through hyperacetylation of p65.

FIGS. 6A-C. Hyperacetylation of p65 by Tat contributes to T-cell hyperactivation (A) Induction of p65 hyperacetylation by wild type and mutant Tat. Expression vectors encoding T7-tagged p65 (0.5 $\mu$g), p300 (2 $\mu$g), wild type and mutant Tat (1 $\mu$g each) were transiently cotransfected in 293 cells as indicated Immunoprecipitations were performed with $\alpha$-T7 agarose or $\alpha$-FLAG agarose to isolate p65 or Tat followed by western blotting with $\alpha$-AcK310 p65, $\alpha$-T7, and $\alpha$-FLAG antibodies. (B) Flow cytometry of Jurkat T cells infected with lentiviral vectors expressing wild type or mutant Tat and GFP. Data are representative of three independent experiments in which infection efficiencies ranged from 75-85% GFP cells. (C) Real-time RT-PCR analysis of IL-2 mRNA levels induced in infected Jurkat T cells after activation with $\alpha$-CD3/28 antibodies. Data are presented as fold induction by $\alpha$-CD3/28 treatment relative to vector (EF-1a-GFP)-infected cells (100%). The average (mean±SEM) of three independent experiments is shown.

Figure 7A:
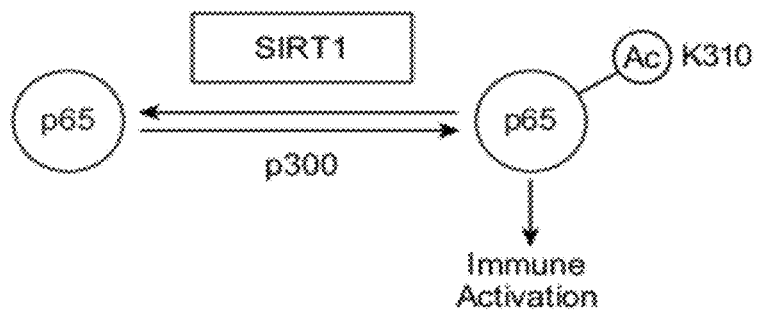
FIGS. 7A and 7B depict a model for Tat effects on SIRT1 deacetylase activity, T-cell activation, and HIV transcription.
Figure 7B:
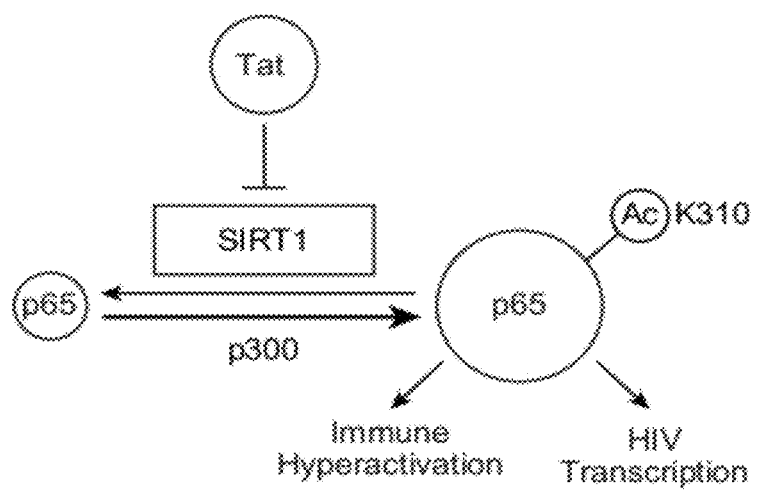

The data presented above show that Tat binds to the SIRT1 catalytic site and impairs the ability of SIRT1 to deacetylate K310 in p65. It was also found that NF-$\kappa$B activity is "superactivated" in the presence of Tat. Based on these results, a model is proposed where Tat hyperactivates T cells through inhibition of SIRT1 and abnormally sustained action of NF-$\kappa$B. In the absence of Tat, a balance of p300 and SIRT1 activities regulates p65 acetylation. This balance tightly controls the activation of cellular genes involved in the immune response of T cells (FIG. 7A). During HIV infection, Tat expression disrupts the balance between p300 and SIRT1 and increases levels of acetylated p65 through inhibition of SIRT1 (FIG. 7B). This increase hyperactivates the function of NF-$\kappa$B and the expression of NF-$\kappa$B-responsive genes including IL-2.

One of the most studied NF-κB-responsive genes is HIV itself. The two NF-κB-binding sites in the HIV enhancer link HIV transcription to the activation status of the infected T cells. This is particularly important at the beginning of the infectious process and during reactivation from latency when Tat levels are limiting. During these times, the action of cellular transcription factors, most importantly NF-κB, is essential for the production of full-length viral transcripts necessary for the initial synthesis of Tat. Once Tat accumulates to sufficient levels, it binds to TAR RNA and dramatically increases the elongation competence of the RNA polymerase II complex through recruitment of the P-TEFb complex. At that time, Tat may also enhance NF-κB function through inhibition of SIRT1 (FIG. 7B).

FIGS. 7A and 7B. Tat blocks the SIRT1 deacetylase activity and superinduces T-cell activation and HIV transcription via NF-κB.

Example 2

SIRT1 Activators Suppress Tat-induced T Cell Hyperactivation

Figure 8A:
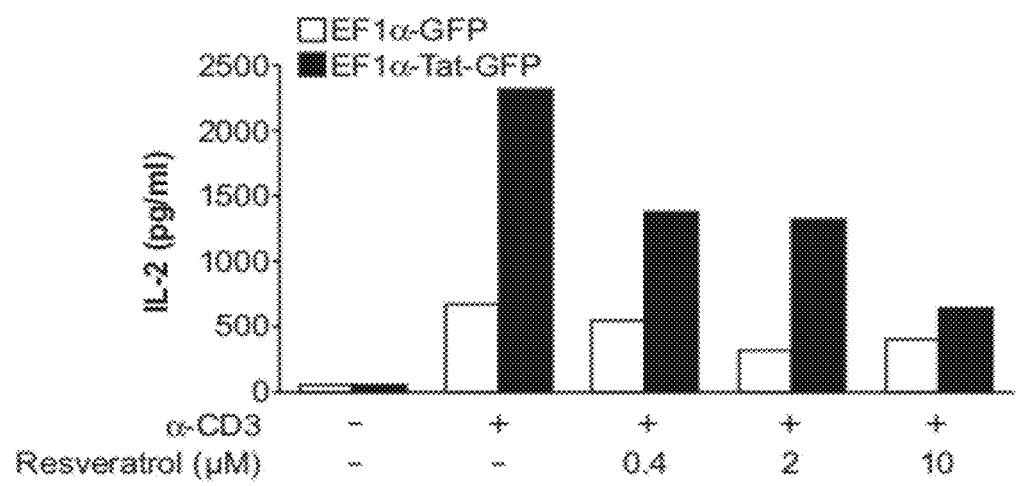
FIGS. 8A and 8B depict the effect of SIRT1 activators on Tat-mediated T cell hyperactivation.

Lentiviral vectors, which contained the heterologous elongation factor 1α (EF-1α) promoter driving Tat and GFP expression, were generated. High titer viral stocks were produced and used to infect Jurkat T cells. Flow cytometry of GFP showed equivalent infection with EF-1α-GFP or EF-1α-Tat-GFP viruses. Infected cultures were stimulated with antibodies specific for the CD3 receptor and treated with increased concentrations of resveratrol (0.4 μM, 2 μM, and 10 μM), a known SIRT1 activator for 16 hrs. IL-2 protein was measured in the culture supernatant by ELISA assay. Following stimulation with α-CD3 antibody, IL-2 protein was super-induced ~4-fold by wild type Tat (FIG. 8A). In cells expressing Tat, ~2300 pg/ml of IL-2 protein was detected in response to α-CD3 treatment, whereas in control cells, only ~600 pg/ml of IL-2 protein was induced. Superinduction of IL-2 in Tat-expressing cells was abolished by resveratrol in a concentration dependent manner (FIG. 8A). Treatment of infected cells with 10 μM of resveratrol completely impaired the ability of Tat to superinduce IL-2 production.

Resveratrol, a polyphenolic compound present in red wine, functions as a (weak) reversible activator of SIRT1 enzymatic activity (Howitz et al., (2003) Nature 425:191-196., Baur et al., (2006) *Nat. Rev. Drug. Discov.*). Recently, novel 1000-fold more potent and structurally unrelated small molecule activators of SIRT1 have been developed and have shown potent activity in obesity and insulin resistance (Milne et al., (2007) *Nature* 450:712-716).

Figure 8B:
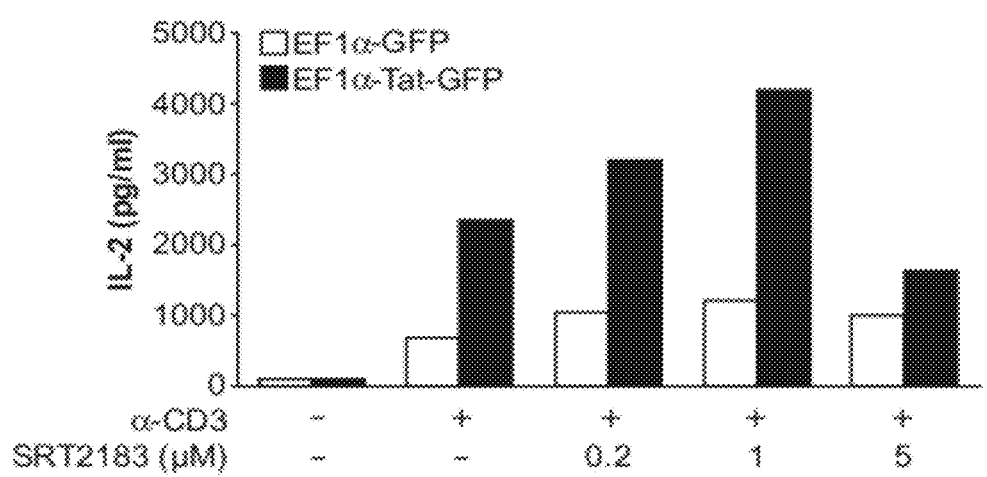

The effects of small molecule of SIRT1 (SRT2180) on T cell hyperactivation in Tat-expressing cells were examined. Jurkat T cells were infected with EF-1α-GFP or EF-1α-Tat-GFP viruses (FIG. 8B). Infected cultures were stimulated with α-CD3 antibody and treated with SRT2183 (0.2, 1, and 5 μM) for 16 hrs. Low concentrations of SRT2183 (0.2 and 1 μM) caused increases in IL-2 protein both in control and Tat expressing cells (FIG. 8B). However, higher concentration of SRT2183 (5 μM) suppressed the production of IL-2 protein in Tat expressing cells while slight increase in IL-2 protein was observed in control cells. These results indicate that activation of SIRT1 by either resveratrol or small molecule counterbalance the block in SIRT1 function by Tat and can suppress elevated levels of IL-2 in Tat-expressing cells.

FIGS. 8A and 8B. Resveratrol and small molecule activator of SIRT1 (SRT2183) suppresses T cell hyperactivation by Tat. (A) IL-2 protein levels measured by ELISA in the supernatant of infected cultures. 24 hrs after infection with EF1α-GFP and EF1α-Tat-GFP viruses, Jurkat T cells were stimulated with α-CD3 antibody in the presence of increased concentrations of resveratrol (0.4, 2, and 10 μM) for 16 hrs. (B) 24 hrs after infection with EF1α-GFP and EF1α-Tat-GFP viruses, Jurkat T cells were stimulated with α-CD3 antibody in the presence of increased concentrations of SRT2183 (0.2, 1, and 5 μM) for 16 hrs. IL-2 protein levels were measured by ELISA in the supernatant of infected cultures.

Example 3

SIRT1 regulates FoxP3 Stability and Treg Differentiation Through Deacetylation of Three Novel Acetylation Sites in FoxP3

The FoxP3 transcription factor is the master regulator of regulatory T cell (Treg) differentiation. High-level FoxP3 expression is required to support the immune suppressive activity of Tregs while Tregs expressing low levels of FoxP3 may cause autoimmunity. Here we show that FoxP3 protein expression is regulated at the posttranscriptional level by the NAD+-dependent SIRT1 deacetylase. Induced Treg differentiation is suppressed when SIRT1 is overexpressed. In contrast, SIRT1 knockdown or treatment with a small molecule inhibitor of SIRT1 (Ex-527) stabilizes FoxP3 protein expression. Importantly, treatment with Ex-527 prevents loss of FoxP3 expression in thymus-derived natural Tregs during ex vivo expansion. Using mass spectrometry of immunoprecipitated FoxP3, we identified three novel acetylation sites in FoxP3 (K31, K262, K267). Mutant FoxP3 proteins, in which the three sites were substituted by arginines, accumulate in cells to higher levels than wildtype FoxP3 and are not further stabilized by treatment with Ex-527. Collectively, our data support a model where SIRT1 deacetylates and destabilizes FoxP3 in Tregs. SIRT1 inhibitors may serve to optimize Treg-based approaches to treat autoimmune diseases or graft rejections.

Results

SIRT1 Plays a Negative Role in the Differentiation of Induced Tregs (iTregs)

Figure 9A:
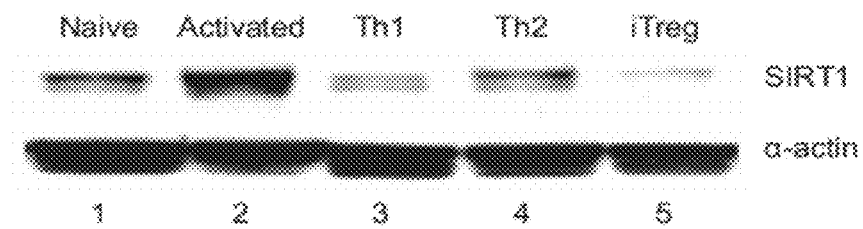
FIGS. 9A and 9B depict the effect of SIRT1 on induced Treg (iTreg) differentiation.

To gain insight into the role of SIRT1 in Treg biology, SIRT1 protein expression during ex vivo Treg differentiation was analyzed. Naïve CD4$^+$ T cells (CD4+CD25-CD69-CD44-) were isolated from mouse spleen and lymph nodes and were activated by anti-CD3/CD28 antibodies alone or in combination with cytokines driving differentiation into T helper (Th) 1, Th2 or induced Treg (iTreg) cells. While SIRT1 expression was increased upon CD3/CD28 activation, it was decreased after T cell differentiation, most noticeably in iTregs (FIG. 9A, lane 5).

Figure 9B:
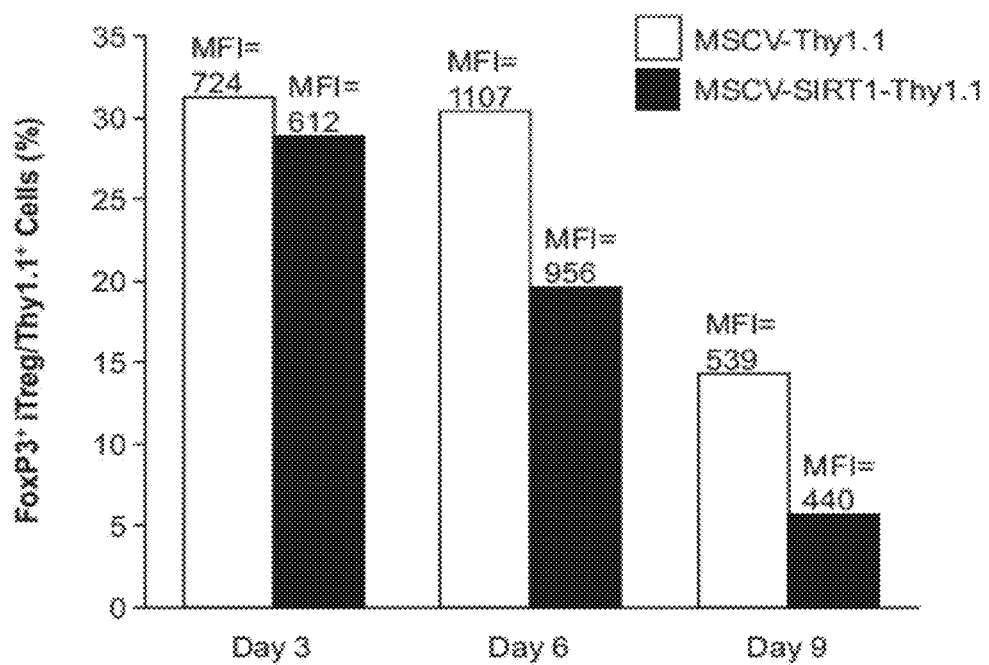

To test whether SIRT1 plays a role in iTreg differentiation, SIRT1 was overexpressed during iTreg differentiation. Activated CD4+ cells were infected with bicistronic retroviral vectors expressing SIRT1 and the Thy1.1 surface marker (MSCV-SIRT1-Thy1.1) or a control vector expressing Thy1.1 alone (MSCV-Thy1.1). Cell were further differentiated into Tregs in the presence of recombinant human TGF-β and recombinant human IL-2 as previously described (Fu et al., 2004). After 3 days, cells were stained for surface Thy1.1 and intracellular FoxP3 and analyzed by flow cytometry. No difference in the number of FoxP3$^+$Thy1.1$^+$ cells was observed in cultures expressing SIRT1 or control cells; however, the mean fluorescence intensity (MFI) of FoxP3 was decreased in cells overexpressing SIRT1 (FIG. 9B). Cells were cultured 3 more days in IL-2 alone and were reanalyzed at day 6 after infection. Both, the number of FoxP3+/Thy1.1+ cells and FoxP3 MFI were decreased in SIRT1-expressing cells (FIG. 9B). The opposite result was observed when SIRT1 was knocked down during iTreg differentiation using lentiviral shRNA vectors. Collectively, these data indicate that SIRT1 decreases the expression of FoxP3 protein and negatively regulates iTreg differentiation.

Binding and Deacetylation of FoxP3 by SIRT1

To test whether SIRT1 controls FoxP3 expression through deacetylation coimmunoprecipitation experiments were performed in 293 T cells. Hemagglutinin (HA)-tagged SIRT1 protein coimmunoprecipitated with FLAG-tagged FoxP3 in cells transfected with SIRT1- and FoxP3 expression vectors, but no signal was obtained when SIRT1 or FoxP3 were expressed alone (FIG. 10A). Next, a series of deletion mutants of FoxP3 (Ono et al., 2007) was tested, to map the SIRT1 interaction site in FoxP3. C-terminal deletion at amino acids 278 reduced SIRT1 binding to FoxP3, pointing to amino acids 279 to 337 as a region involved in FoxP3 binding to SIRT1 (FIG. 10B, lanes 2-4). In addition, the N-terminal deletion at amino aids 187 abrogated binding to SIRT1 identifying a second interaction site with SIRT1 at amino acids 133 and 187 of FoxP3 (FIG. 2B, lane 9).

To further explore the possibility that SIRT1 deacetylates FoxP3, cells expressing FLAG-FoxP3 were subjected to treatment with nicotinamide, a natural byproduct and feedback inhibitor of the sirtuin deacetylation reaction. Nicotinamide treatment increased acetylation levels of FoxP3 in synergy with the histone acetyltransferase p300 supporting the model that SIRT1 is involved in FoxP3 deacetylation (FIG. 10C, lane 3). Interestingly, nicotinamide-induced hyperacetylation of FoxP3 was more pronounced than hyperacetylation induced by trichostatin A (TSA), a class I and II HDAC inhibitor previously shown to increase FoxP3 acetylation (Li et al., 2007; Tao et al., 2007) (FIG. 10C, lane 2). No synergy was observed when cells were treated with nicotinamide and TSA together (FIG. 10C, lane 4). In contrast, acetylation of another transcription factor, AML1/Runx1 was increased to the same extent by TSA and nicotinamide treatment and both agents synergized to further increase acetylation (FIG. 10D).

SIRT1 Destabilizes the FoxP3 Protein via K31, K262, and K267

Figure 11A:
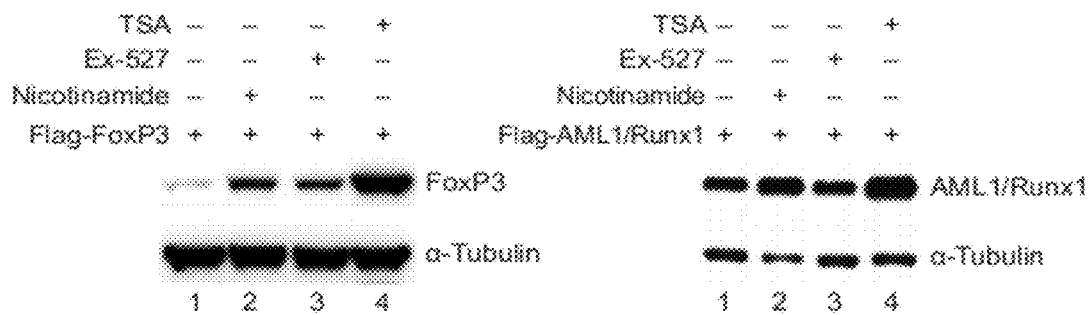
FIGS. 11A-D depict destabilization of FoxP3 protein via deacetylation by SIRT1.
Figure 11B:

During these studies of FoxP3 acetylation, noticed an upregulation of protein expression in response to nicotinamide as well as TSA was noticed. To further study the effect of SIRT1 on FoxP3 protein expression, cells were treated with Ex-527, a specific inhibitor of SIRT1. Ex-527 treatment increased FoxP3 protein expression to a similar extent as nicotinamide, supporting the model that SIRT1 deacetylates and destabilizes FoxP3 (FIG. 11A). No effect of Ex-527 or nicotinamide treatment was observed on FoxP3 mRNA levels. In addition, expression of FLAG-AML1/Runx1, which was driven by the same promoter as FoxP3, was unchanged in response to Ex-527 treatment further excluding transcriptional effects of Ex-527 on FoxP3 expression (FIG. 11B). In contrast, treatment with TSA increased both FoxP3 and AML1/Runx1 expression confirming previously described transcriptional effects of TSA on the CMV promoter. This result indicates that inhibition of SIRT1 deacetylase activity by Ex-527 stabilizes FoxP3 expression at the post-transcriptional level.

To map the acetylation sites in FoxP3, mass spectrometry was performed on FLAG-FoxP3 isolated from 293 T cells. Flag-FoxP3 was expressed in 293 T cells, immunoprecipitated using anti-Flag agarose, eluted with FLAG peptides and analyzed by mass spectrometry. Peptides recovered in the analysis covered 78-82% of the FoxP3 protein. Three acetylated sites were identified: K31, K262, K267 in mouse FLAG-FoxP3 and the corresponding sites: K31, K263 and K268 in human FLAG-FoxP3 (FIG. 11B). Interestingly, peptides containing acetylated K31 and K262 residues were recovered from samples expressing FLAG-Foxp3 alone, while acetylation of K267 was only detected in samples in which p300 was coexpressed and which were also treated with a combination of TSA and nicotinamide (FIG. 11B). This suggests that K267 is a reversible target of p300 and SIRT1/HDACs while K31 and K262 are more stably acetylated in cells. Interestingly, both K262 and K267 are located close to the C-terminal SIRT1 binding region in FoxP3 (aa 278-337).

Figure 11C:
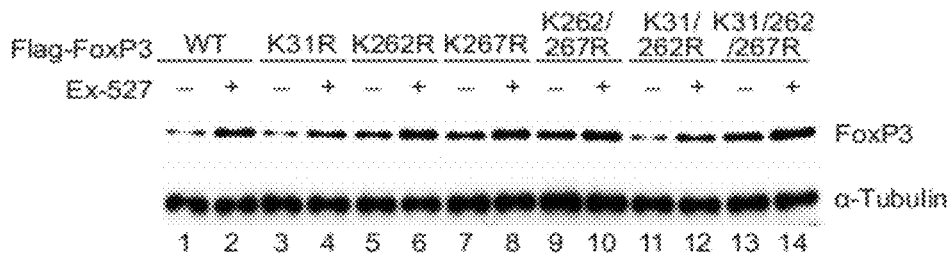

To determine whether the three newly identified acetylated lysine residues regulate FoxP3 stability, mutants were generated in which each of three lysine residues was substituted to arginines (KR), a conservative mutation that preserves the positive charge of the residue. Expression of FLAG-FoxP3 increased in K262R and K267R mutants suggesting that these residues are involved in regulating FoxP3 protein stability (FIG. 11C, lanes 5 and 7). No such effect was observed when K31 was mutated. In addition, treatment with Ex-527 increased expression of the K31R mutant to comparable levels as the wild type FoxP3 protein (FIG. 11C, lanes 3 and 4). This increase was less visible in K262R and K267 R mutants indicating that these residues are targeted by SIRT1 (FIG. 11C, lanes 6 and 8). Expression of the K262/267R double mutant further increased above levels of the single mutants, and Ex-527 treatment could not further increase the expression of the K262/267R double mutant (FIG. 11C, lanes 9 and 10). Mutation of the triple K31/262/267R mutant (3KR) showed a similar effect as the double mutant (FIG. 11C, lanes 13 and 14).

Figure 11D:
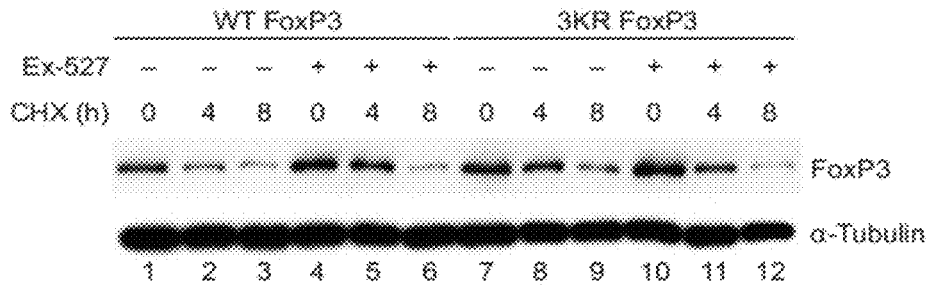

To investigate the effect of SIRT1 inhibition and the three newly identified acetylation sites on FoxP3 protein stability, wild type and 3KR mutant FoxP3 protein expression was measured after treatment with cycloheximide (CHX), a general inhibitor of protein translation. Expression of wild type FoxP3 expression was markedly decreased after 4 h of CHX treatment while treatment with Ex-527 stabilized FoxP3 protein expression at this time point (FIG. 11D, lanes 2 and 5). The 3KR mutant FoxP3 protein mimicked the effect of Ex-527 at the 4 hour-time point, and no further stabilization was observed after Ex-527 treatment (FIG. 11D, lanes 8 and 11). Collectively, these data show that the SIRT1-mediated destabilization of FoxP3 is mediated by the newly identified acetylation sites in FoxP3, mainly K262 and K267.

Treatment with Ex-527 Stabilizes FoxP3 Expression in Induced and Natural Tregs

Figure 12A:
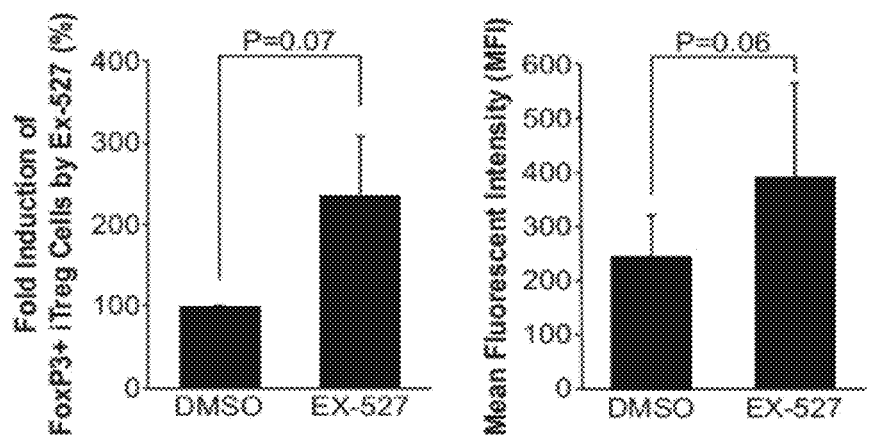
FIGS. 12A and 12B depict the effect of inhibition of SIRT1 activity on differentiation of iTreg cells and FoxP3 expression in nTreg cells.
Figure 12B:
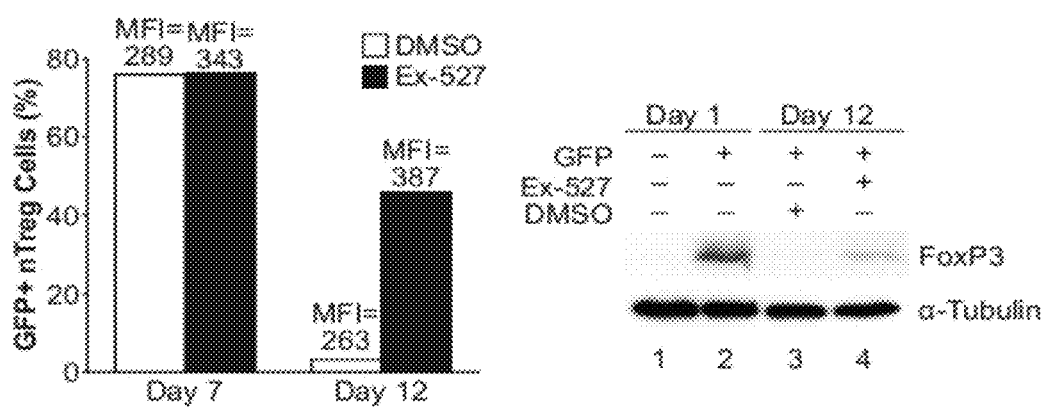

To test the effect of Ex-527 on FoxP3 expression in natural FoxP3-expressing cells, Ex-527 was added to naïve CD4+ T cells undergoing differentiation into iTreg cells. The number of FoxP3-expressing cells increased up to 3-fold in the presence of Ex-527 as compared to cells treated with the drug vehicle alone (FIG. 12A). In addition, the mean fluorescent intensity (MFI) of FoxP3 expression was increased up to 2-fold (FIG. 12B). As expected, no effect of Ex-527 on FoxP3 mRNA levels was observed, confirming that Ex-527 promotes FoxP3 expression in iTreg cells at the post-transcriptional level.

To test the effect of Ex-527 in natural thymus-derived Treg cells, GFP+ cells were isolated from GFP-Foxp3 knock-in mice, in which green fluorescent protein (GFP) is expressed as a fusion protein with FoxP3. Total CD4+ T cells were isolated from spleen and lymph nodes of these mice, and GFP+ T cells were sorted with >95% purity. GFP+ T cells were expanded by anti-CD3/CD28 beads and IL-2 for 5 days when Ex-527 or dimethylsulfoxide (DMSO) was added. Two days later, 75% of cells were GFP-positive regardless whether Ex-527 was added or not; however, the MFI of GFP was increased in Ex-527-treated cells (FIG. 12B, day 7). 7 days later, only 5% of cells remained GFP-positive in control-treated cells versus 45% in Ex-527-treated cultures (FIG. 12B, day 12). In addition, the MR of FoxP3 remained higher in Ex-527-treated cells versus control-treated cells (387 versus 263). At day 12, FoxP3 expression in Ex-527-treated cells remained visible by western blot analysis (FIG. 12B). No FoxP3 expression was detected from either GFP-negative cells or cells expanded in the absence of Ex-527 (FIG. 12B). These data underline the negative role of SIRT1 deactylase activity on FoxP3 expression in the natural context of induced or natural Treg cells. Thus, SIRT1 inhibitors, e.g., Ex-527, can be used to maximize ex vivo or in vivo expansion of Tregs for therapeutic purposes.

FIGS. 9A and 9B. SIRT1 plays a negative role in iTreg differentiation (A) Western blot analysis of SIRT1 in mouse CD4+ T cells. Naïve CD4+ T cells isolated from mouse spleen and lymph node were activated with CD3 and CD28 antibodies and differentiated into Th1, Th2 and iTreg cells as described in material and methods. (B) Flow cytometry of iTregs infected with a bicistronic retroviral vector expressing SIRT1 (MSCV-SIRT1-Thy1.1) or control vector (MSCV-Thy1.1). Thy1.1 is a surface marker that is coexpressed to gate on infected cells. Infection efficiencies were similar in SIRT1-expressing or control-infected cells (~20% Thy1.1+ cells). Shown are the percentage of FoxP3+ cells in the Thy1.1+ population and the mean fluorescence intensity (MFI) of FoxP3 per cell. A and B show one representative experiment of two with the same results.

FIGS. 10A-D. SIRT1 interacts with FoxP3 and inhibition of SIRT1 deacetylase activity increases acetylation of FoxP3. (A) Communoprecipitation/western blot analysis of FLAG-tagged FoxP3 and HA-tagged SIRT1 after transfection of corresponding expression vectors or empty vector controls into 293T cells. (B) Communoprecipitation assay of SIRT1 and FoxP3 deletion mutants. A schematic summary of the binding of FoxP3 mutants to SIRT1 is shown. The forkhead box (FH) indicates the DNA binding domain ZnF, zinc finger domain; LZ, leucine zipper. (C) Immunoprecipitation/Western blot analysis of acetylated FLAG-FoxP3 in response to trichostatin A (TSA) or nicotinamide in 293 T cells. An expression vector for the p300 acetyltransferase was cotransfected with FoxP3. (D) The same experiment as in (C) using HA-AML1/Runx1. Immunoprecipitations were performed with either anti-FLAG antibody coupled to agarose (α-FLAG agarose) (C) or anti-hemagglutinin antibody coupled to agarose (α-HA agarose) (D) and western blotting with rabbit polyclonal antibody to acetyl-lysine (α-acetyl lysine) (α-AcK), α-FLAG or α-HA antibodies.

FIGS. 11A-D. SIRT1 destabilizes FoxP3 protein through deacetylation of three newly identified acetylation sites (A) Western blot analysis of FLAG-FoxP3 or FLAG-AML1/Runx1in 293 T cells treated with nicotinamide (5 mM), Ex-527 (50 µM) or trichostatin A TSA (400 nM) for 16 hours. (B) Scheme of acetylated lysine residues identified by mass spectrometry using immunoprecipitated FLAG-FoxP3 protein. The murine protein is shown. (C) Western blot analysis of wild type or mutant FLAG-FoxP3 proteins in 293 T cells treated with Ex-527 (50 µM) or DMSO as a control. (D) Western blot analysis of wild type or mutant K31/K262/K267R (3KR) FLAG-FoxP3 in 293 cells treated with cycloheximide (CHX) and/or Ex-527 for indicated times.

FIGS. 12A and 12B. Inhibition of SIRT1 activity by Ex-527 promotes differentiation of iTreg cells and FoxP3 expression in nTreg cells. (A) Intracellular flow cytometry (% FoxP3+ cells and MFI) of FoxP3 in induced Tregs treated during differentiation with Ex-527 (50 µM) or DMSO as control. Shown are averages of three independent experiments (mean±SD). (B) Flow cytometry of GFP in natural Treg populations isolated from GFP-FoxP3 knock-in mice, in which GFP is expressed as a fusion protein with FoxP3. GFP+ nTregs were expanded by α-CD3/CD28 beads and hIL-2 (2000 U/ml) for 5 days. Cells were further cultured with either DMSO or Ex-527 for additional 2 and 7 days and FoxP3 expression was analyzed as in (A). Western blot analysis of FoxP3 in cell lysates from GFP−, GFP+, and GFP+ cultures expanded as described in the presence of DMSO or EX-527.

REFERENCES

Chen, L. F., Williams, S. A., Mu, Y., Nakano, H., Duerr, J. M., Buckbinder, L., and Greene, W. C. (2005). NF-kappaB RelA phosphorylation regulates RelA acetylation. Mol Cell Biol 25, 7966-7975.

Fu, S., Zhang, N., Yopp, A. C., Chen, D., Mao, M., Chen, D., Zhang, H., Ding, Y., and Bromberg, J. S. (2004). TGF-beta induces Foxp3+ T-regulatory cells from CD4+ CD25− precursors. Am J Transplant 4, 1614-1627.

Jordan, A., Defechereux, P., and Verdin, E. (2001). The site of HIV-1 integration in the human genome determines basal transcriptional activity and response to Tat transactivation. EMBO J. 20, 1726-1738.

Kwon, H. S., Brent, M. M., Getachew, R., Jayakumar, P., Chen, L. F., Schnolzer, M., McBurney, M. W., Marmorstein, R., Greene, W. C., and Ott, M. (2008). Human immunodeficiency virus type 1 Tat protein inhibits the SIRT1 deacetylase and induces T cell hyperactivation. Cell Host Microbe 3, 158-167.

Li, B., and Greene, M. I. (2007). FOXP3 actively represses transcription by recruiting the HAT/HDAC complex. Cell Cycle, 6, 1432-1436.

Li, B., Samanta, A., Song, X., Iacono, K. T., Bembas, K., Tao, R., Basu, S., Riley, J. L., Hancock, W. W., Shen, Y., et al. (2007). FOXP3 interactions with histone acetyltransferase and class II histone deacetylases are required for repression. Proc Natl Acad Sci USA 104, 4571-4576.

Ono, M., Yaguchi, H., Ohkura, N., Kitabayashi, I., Nagamura, Y., Nomura, T., Miyachi, Y., Tsukada, T., and Sakaguchi, S. (2007). Foxp3 controls regulatory T-cell function by interacting with AML1/Runx1. Nature 446, 685-689.

Pagans, S., Pedal, A., North, B. J., Kaehlcke, K., Marshall, B. L., Don, A., Hetzer-Egger, C., Henklein, P., Frye, R., McBurney, M. W., et al. (2005). SIRT1 Regulates HIV Transcription via Tat Deacetylation. PLoS Biol 3, e41.

Tao, R., de Zoeten, E. F., Ozkaynak, E., Chen, C., Wang, L., Porrett, P. M., Li, B., Turka, L. A., Olson, E. N., Greene, M. I., et al. (2007). Deacetylase inhibition promotes the generation and function of regulatory T cells. Nature Med 13, 1299-1307.

Zhang, J., Lee, S. M., Shannon, S., Gao, B., Chen, W., Chen, A., Divekar, R., McBurney, M. W., Braley-Mullen, H., Zaghouani, H., and Fang, D. (2009). The type III histone deacetylase Sirt1 is essential for maintenance of T cell tolerance in mice. J Clin Invest 119, 3048-3058.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto

What is claimed is:

1. A method of treating chronic immune hyperactivity in an individual, the method comprising administering to an individual having chronic immune hyperactivity an effective amount of a SIRT1 activator, wherein the SIRT1 activator is a compound of the formula:

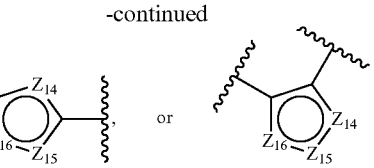

(XVIII)

or a salt thereof, wherein $R^{19}$ is selected from:

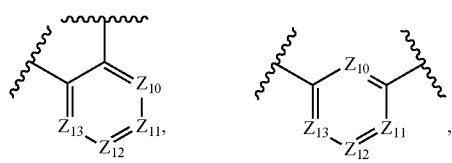

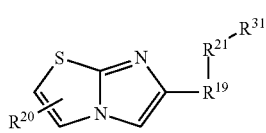

wherein:

each $Z_{10}$, $Z_{11}$, $Z_{12}$ and $Z_{13}$ is independently selected from N, $CR^{20}$ or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, S or O;

zero to one of $Z_{14}$, $Z_{15}$ and $Z_{16}$ is S or O;

zero to two of $Z_{14}$, $Z_{15}$ and $Z_{16}$ is N or $NR_1'$;

zero to one $R^{30}$ is a solubilizing group; and zero to one $R_1'$ is an optionally substituted $C_1$-$C_3$ straight or branched alkyl;

each $R^{20}$ is independently selected from H or a solubilizing group;

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—C(O)—$NR_1'$—, —$CR_1'R_1'$—, —$NR_1'$—C(O)—C(O)—$CR_1'$=$CR_1'$—, —$NR_1'$—S(O)$_2$—$NR_1'$—$NR_1'$—C(O)—$NR_1'$—S(O)$_2$—, —NR₁'—CR₁'R₁'—C(O)—NR₁'—, —CR₁'R₁'—C(O)—NR₁'—, —NR₁'—C(O)—CR₁'=CR₁'—CR₁'R₁'—, —NR₁'—C(=N—CN)—NR₁'—, —NR₁'—C(O)—CR₁'R₁'—O—, —NR₁'—C(O)—CR₁'R₁'—CR₁'R₁'—O—, —NR₁'—S(O)₂—CR₁'R₁'—, —NR₁'—S(O)₂—CR₁'R₁'—CR₁'R₁'—, —NR₁'—C(O)—CR₁'R₁'—; —NR₁'—C(O)—CR₁'R'₁—CR₁'R'₁—, —NR₁'—C(S)—NR₁'—CR₁'R'₁—CR₁'R'₁—, —NR₁'—C(O)—O—,

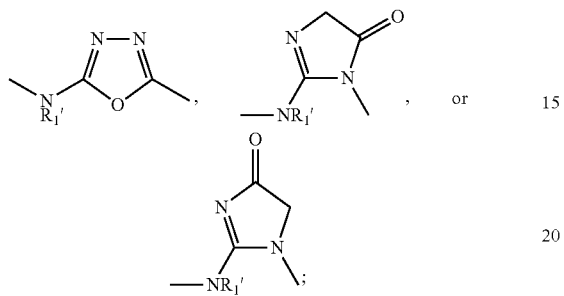

wherein each $R_1'$ is independently selected from H or optionally substituted $C_1$-$C_3$ straight or branched alkyl; and $R^{31}$ is selected from an optionally substituted monocyclic or bicyclic aryl, or an optionally substituted monocyclic or bicyclic heteroaryl, wherein the chronic immune hyperactivity results from an immunodeficiency virus infection.

2. The method of claim 1, wherein the individual is a human.

3. The method of claim 1, wherein the immunodeficiency virus infection is a human immunodeficiency virus-1 (HIV-1) infection.

4. The method of claim 3, further comprising administering to the individual at least one additional therapeutic agent that treats the HIV-1 infection.

5. The method of claim 1, wherein the SIRT1 activator is a selective SIRT1 activator.

6. The method of claim 1, wherein the SIRT1 activator is a compound of the formula:

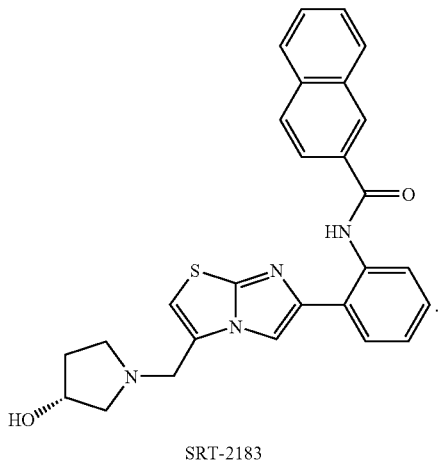 [SMILES: O=C(Nc1ccccc1-c1cn2c(CN3CC[C@@H](O)C3)csc2n1)c1ccc2ccccc2c1 ; "."]

SRT-2183

7. The method of claim 1, wherein the SIRT1 activator is administered orally.

* * * * *

```
                              SEQUENCE LISTING

<160> NUMBER OF SEQ ID NOS: 5

<210> SEQ ID NO 1
<211> LENGTH: 747
<212> TYPE: PRT
<213> ORGANISM: Homo sapiens

<400> SEQUENCE: 1

Met Ala Asp Glu Ala Ala Leu Ala Leu Gln Pro Gly Gly Ser Pro Ser
 1               5                  10                  15

Ala Ala Gly Ala Asp Arg Glu Ala Ala Ser Ser Pro Ala Gly Glu Pro
                20                  25                  30

Leu Arg Lys Arg Pro Arg Arg Asp Gly Pro Gly Leu Glu Arg Ser Pro
            35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Leu Trp Arg Glu Ala Glu
65                  70                  75                  80

Ala Glu Ala Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335
```

-continued

```
Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
        355                 360                 365

Ala Ser Cys Leu Ile Cys Lys Tyr Lys Val Asp Cys Glu Ala Val Arg
    370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
                405                 410                 415

Asn Leu Pro Glu Gln Phe His Arg Ala Met Lys Tyr Asp Lys Asp Glu
            420                 425                 430

Val Asp Leu Leu Ile Val Ile Gly Ser Ser Leu Lys Val Arg Pro Val
        435                 440                 445

Ala Leu Ile Pro Ser Ser Ile Pro His Glu Val Pro Gln Ile Leu Ile
    450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Ser Pro Glu Arg Thr
    530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
        595                 600                 605

Glu Lys Asn Glu Arg Thr Ser Val Ala Gly Thr Val Arg Lys Cys Trp
    610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655

Val Tyr Ser Asp Ser Glu Asp Asp Val Leu Ser Ser Ser Ser Cys Gly
            660                 665                 670

Ser Asn Ser Asp Ser Gly Thr Cys Gln Ser Pro Ser Leu Glu Glu Pro
        675                 680                 685

Met Glu Asp Glu Ser Glu Ile Glu Glu Phe Tyr Asn Gly Leu Glu Asp
    690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745
```

<210> SEQ ID NO 2

```
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: ACETYLATION
<222> LOCATION: 5
<223> OTHER INFORMATION: Acetylated lysine

<400> SEQUENCE: 2

Ser Tyr Gly Arg Lys Lys Lys Arg Arg Gln Arg
 1               5                  10

<210> SEQ ID NO 3
<211> LENGTH: 431
<212> TYPE: PRT
<213> ORGANISM: Homo sapiens

<400> SEQUENCE: 3

Met Pro Asn Pro Arg Pro Gly Lys Pro Ser Ala Pro Ser Leu Ala Leu
 1               5                  10                  15

Gly Pro Ser Pro Gly Ala Ser Pro Ser Trp Arg Ala Ala Pro Lys Ala
                20                  25                  30

Ser Asp Leu Leu Gly Ala Arg Gly Pro Gly Gly Thr Phe Gln Gly Arg
             35                  40                  45

Asp Leu Arg Gly Gly Ala His Ala Ser Ser Ser Leu Asn Pro Met
     50                  55                  60

Pro Pro Ser Gln Leu Gln Leu Pro Thr Leu Pro Leu Val Met Val Ala
 65                  70                  75                  80

Pro Ser Gly Ala Arg Leu Gly Pro Leu Pro His Leu Gln Ala Leu Leu
                 85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300
```

```
Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
            325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
            355                 360                 365

Arg Met Phe Ala Phe Phe Arg Asn His Pro Ala Thr Trp Lys Asn Ala
            370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
                420                 425                 430

<210> SEQ ID NO 4
<211> LENGTH: 429
<212> TYPE: PRT
<213> ORGANISM: Mus musculus

<400> SEQUENCE: 4

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Gly Pro Phe Gln Gly Arg
            35                  40                  45

Asp Leu Arg Ser Gly Ala His Thr Ser Ser Ser Leu Asn Pro Leu Pro
50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
            115                 120                 125

Ser Leu Pro Pro Pro Ser Ala Ala Thr Gly Val Phe Ser Leu Lys Ala
130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
            195                 200                 205

Glu Pro Glu Glu Phe Leu Lys His Cys Gln Ala Asp His Leu Leu Asp
            210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255
```

```
Ala His Leu Ala Gly Lys Met Ala Leu Ala Lys Ala Pro Ser Val Ala
            260                 265                 270

Ser Met Asp Lys Ser Ser Cys Cys Ile Val Ala Thr Ser Thr Gln Gly
            275                 280                 285

Ser Val Leu Pro Ala Trp Ser Ala Pro Arg Glu Ala Pro Asp Gly Gly
            290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
            325                 330                 335

Arg Pro Pro Phe Thr Tyr Ala Thr Leu Ile Arg Trp Ala Ile Leu Glu
            340                 345                 350

Ala Pro Glu Arg Gln Arg Thr Leu Asn Glu Ile Tyr His Trp Phe Thr
            355                 360                 365

Arg Met Phe Ala Tyr Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
            405                 410                 415

Arg Ser Gln Arg Pro Asn Lys Cys Ser Asn Pro Cys Pro
            420                 425

<210> SEQ ID NO 5
<211> LENGTH: 431
<212> TYPE: PRT
<213> ORGANISM: Bos taurus

<400> SEQUENCE: 5

Met Pro Asn Pro Arg Pro Ala Lys Pro Leu Ala Pro Ser Leu Val Leu
1               5                   10                  15

Ser Pro Ser Pro Gly Ala Ser Pro Ser Trp Arg Ala Ala Pro Lys Ala
            20                  25                  30

Ser Asp Gln Leu Gly Thr Lys Ser Pro Gly Thr Thr Phe Gln Gly Arg
        35                  40                  45

Asp Leu Arg Ser Gly Ala His Thr Ser Ser Ser Leu Asn Pro Met
    50                  55                  60

Pro Pro Ser Gln Leu Gln Met Pro Thr Val Pro Leu Val Met Val Ala
65                  70                  75                  80

Pro Ser Gly Ala Arg Leu Gly Pro Ser Pro His Leu Gln Ala Leu Leu
            85                  90                  95

Gln Asp Arg Pro His Phe Val His Gln Leu Ser Thr Val Asp Ala His
            100                 105                 110

Ala Arg Thr Pro Val Leu Gln Val Arg Pro Leu Asp Ser Pro Ala Met
            115                 120                 125

Ile Ser Leu Pro Pro Thr Ala Ala Thr Gly Leu Phe Ser Leu Lys
            130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Ser Pro Gly Met
            165                 170                 175

Pro Arg Lys Asp Ser Thr Leu Ser Thr Val Pro Gln Gly Ser Tyr Ser
            180                 185                 190

Leu Leu Ala Asn Gly Val Cys Lys Trp Pro Gly Cys Glu Lys Val Phe
            195                 200                 205
```

```
Lys Glu Pro Glu Asp Phe Leu Lys His Cys Gln Ala Asp His Leu Leu
    210                 215                 220
Asp Glu Lys Gly Arg Ala Gln Cys Leu Leu Gln Arg Glu Val Val Gln
225                 230                 235                 240
Ser Leu Glu Gln Gln Leu Val Leu Glu Lys Glu Lys Leu Gly Ala Met
                245                 250                 255
Gln Ala His Leu Ala Gly Lys Met Ala Gln Thr Lys Ala Pro Ser Ala
            260                 265                 270
Ala Ser Ser Asp Lys Gly Ser Cys Cys Ile Val Ala Thr Gly Thr Pro
        275                 280                 285
Gly Thr Thr Val Pro Ala Trp Pro Gly Pro Gln Glu Ala Pro Asp Gly
    290                 295                 300
Leu Phe Ala Val Arg Arg His Leu Trp Gly Ser His Gly Asn Ser Thr
305                 310                 315                 320
Phe Pro Glu Phe Phe His Asn Met Asp Tyr Phe Lys Phe His Asn Met
                325                 330                 335
Arg Pro Pro Phe Thr Tyr Ala Thr Leu Ile Arg Trp Ala Ile Leu Glu
            340                 345                 350
Ala Pro Glu Lys Gln Arg Thr Leu Asn Glu Ile Tyr His Trp Phe Thr
        355                 360                 365
Arg Met Phe Ala Phe Phe Arg Asn His Pro Ala Thr Trp Lys Asn Ala
    370                 375                 380
Ile Arg His Asn Leu Ser Leu His Lys Cys Phe Val Arg Val Glu Ser
385                 390                 395                 400
Glu Lys Gly Val Val Trp Thr Val Asp Glu Phe Glu Phe Arg Lys Lys
                405                 410                 415
Arg Ser Gln Arg Pro Ser Arg Cys Ser Asn Pro Thr Pro Gly Pro
            420                 425                 430
```